(12) United States Patent
Venkatesan et al.

(10) Patent No.: US 7,812,014 B2
(45) Date of Patent: Oct. 12, 2010

(54) BICYCLIC 6-ALKYLIDENE-PENEMS AS β-LACTAMASE INHIBITORS

(75) Inventors: Aranapakam Mudumbai Venkatesan, Rego Park, NY (US); Tarek Suhayl Mansour, New City, NY (US); Takao Abe, Saitama (JP); Itsuki Yamamura, Saitama (JP); Tsuyoshi Takasaki, Saitama (JP); Atul Agarwal, Hamden, CT (US); Osvaldo Dos Santos, Kew Gardens, NY (US); Fuk-Wah Sum, Pomona, NY (US); Yang-I Lin, Tappan, NY (US)

(73) Assignee: Wyeth LLC, Madison, NJ (US)

( * ) Notice: Subject to any disclaimer, the term of this patent is extended or adjusted under 35 U.S.C. 154(b) by 0 days.

(21) Appl. No.: 12/195,706

(22) Filed: Aug. 21, 2008

(65) Prior Publication Data
US 2008/0312203 A1    Dec. 18, 2008

Related U.S. Application Data

(60) Continuation of application No. 11/447,814, filed on Jun. 6, 2006, now abandoned, which is a division of application No. 10/427,380, filed on May 1, 2003, now Pat. No. 7,112,582.

(60) Provisional application No. 60/377,052, filed on May 1, 2002.

(51) Int. Cl.
C07D 519/06 (2006.01)
C07D 513/04 (2006.01)
A61P 31/04 (2006.01)
A61K 31/424 (2006.01)
C07D 499/881 (2006.01)
A61K 31/431 (2006.01)

(52) U.S. Cl. .................... 514/210.06; 540/347
(58) Field of Classification Search ............ 540/347; 514/210.06
See application file for complete search history.

(56) References Cited

U.S. PATENT DOCUMENTS

| | | | |
|---|---|---|---|
| 4,206,067 A | 6/1980 | MacKinnon | |
| 4,485,110 A | 11/1984 | Osborne et al. | |
| 4,891,369 A | 1/1990 | Torii et al. | |
| 5,096,899 A * | 3/1992 | Pfaendler et al. | 514/210.06 |
| 5,911,985 A | 6/1999 | Coleman et al. | |
| 6,268,393 B1 | 7/2001 | Xu et al. | |
| 7,018,997 B2 | 3/2006 | Venkatesan et al. | |
| 7,112,582 B2 | 9/2006 | Venkatesan et al. | 514/193 |
| 2003/0080312 A1 | 5/2003 | Seddon et al. | |
| 2004/0043978 A1 | 3/2004 | Venkatesan et al. | |
| 2004/0043980 A1* | 3/2004 | Pfaendler | 514/210.06 |
| 2004/0053913 A1 | 3/2004 | Abe et al. | |
| 2004/0077622 A1 | 4/2004 | Venkatesan et al. | |
| 2004/0132708 A1 | 7/2004 | Abe et al. | |
| 2004/0176349 A1* | 9/2004 | Simpson et al. | 514/210.06 |
| 2005/0101654 A1 | 5/2005 | Weiberth et al. | |
| 2006/0276445 A1* | 12/2006 | Mansour et al. | 514/195 |
| 2006/0276446 A1* | 12/2006 | Mansour et al. | 514/195 |
| 2007/0129344 A1* | 6/2007 | Mansour et al. | 514/193 |

FOREIGN PATENT DOCUMENTS

| | | |
|---|---|---|
| EP | 0 041 768 B1 | 12/1981 |
| EP | 0041768 | 12/1981 |
| EP | 0 120 613 A1 | 10/1984 |
| EP | 0120613 | 10/1984 |
| EP | 0 150 781 A1 | 8/1985 |
| EP | 0 150 984 B1 | 8/1985 |
| EP | 0150781 | 8/1985 |
| EP | 0150984 | 8/1985 |
| EP | 0 154 132 B1 | 9/1985 |
| EP | 0154132 | 9/1985 |
| EP | 0 167 050 A1 | 1/1986 |
| EP | 0167050 | 1/1986 |
| EP | 0 210 065 A1 | 1/1987 |
| EP | 0210065 | 1/1987 |
| EP | 0 210 814 A1 | 2/1987 |
| EP | 0210814 | 2/1987 |
| EP | 0232966 | 8/1987 |
| EP | 0 313 458 | 4/1989 |
| EP | 0 321 187 B1 | 6/1989 |
| EP | 0321186 | 6/1989 |
| EP | 0321187 | 6/1989 |

(Continued)

OTHER PUBLICATIONS

Bush, K., Antimicrob. Agents Chemother. 1993, 37, 851.

(Continued)

*Primary Examiner*—Mark L Berch
(74) *Attorney, Agent, or Firm*—Jennifer A. Kispert; Michael J. Herman

(57) ABSTRACT

The present invention provides a compound of formula I

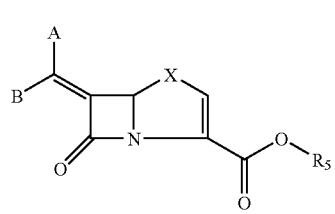

wherein one of A and B is hydrogen and the other an optionally substituted fused bicyclic heteroaryl group as defined herein; X is O; $R_5$ is H, C1-C6 alkyl, C5-C6 cycloalkyl, or $CHR_3OCOC1$-C6 alkyl; and $R_3$ is hydrogen, C1-C6 alkyl, C5-C6 cycloalkyl, optionally substituted aryl, or optionally substituted heteroaryl; or a pharmaceutically acceptable salt thereof; and pharmaceutical compositions and the use thereof for the treatment of bacterial infection or disease in a patient in need thereof.

31 Claims, No Drawings

FOREIGN PATENT DOCUMENTS

| | | |
|---|---|---|
| EP | 0 321 186 B1 | 6/1994 |
| EP | 0232966 B1 | 8/1997 |
| WO | WO-87/00525 | 1/1987 |
| WO | WO87/00525 A1 | 1/1987 |
| WO | WO-91/12815 | 9/1991 |
| WO | WO-93/03042 | 2/1993 |
| WO | WO93/03042 A1 | 2/1993 |
| WO | WO-94/10178 | 5/1994 |
| WO | WO94/10178 A1 | 5/1994 |
| WO | WO-95/17184 | 6/1995 |
| WO | WO95/17184 A1 | 6/1995 |
| WO | WO-95/28935 | 11/1995 |
| WO | WO95/28935 A1 | 11/1995 |
| WO | WO-03/093277 | 11/2003 |
| WO | WO-03/093279 | 11/2003 |
| WO | WO-03/093280 | 11/2003 |

OTHER PUBLICATIONS

Yang, Y.; Janota, K.; Tabei, K.; Huang, N.; Seigal, M.M.; Lin, Y.I. Rasmussen, B.A. and Shlaes D.M., J. Biol. Chem. 2000, 35, 26674-26882.

Abiko, et al., "Concerning the Boron Mediated Aldol Reaction of Carboxylic Esters", J. Org. Chem., 61:2590-2591 (1996).

Bennett, et al., "6-(Substituted Methylene)Penems, Potent Broad Spectrum Inhibitors of Bacterial β-Lactamase: III. Structure-Activity Relationships of the 5-Membered Heterocyclic Derivatives", Journal of Antibiotics, 44(3):331-337 (1991).

Bouffard, et al., "A New Approach to the Diastereoselective Synthesis of Aldols: Introduction of the 6α-(1R-Hydroxyethyl) Side Chain of the Carbapenem and Penem Antiobiotics", Tetrahedron Letters, 26(51):6285-6288 (1985).

Bouffard, et al., "Thienamycin Total Synthesis. 1. Synthesis of Azetidinone Percursors of (±)-Thienamycin and Its Stereoisomers", J. Org Chem., 45:1130-1135 (1980).

Dininno, et al., "Aldol Condensations of Regiospecific Penicillanate and Cephalosporanate Enolates, Hydroxyethylation at C-6 and C-7", J. Org. Chem., 42(18):2960-2965 (1977).

Innis, "Human Milk and Formula Fatty Acids", Journal of Pediatrics, 120(4,Pt. 2):S56-S59 (1992).

Mansour, "Hunig's Base-Magnesium Chloride Mediated Carbon Alkylation and Oxygen Acylation of Benzoylacetonitrile", Tetrahedron Letters, 29(28):3437-3440 (1988).

Mansour, et al., "N-Protected α-Aminomethylketone Analogues of C-Terminal p-Nitrobenzyl-3-Ketoesters of N-Protected Amino Acids", Synthetic Communications, 19(3&4):667-672 (1989).

Office Action that issued from the European Patent Office on Jun. 20, 2006 in EP 03 733 911.6-1211.

Osborne, et al., "A Novel and Stereocontrolled Synthesis of (5R)-(Z)-6-(1Methyl-1,2,3-triazol-4-ylmethylene)penem-3-carboxylic Acid, a Potent Broad Spectrum β-Lactamase Inhibitor", J. Chem. Soc., Chem. Commun., pp. 371-373 (1989).

Osborne, et al., "Synthesis of (5R)-(Z)-6-(1-Methyl-1,2,3-triazol-4-ylmethylene-penem-3-carboxylic Acid, a Potent Broad Spectrum β-Lactamase Inhibitor, from 6-Aminopenicillanic Acid", J. Chem. Soc. Perkin Trans., pp. 179-188 (1994).

Rathke, et al., "Procedures for the Acylationof Diethyl Malonate and Ethyl Acetoacetate with Acid Chlorides Using Tertiary Amine Bases and Magnesium Chloride", J. Org. Chem., 50:2622-2624 (1985).

International Search Report and Written Opinion of the International Searching Authority issued for PCT/US2006/032781, dated May 8, 2007.

Weiss, et al., "In Vitro and In Vivo Activities of Novel 6-Methylidene Penems as Beta-Lactamase Inhibitors", Antimicrobial Agents and Chemotherapy, 48(12):4589-4596 (2004).

Bush, "β-Lactamases of Increasing Clinical Importance", Cur. Pharm. Design, 5:839-845 (1999).

Bush, et al., "Kinetic Interactions of Tazobactam with β-Lactamases from All Major Structural Classes", Antimicrobial Agents and Chemotherapy, 37(4):851-858(1993).

Cignarella, et al., "6-Chloro- and 6-Bromopenicillanic Acids", J. Org. Chem., 27:2668-2669 (1962).

Coleman, "Anti-Infectives: An Update on β-Lactamases and β-Lactamase Inhibitors", Expert Opin. Invest. Drugs, 4(8):693-704 (1995).

Grant and Hackh's Chemical Dictionary, Fifth Edition, p. 412 (1987).

Haslam, "Protection of Carboxyl Groups", *Protective Groups in Organic Chemistry*, Chapter 5, McOmie, ed., Plenum Press, p. 183-215 (1973).

Jones, "Resistance Patterns Among Nosocomial Pathogens: Trends Over the Past Few Years", Chest, 119:397S-404S (2001).

Osborne, et al., "A Novel and Stereocontrolled Synthesis of (5R)-(Z)-6-(1-Methyl-1,2,3-Triazol-4-Ylmethylene)Penem-3-Carboxylic Acid, A Potent Broad Spectrum β-Lactamase Inhibitor", Journal of the Chemical Society, Letchworth, Great Britain, 6:371-373 (1989).

Payne, et al., "β-Lactamase Epidemiology and the Utility of Established and Novel β-Lactamase Inhibitors", Exp. Opin. Invest. Drugs, 9(2):247-261 (2000).

Rietscha, et al., "Collaborative Clinical Pharmacokinetics Service in a Community Hospital", Am. J. Hosp. Pharm., 41:463-477 (1984).

Sanders, "Cefepime: The Next Generation?", Clin. Infect. Dis., 17:369-379 (1993).

Sutherland, "β-Lactam/β-Lactamase Inhibitor Combinations: Development, Antibacterial Activity and Clinical Applications", Infection, 23(4):191-200 (1995).

Yang, Y., et al., J. Biol. Chem. 2000, 35, 26674-26682.

* cited by examiner

BICYCLIC 6-ALKYLIDENE-PENEMS AS β-LACTAMASE INHIBITORS

This application is a continuation of copending divisional application Ser. No. 11/447,814, filed Jun. 6, 2006, which claims priority from non-provisional application Ser. No. 10/427,380, which claims priority from provisional application Ser. No. 60/377,052, filed May 1, 2002, the entire disclosures of which are hereby incorporated by reference.

FIELD OF INVENTION

This invention relates to certain bicyclic 6-alkylidene penems which act as a broad spectrum β-lactamase inhibitors. β-Lactamases hydrolyze β-lactam antibiotics, and as such serve as the primary cause of bacterial resistance. The compounds of the present invention when combined with β-lactam antibiotics will provide an effective treatment against life threatening bacterial infections.

BACKGROUND OF THE INVENTION

Penicillins and cephalosporins are the most frequently and widely used β-lactam antibiotics in the clinic. However, the development of resistance to β-lactam antibiotics by different pathogens has had a damaging effect on maintaining the effective treatment of bacterial infections. (Coleman, K. *Expert Opin. Invest. Drugs* 1995, 4, 693; Sutherland, R. *Infection* 1995, 23 (4) 191; Bush, K, *Cur. Pharm. Design* 1999, 5, 839-845) The most significant known mechanism related to the development of bacterial resistance to the β-lactam antibiotics is the production of class-A, class-B and class-C serine β-lactamases. These enzymes degrade the β-lactam antibiotics, resulting in the loss of antibacterial activity. Class-A enzymes preferentially hydrolyze penicillins where as Class-C lactamases have a substrate profile favoring cephalosporin hydrolysis. (Bush, K.; Jacoby, G. A.; Medeiros, A. A. *Antimicrob. Agents Chemother* 1995, 39, 1211). To date over 250 different β-lactamases have been reported (Payne, D. J,: Du, W and Bateson, J. H. *Exp. Opin. Invest. Drugs* 2000, 247.) and there is a need for a new generation of broad spectrum β-lactamase inhibitors. Bacterial resistance to these antibiotics could be greatly reduced by administering the β-lactam antibiotic in combination with a compound which inhibits these enzymes.

The commercially available β-lactamase inhibitors such as clavulanic acid, sulbactam and tazobactam are all effective against class-A producing pathogens. Clavulanic acid is clinically used in combination with amoxicillin and ticarcillin; similarly sulbactam with ampicillin and tazobactam with piperacillin. However, these compounds are ineffective against class C producing organisms. The mechanism of inactivation of class-A β-lactamases (such as PC1 and TEM-1) has been elucidated. (Bush, K.; *Antimicrob. Agents Chemother.* 1993, 37, 851; Yang, Y.; Janota, K.; Tabei, K.; Huang, N.; Seigal, M. M.; Lin, Y. I.; Rasmussen, B. A. and Shlaes, D. M. *J. Biol. Chem.* 2000, 35, 26674-26682).

In 1981, the Beecham group disclosed 6-alkylidine penems of general structure 1 as inhibitors of β-lactamases. [N. F. Osborne, U.S. Pat. No. 4,485,110 (1984); N. F. Osborne, Eur. Pat. Appl. 81 301683.9, 1981]

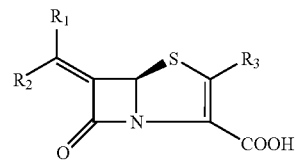

1

$R_1$ and $R_2$ are independently hydrogen or a $C_{1-10}$ hydrocarbon group or mono heterocyclic, and $R_3$ represents a hydrogen or an organic group. Subsequently, the same group disclosed compounds of the general formula 1, wherein $R_1$ comprises a 1,2,3-triazole moiety. [N. F. Osborne, Eur. Pat. Appl. 84301255.0]. The following year, the same group filed 3 patents of the structure 1, wherein $R_1$ is an optionally substituted six membered or five membered mono aromatic ring system. [N. F. Osborne, Eur. Pat. Appl. 85100520.7; Eur. Pat. Appl. 85100521.5; Eur. Pat. Appl. 85300456-2]. European patent applications No. 86305585.1 discloses the synthesis and the utility of (Z)-6-(1-methyl-1,2,3-triazol-4-ylmethylene)-penem-3-carboxylate 2 as a class-A and class-C β-lactamase inhibitor.

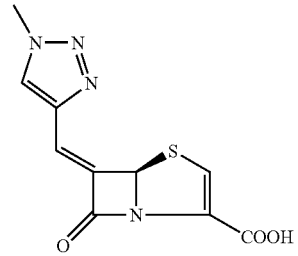

2

Eur. Pat. Appl. 86305584.4 disclosed the preparation of compounds of general formula 1, wherein $R_1$=non-aromatic heterocyclic group and a PCT application [N. J. Broom; P. D. Edwards, N. F. Osborne and S. Coulton PCT WO 87/00525] disclosing $R_1$=fused bicyclic hetero-aromatic group was published. Similarly patent applications [N. J. Broom; G. Brooks; S. Coulton, Eur. Pat. Appl. 88311786.3; N. J. Broom; G. Brooks; B. P. Clarke, Eur. Pat. Appl. 88311787.1) described the preparation and use of compounds of general structure 1, wherein $R_1$ is a substituted five membered hetero-aromatic ring. A process for the preparation of compounds of general formula 1 has been described by Coulton, et al [S. Coulton; J. B. Harbridge; N. F. Osborne and G. Walker Eur. Pat. Appl. No 87300193.7]

In the year 1993, Beecham disclosed [A. V. Stachulski and R. walker, PCT WO 93/03042] the preparation and the use of compounds of general formula 1, in which $R_1$=($C_{1-6}$) alkyl and $R_2$=$CH_2X$ or COY wherein X=halogen or $CONR_2$.

During the last decade three patents have been filed by Beecham describing compounds of general formula 3. [N. J. Broom; F. P. Harrington, PCT WO 94/10178; K. Coleman; J. E. Neale PCT WO 95/28935; K. Coleman; J. E. Neale PCT WO 95/17184] wherein $R_1$=hydrogen or an organic group, and $R_4$ and $R_5$ may be both hydrogen or one or more substituents replacing hydrogen atoms in the ring system shown below.

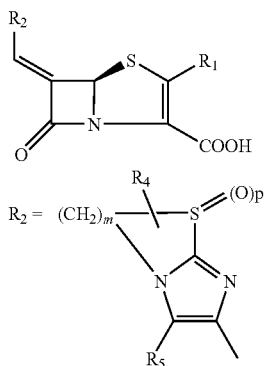

m = 2 or 3; p is 0, 1 or 2

DETAILED DESCRIPTION OF THE INVENTION

The present invention relates to novel, low molecular weight broad spectrum β-lactam compounds, and in particular to a class of bicyclic heteroaryl substituted 6-alkylidene penems which have β-lactamase inhibitory and antibacterial properties. The compounds are therefore useful in the treatment of antibacterial infections in humans or animals, either alone or in combination with other antibiotics.

In accordance with the present invention there are provided compounds of general formula I or a pharmaceutically acceptable salt or in vivo hydrolyzable ester $R_5$ thereof:

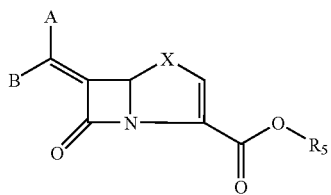

and preferred compounds of the formula:

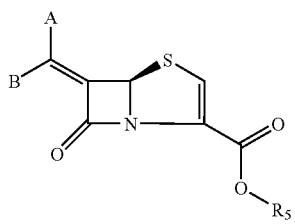

wherein:

One of A and B denotes hydrogen and the other an optionally substituted fused bicyclic heteroaryl group. The expression 'fused bicyclic heteroaryl group' is used in the specification and claims to mean:

A group comprising two fused rings in which one has aromatic character [i.e. Huckel's rule (4n+2)] and the other ring is non-aromatic;

The fused bicyclic heteroaryl group contains one to six heteroatoms selected from the group O, S, N and N—$R_1$;

The fused bicyclic heteroaryl group is bonded to the remainder of the molecule through a carbon atom in the aromatic ring as shown in the formula I;

The aromatic ring of the fused bicyclic heteroaryl group contains five or six ring atoms (including bridgehead atoms) selected from $CR_2$, N, O, S or N—$R_1$. The aromatic ring of the fused bicyclic heteroaryl group contains 0 to 3 heteroatoms selected from the group O, S, N and N—$R_1$;

The non-aromatic ring of the fused bicyclic heteroaryl group contains five to eight ring atoms (including bridgehead atoms) selected from $CR_4R_4$, N, N—$R_1$, O, $S(O)_n$ where n=0-2. The non-aromatic ring of the fused bicyclic heteroaryl group contains 0 to 4 heteroatoms selected from N, N—$R_1$, O or $S(O)_n$ where n=0 to 2.

X is O or S, preferably S;

$R_5$ is H, an in vivo hydrolyzable ester such as C1-C6 alkyl, C5-C6 cycloalkyl, $CHR_3OCOC1$-C6 or salts such as Na, K, Ca; preferably $R_5$ is H or a salt;

$R_1$ is H, optionally substituted —C1-C6 alkyl, optionally substituted -aryl, optionally substituted -heteroaryl or mono or bicyclic saturated heterocycles, optionally substituted —C3-C7 cycloalkyl, optionally substituted —C3-C6 alkenyl, optionally substituted —C3-C6 alkynyl with the proviso that both the double bond and the triple bond should not be present at the carbon atom which is directly linked to N; optionally substituted —C1-C6 per fluoro alkyl, —$S(O)_p$ optionally substituted alkyl or aryl where p is 2, optionally substituted —C=Oheteroaryl, optionally substituted —C=Oaryl, optionally substituted —C=O (C1-C6) alkyl, optionally substituted —C=O(C3-C6) cycloalkyl, optionally substituted —C=O mono or bicyclic saturated heterocycles, optionally substituted C1-C6 alkyl aryl, optionally substituted C1-C6 alkyl heteroaryl, optionally substituted aryl-C1-C6 alkyl, optionally substituted heteroaryl-C1-C6 alkyl, optionally substituted C1-C6 alkyl mono or bicyclic saturated heterocycles, optionally substituted arylalkenyl of 8 to 16 carbon atoms, —$CONR_6R_7$, —$SO_2NR_6R_7$, optionally substituted arylalkyloxyalkyl, optionally substituted -alkyl-O-alkyl-aryl, optionally substituted -alkyl-O-alkyl-heteroaryl, optionally substituted aryloxyalkyl, optionally substituted heteroaryloxyalkyl, optionally substituted aryloxyaryl, optionally substituted aryloxyheteroaryl, optionally substituted C1-C6alkyl aryloxyaryl, optionally substituted C1-C6 alkyl aryloxyheteroaryl, optionally substituted alkyl aryloxy alkylamines, optionally substituted alkoxy carbonyl, optionally substituted aryloxy carbonyl, optionally substituted heteroaryloxy carbonyl. Preferred $R_1$ groups are H, optionally substituted alkyl, optionally substituted aryl, —C=O(C1-C6)alkyl, C3-C6alkenyl, C3-C6alkynyl, optionally substituted cycloalkyl, $SO_2$alkyl, $SO_2$aryl, optionally substituted heterocycles, —$CONR_6R_7$, and optionally substituted heteroaryl.

$R_2$ is hydrogen, optionally substituted C1-C6 alkyl, optionally substituted C2-C6 alkenyl having 1 to 2 double bonds, optionally substituted C2-C6 alkynyl having 1 to 2 triple bonds, halogen, cyano, N—$R_6R_7$, optionally substituted C1-C6 alkoxy, hydroxy; optionally substituted aryl, optionally substituted heteroaryl, $COOR_6$, optionally substituted alkyl aryloxy alkylamines, optionally substituted aryloxy, optionally substituted heteroaryloxy, optionally substituted C3-C6 alkenyloxy, optionally substituted C3-C6 alkynyloxy, C1-C6 alkylamino-C1-C6 alkoxy, alkylene dioxy, optionally substituted aryloxy-C1-C6 alkyl amine, C1-C6 perfluoro alkyl, $S(O)_q$— optionally substituted C1-C6 alkyl, $S(O)_q$— optionally substituted aryl where q is 0, 1 or 2, $CONR_6R_7$, guanidino or cyclic guanidino, optionally substituted C1-C6 alkylaryl, optionally substituted arylalkyl, optionally substituted C1-C6 alkylheteroaryl, optionally substituted heteroaryl-C1-C6 alkyl, optionally substituted C1-C6 alkyl mono or bicyclic saturated heterocycles, optionally substituted arylalkenyl of 8 to 16 carbon atoms, $SO_2NR_6R_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, substituted heteroaryloxyaryl, optionally substituted C1-C6alkyl aryloxyaryl, optionally substituted C1-C6 alkylaryloxyheteroaryl, optionally substituted aryloxyalkyl, optionally substituted heteroaryloxyalkyl, optionally substituted alkylaryloxyalkylamines. Preferred $R_2$ groups are H, optionally substituted alkyl, optionally substituted alkoxy, optionally substituted heteroaryl, halogen, CN, hydroxy, optionally substituted heterocycle, —$CONR_6R_7$, $COOR_6$, optionally substituted aryl, $S(O)_q$-alkyl, and $S(O)_q$-aryl.

$R_3$ is hydrogen, C1-C6 alkyl, C5-C6 cycloalkyl, optionally substituted aryl, optionally substituted heteroaryl; preferred $R_3$ groups are H or C1-C6 alkyl;

$R_4$ is H, optionally substituted C1-C6 alkyl, one of $R_4$ is OH, C1-C6 alkoxy, —S—C1-C6 alkyl, $COOR_6$, —$NR_6R_7$, —$CONR_6R_7$; or $R_4R_4$ may together be =O or $R_4R_4$ together with the carbon to which they are attached may form a spiro system of five to eight members with or without the presence of heteroatoms selected N, O, S=(O)n (where n=0 to 2), N—$R_1$; preferred $R_4$ groups are H, C1-C6 alkyl, $NR_6R_7$ or $R_4R_4$ together with the carbon to which they are attached may form a spiro system of five to eight members with or without the presence of heteroatoms;

$R_6$ and $R_7$ are independently H, optionally substituted C1-C6 alkyl, optionally substituted aryl, optionally substituted heteroaryl, optionally substituted C1-C6 alkyl aryl, optionally substituted arylalkyl, optionally substituted heteroarylalkyl, optionally substituted C1-C6 alkyl heteroaryl, $R_6$ and $R_7$ can be together to form a 3-7 membered saturated ring system optionally having one or two heteroatoms such as N—$R_1$, O, S=(O)$_n$ n=0-2. Preferred $R_6$ and $R_7$ groups are H, C1-C6 alkyl, arylalkyl, heteroarylalkyl or $R_6$ and $R_7$ together forming a 3-7 membered saturated ring system optionally having one or two heteroatoms.

Chemical Definitions

The term alkyl means both straight and branched chain alkyl moieties of 1-12 carbons, preferably of 1-6 carbon atoms.

The term alkenyl means both straight and branched alkenyl moieties of 2-8 carbon atoms containing at least one double bond, and no triple bond, preferably the alkenyl moiety has 1 or two double bonds. Such alkenyl moieties may exist in the E or Z conformations; the compounds of this invention include both conformations. In the case of alkenyl, hetero atoms such as O, S or N—$R_1$ should not be present on the carbon that is bonded to a double bond;

The term alkynyl includes both straight chain and branched alkynyl moieties containing 2-6 carbon atoms containing at least one triple bond, preferably the alkynyl moiety has one or two triple bonds. In the case of alkynyl, hetero atoms such as O, S or N—$R_1$ should not be present on the carbon that is bonded to a double or triple bond;

The term cycloalkyl refers to a alicyclic hydrocarbon group having 3-7 carbon atoms. The term perfluoroalkyl is used herein to refer to both straight- and branched-chain saturated aliphatic hydrocarbon groups having at least one carbon atom and two or more fluorine atoms. Examples include $CF_3$, $CH_2CF_3$, $CF_2CF_3$ and $CH(CF_3)_2$. The term halogen is defined as Cl, Br, F, and I.

If alkyl, alkenyl, alkynyl, or cycloalkyl is "optionally substituted", one or two of the following are possible substituents: nitro, -aryl, -heteroaryl, alkoxycarbonyl-, -alkoxy, -alkoxy-alkyl, alkyl-O—C2-C4alkyl-O—, -cyano, -halogen, -hydroxy, —N—$R_6R_7$, —COOH, —COO-alkyl, -trifluoromethyl, -trifluoromethoxy, arylalkyl, alkylaryl, $R_6R_7$N-alkyl-, HO—C1-C6-alkyl-, alkoxyalkyl-, alkyl-S—, —$SO_2N$—$R_6R_7$, —$SO_2NHR_6$, —$CO_2H$, $CONR_6R_7$, aryl-O—, heteroaryl-O—, —$S(O)_s$-aryl (where s=0-2), -alkyl-O-alkyl-$NR_6R_7$, -alkyl-aryl-O-alkylN-$R_6R_7$, C1-C6alkyl, alkenyl, alkynyl, cycloalkyl, alkoxy-alkyl-O—, $R_6R_7$N-alkyl-, and —$S(O)_s$-heteroaryl (where s=0-2); Preferred substituents for alkyl, alkenyl, alkynyl, and cycloalkyl include: halogen, nitro, aryl, heteroaryl, —COOH, —COO-alkyl, alkoxycarbonyl-, alkoxy, -alkoxy-alkyl, -cyano, hydroxy, and —N—$R_6R_7$.

Aryl is defined as an aromatic hydrocarbon moiety selected from the group: phenyl, α-naphthyl, β-naphthyl, biphenyl, anthryl, tetrahydronaphthyl, fluorenyl, indanyl, biphenylenyl, acenaphthenyl, groups. The preferred aryl groups are phenyl and biphenyl.

Heteroaryl is defined as a aromatic heterocyclic ring system (monocyclic or bicyclic) where the heteroaryl moieties are selected from: (1) furan, thiophene, indole, azaindole, oxazole, thiazole, isoxazole, isothiazole, imidazole, N-methylimidazole, pyridine, pyrimidine, pyrazine, pyrrole, N-methylpyrrole, pyrazole, N-methylpyrazole, 1,3,4-oxadiazole, 1,2,4-triazole, 1-methyl-1,2,4-triazole, 1H-tetrazole, 1-methyltetrazole, benzoxazole, benzothiazole, benzofuran, benzisoxazole, benzimidazole, N-methylbenzimidazole, azabenzimidazole, indazole, quinazoline, quinoline, and isoquinoline; (2) a bicyclic aromatic heterocycle where a phenyl, pyridine, pyrimidine or pyridizine ring is: (a) fused to a 6-membered aromatic (unsaturated) heterocyclic ring having one nitrogen atom; (b) fused to a 5 or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S. Preferred heteroaryl groups are furan, oxazole, thiazole, isoxazole, isothiazole, imidazole, N-methylimidazole, pyridine, pyrimidine, pyrazine, pyrrole, N-methylpyrrole, pyrazole, N-methylpyrazole, 1,3,4-oxadiazole, 1,2,4-triazole, 1-methyl-1,2,4-triazole, 1H-tetrazole, 1-methyltetrazole, quinoline, isoquinoline, and naphthyridine.

If aryl or heteroaryl is 'optionally substituted', one or two of the following are possible substituents: nitro, -aryl, -heteroaryl, alkoxycarbonyl-, -alkoxy, -alkoxy-alkyl, alkyl-O—C2-C4alkyl-O—, -cyano, -halogen, -hydroxy, —N—$R_6R_7$, -trifluoromethyl, -trifluoromethoxy, arylalkyl, alkylaryl, $R_6R_7$N-alkyl-, HO—C1-C6-alkyl-, alkoxyalkyl-, alkyl-S—, —$SO_2N$—$R_6R_7$, —$SO_2NHR_6$—$CO_2H$, $CONR_6R_7$, aryl-O—, heteroaryl-O—, —$S(O)_s$— aryl (where s=0-2), -alkyl-O-alkyl-$NR_6R_7$, -alkyl-aryl-O-alkylN-$R_6R_7$, C1-C6alkyl, alkenyl, alkynyl, cycloalkyl, alkoxy-alkyl-O—, $R_6R_7$N-alkyl-, and —$S(O)_s$-heteroaryl (where s=0-2); Preferred substituents for aryl and heteroaryl include: alkyl, halogen, —N—$R_6R_7$, trifluoromethyl, -trifluoromethoxy, arylalkyl, and alkylaryl.

Arylalkyl is defined as Aryl-C1-C6alkyl-; Arylalkyl moieties include benzyl, 1-phenylethyl, 2-phenylethyl, 3-phenylpropyl, 2-phenylpropyl and the like. The term 'optionally substituted' refers to unsubstituted or substituted with 1 or 2 substituents on the alkyl or aryl moiety as defined above.

Alkylaryl is defined as C1-C6alkyl-aryl-. The term 'optionally substituted' refers to unsubstituted or substituted with 1 or 2 substituents on the aryl or alkyl moiety as defined above.

Heteroaryl-C1-C6-alkyl is defined as a heteroaryl substituted alkyl moiety wherein the alkyl chain is 1-6 carbon atoms (straight or branched). Alkyl heteroaryl moieties include Heteroaryl-$(CH_2)_{1-6}$— and the like. The term 'optionally substituted' refers to unsubstituted or substituted with 1 or 2 substituents on the alkyl or heteroaryl moiety as defined above;

C1-C6 alkylheteroaryl is defined an alkyl chain of 1-6 carbon atoms (straight or branched) attached to a heteroaryl moiety, which is bonded to the rest of the molecule. Ex. C1-C6-alkyl-Heteroaryl-. The term 'optionally substituted' refers to unsubstituted or substituted with 1 or 2 substituents on the alkyl or heteroaryl moiety as defined above;

Saturated or partially saturated heterocycles groups are defined as heterocyclic rings selected from the moieties; aziridinyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothienyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, dihydro-1,4-dioxanyl, tetrahydrofuranyl, tetrahydrothienyl, tetrahydroquinolinyl, and tetrahydroisoquinolinyl. Preferred saturated or partially saturated heterocycles are aziridinyl, azetidinyl, 1,4-dioxanyl, hexahydroazepinyl, piperazinyl, piperidinyl, pyrrolidinyl, morpholinyl, thiomorpholinyl, tetrahydroquinolinyl, tetrahydroisoquinolinyl, dihydroimidazolyl, and dihydroisooxazolyl.

C1-C6 alkyl mono or bicyclic saturated or partially saturated heterocycles is defined as an alkyl group (straight or branched) of C1-C6 attached to a heterocycles (which is defined before) through a carbon atom or a nitrogen atom and the other end of the alkyl chain attached to the rest of the molecule. The terms 'optionally substituted' refers to unsubstituted or substituted with 1 or 2 substituents present on the alkyl or heterocyclic portion of the molecule, as defined before;

Arylalkyloxyalkyl is defined as Aryl-C1-C6alkyl-O—C1-C6alkyl-. The term 'optionally substituted' refers to unsubstituted or substituted with 1 or 2 substituents present on the alkyl and/or aryl portions as defined before;

Alkyloxyalkyl is defined as C1-C6 alkyl-O—C1-C6alkyl-. The term 'optionally substituted' refers to unsubstituted or substituted with 1 or 2 substituents present at the alkyl moiety as defined before;

Aryloxyalkyl is defined as Aryl-O—C1-C6 alkyl-. The term 'optionally substituted' refers to unsubstituted or substituted with 1 or 2 substituents present at the alkyl or aryl moiety as defined before;

Heteroarylalkyloxyalkyl is defined as Heteroaryl-C1-C6alkyl-O—C1-C6alkyl-. The term 'optionally substituted' refers to unsubstituted or substituted with 1 or 2 substituents present on the alkyl or heteroaryl moiety as defined before;

Aryloxyaryl is defined as Aryl-O-Aryl-. The term 'optionally substituted' refers to unsubstituted or substituted with 1 or 2 substituents present on the aryl moiety as defined before;

Aryloxyheteroaryl is defined as Aryl-O-Heteroaryl- or -Aryl-O-Heteroaryl; In this definition either the aryl moiety or the heteroaryl moiety can be attached to the remaining portion of the molecule; The term 'optionally substituted' refers to unsubstituted or substituted with 1 or 2 substituents present on the aryl moiety or on the heteroaryl moiety as defined before;

Alkyl aryloxyaryl is defined as Aryl-O-Aryl-C1-C6alkyl-; The term 'optionally substituted' refers to unsubstituted or substituted with 1 or 2 substituents present at the aryl moiety as defined before;

Alkylaryloxyheteroaryl is defined as Heteroaryl-O-Aryl-C1-C6alkyl-; The term 'optionally substituted' refers to unsubstituted or substituted with 1 or 2 substituents present on the aryl moiety or on the heteroaryl moiety as defined before;

Alkylaryloxyalkylamine is defined as $R_6R_7N$—C1-C6alkyl-O-Aryl-C1-C6alkyl-; The terms 'optionally substituted' refers to unsubstituted or substituted with 1 or 2 substituents present on the alkyl or aryl moiety as defined before; $R_6$ and $R_7$ as defined before;

Alkoxycarbonyl is defined as C1-C6alkyl-O—C=O—; The term 'optionally substituted' refers to unsubstituted or substituted with 1 or 2 substituents present on the alkyl portion of the alkoxy moiety as defined before;

Aryloxycarbonyl is defined as Aryl-O—C=O—; The term 'optionally substituted' refers to unsubstituted or substituted with 1 or 2 substituents present at the aryl moiety as defined before;

Heteroaryloxy carbonyl is defined as Heteroaryl-O—C=O—; The term 'optionally substituted' refers to unsubstituted or substituted with 1 or 2 substituents present at the heteroaryl moiety as defined before;

Alkoxy is defined as C1-C6alkyl-O—; The terms 'optionally substituted' refers to unsubstituted or substituted with 1 or 2 substituents present at the alkyl moiety as defined before;

Aryloxy is defined as Aryl-O—; The term 'optionally substituted' refers to unsubstituted or substituted with 1 or 2 substituents present at the aryl moiety as defined before;

Heteroaryloxy is defined as Heteroaryl-O—; The term 'optionally substituted' refers to unsubstituted or substituted with 1 or 2 substituents present at the heteroaryl moiety as defined before;

Alkenyloxy is defined as C3-C6 alkene-O—; Example allyl-O—, bute-2-ene-O like moieties; The term 'optionally substituted' refers to unsubstituted or substituted with 1 or 2 substituents present at the alkene moiety as defined before, with the proviso that no hetero atom such as O, S or N—$R_1$ is present on the carbon atom, which is attached to a double bond;

Alkynyloxy is defined as C3-C6alkyne-O—; Example CH triple bond C—$CH_2$—O—, like moieties; The term 'optionally substituted' refers to unsubstituted or substituted with 1 or 2 substituents present at the alkyne moiety as defined before, with the proviso that no hetero atom such as O, S or N—$R_1$ is present on a carbon atom which is attached to a double or triple bond;

Alkylaminoalkoxy is defined as $R_6R_7N$—C1-C6-alkyl-O—C1-C6-alkyl-, where the terminal alkyl group attached to the oxygen is connected to the rest of the molecule;

The terms $R_6$ and $R_7$ are defined above; The term 'optionally substituted' refers to unsubstituted or substituted with 1 or 2 substituents present at the alkyl moiety as defined before;

Alkylenedioxy is defined as —O—CH$_2$—O— or —O—(CH$_2$)$_2$—O—;

Aryloxyalkylamine is defined as R$_6$R$_7$N—C1-C6-alkyl-O-Aryl-, where the aryl is attached to the rest of the molecule; The term 'optionally substituted' refers to unsubstituted or substituted with 1 or 2 substituents present at the alkyl or aryl moiety as defined before;

Arylalkenyl is defined as Aryl-C2-C8alkene-, with the proviso that no hetero atom such as O, S or N—R$_1$ is present on the carbon atom, which is attached to a double bond; The term 'optionally substituted' refers to unsubstituted or substituted with 1 or 2 substituents present on the alkene or aryl moiety as defined before;

Heteroaryloxyalkyl is defined as Heteroaryl-O—C1-C6alkyl-; The term 'optionally substituted' refers to unsubstituted or substituted with 1 or 2 substituents present at the heteroaryl moiety as defined before;

Heteroaryloxyaryl is defined as Heteroaryl-O-aryl-, where the aryl moiety is attached to the rest of the molecule; The term 'optionally substituted' refers to unsubstituted or substituted with 1 or 2 substituents present at the heteroaryl moiety or the aryl moiety as defined before;

Alkoxy, alkoxyalkyl, alkoxyalkyloxy and alkylthioalkyloxy are moieties wherein the alkyl chain is 1-6 carbon atoms (straight or branched). Aryloxy, heteroaryloxy, arylthio and heteroarylthio are moieties wherein the aryl and heteroaryl groups are as herein before defined. Arylalkyloxy, heteroarylalkyloxy, arylalkylthio and heteroarylalkylthio are moieties wherein the aryl and heteroaryl groups are as herein before defined and wherein the alkyl chain is 1-6 carbons (straight or branched). Aryloxyalkyl, heteroaryloxyalkyl, aryloxyalkyloxy and heteroaryloxyalkyloxy are substituents wherein the alkyl radical is 1-6 carbon atoms. The terms monoalkylamino and dialkylamino refer to moieties with one or two alkyl groups wherein the alkyl chain is 1-6 carbons and the groups may be the same or different. The terms monoalkylaminoalkyl and dialkylaminoalkyl refer to monoalkylamino and dialkylamino moieties with one or two alkyl groups (the same or different) bonded to the nitrogen atom which is attached to an alkyl group of 1-3 carbon atoms. Examples of fused bicyclic heteroaryl groups are optionally substituted ring systems such as one of the following 4,5,6,7-tetrahydrothieno[3,2-c]pyridine, optionally substituted by e.g., arylalkyl such as benzyl; by alkoxyarylalkyl such as 4-methoxybenzyl; by C1-C6alkyl such as methyl; by heteroarylalkyl such as pyridin-3-ylmethyl; by arylalkylCO— such as phenylacetyl; or heteroarylCO— such as pyridin-3-ylcarbonyl; e.g. by alkylCO-such as acetyl;

5,6,7,8-tetrahydroimidazo[1,2-a]pyrazine, optionally substituted e.g., by C1-C6alkyl such as methyl;
5,6-dihydro-8H-imidazo[2,1-c][1,4]thiazine;
6,7-Dihydro-5H-pyrrolo[1,2-a]imidazole
5,6-Dihydro-8H-imidazo[2,1-c][1,4]oxazine
5,6-Dihydro-4H-pyrrolo[1,2-b]pyrazole
4,5,6,7-tetrahydropyrazolo[1,5-a]pyridine
6-oxo-5,6,7,8-tetrahydro-imidazo[1,2-a]pyrazine, optionally substituted e.g., by C1-C6alkyl such as methyl;
6,7-Dihydro-4H-pyrazolo[5,1-c][1,4]thiazine;
4H-5-thia-1,6a-diazapentalene;
7H-Imidazo[1,2-c]thiazole;
4-oxo-6,7-dihydro-4H-pyrazolo[5,1-c][1,4]oxazine;
6,7-Dihydro-4H-thieno[3,2-c]pyran;
6,7-Dihydro-4H-thieno[3,2-c]thiopyran;
6,7-dihydro-4H-thieno[3,2-c]pyridine, optionally substituted by C2-C7alkoxycarbonyl;
6,7,8,9-tetrahydro-5H-imidazo[1,2-a]azepine;

5,6,7,8-tetrahydroimidazo[1,2-a]pyrazine, optionally substituted by arylalkyl such as benzyl;
5,5-Dioxo-4,5,6,7-tetrahydro-5λ$^6$-pyrazolo[5,1-c][1,4]thiazine;
4,5,6,7-tetrahydropyrazolo[1,5-a]pyrazine;
5,6-Dihydro-4H-cyclopenta[b]furan;
4,5-Dihydro-6-thia-1,7a-diazaindene;
5,6-Dihydro-8-H-imidazo[2,1-c][1,4]thiazine;
4H-5-thia-1,6a-diazapentalene;
2,3-Dihydropyrazolo[5,1-b]thiazole;
2,3-Dihydropyrazolo[5,1-b]oxazole;
6,7-dihydro-4H-pyrazolo[5,1-c][1,4]oxazine;
6,7-5H-Dihydropyrazolo[5,1-b]oxazine; and
4,5,6,7-tetrahydropyrazolo[1,5-a]pyrazine optionally substituted, e.g., by alkoxyalkylCO— such as 2-methoxyacetyl; or by alkyloxyalkylCO— such as methoxyacetyl.

Examples of Bicyclic Heteroarylgroup:

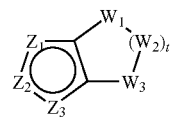

1-A

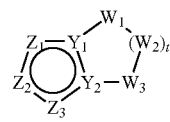

1-B

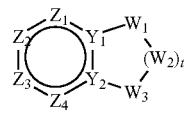

1-C

In formula 1-A Z1, Z2 and Z3 are independently CR$_2$, N, O, S or N—R$_1$ and one of Z1-Z3 is carbon and is bonded to the remainder of the molecule as shown in formula I. When one of Z's is CR$_2$ the other two Zs can be either two N or one N and O, S, N—R$_1$ in any combinations with out disrupting the aromaticity; when two Z,s=CR$_2$ the other Z can be optionally selected from one N, O, S or N—R$_1$ in any combination with out disrupting the aromaticity;

W$_1$, W$_2$ and W$_3$ are independently CR$_4$R$_4$, S, SO, SO$_2$, O, N—R$_1$, C=O; with the proviso that no S—S or O—O or S—O bond formation can occur to form the saturated ring system; t=1 to 4.

In formula 1-B Z1, Z2 and Z3 are independently CR$_2$, N, O, S or N—R$_1$ and one of Z1-Z3 is carbon and is bonded to the remainder of the molecule as shown in formula I. When one of Z's=CR$_2$, then the other two Z's can be independently CR$_2$, N, O, S or N—R$_1$ in any combinations with out disrupting the aromaticity;

When two Z's=N, then the other carbon in the ring is bonded to the penem portion of the molecule as shown in formula I.

W$_1$, W$_2$ and W$_3$ are independently CR$_4$R$_4$, S, SO, SO$_2$, O, N—R$_1$, t=1 to 4;

Y$_1$ and Y$_2$=N or C; with the proviso that when the aromatic heterocycle is imidazole, the saturated ring may not contain a S adjacent to the bridgehead carbon.

In formula 1-C Z1, Z2, Z3 and Z4 are independently CR$_2$ or N and one of Z1-Z4 is carbon and is bonded to the remainder of the molecule.

$W_1$, $W_2$ and $W_3$ are independently $CR_4R_4$, S, SO, $SO_2$, O, or N—$R_1$; with the proviso that no S—S or O—O or S-0 bond formation can occur to form the saturated ring system; t=1 to 4.

$Y_1$ and $Y_2$ are independently C or N.

The more preferred embodiment of the formula 1-A:

1. t=1 to 3.
2. In formula 1-A Z1 is N, S, N—$R_1$ or O and one of Z2 or Z3 is $CR_2$ and the other of Z2 or Z3 is carbon and is bonded to the remainder of the molecule as shown in formula I.
3. In formula 1-A Z3 is N, S, N—$R_1$ or O and one of Z2 or Z1 is $CR_2$ and the other of Z2 or Z1 is carbon and is bonded to the remainder of the molecule as shown in formula I.
4. In formula 1-A Z2 is N, S, N—$R_1$ or O and one of Z1 or Z3 is $CR_2$ and the other of Z1 or Z3 is carbon bonded to the remainder of the molecule as shown in formula I.
5. In formula 1-A Z1 is N, N—$R_1$, O or S and Z2 is N, O or S and Z3 is a carbon bonded to the penem portion of the molecule as shown in formula I.
6. In formula 1-A Z3 is N, N—$R_1$, O or S and Z2 is N, O or S and Z1 is a carbon bonded to the penem portion of the molecule as shown in formula I.
7. In formula 1-A Z1 is N, N—$R_1$, O or S and Z3 is N, O or S and Z2 is a carbon bonded to the penem portion of the molecule as shown in formula I.
8. In formula 1-A Z1 is N, S, N—$R_1$ or O and Z2 or Z3 is $CR_2$ and the other of Z2 or Z3 is carbon and is bonded to the remainder of the molecule; $W_1$, $W_2$ and $W_3$ are independently $CR_4R_4$.
9. In formula 1-A Z3 is N, S, N—$R_1$ or O and one of Z2 or Z1 is $CR_2$ and the other of Z2 or Z1 is carbon and is bonded to the remainder of the molecule; $W_1$, $W_2$, and $W_3$ are independently $CR_4R_4$.
10. In formula 1-A Z2 is N, S, N—$R_1$ or O and one of Z1 or Z3 is $CR_2$ and the other of Z1 or Z3 is carbon and is bonded to the remainder of the molecule; $W_1$, $W_2$, and $W_3$ are independently $CR_4R_4$.
11. In formula 1-A Z1 is N, N—$R_1$, O or S and Z2 is N, O or S; Z3 is a carbon bonded to the penem portion of the molecule; $W_1$, $W_2$, $W_3$ are independently $CR_4R_4$.
12. In formula 1-A Z3 is N, N—$R_1$, O or S; Z2 is N, O or S; Z1 is a carbon bonded to the penem portion of the molecule; $W_1$, $W_2$, $W_3$ are independently $CR_4R_4$.
13. In formula 1-A Z1 is N, N—$R_1$, O or S; Z3 is N, O or S; Z2 is a carbon bonded to the penem portion of the molecule; $W_1$, $W_2$, $W_3$ are independently $CR_4R_4$.
14. In formula 1-A Z3 is N, N—$R_1$, O or S; Z1 is N, O or S; Z2 is a carbon bonded to the penem portion of the molecule; $W_1$, $W_2$, $W_3$ are independently $CR_4R_4$.
15. In formula 1-A Z1 is N, S, N—$R_1$ or O; one of Z2 or Z3 is $CR_2$ and the other of Z2 or Z3 is carbon and is bonded to the remainder of the molecule, t=1-3; one $W_2$ is N—$R_1$, O or $S(O)_n$ n=0-2 and another $W_2$ is $CR_4R_4$.
16. In formula 1-A Z3 is N, S, N—$R_1$ or O; one of Z2 or Z1 is $CR_2$ and the other of Z2 or Z1 is carbon and is bonded to the remainder of the molecule, t=1-3; one $W_2$ is N—$R_1$, O or $S(O)_n$ n=0-2 and another $W_2$=$CR_4R_4$.
17. In formula 1-A Z2 is N, S, N—$R_1$ or O; one of Z1 or Z3 is $CR_2$ and the other of Z1 or Z3 is carbon and is bonded to the remainder of the molecule; t=1-3; one $W_2$ is N—$R_1$, O or $S(O)_n$ n=0-2 and another $W_2$ is $CR_4R_4$.
18. In formula 1-A when Z1=N, N—$R_1$, O or S and Z2=N, O or S and Z3=a carbon bonded to the penem portion of the molecule where t=1-3 then one $W_2$=N—$R_1$, O or $S(O)_n$ n=0-2 and other $W_2$=$CR_4R_4$.
19. In formula 1-A Z3=N, N—$R_1$, O or S and Z2=N, O or S and Z1=a carbon bonded to the penem portion of the molecule where t=1-3 then one $W_2$=N—$R_1$, O or $S(O)_n$ n=0-2 and other $W_2$=$CR_4R_4$.
20. In formula 1-A when Z1=N, N—$R_1$, O or S and Z3=N, O or S and Z2=a carbon bonded to the penem portion of the molecule where t=1-3 then one $W_2$=N—$R_1$, O or $S(O)_n$ n=0-2 and other $W_2$=$CR_4R_4$.
21. In formula 1-A Z1 is N, S, N—$R_1$ or O and Z2 or Z3=$CR_2$ and the other of Z2 or Z3 is carbon and is bonded to the remainder of the molecule; then $W_1$ and $W_3$=$CH_2$ or both hydrogens on the methylene linkage can be substituted to form a spiro system with or without the presence of hetero atoms selected from O, S=$(O)_n$ (n=0 to 2), N—$R_1$ to form five to eight membered cyclic system; t=1-3; one $W_2$=N—$R_1$, O or $S(O)_n$ n=0-2 and other $W_2$=$CR_4R_4$.
22. In formula 1-A Z3=N, S, N—$R_1$ or O and Z2 or Z1=$CR_2$ and the other of Z2 or Z1 is carbon and is bonded to the remainder of the molecule; then $W_1$ and $W_3$=$CR_4R_4$; where t=1-3 then one $W_2$=N—$R_1$, O or $S(O)_n$ n=0-2 and other $W_2$=$CR_4R_4$.
23. In formula 1-A Z2=N, S, N—$R_1$ or O and Z1 or Z3=$CR_2$ and the other of Z1 or Z3 is carbon and is bonded to the remainder of the molecule; then $W_1$ and $W_3$=$CR_4R_4$, where t=1-3 then one $W_2$=N—$R_1$, O or $S(O)_n$ n=0-2 and other $W_2$=$CR_4R_4$.
24. In formula 1-A when Z1=N, N—$R_1$, O or S and Z2=N, O or S then Z3=a carbon bonded to the penem portion of the molecule; then $W_1$ and $W_3$=$CR_4R_4$, where t=1-3 then one $W_2$=N—$R_1$, O or $S(O)_n$ n=0-2 and other $W_2$=$CR_4R_4$.
25. In formula 1-A Z3=N, N—$R_1$, O or S and Z2=N, O or S then Z1=a carbon bonded to the penem portion of the molecule; then $W_1$ and $W_3$=$CR_4R_4$, where t=1-3 then one $W_2$=N—$R_1$, O or $S(O)_n$ n=0-2 and other $W_2$=$CR_4R_4$.
26. In formula 1-A when Z1=N, N—$R_1$, O or S and Z3=N, O or S then Z2=a carbon bonded to the penem portion of the molecule; then $W_1$ and $W_3$=$CR_4R_4$ t=1-3; one $W_2$ is N—$R_1$, O or $S(O)_n$ n=0-2 and another $W_2$ is $CR_4R_4$.
27. In formula 1-A Z3 is N, N—$R_1$, O or S; Z1 is N, O or S; Z2 is a carbon bonded to the remainder of the molecule; $W_1$ and $W_3$ are independently $CR_4R_4$; t=1-3; one $W_2$ is N—$R_1$, O or $S(O)_n$ n=0-2 and another $W_2$ is $CR_4R_4$.

The more preferred embodiments of the formula 1-B:

28. In formula 1-B t=3.
29. In formula 1-B Z1 and Z3 are N; Y1 is N; Y2 is C and Z2 is carbon and is bonded to the remainder of the molecule as shown in formula 1.
30. In formula 1-B Z2 and Z3 are N; Y1 is N; Y2 is C and Z1 is carbon and is bonded to the remainder of the molecule as shown in formula I.
31. In formula 1-B Z1 is N, Y1 is N, Y2 is C, one of $Z_2$ or $Z_3$ is $CR_2$ and the other of Z2 or Z3 is a carbon and is bonded to the remainder of the molecule as shown in formula I.
32. In formula 1-B Z1 is N, Y1 is C, Y2 is N, one of $Z_2$ or $Z_3$ is $CR_2$ and the other of Z2 or Z3 is a carbon and is bonded to the remainder of the molecule as shown in formula I.
33. In formula 1-B Z1 is N, Y1 is N, Y2 is C, one of $Z_2$ or $Z_3$ is $CR_2$ and the other of Z2 or Z3 is a carbon and is bonded to the remainder of the molecule as shown in formula I, $W_1$ and $W_3$ are independently $CR_4R_4$; t=1-3; one $W_2$ is N—$R_1$, O, S=$(O)_n$ (n=0-2), and another $W_2$ is $CR_4R_4$.
34. In formula 1-B Z1 is N, Y1 is C, Y2 is N, one of $Z_2$ or $Z_3$ is $CR_2$ and the other of Z2 or Z3 is a carbon and is bonded to the remainder of the molecule as shown in formula I; $W_1$ and $W_3$ are independently $CR_4R_4$; t=1-3; one $W_2$ is N—$R_1$, O, S=$(O)_n$ (n=0-2), and another $W_2$ is $CR_4R_4$.

35. In formula 1-B Z3 is N; Y1 is N; Y2 is C; one of Z1 or Z2 is $CR_2$ and the other of $Z_1$ or $Z_2$ is carbon and is bonded to the remainder of the molecule as shown in formula I.

36. In formula 1-B Z2 is N; Y1 is N; Y2 is C; one of Z1 or Z3 is $CR_2$ and the other of $Z_1$ or $Z_3$ is carbon and is bonded to the remainder of the molecule as shown in formula I.

37. In formula 1-B Z1 and Z2 are N; Y1 is N; Y2 is C; and Z3 is carbon and is bonded to the remainder of the molecule as shown in formula I.

38. In formula 1-B Z1, Z2 and Z3 are independently $CR_2$; Y1 is C; Y2 is N; except one of Z1-Z3 is carbon and is bonded to the remainder of the molecule as shown in formula I.

39. In formula 1-B Z1 and Z3 are N; Y1 is N; Y2 is C; Z2 is carbon and is bonded to the remainder of the molecule as shown in formula I; and t=1-3.

40. In formula 1-B Z2 and Z3 are N; Y1 is N; Y2 is C; and Z1 is carbon and is bonded to the remainder of the molecule; and t=1-3;

41. In formula 1-B Z2 and Z3 are N, Y1 is C and Y2=N and Z1 is carbon and is bonded to the remainder of the molecule and t=1-3;

42. In formula 1-B Z2 and Z3 are N; Y1 is N; Y2 is C; Z1 is carbon and is bonded to the remainder of the molecule; $W_1$ and $W_3$ are independently $CH_2$ or both hydrogens on the methylene linkage can be substituted to form a spiro system with or without the presence of hetero atoms selected from O, $S(O)_n$ n=0-2, N—$R_1$ to form five to eight membered cyclic system; t=1-3 and $W_2$ is $CH_2$, N—$R_1$, O, $S(O)_n$ where n=0-2.

43. In formula 1-B Z3 is N; Y1 is N; Y2 is C; Z1 is $CR_2$ and Z2 is the carbon atom bonded to the remainder of the molecule.

44. In formula 1-B Z3 is N; Y1 is N; Y2 is C; Z1 is $CR_2$; Z2 is the carbon atom bonded to the remainder of the molecule; $W_1$, $W_2$ and $W_3$ are independently $CR_4R_4$; t=1 to 3.

45. In formula 1-B Z3 is N; Y1 is N; Y2 is C; Z1 is $CR_2$; Z2 is the carbon atom bonded to the remainder of the molecule; $W_1$ and $W_3$ are independently $CR_4R_4$; and one of $W_2$ is N—$R_1$, O or $S(O)_n$, and another $W_2$ is $CR_4R_4$; t=1-3.

46. In formula 1-B Z3 is N; Y1 is N; Y2 is C; Z1 is $CR_2$; Z2 is the carbon atom bonded to the remainder of the molecule; $W_1$ and $W_2$ are independently $CR_4R_4$; $W_3$ is N—$R_1$, O or $S(O)_n$; and t=2.

47. In formula 1-B Z3 is N; Y1 is N; Y2 is C; Z1 is $CR_2$; Z2 is the carbon atom bonded to the remainder of the molecule; $W_1$ and $W_3$ are independently $CR_4R_4$; $W_2$ is N—$R_1$, O or $S(O)_n$; and t=1.

48. In formula 1-B Z2 is N; Y1 is N; Y2 is C; Z3 is $CR_2$; Z1 is the carbon bonded to the remainder of the molecule; $W_1$ and $W_2$ is $CH_2$ or both hydrogens on the methylene linkage can be substituted to form a spiro system with or without the presence of hetero atoms selected from O, $S(O)_n$ n=0-2, N—$R_1$ to form five to eight membered cyclic system; $W_3$ is N—$R_1$, O or $S(O)_n$; and t=3.

49. In formula 1-B Z2 is N; Y1 is N; Y2 is C, Z3 is $CR_2$; Z1 is the carbon bonded to the remainder of the molecule; $W_1$ and $W_3$ are independently $CH_2$ or both hydrogens on the methylene linkage can be substituted to form a spiro system with or without the presence of hetero atoms selected from O, $S(O)_n$ n=0-2, N—$R_1$ to form five to eight membered cyclic system; and one $W_2$ is N—$R_1$, O or $S(O)_n$ and another $W_2$ is CR4R4; and t=2.

50. In formula 1-B Z2 is N; Y1 is N; Y2 is C; Z3 is $CR_2$; Z1 is the carbon bonded to the remainder of the molecule; $W_1$ and $W_3$ are independently $CH_2$ or both hydrogens on the methylene linkage can be substituted to form a spiro system with or without the presence of hetero atoms selected from O, $S(O)_n$ n=0-2, N—$R_1$ to form five to eight membered cyclic system; $W_2$ is N—$R_1$, O or $S(O)_n$; and t=1.

51. In formula 1-B Z2 is N; Y1 is N; Y2 is C; Z1 is $CR_2$; Z3 is the carbon bonded to the remainder of the molecule; $W_1$ and $W_3$ are independently $CR_4R_4$; one of $W_2$ is N—$R_1$, O or $S(O)_n$ and another $W_2$ is $CR_4R_4$; and t=3.

52. In formula 1-B Z2 is N; Y1 is N; Y2 is C; Z1 is $CR_2$; Z3 is the carbon bonded to the remainder of the molecule; $W_1$ and $W_3$ are independently $CR_4R_4$; one $W_2$ is N—$R_1$, O or $S(O)_n$, and another $W_2$ is $CR_4R_4$; and t=2.

53. In formula 1-B Z2 is N; Y1 is N; Y2 is C; Z1 is $CR_2$; Z3 is the carbon bonded to the remainder of the molecule; $W_1$ and $W_3$ are independently $CR_4R_4$; $W_2$ is N—$R_1$, O or $S(O)_n$; and t=1.

54. In formula 1-B Z1 and Z2 are N; Y1 is N; Y2 is C; Z3 is carbon and is bonded to the remainder of the molecule; $W_1$ and $W_3$ are independently $CR_4R_4$; one of $W_2$ is N—$R_1$, O or $S(O)_n$ and another $W_2$ is $CR_4R_4$; and t=3.

55. In formula 1-B Z1 and Z2 are N; Y1 is N; Y2 is C; Z3 is carbon and is bonded to the remainder of the molecule; $W_1$ and $W_3$ are independently CR4R4; one of $W_2$ is N—$R_1$, O or $S(O)_n$ and another $W_2$ is CR4R4; and t=2.

56. In formula 1-B Z1 and Z2 are N; Y1 is N; Y2 is C; Z3 is carbon and is bonded to the remainder of the molecule; $W_1$ and $W_3$ are independently CR4R4; $W_2$ is N—$R_1$, O or $S(O)_n$; and t=1

57. In formula 1-B Z1 and Z2 are independently $CR_2$; Y1 is C; Y2 is N; Z3 is carbon and is bonded to the remainder of the molecule; $W_1$ and $W_3$ are independently CR4R4; one of $W_2$ is N—$R_1$, O or $S(O)_n$; another $W_2$ is CR4R4; and t=3.

58. In formula 1-B Z1 and Z2 are independently $CR_2$; Y1 is C and Y2 is N and Z3 is carbon and is bonded to the remainder of the molecule; $W_1$ and $W_3$ are independently CR4R4; and one $W_2$ is N—$R_1$, O or $S(O)_n$ and the other $W_2$ is CR4R4; and t=2.

59. In formula 1-B Z1 and Z2 are independently $CR_2$; Y1 is C; Y2 is N; Z3 is carbon and is bonded to the remainder of the molecule; $W_1$ and $W_3$ are independently $CR_4R_4$; $W_2$ is N—$R_1$, O or $S(O)_n$; and t=1.

60. In formula 1-B Z1 and Z3 are independently $CR_2$; Y1 is C; Y2 is N; Z2 is carbon and is bonded to the remainder of the molecule; $W_1$ and $W_3$ are independently $CR_4R_4$; one $W_2$ is N—$R_1$, O or $S(O)_n$; another $W_2$ is $CR_4R_4$; and t=3.

61. In formula 1-B Z1 and Z3 are independently $CR_2$; Y1 is C; Y2 is N; Z2 is carbon and is bonded to the remainder of the molecule; $W_1$ and $W_3$ are independently $CR_4R_4$; and one $W_2$ is N—$R_1$, O or $S(O)_n$ and the other $W_2$ is $CR_4R_4$; and t=2.

62. In formula 1-B Z1 and Z3 are independently $CR_2$; Y1 is C; Y2 is N; Z2 is carbon and is bonded to the remainder of the molecule; $W_1$ and $W_3$ are independently $CR_4R_4$; $W_2$ is N—$R_1$, O or $S(O)_n$; and t=1.

63. In formula 1-B Z3 and Z2 are independently $CR_2$; Y1 is C; Y2 is N; Z1 is carbon and is bonded to the remainder of the molecule; $W_1$ and $W_2$ are independently $CR_4R_4$; one $W_2$ is N—$R_1$, O or $S(O)_n$; another $W_2$ is $CR_4R_4$; and t=3.

64. In formula 1-B Z3 and Z2 are independently $CR_2$; Y1 is C; Y2 is N; Z1 is carbon and is bonded to the remainder of the molecule; $W_1$ and $W_3$ are independently $CR_4R_4$; one $W_2$ is N—$R_1$, O or $S(O)_n$; the other $W_2$ is $CR_4R_4$; and t=2.

65. In formula 1-B Z3 and Z2 are independently $CR_2$; Y1 is C; Y2 is N; Z1 is carbon and is bonded to the remainder of the molecule; $W_1$ and $W_3$ are independently $CR_4R_4$; $W_2$ is N—$R_1$, O or $S(O)_n$; and t=1.

66. In formula 1-B Z3 is N; Y1 is N; Y2 is C; one of Z1 and Z2 is $CR_2$ and the other is C; $W_1$ is $CR_4R_4$; $W_2$ is $CR_4R_4$; $W_3$ is $CH_2$, N—$R_1$ or O; and t=1.

67. In formula 1-B Z3 is N; Y1 is N; Y2 is C; one of Z1 and Z2 is CR$_2$ and the other is C; W$_1$ is CR$_4$R$_4$; W$_2$ is C=O; W$_3$ is N—R$_1$; and t=1.

68. In formula 1-B Z3 is N; Y1 is N; Y2 is C; one of Z1 and Z2 is CR$_2$ and the other is C; W$_1$ is N—R$_1$; W$_2$ is C=O; W$_3$ is CR$_4$R$_4$; and t=1.

69. In formula 1-B Z3 is N; Y1 is N; Y2 is C; one of Z1 and Z2 is CR$_2$ and the other is C; W$_1$ is C=O; W$_2$ is N—R$_1$; W$_3$ is CH$_2$; and t=1.

The more preferred embodiments of the formula 1-C are:

70. In formula 1-C Z1, Z2, Z3 and Z4 are independently CR$_2$; one of Z1-Z4 is carbon and is bonded to the remainder of the molecule; Y$_1$ and Y$_2$ are C; t=1 to 3; and W$_1$, W$_2$ and W$_3$ are independently CR$_4$R$_4$, S, SO, SO$_2$, O, or N—R$_1$.

71. In formula 1-C Z1, Z2, Z3 and Z4 are independently CR$_2$ and one of Z1-Z4 is carbon and is bonded to the remainder of the molecule; Y$_1$ and Y$_2$=C or N; t=1 to 3; W$_1$, W$_2$ and W$_3$ are independently CR$_4$R$_4$, S, SO, SO$_2$, O, or N—R$_1$.

72. In formula 1-C Z1, Z2, Z3 and Z4 are independently CR$_2$; Y$_1$ and Y$_2$ are N; t=1 to 3; W$_1$, W$_2$ and W$_3$ are independently CR$_4$R$_4$, S, SO, SO$_2$, O, or N—R$_1$.

73. In formula 1-C Z1 is N and Z2, Z3 and Z4 are independently CR$_2$; Y$_1$ and Y$_2$ are C; t=1 to 3; W$_1$, W$_2$ and W$_3$ are independently CR$_4$R$_4$, S, SO, SO$_2$, O, or N—R$_1$.

74. In formula 1-C Z1 is N and Z2, Z3 and Z4 are independently CR$_2$; one of Z1-Z4 is carbon and is bonded to the remainder of the molecule; Y$_1$ is C; Y$_2$ is N; t=1 to 3; and W$_1$, W$_2$ and W$_3$ are independently CR$_4$R$_4$, S, SO, SO$_2$, O, or N—R$_1$.

75. In formula 1-C Z2=N and Z1, Z3 and Z4 are independently CR$_2$; one of Z1-Z4 is carbon and is bonded to the remainder of the molecule; Y$_1$ and Y$_2$ are C; t=1 to 3; and W$_1$, W$_2$ and W$_3$ are independently CR$_4$R$_4$, S, SO, SO$_2$, O, or N—R$_1$.

76. In formula 1-C Z2 is N and Z1, Z3 and Z4 are independently CR$_2$; one of Z1-Z4 is carbon and is bonded to the remainder of the molecule; Y$_1$ is C; Y$_2$ is N; t=1 to 3; and W$_1$, W$_2$ and W$_3$ are independently CR4R4, S, SO, SO$_2$, O, or N—R$_1$.

77. In formula 1-C Z3 is N; Z1, Z2 and Z4 are independently CR$_2$; one of Z1-Z4 is carbon and is bonded to the remainder of the molecule; Y$_1$ and Y$_2$ are C; t=1 to 3; and W$_1$, W$_2$ and W$_3$ are independently CR$_4$R$_4$, S, SO, SO$_2$, O, or N—R$_1$.

78. In formula 1-C Z3 is N and Z1, Z2 and Z4 are independently CR$_2$; one of Z1-Z4 is carbon and is bonded to the remainder of the molecule; Y$_1$ is C and Y$_2$ is N; t=1 to 3; and W$_1$, W$_2$ and W$_3$ are independently CR4R4, S, SO, SO$_2$, O, or N—R$_1$.

79. In formula 1-C Z4 is N and Z1, Z2 and Z3 are independently CR$_2$; one of Z1-Z4 is carbon and is bonded to the remainder of the molecule; Y$_1$ and Y$_2$ are C; t=1 to 3; and W$_1$, W$_2$ and W$_3$ are independently CR$_4$R$_4$, S, SO, SO$_2$, O, or N—R$_1$.

80. In formula 1-C Z4 is N and Z1, Z2 and Z3 are independently CR$_2$; one of Z1-Z4 is carbon and is bonded to the remainder of the molecule; Y$_1$ is N; Y$_2$ is C; t=1 to 3; and W$_1$, W$_2$ and W$_3$ are independently CR$_4$R$_4$, S, SO, SO$_2$, O, or N—R$_1$.

81. In formula 1-C Z1 is N and Z2, Z3 and Z4 are independently CR$_2$; one of Z1-Z4 is carbon and is bonded to the remainder of the molecule; Y$_1$ and Y$_2$ are C; t=1 to 3; and W$_1$, W$_2$ and W$_3$ are independently CR$_4$R$_4$, S, SO, SO$_2$, O, or N—R$_1$.

82. In formula 1-C Z1 and Z2 are N and Z3 or Z4 are independently CR$_2$; one of Z1-Z4 is carbon and is bonded to the remainder of the molecule; Y$_1$ is C; Y$_2$ is N; t=1 to 3; and W$_1$, W$_2$ and W$_3$ are independently CR4R4, S, SO, SO$_2$, O, or N—R$_1$.

83. In formula 1-C Z1 and Z3 are N and Z2 or Z4 are independently CR$_2$; one of Z1-Z4 is carbon and is bonded to the remainder of the molecule; Y$_1$ is C; Y$_2$ is N; t=1 to 3; and W$_1$, W$_2$ and W$_3$ are independently CR4R4, S, SO, SO$_2$, O, or N—R$_1$.

84. In formula 1-C Z1 and Z4 are N and Z2 or Z3 are independently CR$_2$; one of Z1-Z4 is carbon and is bonded to the remainder of the molecule; Y$_1$ is N; Y$_2$ is C; t=1 to 3; and W$_1$, W$_2$ and W$_3$ are independently CR4R4, S, SO, SO$_2$, O, or N—R$_1$.

85. In formula 1-C Z1, Z2, Z3 are N and Z4 is carbon and is bonded to the remainder of the molecule; Y$_1$ is C; Y$_2$ is N; t=1 to 3; and W$_1$, W$_2$ and W$_3$ are independently CR4R4, S, SO, SO$_2$, O, or N—R$_1$.

86. In formula 1-C Z1, Z3 and Z4 are N and Z2 is carbon and is bonded to the remainder of the molecule; Y$_1$ and Y$_2$ are C; t=1 to 3; and W$_1$, W$_2$ and W$_3$ are independently CR4R4, S, SO, SO$_2$, O, or N—R$_1$.

87. In formula 1-C Z1, Z2 and Z4 are N and Z3 is carbon and is bonded to the remainder of the molecule; Y$_1$ and Y$_2$ are C and t=1 to 3; and W$_1$, W$_2$ and W$_3$ are independently CR4R4, S, SO, SO$_2$, O, or N—R$_1$.

88. In formula 1-C Z2, Z3, Z4 are N and Z1 is carbon and is bonded to the remainder of the molecule; Y$_1$ and Y$_2$ are C and t=1 to 3; and W$_1$, W$_2$ and W$_3$ are independently CR4R4, S, SO, SO$_2$, O, or N—R$_1$.

More preferred compounds of the present invention are:

1. (5R,6Z)-6-[(5-benzyl-4,5,6,7-tetrahydrothieno[3,2-c]pyridin-2-yl)methylene]-7oxo-4-thia-1-azabicyclo[3.2.0]hept-2-ene-2-carboxylic acid.

2. (5R),(6Z)-6-(7-Methyl-5,6,7,8-tetrahydroimidazo[1,2-a]pyrazin-2-ylmethylene)-7-oxo-4-thia-1-aza-bicyclo[3.2.0]hept-2-ene-2-carboxylic acid, sodium salt.

3. (5R),(6Z)-7-Oxo-6-(5,6,7,8-tetrahydroimidazo[1,2-a]pyrazin-2-ylmethylene)-4-thia-1-azabicyclo[3.2.0]hept-2-ene-2-carboxylic acid, sodium salt.

4. (5R,6Z)-6-{[5-(4-methoxybenzyl)-4,5,6,7-tetrahydrothieno[3,2-c]pyridin-2-yl)]methylene}-7oxo-4-thia-1-azabicyclo[3.2.0]hept-2-ene-2-carboxylic acid, sodium salt.

5. (5R),(6Z)-6-(5,6-dihydro-8H-imidazo[2,1-c][1,4]thiazin-2-ylmethylene)-7-oxo-4-thia-1-azabicyclo[3.2.0]hept-2-ene-2-carboxylic acid, sodium salt 6. (5R),(6Z)-6-(6,7-Dihydro-5H-pyrrolo[1,2-a]imidazol-2-ylmethylene)-7-oxo-4-thia-1-aza-bicyclo[3.2.0]hept-2-ene-2-carboxylic acid, sodium salt.

7. (5R),(6Z)-6-(5,6-Dihydro-8H-imidazo[2,1-c][1,4]oxazin-2-ylmethylene)-7-oxo-4-thia-1-azabicyclo[3.2.0]hept-2-ene-2-carboxylic acid, sodium salt 8. (5R),(6Z)-6-(5,6-Dihydro-4H-pyrrolo[1,2-b]pyrazol-2-ylmethylene)-7-oxo-4-thia-1-azabicyclo[3.2.0]hept-2-ene-2-carboxylic acid, sodium salt 9. (5R)(6Z)-7-Oxo-6-(4,5,6,7-tetrahydropyrazolo[1,5-a]pyridin-2-ylmethylene)-4-thia-1-azabicyclo[3.2.0]hept-2-ene-2-carboxylic acid, sodium salt 10. (5R),(6Z)-6-(7-Methyl-6-oxo-5,6,7,8-tetrahydro-imidazo[1,2-a]pyrazin-2-ylmethylene)-7-oxo-4-thia-1-azabicyclo[3.2.0]hept-2-ene-2-carboxylic acid sodium salt 11. (5R)(6Z)-6-(6,7-Dihydro-4H-pyrazolo[5,1-c][1,4]thiazin-2-ylmethylene)-7-oxo-4-thia-1-azabicyclo[3.2.0]hept-2-ene-2-carboxylic acid, sodium salt 12. (5R)(6Z)-7-Oxo-6-(4H-5-thia-1,6a-diazapentalen-2-ylmethylene)-4-thia-1-azabicyclo[3.2.0]hept-2-ene-2-carboxylic acid, sodium salt 13. (5R)(6Z)-6-(7H-imidazo[1,2-c]thiazol-2-ylmethylene)-7-oxo-4-thia-1-azabicyclo[3.2.0]hept-2-ene-2-carboxylic acid, sodium salt
14. (5R,6Z)-7-oxo-6-[(4-oxo-6,7-dihydro-4H-pyrazolo[5,1-c][1,4]oxazin-2-yl)methylene]-4-thia-1-azabicyclo[3.2.0]hept-2-ene-2-carboxylic Acid
15. 6-(6,7-Dihydro-4H-thieno[3,2-c]pyran-2-ylmethylene)-7-oxo-4-thia-1-aza-bicyclo[3.2.0]hept-2-ene-2-carboxylic acid
16. 6-(6,7-Dihydro-4H-thieno[3,2-c]thiopyran-2-ylmethylene)-7-oxo-4-thia-1-aza-bicyclo[3.2.0]hept-2-ene-2-carboxylic acid
17. 6-(5-Methyl-4,5,6,7-tetrahydro-thieno[3,2-c]pyridin-2-ylmethylene)-7-oxo-4-thia-1-aza-bicyclo[3.2.0]hept-2-ene-2-carboxylic acid
18. 2-(2-Carboxy-7-oxo-4-thia-1-aza-bicyclo[3.2.0]hept-2-en-6-ylidenemethyl)-6,7-dihydro-4H-thieno[3,2-c]pyridine-5-carboxylic acid ethyl ester
19. 7-Oxo-6-(6,7,8,9-tetrahydro-5H-imidazo[1,2-a]azepin-2-ylmethylene)-4-thia-1-aza-bicyclo[3.2.0]hept-2-ene-2-carboxylic acid
20. (5R),(6Z)-6-(7-Benzyl-5,6,7,8-tetrahydroimidazo[1,2-a]pyrazin-2-ylmethylene)-7-oxo-4-thia-1-azabicyclo[3.2.0]hept-2-ene-2-carboxylic acid
21. (5R,6Z)-7-oxo-6-{[5-(pyridin-3-ylmethyl)-4,5,6,7-tetrahydrothieno[3,2-c]pyridin-2-yl)]methylene}-7oxo-4-thia-1-azabicyclo[3.2.0]hept-2-ene-2-carboxylic acid
22. (5R,6Z)-7-oxo-6-{[5-(pyridin-3-ylcarbonyl)-4,5,6,7-tetrahydrothieno[3,2-c]pyridin-2-yl)]methylene}-7oxo-4-thia-1-azabicyclo[3.2.0]hept-2-ene-2-carboxylic acid
23. (5R,6Z)-7-oxo-6-{[5-(phenylacetyl)-4,5,6,7-tetrahydrothieno[3,2-c]pyridin-2-yl)]methylene}-7oxo-4-thia-1-azabicyclo[3.2.0]hept-2-ene-2-carboxylic acid;
24. (5R),(6Z)-6-(5,5-Dioxo-4,5,6,7-tetrahydro-5$\lambda^6$-pyrazolo[5,1-c][1,4]thiazin-2-ylmethylene)-7-oxo-4-thia-1-azabicyclo[3.2.0]hept-2-ene-2-carboxylic acid, sodium salt;
25. (5R),(6Z)-7-Oxo-6-(4,5,6,7-tetrahydropyrazolo[1,5-a]pyrazin-2-ylmethylene)-4-thia-1-aza-bicyclo[3.2.0]hept-2-ene-2-carboxylic acid, sodium salt
26. (5R)(6Z)-6-(5,5-Dimethyl-4H-1,6a-diazapentalen-2-ylmethylene)-7-oxo-4-thia-1-azabicyclo[3.2.0]hept-2-ene-2-carboxylic acid, sodium salt 5,5-Dimethyl-2-piperidone;
27. (5R),(6Z)-6-(5,6-Dihydro-4H-cyclopenta[b]furan-2-ylmethylene)-7-oxo-4-thia-1-azabicyclo[3.2.0]hept-2-ene-2-carboxylic acid, sodium salt;
28. (5R)(6Z)-6-(4,5-Dihydro-6-thia-1,7a-diazainden-2-ylmethylene)-7-oxo-4-thia-1-azabicyclo[3.2.0]hept-2-ene-2-carboxylic acid, sodium salt;
29. (5R),(6Z)-6-(6,6-Dimethyl-5,6,7,8-tetrahydroimidazo[1,2-a]pyrizin-2-ylmethylene)-7-oxo-4-thia-1-azabicyclo[3.2.0]hept-2-ene-2-carboxylic acid, sodium salt;
30. (5R),(6Z)-6-(5,6-Dihydro-8-H-imidazo[2,1-c][1,4]thiazin-3-ylmethylene)-7-oxo-4-thia-1-azabicyclo[3.2.0]hept-2-ene-2-carboxylic acid;
31. (5R)(6Z)-7-Oxo-6-(4H-5-thia-1,6a-diazapentalen-2-ylmethylene)-4-thia-1-azabicyclo[3.2.0]hept-2-ene-2-carboxylic acid, sodium salt;
32. (5R)(6Z)-6-(2,3-Dihydropyrazolo[5,1-b]thiazol-6-ylmethylene)-7-oxo-4-thia-1-azabicyclo[3.2.0]hept-2-ene-2-carboxylic acid, sodium salt;
33. (5R)(6Z)-6-(2,3-Dihydropyrazolo[5,1-b]oxazol-6-ylmethylene)-7-oxo-4-thia-1-azabicyclo[3.2.0]hept-2-ene-2-carboxylic acid, sodium salt;
34. (5R,6Z)-6-[(5-acetyl-4,5,6,7-tetrahydrothieno[3,2-c]pyridin-2-yl)methylene]-oxo-4-thia-1-azabicyclo[3.2.0.]hept-2-ene-2-carboxylic acid (E+Z Isomers mixture, Sodium salt);
35. (5R,6Z)-6-(6,7-dihydro-4H-pyrazolo[5,1-c][1,4]oxazin-2-ylmethylene)-7-oxo-4-thia-1-azabicyclo[3.2.0]hept-2-ene-2-carboxylic acid;
36. (5R)(6Z)-6-(6, 7-5H-Dihydropyrazolo[5,1-b]oxazin-2-ylmethylene)-7-oxo-4-thia-1-azabicyclo[3.2.0]hept-2-ene-2-carboxylic acid, sodium salt;
37. (5R),(6Z)-6-[5-(3-carboxypropionyl)-4,5,6,7-tetrahydropyrazolo[1,5-a]pyrazin-2-ylmethylene]-7-oxo-4-thia-1-azabicyclo[3.2.0]hept-2-ene-carboxylic acid, disodium salt;
38. (5R),(6Z)-6-[5-(2-methoxyacetyl)-4,5,6,7-tetrahydropyrazolo[1,5-a]pyrazin-2-ylmethylene]-7-oxo-4-thia-1-azabicyclo[3.2.0]hept-2-ene-carboxylic acid, sodium salt;
39. (5R),(6Z)-6-[5-(2-methoxyacetyl)-4,5,6,7-tetrahydropyrazolo[1,5-a]pyrazin-2-ylmethylene]-7-oxo-4-thia-1-azabicyclo[3.2.0]hept-2-ene-carboxylic acid, sodium salt; and
40. (5R),(6Z)-6-[5-(2-methoxyacetyl)-4,5,6,7-tetrahydropyrazolo[1,5-a]pyrazin-2-ylmethylene]-7-oxo-4-thia-1-azabicyclo[3.2.0]hept-2-ene-carboxylic acid, sodium salt.

Especially preferred compounds of the present invention include:

(5R),(6Z)-6-(5,6-dihydro-8H-imidazo[2,1-c][1,4]thiazin-2-ylmethylene)-7-oxo-4-thia-1-azabicyclo[3.2.0]hept-2-ene-2-carboxylic acid, sodium salt;

(5R),(6Z)-6-(6,7-Dihydro-5H-pyrrolo[1,2-a]imidazol-2-ylmethylene)-7-oxo-4-thia-1-aza-bicyclo[3.2.0]hept-2-ene-2-carboxylic acid, sodium salt;

(5R),(6Z)-6-(5,6-Dihydro-8H-imidazo[2,1-c][1,4]oxazin-2-ylmethylene)-7-oxo-4-thia-1-azabicyclo[3.2.0]hept-2-ene-2-carboxylic acid, sodium salt; and (5R)(6Z)-7-Oxo-6-(4H-5-thia-1,6a-diazapentalen-2-ylmethylene)-4-thia-1-azabicyclo[3.2.0]hept-2-ene-2-carboxylic acid, sodium salt.

The compounds according to the present invention have β-lactamase inhibitory and antibacterial properties and are useful for the treatment of infections in humans and animals. It should be noted that the compounds of the present invention, when used in combination with β-lactam antibiotics will result in the increased antibacterial activity (synergistic effect) against class-A and class-C producing organisms. β-Lactam antibiotics include penicillin antibiotics such as piperacillin, amoxycillin, ticarcillin, benzylpenicillins, ampicillin, sulbenicillin, other known penicillins and cephalosporins such as cefatrizine, cephaloridine, cephalothin, cefazolin, cephalexin, cephradine, other known cephalosporins, aztreonam and latamoxef (Moxalactam). Most preferably compounds of this present invention are used with piperacillin or amoxicillin which has a broad spectrum of activity against Gram positive and Gram negative pathogens.

The compounds of the present invention may be provided prior to, simultaneously with, or subsequent to a β-lactam antibiotic ("co-administration"). By "provided", it is intended to include administering the compound directly or in vivo, e.g. pro-drugs. When the compounds of the present invention are co-administered with a β-lactam antibiotic, the ratio of the amount of the compound to the amount of the β-lactam antibiotic may vary in a wide range. The ratio of β-lactam antibiotic to β-lactamase inhibitor may vary from 1:1 to 100:1. Preferably the ratio of the β-lactam antibiotic to β-lactamase inhibitor is less than 10:1. The composition of the present invention may be in a form suitable for oral (PO), intravenous (IV) or topical administration. The compositions of the invention may be in a form of tablets, capsules, creams, syrups, suspension, sterile solutions suitable for injection or infusion. Preferably, the compounds of the present invention are co-administered with piperacillin intravenously or amoxicillin intravenously or orally.

A compound's structural formula includes any tautomers, any stereoisomers (except where stereochemistry is clearly noted) and any crystalline forms.

$IC_{50}$ Determination for the Penem Inhibitor

β-Lactamase inhibitory activity of the penem inhibitors was determined spectrophotometrically as described by Bush et al., [Bush, K., Macalintal, C., Rasmussen, B. A., Lee, V. and Yang, Y. *Antimicrobial Agents and Chemotherapy* 1993, 37, 851]. Homogeneously purified class A β-lactamases TEM-1 from *E. coli* and Imi-1 from *Enterobacter cloacae*, class B enzyme CcrA from *Bacteroides fragilis* and class C enzyme AmpC from *Enterobacter cloaca* were employed in the assay. The enzyme concentrations for TEM-1, Imi-1, CcrA and AmpC were 4.3, 7.1, 1.2 and 2.1 nM, respectively. A wide range of inhibitor concentrations were prepared in 50 mM $PO_4$, pH 7.0 to include the possible $IC_{50}$ values. The substrate used to initiate the enzyme reaction was nitrocefin at 50 μg/ml in the same buffer as the inhibitor. Initially the enzyme and inhibitor (20 μl each) were preincubated for 10 minutes at 25° C. prior to the addition of 160 μl volume of nitrocefin. Initial rates of hydrolysis were monitored for 5 minutes at 495 nm using a Molecular Devices Spectra Max 250 with kinetic protocol of SoftMax Program. Readings from the Spectra Max 250 were exported and transferred to Microsoft Excel. The percent of inhibition of each inhibitor concentration was calculated based on the control enzyme activity. The inhibitor concentration that caused a 50% reduction in the enzymatic activity ($IC_{50}$) was determined graphically.

TABLE 1

| | IC50 (nM) | | |
|---|---|---|---|
| | Class A | Class B | Class C |
| Compound | TEM-1 | Imi | Ccr | AmpC |
| Example 1 | 4.2 | 2.1 | 260 | 12 |
| Example 2 | 4.4 | 22 | 120 | 5.8 |
| Example 3 | 5.4 | 28 | 320 | 6.2 |
| Example 7 | 0.4 | 7.8 | 66 | 4.8 |
| Example 8 | 1.2 | 50 | 14 | 1.5 |
| Example 9 | 2.2 | 90 | 62 | 3.2 |
| Example 10 | 10 | 65 | 140 | 3.0 |
| Example 11 | 1.0 | 18 | 61 | 1.2 |
| Example 12 | 1.4 | 56 | 110 | 1.5 |
| Example 13 | 2.9 | 16 | 160 | 3.1 |

TABLE 1-continued

| | IC50 (nM) | | |
|---|---|---|---|
| | Class A | Class B | Class C |
| Compound | TEM-1 | Imi | Ccr | AmpC |
| Example 14 | 2.5 | 68 | 26 | 3.8 |
| Example 15 | 1.2 | 8.6 | 14 | 3.8 |
| Example 16 | 3.1 | 25 | 12 | 4.2 |
| Example 17 | 12 | 24 | 28 | 26 |
| Example 18 | 2.8 | 50 | 120 | 9.2 |
| Example 19 | 4.8 | 2700 | 170 | 4.6 |
| Example 20 | 1.4 | 9.6 | 18 | 3.1 |
| Example 21 | 9.8 | 40 | 280 | 18 |
| Example 22 | 6.1 | 42 | 110 | 11 |
| Example 23 | 4.6 | 40 | 140 | 7.8 |
| Example 24 | 1.1 | 56 | 4 | 1.5 |
| Example 25 | 1.1 | 123 | 162 | 2.7 |
| Example 26 | 0.73 | 54 | 89 | 2.3 |
| Example 27 | 2 | 5.5 | 73 | 2 |
| Example 28 | ND | ND | ND | ND |
| Example 29 | ND | ND | ND | ND |
| Example 30 | 2.9 | 2300 | 7.8 | 2.5 |
| Example 31 | 1.4 | 56 | 110 | 1.5 |
| Example 32 | ND | ND | ND | ND |
| Example 33 | 1.1 | 59 | 41 | 0.85 |
| Example 34 | 4.2 | 34 | 99 | 6.5 |
| Example 35 | 4.2 | 230 | 30 | 6.1 |
| Example 36 | 6.3 | 413 | 140 | 4.5 |

ND = Not Determined

Antimicrobial susceptibility testing. The in vitro activities of the antibiotics were determined by the microbroth dilution method as recommended by the National Committee for Clinical Laboratory Standards (NCCLS). (NCCLS. 2000. Methods for Dilution Antimicrobial Susceptibility Tests for Bacteria That Grow Aerobically; Approved Standards: M7-A5, vol. 19. National Committe for Clinical Laboratory Standards, Villanova, Pa.). Mueller-Hinton II broth (MHBII) (BBL Cockeysville, Md.), was used for the testing procedure. Microtiter plates containing 50 μl per well of two-fold serial dilutions of piperacillin combined with a constant amount (4 ug/ml) of a B-lactamase inhibitor were inoculated with 50 μl of inoculum to yield the appropriate density ($10^5$ CFU/ml) in 100·l final volume. The plates were incubated for 18-22 hours at 35° C. in ambient air. The minimal inhibitory concentration (MIC) for all isolates was defined as the lowest concentration of antimicrobial agent that completely inhibits the growth of the organism as detected by the unaided eye. The MIC data obtained by the above said procedure are enlisted in Table 2.

TABLE 2

| Minimal Inhibitory Concentration (μg/ml) Data: Inc: 35° C. for 18 hours | | | | | | | | |
|---|---|---|---|---|---|---|---|---|
| Example 1 | E. Coli GC2844 | E. Coli GC2847 (TEM-1) | E. Coli GC2920 (IRT-2) | E. Coli GC2894 (Ampc) | E. Cloacae GC1477 (Ampc) | P. aeruginos GC1764 (Ampc) | S. Marcescens GC1781 Sme-1 + Ampc | E. Coli GC22033 | S. aureus GC2216 |
| 1 | 2 | 2 | 2 | 16 | 32 | 32 | 0.5 | 1 | 0.12 |
| 2 | 2 | 16 | 2 | 2 | >64 | 8 | 1 | 1 | 0.25 |
| 3 | 2 | 2 | 1 | 2 | 64 | 16 | 1 | 2 | 0.5 |
| 4 | 2 | 8 | 2 | 2 | 64 | 32 | 2 | 2 | 0.50 |
| 7 | 2 | 2 | 4 | 2 | 16 | 1 | 1 | 1 | <0.06 |
| 8 | 2 | 2 | 2 | 2 | 8 | 0.25 | 2 | 2 | <0.06 |
| 9 | 1 | 2 | 1 | 2 | 16 | 4 | 1 | 2 | <0.06 |
| 10 | 1 | 32 | 1 | 16 | >64 | 4 | 1 | 1 | <0.06 |
| 11 | 2 | 4 | 2 | 2 | 32 | 2 | 1 | 1 | <0.06 |
| 12 | 2 | 4 | 2 | 2 | 32 | 1 | 1 | 1 | <0.06 |
| 13 | 0.5 | 1 | 2 | 0.5 | 16 | 1 | 0.5 | 2 | <0.06 |
| 14 | 1 | 32 | 0.50 | 64 | >64 | 64 | 16 | 2 | 1 |

TABLE 2-continued

Minimal Inhibitory Concentration (μg/ml) Data: Inc: 35° C. for 18 hours

| Example 1 | E. Coli GC2844 | E. Coli GC2847 (TEM-1) | E. Coli GC2920 (IRT-2) | E. Coli GC2894 (Ampc) | E. Cloacae GC1477 (Ampc) | P. aeruginos GC1764 (Ampc) | S. Marcescens GC1781 Sme-1 + Ampc | E. Coli GC22033 | S. aureus GC2216 |
|---|---|---|---|---|---|---|---|---|---|
| 15 | 2 | 16 | 2 | 8 | 32 | 8 | 2 | 2 | <0.06 |
| 16 | 2 | 16 | 1 | 4 | 32 | 16 | 2 | 1 | 0.12 |
| 17 | 2 | 8 | 2 | 4 | 32 | 4 | 1 | 2 | 0.25 |
| 18 | 2 | 16 | 2 | 32 | >64 | 64 | 2 | 2 | 0.50 |
| 19 | 2 | 8 | 2 | 8 | >64 | 64 | 4 | 2 | 0.5 |
| 20 | 2 | 32 | 2 | 32 | >64 | 64 | 2 | 2 | <0.06 |
| 21 | 2 | 32 | 2 | 32 | >64 | 64 | 2 | 1 | 0.25 |
| 22 | 2 | >64 | 2 | 64 | >64 | 64 | 4 | 2 | 0.5 |
| 23 | 2 | 64 | 2 | 32 | >64 | 64 | 4 | 2 | 0.5 |
| 24 | 2 | 4 | 2 | 4 | 64 | 2 | 1 | 2 | ND |
| 25 | 2 | 4 | 2 | 2 | 32 | 0.5 | 2 | 2 | ND |
| 26 | 2 | 8 | 2 | 16 | 32 | 8 | 2 | 4 | ND |
| 27 | 2 | 4 | 2 | 16 | 32 | 16 | 2 | 2 | ND |
| 28 | 2 | 4 | 2 | 4 | 16 | 2 | 2 | 2 | ND |
| 29 | 2 | 8 | 2 | 8 | 32 | 8 | 2 | 2 | ND |
| 30 | 2 | 8 | 1 | 2 | 16 | 8 | 8 | 2 | 0.06 |
| 31 | 2 | 4 | 2 | 2 | 32 | 1 | 0.5 | 1 | 0.5 |
| 32 | 2 | 2 | 2 | 2 | 16 | 2 | 1 | 2 | ND |
| 33 | 2 | 4 | 4 | 2 | 16 | 0.5 | 1 | 4 | 0.06 |
| 34 | 4 | 32 | 4 | 32 | >64 | 32 | 2 | 2 | ND |
| 35 | 2 | 4 | 2 | 2 | 64 | 1 | 8 | 2 | 0.25 |
| 36 | 2 | 4 | 2 | 2 | 16 | 1 | 1 | 4 | 0.06 |

ND = Not Determined

In Vivo Antibacterial Protection

Materials:

Animals:

Female mice strain CD-1, approximately 18-22 grams, were received from Charles River Laboratories and quarantined 7 days prior to use. In addition, mice may be rendered neutropenic using cytoxan.

Infections:

Clinical isolates that have been adapted to cause infection in mice, are used in the experiment, including infections with strains of E. coli, K. pneumoniae, M. morganii, E. cloacae, S. marcescens, C. freundii, staphylococci, streptococci, P. aeruginosa and N. gonorrhoeae.

Preparation:

Animals are housed five to a cage with free access to food and water, in accordance with NIH guidelines.

Experimental Protocol:

Mice are challenged by injecting 0.5 ml intraperitoneally or 0.05 ml intranasally of a predetermined bacterial inoculum suspended in broth, saline or hog gastric mucin (supplemented with dried bovine hemoglobin for N. gonorrhoeae). The bacterial inoculum is equivalent to 10-100 LD$_{50}$s of the specific infecting strain and will result in death of the non-treated control animals within 7 days: "Bacterial Virulence in Mice". Antibacterial doses (dose concentration prepared by two fold serial dilutions of the antibiotic) are dissolved or suspended in 0.2% aqueous agar or methocel, phosphate buffered saline or an adjuvant are administered orally, subcutaneously or intravenously in the following manner:

a) Orally or subcutaneously: Dose volume of 0.5 ml administered ½ hr after infection. A second dose may be administered 3 hr. after infection for treatment of infections with more virulent organisms.
  b) Intravenously: Dose volume of 0.2 ml, administered ½ hr. after infection. For the treatment of infections with more virulent organisms, more doses, up to 48 hr may be administered. (Intravenous dosing will not exceed 3 doses/24 hr period.)
  c) Oral pretreatment: Under special circumstances, the pH of the stomach needs to be adjusted in order to increase the gastric stability of the antibiotic. For this purpose, 0.5 ml of phosphate buffered saline (pH7.8, 0.06M) (or specific approved adjuvant) is administered orally ½ hr after infection, followed 5 minutes later by 0.5 ml of antibiotic (also orally) contained in phosphate buffered saline (pH7.8, 0.06M).

Animal Species

A detailed explanation as to the number of animals needed for the determination of in vivo efficacy follows:

A) Novel antibiotics are tested at 5 different dose levels with 5 mice per dose level at each of three routes of administration (oral, subcutaneous and intravenous). Initially the three routes of administration should be investigated so as to determine if the drug is orally absorbed and/or which is the most effective route. This would require 25 mice/route with 3 routes/antibiotic or 75 mice per novel compound tested. One to two novel antibiotics will be tested per experiment (75-150 mice)

B) The effectiveness of the new compound must be compared to that of a standard, or antibiotic of known effectiveness. Known or previously tested antibiotics are tested at 5 dose levels with 5 mice per dose level by a single route of administration, for a total of 25 mice/antibiotic. Usually 3-6 antibiotics will be tested per experiment. (75-150 mice).

C) Untreated controls—In each of the above tests, untreated animals are infected with 3 different concentrations of bacterial inoculum with 10 mice per concentration (30 mice total in each and every test). These untreated controls are used to determine and maintain the infection level between 10-100 LD50s as required for test to test comparison and validity.

Determination of Protective Effects of Antibacterial Agents:

The protective effects of the antibacterial agent(s) are measured by the survival of the infected untreated as compared to the treated animals. For this determination, animals are observed for 7 days after treatment. A census of survivors is taken twice daily and at that time dead as well as moribund animals are removed. The 7 day survival ratio from three separate tests are pooled for estimation of median effective dose (ED50) by computerized program for probit analysis (Cleeland, R. and E. Squires. 1991. Evaluation of New Antimicrobials in Vitro and in Experimental Animal Infections. In "Antibiotics in Laboratory Medicine", 3rd. ed., edited by Victor Lorian. Willams and Wilkins Baltimore, Md. pp. 752-783). The test is performed three times on separate days to provide a statistically valid number of animals and to minimize variation in test results on a day to day and test to test basis.

TABLE 3

| Example | $ED_{50}$ mg/kg | Ratio of Piperacillin vs. Inhibitor |
|---|---|---|
| 1 | 32-64 | 2:1 |
| 2 | >64 | 2:1 |
| 3 | 16-32 | 4:1 |
| 4 | 32-64 | 4:1 |
| 7 | 22.8 | 4:1 |
| 8 | 18.9 | 4:1 |
| 9 | 31.3 | 4:1 |
| 10 | | |
| 11 | 13.9 | 4:1 |
| 12 | 20.0 | 4:1 |
| 13 | 18.0 | |
| 14 | | |
| 15 | | |
| 16 | | |
| 17 | 37.9 | 4:1 |
| 18 | | |
| 19 | 59.2 | 4:1 |
| 20 | | |
| 21 | | |
| 22 | 128 | 4:1 |
| 23 | 128 | 4:1 |
| 24 | 64 | |
| 25 | 30 | |
| 26 | 30 | |
| 27 | 28 | |
| 28 | 31 | |
| 29 | 46 | |
| 30 | ND | |
| 31 | 20 | |
| 32 | 46 | |
| 33 | >64 | |
| 34 | 32 | |

TABLE 3-continued

| Example | $ED_{50}$ mg/kg | Ratio of Piperacillin vs. Inhibitor |
|---|---|---|
| 35 | 19 | |
| 36 | 90 | |

Process of Invention

Compounds of the general formula I can be prepared by a novel, mild and a facile way, by condensing an appropriately substituted aldehyde 4 with a 6-bromo-penem derivative of structure 1. (Scheme 1) in the presence of anhydrous $MgBr_2$ or $MgBr_2$:etherate and a base such as triethylamine or DBU or DMAP, preferably at −20° C. to −40° C. The intermediate aldol product 5 can be functionalized with acid chlorides or anhydrides to an acetate, triflate or a tosylate 6. Compound 6 can be smoothly converted to the desired product by a reductive elimination process using a metal such as activated zinc and phosphate buffer at 20° C. to 35° C. at a pH of 6.5 to 8.0. If the protecting group on the carboxylate oxygen is a para-nitrobenzyl substituent then the reductive elimination and deprotection can be achieved by a single step. However, if the protecting group is other than a para-nitrobenzyl substituent, a two step procedure can be followed depending up on the nature of the protecting group. The product can be isolated as a free acid or as an alkali metal salt. The above mentioned two step procedure can be carried out in one step by carrying out the entire process without isolating the intermediate 6. This is a very general, relatively simple and efficient procedure in terms of yield and economic feasibility. This procedure can be adopted to large scale synthesis and is amenable to a variety of aldehydes. Alternatively, compound 6 can be hydrogenated at 40 psi pressure in the presence of Pd/C (10%) in THF and 6.5 phosphate buffer to yield the final product.

The above mentioned aldol condensation reaction is very versatile and it can be applied to any bromopenem derivative, where the carboxy group is protected other than 4-nitrobenzyl moiety. Example of other protecting group include benzyl, para-methoxy benzyl derivative, benzyhydrol, trityl, alkyl and allyl derivatives. However, when the protecting group is other than 4-nitrobenzyl group, a separate deprotection step need to be carried out after the reductive elimination procedure. The chemistry involved in the deprotection step is well known to people who are skilled in that art.

SCHEME 1

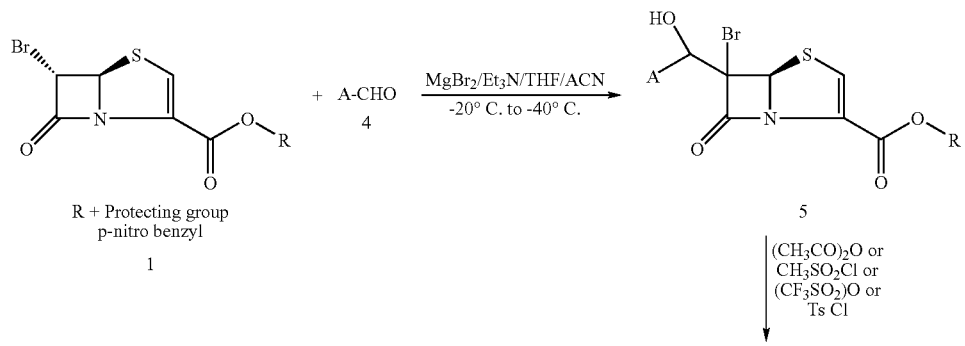

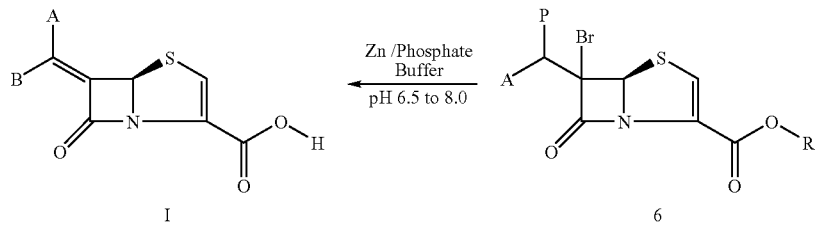

The required aldehydes 4 for the above mentioned transformations can be prepared from their respective alcohol derivatives by $MnO_2$ oxidation or by Swern oxidation. In some cases the required aldehyde functionality can be introduced directly in the heterocyclic moiety by a Vilsmier Haack reaction using $DMF/POCl_3$. The aldehydes required for the present investigation may be prepared as depicted in Schemes 2 to 5. The N-(tert-butoxycarbonyl)- (ie) t-Boc protected-4-piperidone is treated with $DMF/POCl_3$ to yield 4-chloro-3-formyl derivative. (Scheme 2). This reaction can be conducted on tetrahydro-4H-pyran-4-one and the corresponding tetrahydro-4H-thiopyran-4-one derivative to give the corresponding oxygen and the sulfur derivatives. This reaction can also be conducted on five to eight membered cyclic ketones derivatives. The chloro formyl intermediate can be reacted with 2-mercapto ethyl acetate to give the thieno derivative. The ester can be converted to alcohol, which can be converted to the starting aldehyde functionality. Scheme 3 illustrates the preparation of the imidazolo-tetrahydro pyridine derivative and imidazolo pyrazine derivative. 2-aminopyridine or 2-aminopyrazine can be reacted with ethyl bromopyruvate in boiling ethanol to give the cyclized derivative (Scheme 3). Reduction of one ring can be achieved.

Scheme 2

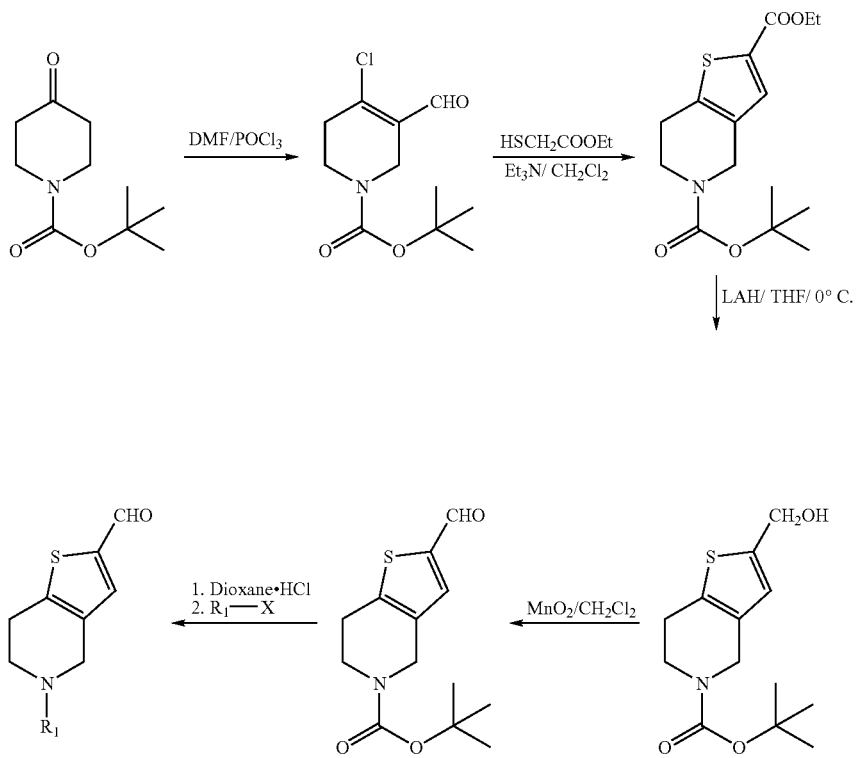

This above mentioned sequence can be conducted starting from tetrahydro-4H-pyran-4-one and the corresponding tetrahydro-4H-thiopyran-4-one. The Vilsmier reaction can be performed on five to eight membered cyclic ketones.

Scheme 3

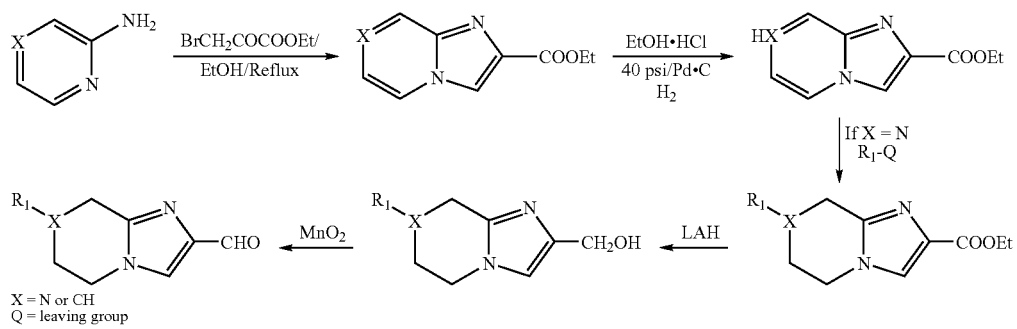

X = N or CH
Q = leaving group by hydrogenating it over Pd/C under 40 psi pressure in a par apparatus. Subsequently the ester group can be reduced to alcohol and converted to the aldehyde. In the case of X=N the intermediate amino ester can be derivatized using an appropriate $R_1Q$ (where Q is a leaving group or a condensing group). In the case of Scheme 3, where $R_1$=H can be synthesized by the procedure outlined in Scheme 4.

Scheme 4

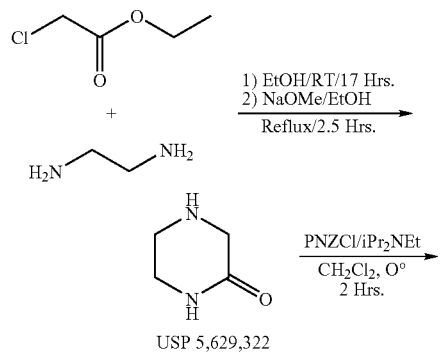

-continued

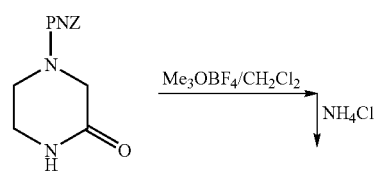

Additional aldehydes may be synthesized as outlined in Schemes 5-7.

Scheme 5

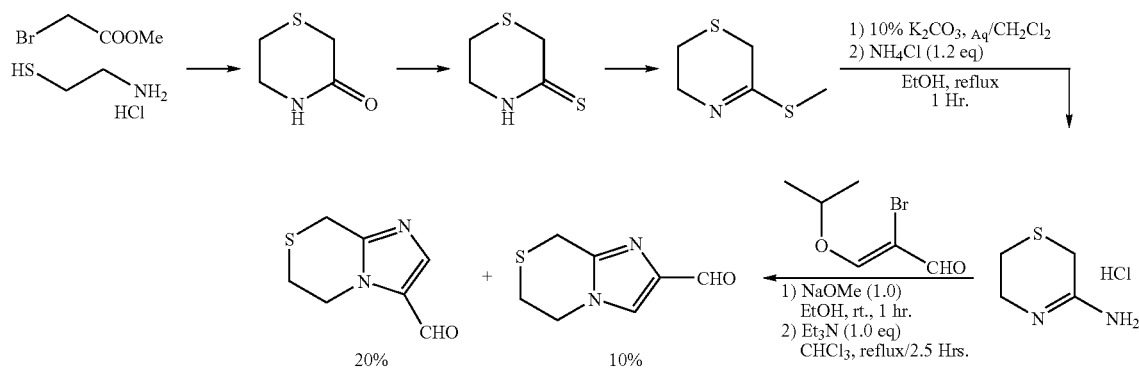

Aldehydes required for examples 24-32 and 34, 35 were prepared by the route indicated schemes 8 to 18.
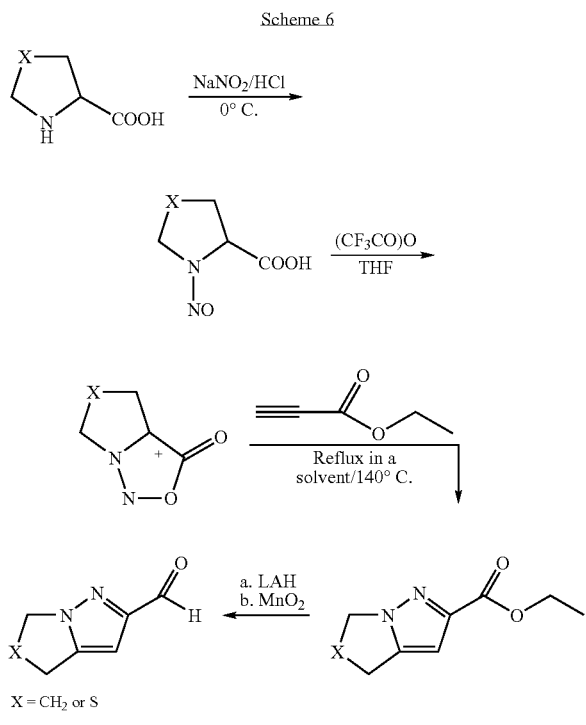
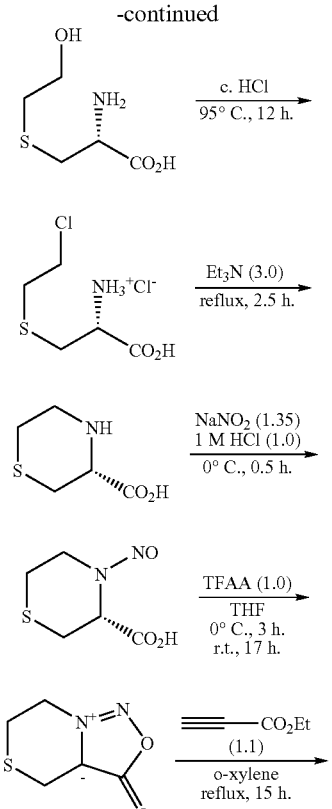
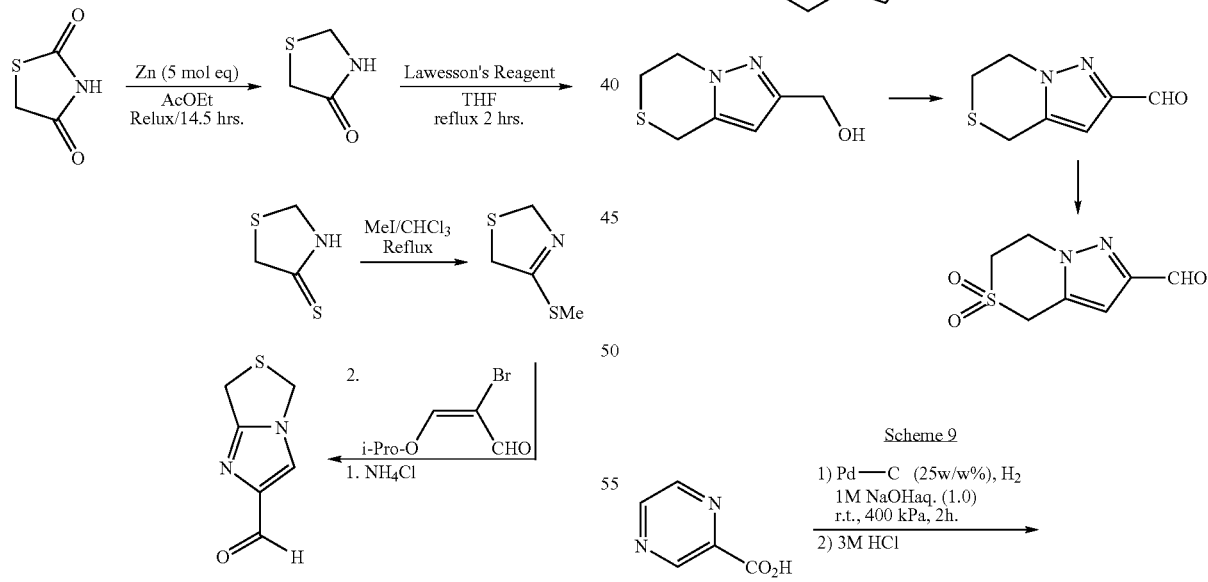

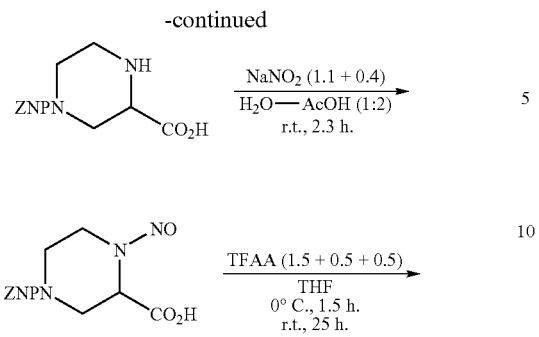
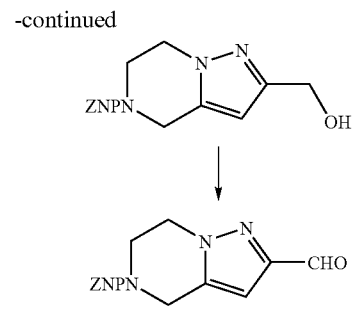
Scheme 10
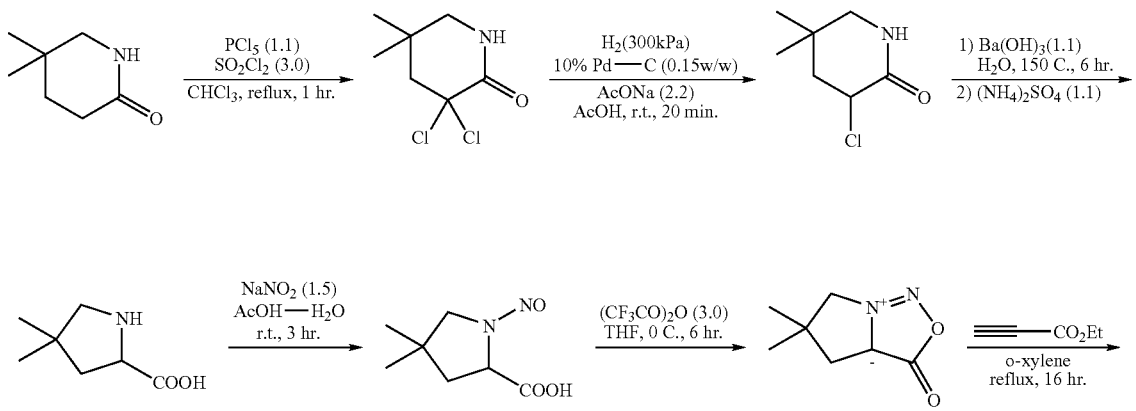
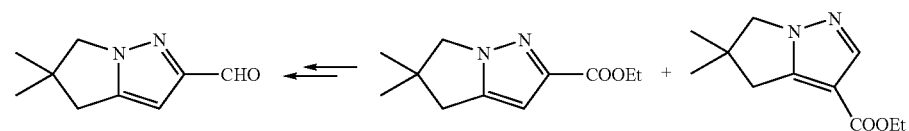
Scheme 11
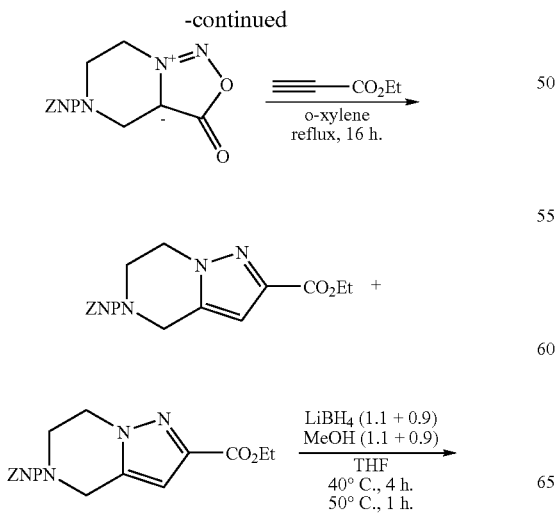
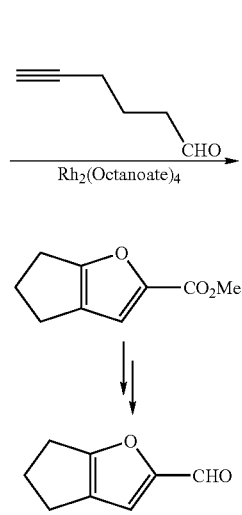

Scheme 12
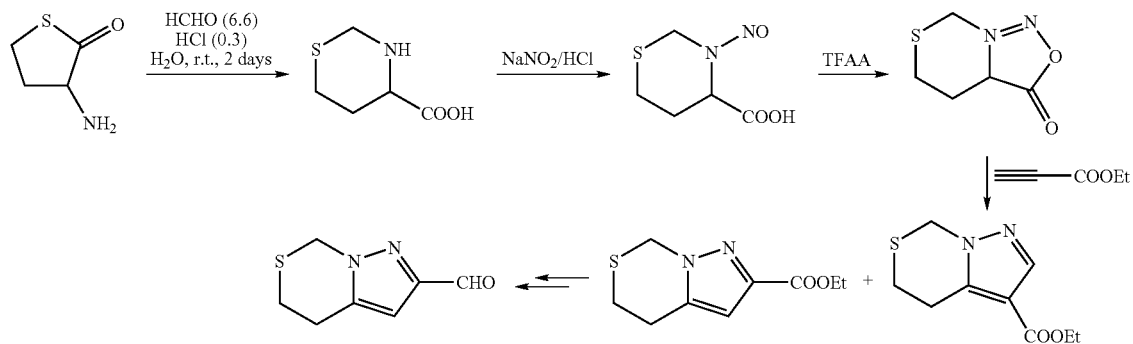
Scheme 13
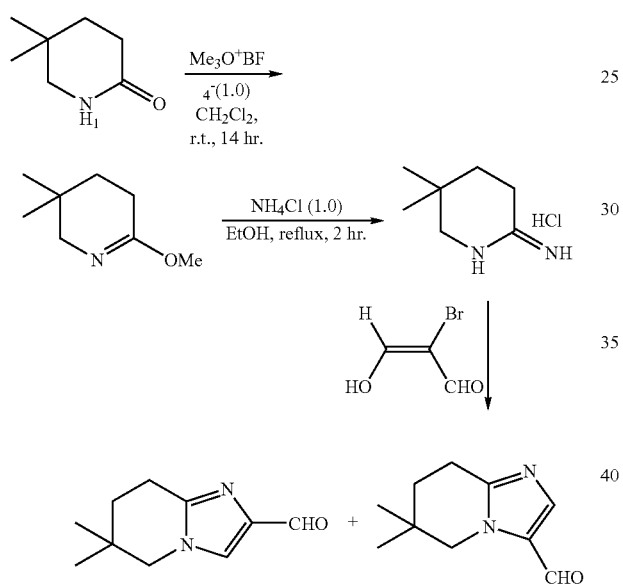
Scheme 14
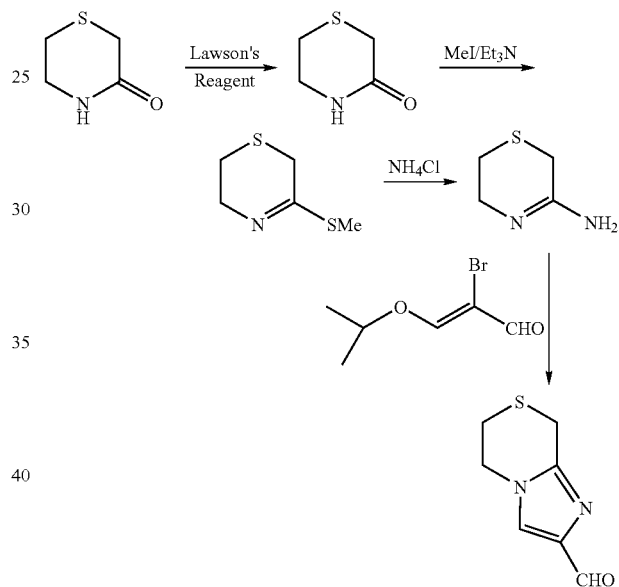
Scheme 15
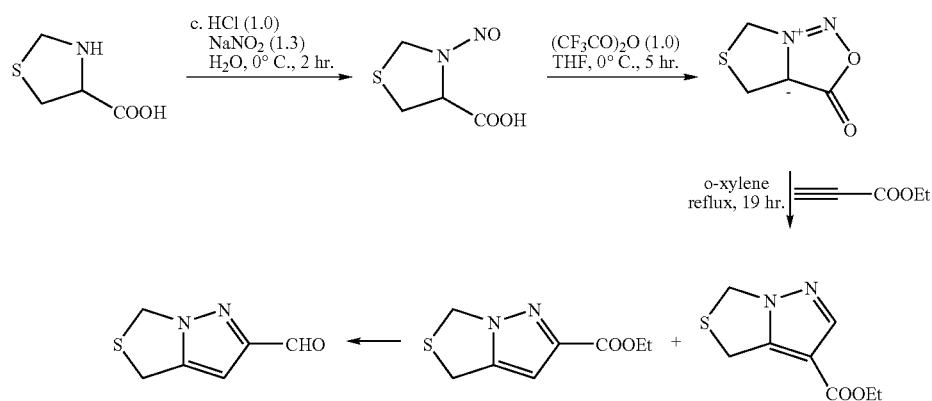

Scheme 16

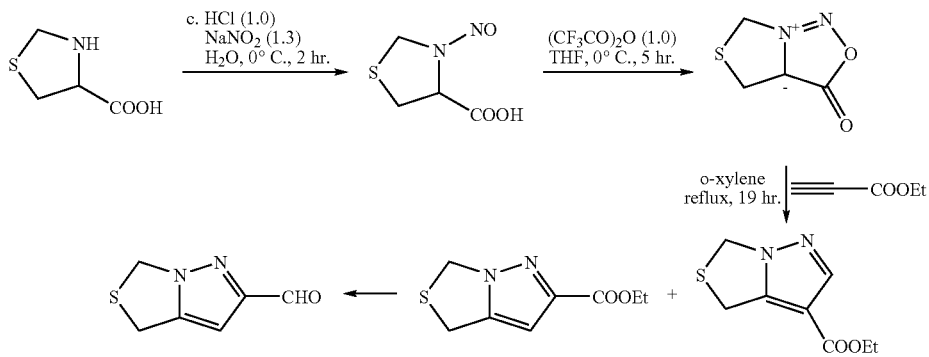

Scheme 17

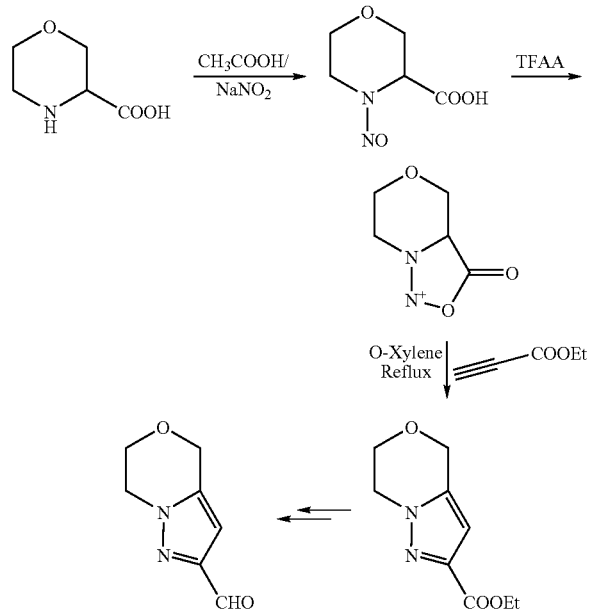

Scheme 18

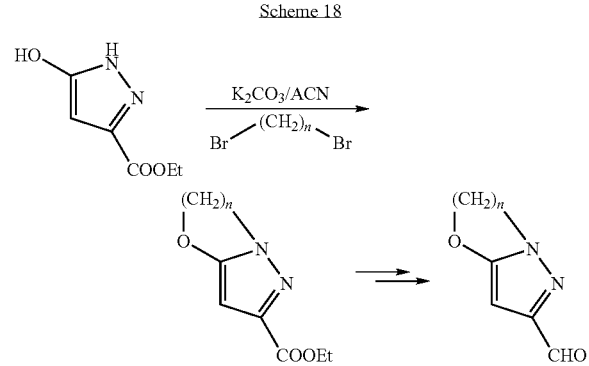

n = 2, 3

EXPERIMENTALS

Example 1

Preparation of (5R,6Z)-6-[(5-benzyl-4,5,6,7-tetrahydrothieno[3,2-c]pyridin-2-yl)methylene]-7oxo-4-thia-1-azabicyclo[3.2.0]hept-2-ene-2-carboxylic acid Step 1: Ethyl 5-benzoyl-4,5,6,7-tetrahydrothieno[3,2-c]pyridine-2-carboxylate To a stirred dry DMF (7.3 g, 100 mmol), POCl$_3$ (12.25 g, 80 mmol) was slowly added between 0° C. to 5° C. After the addition the solidified mass was dissolved in CH$_2$Cl$_2$ (20 ml) and stirred at room temperature for 2 hrs. Again the temperature was cooled to 0° C. and 1-benzoyl-4-piperidone in CH$_2$Cl$_2$ was added slowly. After the addition the reaction mixture was stirred at room temperature for 2 hrs and poured over crushed ice and sodium acetate. It was stirred for 30 minutes at room temperature. Extracted with CH$_2$Cl$_2$; washed well with water; dried over anhydrous MgSO$_4$ and concentrated. The crude product was dissolved in CH$_2$Cl$_2$ and ethylmercaptoacetae (9.6 g, 80 mmol)/Et$_3$N (10.1 g, 100 mmol) was added slowly at room temperature. The reaction mixture was refluxed for 2 hrs and quenched with water. CH$_2$Cl$_2$ layer was washed well with water; dried over anhydrous MgSO$_4$; filtered and concentrated. The product was purified by SiO$_2$ column chromatography by eluting it with 50% ethylacetate; hexane. Yellow oil; Yield: 6.4 gms (25%); M+H 316.

Step: 2 (5-benzyl-4,5,6,7-tetrahydrothieno[3,2-c]pyridin-2-yl)methanol

To stirred suspension of LAH (2.0 gms) a solution of ethyl 5-benzoyl-4,5,6,7-tetrahydrothieno[3,2-c]pyridine-2-carboxylate (6.0 g, 19 mmol) in THF was added slowly at 0° C. After addition reaction mixture was stirred for 30 minutes and quenched with saturated NH$_4$Cl. It was diluted with CHCl$_3$ and filtered. The filtrate was washed with saturated brine solution and dried over anhydrous MgSO$_4$. It was filtered and taken to next step with out purifications. Yield: 4.5 g 91%. Yellow liquid.

Step 3: 2-Formyl (5-benzyl-4,5,6,7-tetrahydrothieno[3,2-c]pyridine

To a stirred solution of (5-benzyl-4,5,6,7-tetrahydrothieno[3,2-c]pyridin-2-yl)methanol (4.0 g, 15.4 mmol) in CH$_2$Cl$_2$ (300 ml) active MnO$_2$ (20 g, excess) was added and stirred at room temperature for 18 hrs. At the end, the reaction mixture was filtered through celite and washed with CHCl$_3$. Reaction mixture was washed well with water; dried and concentrated. The product was found to be pure and taken to next step without purifications. Yield: 3.0 g (76%); (M+H: 257).

Step 4: 4-Nitrobenzy-6-[(acetyloxy)(5-benzyl-4,5,6,7-tetrahydrothieno[3,2-c]pyridin-2-yl)methyl]-6-bromo-7-oxo-4-thia-1-azabicyclo[3.2.0]hept-2-ene-2-carboxylate 2-Formyl (5-benzyl-4,5,6,7-tetrahydrothieno[3,2-c]pyridine (565 mg, 2.2 mmol) and the dry THF solution (20 mL) of (5R,6S)-6-bromo-7-oxo-4-thia-1-aza-bicyclo[3.2.0]hept-2-ene-2-carboxylic acid 4-nitro-benzyl ester (772 mg, 2.0 mmol) were added successively to the dry acetonitrile (15 mL) solution of anhydrous MgBr$_2$:O(Et)$_2$ (390 mg, 1.5 mmol) under an argon atmosphere at room temperature. After cooling to −20° C., Et$_3$N (2.0 mL) was added in one portion. The reaction vessel was covered with foil to exclude light. The reaction mixture was stirred for 2 h at −20° C. and treated with acetic anhydride (1.04 mL) in one portion. The reaction mixture was warmed to 0° C. and stirred for 15 h at 0° C. The mixture was diluted with ethyl acetate and washed with 5% citric acid aqueous solution, saturated sodium hydrogen carbonate, and brine. The organic layer was dried (MgSO$_4$) and filtered through a pad of Celite. The pad was washed with ethyl acetate. The filtrate was concentrated under reduced pressure. The residue was applied to silica gel column chromatography, then the column was eluted with ethyl acetate:hexane (1:1). Collected fractions were concentrated under reduced pressure and the mixture of diastereo isomers were taken to next step. Pale yellow amorphous solid; Yield: 550 mg, 40%; M+H 687.

Step 5: (5R,6Z)-6-[(5-benzyl-4,5,6,7-tetrahydrothieno[3,2-c]pyridin-2-yl)methylene]-7-oxo-4-thia-1-azabicyclo[3.2.0]hept-2-ene-2-carboxylic acid 4-Nitrobenzy-6-[(acetyloxy)(5-benzyl-4,5,6,7-tetrahydrothieno[3,2-c]pyridin-2-yl)methyl]-6-bromo-7-oxo-4-thia-1-azabicyclo[3.2.0]hept-2-ene-2-carboxylate (450 mg, 0.65 mmol) was dissolved in THF (20 mL) and acetonitrile (10 mL). Freshly activated Zn dust (5.2 g) was added rapidly with 0.5 M phosphate buffer (pH 6.5, 28 mL). The reaction vessel was covered with foil to exclude light. The reaction mixture was vigorously stirred for 2 hours at room temperature. The reaction mixture was filtered, cooled to 3° C., and 0.1 M NaOH was added to adjust pH to 8.5. The filtrate was washed with ethyl acetate and the aqueous layer was separated. The aqueous layer was concentrated under high vacuum at 35° C. to give yellow precipitate. The product was purified by HP21 resin reverse phase column chromatography. Initially the column was eluted with deionized water (2 lits) and latter with 10% CAN:Water. The fractions containing the product were collected and concentrated at reduced pressure at room temperature. The yellow solid was washed with acetone and filtered. Dried. Yield: 50 mg, 18%; as yellow crystals; mp. 198° C.; (M+H) 411.

$^1$H NMR (DMSO-d$_6$) δ d 2.7 (m, 2H), 2.8 (bm, 2H), 3.4 (m, 2H), 3.8 (s, 2H), 6.3 (s, 1H), 6.5 (s, 1H), 7.1 (s, 1H), 7.28 (s, 1H), 7.4 (s, 5H).

Example 2

Preparation of (5R),(6Z)-6-(7-Methyl-5,6,7,8-tetrahydroimidazo[1,2-a]pyrazin-2-ylmethylene)-7-oxo-4-thia-1-aza-bicyclo[3.2.0]hept-2-ene-2-carboxylic acid, sodium salt

Step 1: Imidazo[1,2-a]pyrazine-2-carboxylic acid ethyl ester

Ethyl bromopyruvate (62.9 g) was added to the DME (258 mL) solution of 2-aminopyrazine (24.8 g) at room temperature and stirred for 2.5 h. The reaction mixture was cooled to 0° C. and stirred for 30 min to afford a pale brown precipitate. The precipitate was filtered and washed with Et$_2$O to give pale brown crystals. The suspension of the precipitate (66.1 g) in EtOH (1.29 L) was heated at reflux temperature to turn to clear solution. After refluxing for 2 h, the reaction mixture was concentrated under reduced pressure, then mixed with CHCl$_3$ and saturated NaHCO$_3$aq. The mixture was filtered through a pad of Celite and the separated organic layer was dried (MgSO$_4$) and filtered. The filtrate was concentrated under reduced pressure. The residue was applied to silica gel column chromatography, then the column was eluted with CHCl$_3$-MeOH (99/1~97/3), and collected fractions were concentrated under reduced pressure followed by recrystallization from CHCl$_3$-Et$_2$O. The titled compound was obtained as pale pink crystals. Yield: 10.9 g, 22%).

$^1$H NMR (CDCl$_3$) δ d 1.46 (t, 3H, J=7.2 Hz), 4.49 (q, 2H, J=7.2 Hz), 7.96 (d, 1H, J=4.7 Hz), 8.08 (dd, 1H, J=1.2, 4.7 Hz), 8.26 (s, 1H), 9.21 (d, 1H, J=1.2 Hz).

Step 2: 5,6,7,8-Tetrahydroimidazo[1,2-a]pyrazine-2-carboxylic acid ethyl ester, Hydrochloride 0.46 M HCl-EtOH (169 mL) and 10% Pd—C (50% wet) (1.37 g) were added to the EtOH (546 mL) solution of imidazo[1,2-a]pyrazine-2-carboxylic acid ethyl ester (13.7 g). The mixture was hydrogenated under H$_2$ at 40 psi at room temperature for 15 h. The reaction mixture was filtered and Pd—C was washed with EtOH. The filtrate was concentrated under reduced pressure. The residue was applied to silica gel column chromatography, then the column was eluted with CHCl$_3$-MeOH (9/1~2/1). The titled compound was obtained as brown crystals Yield: 10.4 g, 63%.

$^1$H NMR (CDCl$_3$) δ d 1.38 (t, 3H, J=7.1 Hz), 3.90 (t, 2H, J=5.7 Hz), 4.40 (q, 2H, J=7.1 Hz), 4.59 (t, 2H, J=5.7 Hz), 4.80 (s, 2H), 8.20 (s, 1H).

Step 3: 7-Methyl-5,6,7,8-tetrahydroimidazo[1,2-a]pyrazine-2-carboxylic acid ethyl ester Et$_3$N (3.44 mL), 37% HCHO aq. (2.02 mL) and NaBH$_3$CN (1.78 g) were added successively to the MeOH (75 mL) solution of 5,6,7,8-tetrahydroimidazo[1,2-a]pyrazine-2-carboxylic acid ethyl ester, hydrochloride (5.2 g) at room temperature and stirred for 3.5 h under a nitrogen atmosphere. The mixture was diluted with CH$_2$Cl$_2$ and washed with 50% K$_2$CO$_3$ aq. The organic layer was dried (K$_2$CO$_3$) and filtered. The filtrate was concentrated under reduced pressure. The residue was applied to silica gel column chromatography, then the column was eluted with CHCl$_3$-acetone (1/1~1/2). The titled compound was obtained as orange oil. Yield: 2.68 g, 57%).

$^1$H NMR (CDCl$_3$) δ d 1.37 (t, 3H, J=7.1 Hz), 2.50 (s, 3H), 2.85 (t, 2H, J=5.5 Hz), 3.69 (s, 2H), 4.06 (t, 2H, J=5.5 Hz), 4.36 (t, 2H, J=7.1 Hz), 7.52 (s, 1H).

Step 4: 7-Methyl-5,6,7,8-tetrahydroimidazo[1,2-a]pyrazine-2-carbaldehyde 1.01 M solution of DIBAL in toluene (13.6 mL) was added to the dry $CH_2Cl_2$ (86 mL) solution of 7-methyl-5,6,7,8-tetrahydroimidazo[1,2-a]pyrazine-2-carboxylic acid ethyl ester (1.8 g) under a nitrogen atmosphere at −78° C. and stirred for 2 h. The mixture was quenched with 1M HCl. The reaction mixture was filtered through a pad of Celite. The filtrate was washed with 50% $K_2CO_3$ aq. and the aqueous layer was extracted with $CH_2Cl_2$ three times. The combined organic layer was dried ($K_2CO_3$) and filtered. The filtrate was concentrated under reduced pressure. The residue was applied to silica gel column chromatography, then the column was eluted with $CHCl_3$-MeOH (19/1~9/1). The titled compound 5 was obtained as colorless crystals. Yield: 591 mg, 42%).

$^1$H NMR (CDCl$_3$) δ d 2.51 (s, 3H), 2.87 (t, 2H, J=5.5 Hz), 3.70 (s, 2H), 4.10 (t, 2H, J=5.5 Hz), 7.53 (s, 1H), 9.82 (d, 1H, J=1.4 Hz).

Step 5: (5R,6RS)-6-[(RS)-Acetoxy(7-methyl-5,6,7,8-tetrahydroimidazo[1,2-a]pyrazin-2-yl)methyl]-6-bromo-7-oxo-4-thia-1-azabicyclo[3.2.0]hept-2-ene-2-carboxylic acid 4-nitrobenzyl ester (diastereo mixture)

7-Methyl-5,6,7,8-tetrahydroimidazo[1,2-a]pyrazine-2-carbaldehyde (1.19 g) was added to the dry acetonitrile (97 mL) solution of anhydrous $MgBr_2$ (4.05 g) under a nitrogen atmosphere at room temperature. The dry THF solution (97 mL) of (5R,6S)-6-bromo-7-oxo-4-thia-1-aza-bicyclo[3.2.0]hept-2-ene-2-carboxylic acid 4-nitro-benzyl ester (3.32 g) was added to the mixture, cooled to −20° C., and Et$_3$N (3.0 mL) was added in one portion. The reaction vessel was covered with foil to exclude light. The reaction mixture was stirred for 4.5 h at −20° C. and treated with acetic anhydride (1.36 mL) in one portion. The reaction mixture was warmed to 0° C. and stirred for 17 h at 0° C. The mixture was diluted with ethyl acetate and washed with 5% citric acid aqueous solution, saturated sodium hydrogen carbonate, and brine. The organic layer was dried (MgSO$_4$) and filtered. The filtrate was concentrated under reduced pressure. The residue was applied to silica gel column chromatography, then the column was eluted with $CHCl_3$-acetone (9/1~2/1). The titled compound was obtained as two diastereo mixture. Red oil, Yield: 1.13 g.

$^1$H NMR (CDCl$_3$) δ d 1.20 (s, 0.81×3H), 2.24 (s, 0.19×3H), 2.48 (s, 3H), 2.80~2.84 (m, 2H), 3.57~3.67 (m, 2H), 3.97~4.02 (m, 2H), 5.27 (d, 1H, J=13.6 Hz), 5.42 (d, 0.19× 1H, J=13.6 Hz), 5.45 (d, 0.81×1H, J=13.6 Hz), 6.07 (s, 0.19× 1H), 6.30 (s. 0.81×2H), 6.79 (s, 0.19×1H), 6.80 (s, 0.19×1H), 7.02 (s, 0.81×1H), 7.44 (s, 0.19×1H), 7.47 (s, 0.81×1H), 7.60 (d, 0.19×2H, J=8.2 Hz), 7.62 (d, 0.81×2H, J=8.6 Hz), 8.22~8.26 (m, 2H).

Step 6: (5R),(6Z)-6-(7-Methyl-5,6,7,8-tetrahydroimidazo[1,2-a]pyrazin-2-ylmethylene)-7-oxo-4-thia-1-aza-bicyclo[3.2.0]hept-2-ene-2-carboxylic acid, sodium salt (5R,6RS)-6-[(RS)-Acetoxy(7-methyl-5,6,7,8-tetrahydroimidazo[1,2-a]pyrazin-2-yl)methyl]-6-bromo-7-oxo-4-thia-1-azabicyclo[3.2.0]hept-2-ene-2-carboxylic acid 4-nitrobenzyl ester (1.11 g) was dissolved in THF (32 mL) and acetonitrile (32 mL). Freshly activated Zn dust (4.46 g) was added rapidly with 0.5 M phosphate buffer (pH 6.5, 48 mL). The reaction vessel was covered with foil to exclude light. The reaction mixture was vigorously stirred for 2 h at room temperature. The reaction mixture was filtered through a pad of Celite, cooled to 3° C., and 1 M NaOH was added to adjust pH to 7.5. The filtrate was washed with ethyl acetate and the aqueous layer was separated. The aqueous layer was concentrated under high vacuum at 35° C. The concentrate was applied to Diaion HP-21 (20 mL, Mitsubishi Kasei Co. Ltd.) resin column chromatography. After adsorbing, the column was eluted with $H_2O$-MeCN (1/0~95/5). The combined fractions were concentrated under high vacuum at 35° C. and lyophilized to give the title compound as a yellow amorphous solid. Yield: 417 mg, 65%: mp 200° C. (dec); $^1$H NMR ($D_2O$) δ d 2.32 (s, 3H), 2.79~2.81 (m, 2H), 3.54 (s, 2H), 3.95 (t, 2H, J=5.6 Hz), 6.39 (s, 1H), 6.85 (s, 1H), 6.87 (s, 1H), 7.26 (s, 1H).

Example 3

Preparation of (5R),(6Z)-7-Oxo-6-(5,6,7,8-tetrahydroimidazo[1,2-a]pyrazin-2-ylmethylene)-4-thia-1-azabicyclo[3.2.0]hept-2-ene-2-carboxylic acid, sodium salt 2-oxopiperazine 2-oxopiperazine may be prepared according to procedures in U.S. Pat. No. 5,629,322.

Step 1: 4-p-Nitrobenzyloxycarbonyl-2-oxopiperazine

The 48.7% solution of p-nitrobenzyloxycarbonyl chloride in 1,4-Dioxane (10.7 mL) was added to the dichloromethane (110 mL) solution of 2-oxpiperazine (2.21 g) and diisopropylethylamine (4.6 mL) at 0° C. and stirred for 0.5 h at 0° C. Water (300 mL) was added to the reaction mixture, and extracted with dichloromethane (3×100 mL). The organic layer was dried (MgSO$_4$) and filtered. The filtrate was concentrated under reduce pressure. The residue was applied to silica gel column chromatography, eluted with $CHCl_3$-methanol (30: 1), and the title compound was obtained as white solid (7.1 g, quant.).

$^1$H NMR (d, CDCl$_3$) □ 3.42-3.45 (m, 2H), 3.74 (t, 2H, J=5.4 Hz), 4.19 (s, 2H), 5.26 (s, 2H), 6.39 (brs, 1H), 7.52 (d, 2H, J=8.6 Hz), 8.24 (d, 2H, J=8.6 Hz).

Step 2: 5-Methoxy-4-p-nitrobenzyloxycarbonyl-1,2, 3,6-tetrahydropyrazine

Trimethyloxonium tetrafluoroborate (97%, 3.7 g) was added to the dry dichloromethane (120 mL) solution of 4-p-nitrobenzyloxycarbonyl-2-oxopiperazine (6.7 g) at room temperature and stirred for 17 hours. The reaction mixture was treated with saturated sodium hydrogen carbonate aqueous solution, and the organic layer was separated. The aqueous layer was extracted with ethyl acetate (3×100 mL), then the combined organic layer was washed with saturated sodium hydrogen carbonate aqueous solution and brine. The organic layer was dried (MgSO$_4$) and filtered. The filtrate was concentrated under reduce pressure and the title compound was obtained as a pale brown solid. Yield; 5.7 g, 80.6.

$^1$H NMR (d, CDCl$_3$) □ 3.48 (m, 2H), 3.57 (m, 2H), 3.70 (s, 3H), 3.97 (s, 2H), 5.26 (s, 2H), 7.52 (d, 2H, J=8.7 Hz), 8.23 (d, 2H, J=8.7 Hz).

Step 3: 2-Imino-4-p-nitrobenzyloxycarbonyl piperazine

The mixture of 5-methoxy-4-p-nitrobenzyloxycarbonyl-1, 2,3,6-tetrahydropyrazine (5.7 g) and ammonium chloride (1.6 g) in dry ethanol (100 mL) was heated to reflux for 4 hours. The reaction mixture was then concentrated under reduced pressure. Dichloromethane (100 mL) was added to the residue and extracted with water (3×50 mL) then the combined aqueous layer was washed with dichloromethane. The aqueous layer was neutralized with 10% potassium carbonate aqueous solution and then extracted with dichloromethane (8×50 mL). The combined organic layer was dried ($MgSO_4$) and filtered. The filtrate was concentrated under reduced pressure and the title compound was obtained as a white solid. Yield: 4.9 g, 91.2%.

$^1$H NMR (d, $CDCl_3$) δ 3.49 (brs, 4H), 3.98 (brs, 2H), 5.26 (s, 2H), 7.52 (d, 2H, J=8.6 Hz), 8.23 (d, 2H, J=8.6 Hz).

Step 4: 7-p-Nitrobenzyloxycarbonyl-5,6,7,8-tetrahydroimidazo[1,2-a]pyrazine-2-carbaldehyde (9) and 7-p-nitrobenzyloxycarbonyl-5,6,7,8 tetrahydroimidazo[1,2-a]pyrazine-3-carbaldehyde The mixture of 2-bromo-3-hydroxypropenal (2.8 g), p-toluenesulfonic acid monohydrate (33 mg) and 2-propanol (3.5 mL) in cyclohexane (28 mL) was azeotroped until the vapor temperature rose to 80° C. The reaction mixture was concentrated under reduce pressure. The residue was dissolved in dry acetonitrile (30 mL). The dry acetonitrile (310 mL) solution of 2-imino-4-p-nitrobenzyloxycarbonyl piperazine (4.7 g) was added at room temperature. The reaction mixture was stirred at room temperature for 3 h, and then the reaction solution was removed in vacuo. The residue was dissolved in ethyl acetate (170 mL) and triethylamin (2.4 mL) was added, then the reaction mixture was heated to reflux for 1.5 h. The reaction mixture was cooled to room temperature, and then water (170 mL) was added to the reaction mixture and separated. The aqueous layer was extracted with dichloromethane (2×100 mL). The combined organic layer was dried ($MgSO_4$) and filtered. The filtrate was concentrated under reduce pressure. The residue was applied to silica gel column chromatography, eluted with $CHCl_3$-methanol (50:1), and the title compound was obtained as a brown solid, (Yield: 2.9 g, 51.6%) and its regio isomer (orange amorphous solid, Yield; 0.8 g, 14.9%) were obtained.

$^1$H NMR (d, $CDCl_3$) 3.99 (t, 2H, J=5.4 Hz), 4.14 (t, 2H, J=5.4 Hz), 4.85 (s, 2H), 5.29 (s, 2H), 7.54 (d, 2H, J=8.6 Hz), 7.57 (s, 1H), 8.24 (d, 2H, J=8.6 Hz), 9.85 (s, 1H).

Regio isomer $^1$H NMR (d, $CDCl_3$) δ 3.95 (t, 2H, J=5.4 Hz), 4.44 (t, 2H, J=5.4 Hz), 4.87 (s, 2H), 5.29 (s, 2H), 7.54 (d, 2H, J=8.7 Hz), 7.78 (s, 1H), 8.24 (d, 2H, J=8.7 Hz), 9.71 (s, 1H).

Step 5: (5R)-6-[Acetoxy-(7-p-nitrobenzyloxycarbonyl-5,6,7,8-tetrahydroimidazo[1,2-a]pyrazin-2-yl)-methyl]-6-bromo-7-oxo-4-thia-1azabicyclo[3.2.0]hept-2-ene-2-carboxylic acid p-nitrobenzyl ester The dry acetonitrile (25 mL) solution of 7-p-nitrobenzyloxycarbonyl-5,6,7,8-tetrahydroimidazo[1,2-a]pyrazine-2-carbaldehyde (1.6 g) was added to the dry acetonitrile (55 mL) solution of $MgBr_2$ (2.2 g) under an nitrogen atmosphere at room temperature then the mixture was stirred for 10 min. The dry THF (80 mL) solution of (5R,6S)-6-bromo-7-oxo-4-thia-1-aza-bicyclo[3.2.0]hept-2-ene-2-carboxylic acid 4-nitro-benzyl ester (1.8 g) was added, the mixture was cooled to −20° C. then triethylamine (1.6 mL) was added in one portion. The reaction vessel was covered with foil to exclude light. The reaction mixture was stirred for 3 h at −20° C. and treated with 4,4-dimethylamino pyridine (58.3 mg) and acetic anhydride (0.89 mL) in one portion. The reaction mixture was warmed to 0° C. and stirred for 15 h at 0° C. 10% Citric acid aqueous solution (320 mL) was added to the reaction mixture and the aqueous layer was extracted with ethyl acetate (3×160 mL). The organic layer was washed with water, saturated sodium hydrogen carbonate and brine, dried ($MgSO_4$) and filtered. The filtrate was concentrated under reduced pressure. The residue was applied to silica gel column chromatography, eluted with $CH_2Cl_2$-acetone (20:1), and the title compound was obtained as two diastereo mixture (81:19, brown foamy amorphous solid. Yield: 2.1 g, 59.9%.

$^1$H NMR (d, $CDCl_3$) δ 2.01 (s, 2.43H), 2.24 (s, 0.57H), 3.93-, 3.96 (m, 2H), 4.02-4.05 (m, 2H), 4.74-4.76 (m, 2H), 5.28 (d, 1H, J=13.5 Hz), 5.28 (s, 2H), 5.45 (d, 1H, J=13.5 Hz), 6.07 (s, 0.19H), 6.29 (s, 0.81H), 6.31 (s, 0.81H), 6.80 (s, 0.19H), 6.83 (s, 0.19H), 7.08 (s, 0.81H), 7.43 (s, 0.19H), 7.46 (s, 0.81H), 7.54 (d, 2H, J=8.6 Hz), 7.61 (d, 2H, J=8.8 Hz), 8.24 (d, 4H, J=8.3 Hz).

Step 6: (5R),(6Z)-7-Oxo-6-(5,6,7,8-tetrahydroimidazo[1,2-a]pyrazin-2-ylmethylene)-4-thia-1-azabicyclo[3.2.0]hept-2-ene-2-carboxylic acid, sodium salt (5R)-6-[Acetoxy-(7-p-nitrobenzyloxycarbonyl-5,6,7,8-tetrahydroimidazo[1,2-a]pyrazin-2-yl)-methyl]-6-bromo-7-oxo-4-thia-1 azabicyclo[3.2.0]hept-2-ene-2-carboxylic acid p-nitrobenzyl ester (2.0 g) was dissolved in THF (63 mL). Freshly activated Zn dust (7.9 g) was added rapidly with 0.5 mol/L phosphate buffer (pH 6.5, 63 mL). The reaction vessel was covered with foil to exclude light. The reaction mixture was vigorously stirred for 2 h at room temperature. The reaction solution was filtered through a pad of Celite and the pad was washed with water (150 mL) and n-butanol (150 mL). The aqueous layer was separated and then the organic layer was extracted with water (2×50 mL). The combined aqueous layer was concentrated to 61 g and applied to Diaion HP-21 resin (80 mL, Mitsubishi Kasei Co. Ltd.) column chromatography. After adsorbing, the column was eluted with water and then 5% acetonitrile aqueous solution. The combined fractions were concentrated under high vacuum at 35° C. and lyophilized to give the title compound as a yellow amorphous solid. Yield: 172 mg, 20.1%: mp 150° C. (dec); $^1$H NMR (d, $D_2O$) δ3.02 (t, 2H, J=5.6 Hz), 3.82 (s, 2H), 3.89 (d, 2H, J=5.6 Hz), 6.38 (s, 1H), 6.84 (s, 1H), 6.87 (s, 1H), 7.24 (s, 1H); IR (KBr)

Example 4

Preparation of (5R,6Z)-6-{[5-(4-methoxybenzyl)-4, 5,6,7-tetrahydrothieno[3,2-c]pyridin-2-yl)]methylene}-7oxo-4-thia-1-azabicyclo[3.2.0]hept-2-ene-2-carboxylic acid

Step 1: 5-tert-butyl 2-ethyl 6,7-dihydrothieno[3,2-c] pyridine-2,5(4H)-dicarboxylate 5-tert-butyl 2-ethyl 6,7-dihydrothieno[3,2-c]pyridine-2,5 (4H)-dicarboxylate was prepared according to the procedure as outlined in Example 1, (Step 1). Starting from tert-butyl-1-piperidinecarboxylate (9.9 g, 50 mmol), $POCl_3$ (6.3 g, 40 mmol) and DMF (3.8 g, 50 mmol). The chloroformyl intermediate was reacted with ethyl mercaptoacetate (6.0 g, 50 mmol) and $Et_3N$. The product was purified by $SiO_2$ column chromatography by eluting it with 3:1 hexane; ethylacetate. Yield: 8.7 g, 56%; White liquid. (M+H) 312.

Step 2: tert-butyl 2-(hydroxymethyl)-6,7-dihydrothieno[3,2-c]pyridine-5(4H)-carboxylate tert-butyl 2-(hydroxymethyl)-6,7-dihydrothieno[3,2-c]pyridine-5(4H)-carboxylate was prepared according to the procedure outlined in Example 1, (Step 2). Starting from 5-tert-butyl 2-ethyl 6,7-dihydrothieno[3,2-c]pyridine-2,5(4H)-dicarboxylate (1.0 g, 3.21 mmol) and LiAlH$_4$ (500 mg, excess), 807 mg (92% yield) of the alcohol derivative was isolated as white liquid. (M+H) 270.

Step 3: tert-butyl 2-(formyl)-6,7-dihydrothieno[3,2-c]pyridine-5(4H)-carboxylate tert-butyl 2-(formyl)-6,7-dihydrothieno[3,2-c]pyridine-5(4H)-carboxylate was prepared according to the procedure outlined in Example 1, (Step 3). Starting from tert-butyl 2-(hydroxymethyl)-6,7-dihydrothieno[3,2-c]pyridine-5(4H)-carboxylate (1.0 g 3.7 mmol) in methylene chloride (100 ml) and active MnO$_2$ (5 g, excess), 800 g (81% Yield) of the aldehyde derivative was isolated as brown solid. (M+H) 268.

Step 4: 2-(formyl)-6,7-dihydrothieno[3,2-c]-5(4H)-pyridine 2-(formyl)-6,7-dihydrothieno[3,2-c]-5(4H)-pyridine was prepared starting from tert-butyl 2-(formyl)-6,7-dihydrothieno[3,2-c]pyridine-5(4H)-carboxylate (1.0 g 3.7 mmol) was dissolved in CH$_2$Cl$_2$ (20 ml), MeOH (90% 20 ml) and 1N. HCl in dioxane (10 ml). The reaction mixture was stirred at room temperature for 48 hrs. At the end reaction mixture was concentrated to dryness and taken to next step without purification. Yield: 750 mg (HCl salt, Quantitative); M+H 168.

Step 5: 2-Formyl [5-(4-methoxybenzyl)-4,5,6,7-tetrahydrothieno][3,2-c]pyridine To a stirred solution of 2-(formyl)-6,7-dihydrothieno[3,2-c]-5(4H)-pyridine (1.4 g, 5.2 mmol) in DMF (20 ml), 4-methoxybenzyl chloride (0.94 g, 6.2 mmol) and N,N-diisopropylethylamine (10 ml, excess) was added at room temperature. The reaction mixture was stirred for 24 hrs and quenched with water. The reaction mixture was extracted with chloroform; washed well with water and dried over anhydrous MgSO$_4$. It was filtered and concentrated. The product was purified by SiO$_2$ column chromatography by eluting it with ethylacetate. Pale yellow oil. Yield: 470 mg, 35%; M+H 288.

Step 6: 4-Nitrobenzy-6-[(acetyloxy)[5(4-methoxybenzyl)-4,5,6,7-tetrahydrothieno[3,2-c]pyridin-2-yl)methyl]-6-bromo-7-oxo-4-thia-1-azabicyclo[3.2.0]hept-2-ene-2-carboxylate 2-Formyl [5-(4-methoxybenzyl)-4,5,6,7-tetrahydrothieno][3,2-c]pyridine (574 mg, 2.0 mmol) and the dry THF solution (20 mL) of (5R,6S)-6-bromo-7-oxo-4-thia-1-aza-bicyclo[3.2.0]hept-2-ene-2-carboxylic acid 4-nitro-benzyl ester (772 mg, 2.0 mmol) were added successively to the dry acetonitrile (15 mL) solution of anhydrous MgBr$_2$:O(Et)$_2$ (390 mg, 1.5 mmol) under an argon atmosphere at room temperature. After cooling to −20° C., Et$_3$N (2.0 mL) was added in one portion. The reaction vessel was covered with foil to exclude light. The reaction mixture was stirred for 2 h at −20° C. and treated with acetic anhydride (1.04 mL) in one portion. The reaction mixture was warmed to 0° C. and stirred for 15 h at 0° C. The mixture was diluted with ethyl acetate and washed with 5% citric acid aqueous solution, saturated sodium hydrogen carbonate, and brine. The organic layer was dried (MgSO$_4$) and filtered through a pad of Celite. The pad was washed with ethyl acetate. The filtrate was concentrated under reduced pressure. The residue was applied to silica gel column chromatography, then the column was eluted with ethyl acetate:hexane (1:1). Collected fractions were concentrated under reduced pressure and the mixture of diastereo isomers were taken to next step. Pale yellow amorphous solid; Yield: 550 mg, 40%; M+H 714 and 716.

Step 7: (5R,6Z)-6-{[5-(4-methoxybenzyl)-4,5,6,7-tetrahydrothieno[3,2-c]pyridin-2-yl)]methylene}-7oxo-4-thia-1-azabicyclo[3.2.0]hept-2-ene-2-carboxylic acid 4-Nitrobenzy-6-[(acetyloxy)[5(4-methoxybenzyl)-4,5,6,7-tetrahydrothieno[3,2-c]pyridin-2-yl)methyl]-6-bromo-7-oxo-4-thia-1-azabicyclo[3.2.0]hept-2-ene-2-carboxylate (300 mg, 0.42 mmol) was dissolved in THF (20 mL) and acetonitrile (10 mL). Freshly activated Zn dust (5.2 g) was added rapidly with 0.5 M phosphate buffer (pH 6.5, 28 mL). The reaction vessel was covered with foil to exclude light. The reaction mixture was vigorously stirred for 2 h at room temperature. The reaction mixture was filtered, cooled to 3° C., and 0.1 M NaOH was added to adjust pH to 8.5. The filtrate was washed with ethyl acetate and the aqueous layer was separated. The aqueous layer was concentrated under high vacuum at 35° C. to give yellow precipitate. The product was purified by HP21 resin reverse phase column chromatography. Initially the column was eluted with deionized water (2 lits) and latter with 10% CAN:Water. The fractions containing the product were collected and concentrated at reduced pressure at room temperature. The yellow solid was washed with acetone and filtered. Dried. Yield: 50 mg, 18%; as yellow crystals; mp. 127° C.; (M+H) 441.

$^1$H NMR (DMSO-d$_6$) δ d 2.7 (m, 2H), 2.8 (bm, 2H), 3.4 (m, 2H), 3.74 (s, 3H) 3.8 (s, 2H), 6.6 (s, 1H), 6.88 (dd, 2H), 7.14 (s, 1H), 7.24 (dd, 2H), 7.4 (s, 1H), 7.59 (s, 1H).

Example 5

Preparation of (5R),(6Z)-6-(5,6-dihydro-8H-imidazo[2,1-c][1,4]thiazin-2-ylmethylene)-7-oxo-4-thia-1-azabicyclo[3.2.0]hept-2-ene-2-carboxylic acid, sodium salt

Step 1: 5-Methylthio-3,6-dihydro-2H-[1,4]thiazine hydroiodide

5-Methylthio-3,6-dihydro-2H-[1,4]thiazine hydroiodide was prepared by the method as outlined in U.S. Pat. No. 5,629,322.

Step 2: 3-Iminothiomorpholin hydrochloride

5-Methylthio-3,6-dihydro-2H-[1,4]thiazine hydroiodide (7.1 g) was dissolved with 10% K$_2$CO$_3$ aqueous solution (150 mL) and the aqueous layer was extracted with CH$_2$Cl$_2$ (5×70 mL). The combined organic layer was dried (MgSO$_4$), filtered and concentrated under reduce pressure. Ammonium chloride (1.7 g) was added to the obtained residue in dry ethanol (128 mL) and heated to reflux for 1 h. The reaction mixture was cooled to room temperature. The reaction solution was removed in vacuo and the Iminothiomorpholin hydrochloride was obtained as brown solid (4.3 g, quant.).

¹H NMR (d, DMSO-d⁶) δ3.15 (t, 2H, J=5.9 Hz), 3.74 (t, 2H, J=5.9 Hz), 3.83 (s, 2H), 8.97 (brs, 1H), 9.38 (brs, 1H), 9.99 (brs, 1H).

Step 3: 5,6-Dihydro-8H-imidazo[2,1-c][1,4]thiazine-2-carbaldehyde and 5,6-Dihydro-8H-imidazo[2,1-c][1,4]thiazine-3-carbaldehyde The mixture of 2-bromo-3-hydroxypropenal (7, 4.3 g), p-toluenesulfonic acid monohydrate (52 mg) and 2-propanol (5.3 mL) in cyclohexane (43 mL) was azeotroped until the vapor temperature rose to 80° C. The reaction mixture was concentrated under reduce pressure. The residue was dissolved in dry ethanol (28 mL). The mixture of the dry ethanol (143 mL) solution of 3-iminothiomorpholin hydrochloride (4.3 g) and 28% methanol solution of sodium methylate (5.0 mL) were added at room temperature. The reaction mixture was stirred at room temperature for 1 h, and then the reaction solution was removed in vacuo. The residue was dissolved in chloroform (128 mL) and triethylamine (3.6 mL) was added, then the reaction mixture was heated to reflux for 2.5 h. The reaction mixture was cooled to room temperature and then concentrated under reduce pressure. The residue was dissolved with dichloromethane (300 mL) and washed with 50% K₂CO₃ aqueous solution (2×100 mL). The organic layer was dried (MgSO₄) and filtered. The filtrate was concentrated under reduce pressure. The residue was applied to silica gel column chromatography, eluted with CHCl₃-acetone (10:1), and 5,6-Dihydro-8H-imidazo[2,1-c][1,4]thiazine-2-carbaldehyde (brown solid, 445 mg, 10.3%) and 5,6-Dihydro-8H-imidazo[2,1-c][1,4]thiazine-3-carbaldehyde (brown solid, 872 mg, 20.2%) were obtained.

5,6-Dihydro-8H-imidazo[2,1-c][1,4]thiazine-2-carbaldehyde: ¹H NMR (d, CDCl₃) δ 3.07 (t, 2H, J=5.7 Hz), 3.95 (s, 2H), 4.33 (t, 2H, J=5.7 Hz), 7.55 (s, 1H), 9.83 (s, 1H).

5,6-Dihydro-8H-imidazo[2,1-c][1,4]thiazine-3-carbaldehyde: ¹H NMR (d, CDCl₃) δ3.05 (t, 2H, J=5.7 Hz), 3.98 (s, 2H), 4.61 (t, 2H, J=5.7 Hz), 7.73 (s, 1H), 9.69 (s, 1H).

Step 4: (5R),(6Z)-6-(5,6-dihydro-8H-imidazo[2,1-c][1,4]thiazin-2-ylmethylene)-7-oxo-4-thia-1-azabicyclo[3.2.0]hept-2-ene-2-carboxylic acid, sodium salt The dry acetonitrile (20 mL) solution of 5,6-dihydro-8H-imidazo[2,1-c][1,4]thiazine-2-carbaldehyde (392 mg) was added to the dry acetonitrile (20 mL) solution of MgBr₂ (1.1 g) under a nitrogen atmosphere at room temperature then the mixture was stirred for 10 min. The dry THF (40 mL) solution of (5R,6S)-6-bromo-7-oxo-4-thia-1-aza-bicyclo[3.2.0]hept-2-ene-2-carboxylic acid 4-nitro-benzyl ester (1.0 g) was added and the mixture was cooled to −20° C. then triethylamine (0.8 mL) was added in one portion. The reaction vessel was covered with foil to exclude light. The reaction mixture was stirred for 3.5 h at −20° C. and treated with 4-dimethylamino pyridine (30 mg) and acetic anhydride (0.44 mL) in one portion. The reaction mixture was warmed to 0° C. and stirred for 14 h at 0° C. 10% Citric acid aqueous solution (240 mL) was added to the reaction mixture and the aqueous layer was extracted with ethyl acetate (3×100 mL). The combined organic layer was washed with water, saturated sodium hydrogen carbonate and brine, dried (MgSO₄) and filtered. The filtrate was concentrated under reduced pressure. The residue was roughly purified by silica gel column chromatography, eluted with CH₂Cl₂-acetone (50:1), and crude (5R)-6-[acetoxy-(5,6-dihydro-8H-imidazo[2,1-c][1,4]thiazin-2-yl)methyl]-6-bromo-7-oxo-4-thia-1-azabicyclo[3.2.0]hept-2-ene-2-carboxylic acid p-nitrobenzyl ester was obtained as solid.

The solid obtained above was purified by SiO₂ column chromatography by eluting it with 505 ethylacetate:hexane. The pale yellow solid obtained was dissolved in THF (17 mL). Freshly activated Zn dust (2.2 g) was added rapidly with 0.5 mol/L phosphate buffer (pH 6.5, 17 mL). The reaction vessel was covered with foil to exclude light. The reaction mixture was vigorously stirred for 2 h at room temperature. The reaction solution was filtered through a pad of Celite and the pad was washed with water (40 mL) and n-butanol (30 mL). The aqueous layer was separated and then the organic layer was extracted with 0.5 mol/L phosphate buffer (pH 6.5, 2×10 mL). The combined aqueous layer was concentrated to 23 g, 1 mol/L NaOH was added to adjust pH to 7.25 and applied to Diaion HP-21 resin (30 mL, Mitsubishi Kasei Co. Ltd.) column chromatography. After adsorbing, the column was eluted with water and then 10% acetonitrile aqueous solution. The combined active fractions were concentrated under high vacuum at 35° C. and lyophilized to give (5R),(6Z)-6-(5,6-dihydro-8H-imidazo[2,1-c][1,4]thiazin-2-ylmethylene)-7-oxo-4-thia-1-azabicyclo[3.2.0]hept-2-ene-2-carboxylic acid, sodium salt as a yellow amorphous solid (168 mg, 20.9%).

mp 135° C. (dec); ¹H NMR (d, D₂O) δ3.00 (t, 2H, J=5.7 Hz), 3.80 (AB, 2H, J=16.7, 18.1 Hz), 4.19 (t, 2H, J=5.7 Hz), 6.44 (d, 1H, J=0.8 Hz), 6.89 (s, 1H), 6.93 (s, 1H), 7.29 (s, 1H); M+H=322.

Example 6

Preparation of (5R),(6Z)-6-(6,7-Dihydro-5H-pyrrolo[1,2-a]imidazol-2-ylmethylene)-7-oxo-4-thia-1-azabicyclo[3.2.0]hept-2-ene-2-carboxylic acid, sodium salt Step 1: 6,7-Dihydro-5H-pyrrolo[1,2-a]imidazole-2-carbaldehyde 28% Sodium methoxide (5.26 g) was added to the EtOH (250 mL) solution of 4,5-dihydro-3H-pyrrol-2-ylamine hydrochloride (3.27 g) at room temperature. After stirring for 5 min at room temperature, 2-bromo-3-propoxy-propenal (5.79 g) was added to the mixture at room temperature, then the reaction mixture was stirred for 1 h at room temperature. The reaction mixture was taken to dryness in vacuo. The residue was dissolved in CHCl₃ (300 mL) and triethylamine (3.8 mL) was added. The mixture was heated to reflux for 3 hours. The reaction mixture was cooled to room temperature, washed with 50% K2CO3, dried over anhydrous K2CO3, filtered, and evaporated under reduced pressure. The residue was applied with silicagel column chromatography, eluted with CHCl3-acetone (2:1), and 6,7-Dihydro-5H-pyrrolo[1,2-a]imidazole-2-carbaldehyde (41%, 1.51 g) was obtained as a pale yellow solid.

¹H NMR (d, CDCl₃): δ 2.62-2.7 (m, 2H), 2.90-2.94 (m, 2H), 4.07 (t, 2H, J=7.2 Hz), 7.59 (s, 1H), 9.80 (s, 1H).

Step 2: (5R),(6Z)-6-(6,7-Dihydro-5H-pyrrolo[1,2-a]imidazol-2-ylmethylene)-7-oxo-4-thia-1-aza-bicyclo[3.2.0]hept-2-ene-2-carboxylic acid, sodium salt 6,7-Dihydro-5H-pyrrolo[1,2-a]imidazole-2-carbaldehyde (1.36 g) was added to the dry acetonitrile (155 mL) solution of anhydrous MgBr₂ (5.64 g) under an argon atmosphere at room temperature. The dry THF solution (155 mL) of (5R, 6S)-6-bromo-7-oxo-4-thia-1-aza-bicyclo[3.2.0]hept-2-ene-2-carboxylic acid 4-nitro-benzyl ester (3.86 g) was added to the mixture, cooled to −20° C., and Et₃N (4.18 mL) was added in one portion. The reaction vessel was covered with foil to exclude light. The reaction mixture was stirred for 3 h at −20° C. and treated with acetic anhydride (1.89 mL) and DMAP (370 mg) in one portion. The reaction mixture was warmed to 0° C. and stirred for 14.5 h at 0° C. The mixture was diluted with ethyl acetate and washed with 1 M citric acid aqueous solution, saturated sodium hydrogen carbonate, and brine. The organic layer was dried ($MgSO_4$) and filtered. The pad was washed with ethyl acetate. The filtrate was concentrated under reduced pressure. The residue was dissolved in THF (166 mL) and acetonitrile (77 mL). Freshly activated Zn dust (23.2 g) was added rapidly with 0.5 M phosphate buffer (pH 6.5, 243 mL). The reaction vessel was covered with foil to exclude light. The reaction mixture was vigorously stirred for 2 h at room temperature. The reaction mixture was filtered, cooled to 3° C., and 1 M NaOH was added to adjust pH to 8. The filtrate was washed with ethyl acetate and the aqueous layer was separated. 1 M NaOH was added to the aqueous layer again to adjust pH to 8. The resultant mixture was concentrated under high vacuum at 35° C. The concentrate was applied to Diaion HP-21 (20 mL, Mitsubishi Kasei Co. Ltd.) resin column chromatography. After adsorbing, the column was eluted with $H_2O$-MeCN (1/0~9/1) to give the purified active fractions of (5R),(6Z)-6-(6,7-Dihydro-5H-pyrrolo [1,2-a]imidazol-2-ylmethylene)-7-oxo-4-thia-1-aza-bicyclo [3.2.0]hept-2-ene-2-carboxylic acid, sodium salt. The combined fractions were concentrated under high vacuum at 35° C. and lyophilized to give the titled as a yellow amorphous solid (681 mg, 24%, pH 7.8).

mp 190° C. (dec); $^1$H NMR (d, $D_2O$): δ: 2.48-2.56 (m, 2H), 2.74-2.79 (m, 2H), 3.94-3.99 (m, 2H), 6.47 (d, 1H, J=0.7 Hz), 6.94 (s, 1H), 6.95 (s, 1H), 7.36 (s, 1H); (M+H) 291.

Example 7

Preparation of (5R),(6Z)-6-(5,6-Dihydro-8H-imidazo [2,1-c][1,4]oxazin-2-ylmethylene)-7-oxo-4-thia-1-azabicyclo[3.2.0]hept-2-ene-2-carboxylic acid, sodium salt Step 1: Morpholin-3-one Morpholin-3-one was prepared in the method of U.S. Pat. No. 5,349,045.

Step 2: Morpholin-3-thione

A mixture of morpholin-3-one (4.7 g) and Lawesson's reagent (10.3 g) in dry THF (94 mL) was heated to reflux for 1.5 h. The reaction mixture was cooled to room temperature and the reaction solvent was removed in vacuo. The residue was applied to silica gel column chromatography and eluted with $CHCl_3$-methanol (50:1) to obtain a yellow solid. Recrystallization of the crude product from hexane-ethyl acetate gave the title (4.0 g, 72.2%) as yellow powder.

$^1$H NMR ($CDCl_3$) δ 3.45 (t, 2H, J=5.1 Hz), 3.91 (t, 2H, J=5.1 Hz), 4.55 (s, 2H).

Step 3: 5-Methylthio-3,6-dihydro-2H-[1,4]oxazine

A mixture of morpholin-3-thione (4.7 g) and methyl iodide (13 mL) in dry $CH_2Cl_2$ (140 mL) was stirred at room temperature for 15 h. The reaction mixture was filtered and the solid was washed with $CH_2Cl_2$. The obtained solid was dissolved with 50% $K_2CO_3$ solution (150 mL) and the aqueous layer was extracted with $CH_2Cl_2$ (8×100 mL). The combined $CH_2Cl_2$ layer was dried ($MgSO_4$) and filtered. The filtrate was concentrated under reduce pressure and the title was obtained as pale yellow oil (3.6 g, 67.8%).

$^1$H NMR ($CDCl_3$) δ 2.32 (s, 3H), 3.71-3.74 (m, 4H), 4.14-4.15 (m, 2H).

Step 4: 3-Iminomorpholin hydrochloride

A mixture of 5-methylthio-3,6-dihydro-2H-[1,4]oxazine (3.6 g) and ammonium chloride (1.5 g) in dry ethanol (136 mL) was heated to reflux for 1 h. The reaction mixture was cooled to room temperature. The reaction solvent was removed in vacuo and the title was obtained as a pale brown solid (3.6 g, 97.7%).

$^1$H NMR (DMSO-$d^6$) δ 3.34 (m, 2H), 3.86 (t, 2H, J=5.2 Hz), 4.47 (s, 2H).

Step 5: 5,6-Dihydro-8H-imidazo[2,1-c][1,4]oxazine-2-carbaldehyde (9) and 5,6-dihydro-8H-imidazo[2,1-c][1,4]oxazine-3-carbaldehyde The mixture of 2-bromo-3-hydroxypropenal (4.1 g), p-toluenesulfonic acid monohydrate (52 mg) and 2-propanol (5.2 mL) in cyclohexane (42 mL) was azeotroped until the vapor temperature rose to 80° C. The reaction mixture was concentrated under reduce pressure. The residue was dissolved in dry ethanol (50 mL). A mixture of the dry ethanol (200 mL) solution of 3-iminomorpholin hydrochloride (3.4 g) and 28% methanol solution of sodium methylate (4.8 g) was added at room temperature. The reaction mixture was stirred at room temperature for 2 h, and then the reaction solvent was removed in vacuo. The residue was dissolved in chloroform (125 mL) and triethylamine (3.5 mL) was added, then the reaction mixture was heated to reflux for 2 h. The reaction mixture was cooled to room temperature and then concentrated under reduce pressure. The residue was dissolved in dichloromethane (300 mL) and washed with 50% $K_2CO_3$ aqueous solution (2×100 mL). The organic layer was dried ($MgSO_4$) and filtered. The filtrate was concentrated under reduce pressure. The residue was applied to silica gel column chromatography and eluted with $CHCl_3$-acetone (4:1) to obtain the title (pale orange solid, 1.4 g, 36.3%) and the other regio isomer. (pale orange solid, 609 mg, 16.1%).

Desired product: $^1$H NMR ($CDCl_3$) δ 4.08-4.15 (m, 4H), 4.88 (s, 2H), 7.58 (s, 1H), 9.85 (s, 1H).

The unwanted regio isomer: $^1$H NMR ($CDCl_3$) δ 4.06 (t, 2H, J=5.2 Hz), 4.40 (t, 2H, J=5.2 Hz), 4.90 (s, 2H), 7.75 (s, 1H), 9.72 (s, 1H).

Step 6: 5R),(6Z)-6-(5,6-Dihydro-8H-imidazo[2,1-c] [1,4]oxazin-2-ylmethylene)-7-oxo-4-thia-1-azabicyclo[3.2.0]hept-2-ene-2-carboxylic acid, sodium salt The dry acetonitrile (66 mL) solution of 5,6-dihydro-8H-imidazo[2,1-c][1,4]oxazine-2-carbaldehyde (1.2 g) was added to the dry acetonitrile (66 mL) solution of $MgBr_2$ (3.6 g) under a nitrogen atmosphere at room temperature then the mixture was stirred for 10 min. The dry THF (132 mL) solution of p-nitrobenzyl (5R,6S)-6-bromopenem-3-carboxylate (3.4 g) was added and the mixture was cooled to −20° C. then triethylamine (2.8 mL) was added in one portion. The reaction vessel was covered with foil to exclude light. The reaction mixture was stirred for 4 h at −20° C. and treated with 4-dimethylamino pyridine (100 mg) and acetic anhydride (1.5 mL) in one portion. The reaction mixture was warmed to 0° C. and stirred for 18 h at 0° C. 10% Citric acid aqueous solution (1 L) was added to the reaction mixture and the aqueous layer was extracted with ethyl acetate (3×500 mL).

The combined organic layer was washed with water, saturated sodium hydrogen carbonate and brine, dried (MgSO$_4$) and filtered. The filtrate was concentrated under reduced pressure and crude (5R)-6-[acetoxy-(5,6-dihydro-8H-imidazo[2,1-c][1,4]oxazin-2-yl)methyl]-6-bromo-7-oxo-4-thia-1-azabicyclo[3.2.0]hept-2-ene-2-carboxylic acid p-nitrobenzyl ester was obtained as brown amorphous solid.

Freshly activated Zn dust (14 g) was added rapidly with 0.5 mol/L phosphate buffer (pH 6.5, 72 mL) to the THF (72 mL) solution of (5R)-6-[acetoxy-(5,6-dihydro-8H-imidazo[2,1-c][1,4]oxazin-2-yl)methyl]-6-bromo-7-oxo-4-thia-1-azabicyclo[3.2.0]hept-2-ene-2-carboxylic acid p-nitrobenzyl ester. The reaction vessel was covered with foil to exclude light. The reaction mixture was vigorously stirred for 2.5 h at room temperature. The reaction solution was filtered through a pad of Celite and the pad was washed with water (170 mL) and n-butanol (170 mL). The aqueous layer was separated and then the organic layer was extracted with 0.5 mol/L phosphate buffer (pH 6.5, 2×50 mL). The combined aqueous layer was concentrated to 90 g, 1 mol/L NaOH was added to adjust pH to 7.5 and applied to Diaion HP-21 resin (120 mL, Mitsubishi Kasei Co. Ltd.) column chromatography. After adsorbing, the column was eluted with water and then 5% acetonitrile aqueous solution. The combined active fractions was concentrated under high vacuum at 35° C. and lyophilized to give the title as a yellow amorphous solid (756 mg, 29.1%).

Mp 130° C. (dec); $^1$H NMR (DMSO-d$_6$) δ 3.98-4.01 (m, 2H), 4.04-4.07 (m, 2H), 4.74 (AB, 2H, J=15.3, 22.9 Hz), 6.40 (d, 1H, J=0.8 Hz), 6.55 (s, 1H), 6.95 (d, 1H, J=0.6 Hz), 7.54 (s, 1H); IR (KBr) 3412, 1741, 1672, 1592, 1549 cm$^{-1}$; $\lambda^{max}$ (H$_2$O) 304 nm.

Example 8

Preparation of (5R),(6Z)-6-(5,6-Dihydro-4H-pyrrolo[1,2-b]pyrazol-2-ylmethylene)-7-oxo-4-thia-1-azabicyclo[3.2.0]hept-2-ene-2-carboxylic acid, sodium salt Step 1:
5,6-Dihydro-4H-pyrrolo[1,2-b]pyrazole-2-carboxylic acid ethyl ester The titled compound was prepared in the same way of Ranganathan and co-workers (*Indian J. Chem.* 1991, 30 B, 169-175).

Step 2:
(5,6-Dihydro-4H-pyrrolo[2-b]pyrazol-2-yl)methanol

MeOH (2.73 mL) was added to the THF (180 mL) solution of LiBH$_4$ (1.63 g) under a nitrogen atmosphere at room temperature, and then 5,6-dihydro-4H-pyrrolo[1,2-b]pyrazole-2-carboxylic acid ethyl ester (8.11 g) was added to the suspension and stirred for 2 h at 40° C. The mixture was quenched with 1 mol/L HCl at pH 1 and stirred for 1 h at room temperature. Solid K$_2$CO$_3$ was added to the solution to adjust pH to 8 and the mixture was extracted with AcOEt. The organic layer was dried (MgSO$_4$) and filtered. The filtrate was concentrated under reduced pressure to afford the title compound as brown crystals (4.87 g, 78%).

$^1$H NMR (CDCl$_3$) δ 2.44 (t, 1H, J=5.8 Hz), 2.54-2.62 (m, 2H), 2.87 (t, 2H, J=7.4 Hz), 4.10 (t, 2H, J=7.2 Hz), 4.63 (d, 2H, J=5.8 Hz), 5.96 (s, 1H).

Step 3: 5,6-Dihydro-4H-pyrrolo[1,2-b]pyrazole-2-carbaldehyde

MnO$_2$ (activated) (24.4 g) was added to the CHCl$_3$ (350 mL) solution of (5,6-dihydro-4H-pyrrolo[1,2-b]pyrazol-2-yl)methanol (4.87 g) and refluxed for 1 h under a nitrogen atmosphere. The reaction mixture was filtered through a pad of Celite. The filtrate was reduced under reduced pressure. The residue was applied to silica gel column chromatography, then the column was eluted with n-hexane-AcOEt (1/1-1/2). The title compound was obtained as yellow oil (4.35 g, 91%).

$^1$H NMR (CDCl$_3$) δ 2.63-2.71 (m, 2H), 2.95 (t, 2H, J=7.4 Hz), 4.22 (t, 2H, J=7.4 Hz), 6.52 (s, 1H), 9.89 (s, 1H).

Step 4: (5R),(6Z)-6-(5,6-Dihydro-4H-pyrrolo[1,2-b]pyrazol-2-ylmethylene)-7-oxo-4-thia-1-azabicyclo[3.2.0]hept-2-ene-2-carboxylic acid, sodium salt 5,6-Dihydro-4H-pyrrolo[1,2-b]pyrazole-2-carbaldehyde (1.36 g) was added to the dry acetonitrile (148 mL) solution of anhydrous MgBr$_2$ (5.52 g) under a nitrogen atmosphere at room temperature. The dry THF solution (148 mL) of (5R,6S)-6-bromo-7-oxo-4-thia-1-azabicyclo[3.2.0]hept-2-ene-2-carboxylic acid 4-nitrobenzyl ester (cont. 97%) (3.97 g) was added to the mixture, cooled to −20° C., and Et$_3$N (4.18 mL) was added in one portion. The reaction vessel was covered with foil to exclude light. The reaction mixture was stirred for 4 h at −20° C. and treated with acetic anhydride (1.89 mL) and DMAP (123 mg) in one portion. The reaction mixture was warmed to 0° C. and stirred for 14 h at 0° C. The mixture was diluted with ethyl acetate and washed with 5% citric acid aqueous solution, saturated sodium hydrogen carbonate, water and brine. The organic layer was dried (MgSO$_4$) and filtered. The filtrate was concentrated under reduced pressure.

The residue was dissolved in THF (106 mL) and acetonitrile (49 mL). Freshly activated Zn dust (22.5 g) was added rapidly with 0.5 M phosphate buffer (pH 6.5, 155 mL). The reaction vessel was covered with foil to exclude light. The reaction mixture was vigorously stirred for 1.5 h at room temperature. The reaction mixture was filtered through a pad of Celite. The filtrate was washed with ethyl acetate and the aqueous layer was separated. The aqueous layer was cooled to 3° C. and 1 M NaOH was added to adjust pH to 8.0. The mixture was concentrated under high vacuum at 35° C. The concentrate was applied to Diaion HP-21 (79 mL, Mitsubishi Kasei Co. Ltd.) resin column chromatography. After adsorbing, the column was eluted with H$_2$O-MeCN (1/0-9/1). The combined fractions were concentrated under high vacuum at 35° C. and lyophilized to give the title compound as a yellow amorphous solid (848 mg, 29%, pH 7.1).

Mp 190° C. (dec); $^1$H NMR (D$_2$O) δ 2.49 (m, 2H), 2.78 (t, 2H, J=7.4 Hz), 4.02 (t, 2H, J=7.4 Hz), 6.01 (s, 1H), 6.29 (s, 1H), 6.90 (s, 2H).

Example 9

Preparation of (5R)(6Z)-7-Oxo-6-(4,5,6,7-tetrahydropyrazolo[1,5-a]pyridin-2-ylmethylene)-4-thia-1-azabicyclo[3.2.0]hept-2-ene-2-carboxylic acid, sodium salt Step 1:
Tetrahydropyridino[1,2-c][1,2,3]oxadiazolone Conc. HCl (1.96 mL) and NaNO$_2$ (2.2 g) were added to the H$_2$O (21 mL) solution of DL-pipecolic acid (3.04 g) under a nitrogen atmosphere at 0° C. and stirred for 1 h. The solution was extracted with CH$_2$Cl$_2$ and organic layer was washed with brine. The mixture was dried over Na$_2$SO$_4$ and concentrated under reduced pressure to afford crude (2RS)-1-nitrosopiperidine-2-carboxylic acid as pale yellow crystals.

Trifluoroacetic anhydride (1.93 g) was added to the THF (92 mL) solution of crude (2RS)-1-nitrosopiperidine-2-carboxylic acid under a nitrogen atmosphere at 0° C. and stirred for 5 h at 0° C. and for 2 h at room temperature. The solution was concentrated under a reduced pressure. The residue was applied to silica gel column chromatography, then the column was eluted with n-hexane-AcOEt (1/1-0/1). The titled compound was obtained as colorless crystals (1.10 g, 33%).

$^1$H NMR (CDCl$_3$) δ 1.93-1.99 (m, 2H), 2.08-2.15 (m, 2H), 2.65 (t, 2H, J=6.5 Hz), 4.26 (t, 2H, J=6.1 Hz).

Step 2: 4,5,6,7-Tetrahydropyrazolo[1,5-a]pyridine-2-carboxylic acid ethylester Ethyl propiolate (804 mg) was added to the o-xylene (15 mL) solution of tetrahydropyridino[1,2-c][1,2,3]oxadiazolone (1.04 g) under a nitrogen atmosphere and refluxed for 16 h. The solution was concentrated under a reduced pressure. The residue was applied to silica gel column chromatography, then the column was eluted with n-hexane-AcOEt (2/1-1/1). The titled compound was obtained as yellow oil (871 mg, 65%), and 4,5,6,7-tetrahydropyrazolo[1,5-a]pyridine-3-carboxylic acid ethyl ester was obtained as yellow oil (345 mg, 26%).

$^1$H NMR (CDCl$_3$) δ1.39 (t, 3H, J=7.1 Hz), 1.84-1.91 (m, 2H), 2.02-2.09 (m, 2H), 2.82 (t, 2H, J=6.4 Hz), 4.22 (t, 2H, J=6.2 Hz), 4.39 (q, 2H, J=7.1 Hz), 6.53 (s, 1H).

Step 3: (4,5,6,7-Tetrahydropyrazolo[1,5-a]pyridin-2-yl)methanol

MeOH (0.29 mL) was added to the THF (19 mL) solution of LiBH$_4$ (cont. 90%) (174 mg) under a nitrogen atmosphere at room temperature, then 4,5,6,7-tetrahydropyrazolo[1,5-a]pyridine-2-carboxylic acid ethyl ester (862 mg) was added to the suspension and stirred for 1 h at room temperature and 1.5 h at 40° C. The mixture was quenched with 1 mol/L HCl at pH 1 and stirred for 1 h at room temperature. Solid K$_2$CO$_3$ was added to the solution to adjust pH to 8 and the mixture was extracted with AcOEt. The organic layer was dried (MgSO$_4$) and filtered. The filtrate was concentrated under reduced pressure to afford titled compound as pale yellow oil (691 mg, 95%).

$^1$H NMR (CDCl$_3$) δ 1.80-1.87 (m, 2H), 1.98-2.05 (m, 2H), 2.77 (t, 2H, J=6.4 Hz), 2.81-2.84 (br, 1H), 4.09 (t, 2H, J=6.1 Hz), 4.62 (d, 2H, J=5.3 Hz), 5.96 (s, 1H).

Step 4: 4,5,6,7-Tetrahydropyrazolo[1,5-a]pyridine-2-carbaldehyde

MnO$_2$ (activated) (3.36 g) was added to the CHCl$_3$ (44 mL) solution of (4,5,6,7-tetrahydropyrazolo[1,5-a]pyridin-2-yl)methanol (673 mg) and refluxed for 1 h under a nitrogen atmosphere. The reaction mixture was filtered through a pad of Celite. The filtrate was reduced under reduced pressure. The residue was applied to silica gel column chromatography, then the column was eluted with n-hexane-AcOEt (2/1-½). The titled compound was obtained as pale yellow oil (510 mg, 77%).

$^1$H NMR (CDCl$_3$) δ 1.90 (m, 2H), 2.10 (m, 2H), 2.84 (t, 2H, J=6.4 Hz), 4.23 (t, 2H, J=6.2 Hz), 6.52 (s, 1H), 9.92 (s, 1H).

Step 5: (5R)(6Z)-7-Oxo-6-(4,5,6,7-tetrahydropyrazolo[1,5-a]pyridin-2-ylmethylene)-4-thia-1-azabicyclo[3.2.0]hept-2-ene-2-carboxylic acid, sodium salt 4,5,6,7-Tetrahydropyrazolo[1,5-a]pyridine-2-carbaldehyde (483 mg) was added to the dry acetonitrile (48 mL) solution of anhydrous MgBr$_2$ (1.81 g) under a nitrogen atmosphere at room temperature. The dry THF solution (48 mL) of (5R,6S)-6-bromo-7-oxo-4-thia-1-azabicyclo[3.2.0]hept-2-ene-2-carboxylic acid 4-nitrobenzyl ester (cont. 97%) (1.28 g) was added to the mixture, cooled to −20° C., and Et$_3$N (1.35 mL) was added in one portion. The reaction vessel was covered with foil to exclude light. The reaction mixture was stirred for 2 h at −20° C. and treated with acetic anhydride (0.61 mL) and DMAP (40 mg) in one portion. The reaction mixture was warmed to 0° C. and stirred for 16 h at 0° C. The mixture was diluted with ethyl acetate and washed with 5% citric acid aqueous solution, saturated sodium hydrogen carbonate, water and brine. The organic layer was dried (MgSO$_4$) and filtered. The filtrate was concentrated under reduced pressure.

The residue was dissolved in THF (35 mL) and acetonitrile (16 mL). Freshly activated Zn dust (7.43 g) was added rapidly with 0.5 M phosphate buffer (pH 6.5, 51 mL). The reaction vessel was covered with foil to exclude light. The reaction mixture was vigorously stirred for 1.5 h at room temperature. The reaction mixture was filtered through a pad of Celite. The filtrate was washed with ethyl acetate and the aqueous layer was separated. The aqueous layer was cooled to 3° C. and 1 M NaOH was added to adjust pH to 8.0. The mixture was concentrated under high vacuum at 35° C. The concentrate was applied to Diaion HP-21 (105 mL, Mitsubishi Kasei Co. Ltd.) resin column chromatography. After adsorbing, the column was eluted with H$_2$O-MeCN (1/0-85/15). The combined fractions were concentrated under high vacuum at 35° C. and lyophilized to give the title compound as a yellow amorphous solid (427 mg, 41%, pH 7.7).

Mp 190° C. (dec); $^1$H NMR (D$_2$O) δ 1.67-1.71 (m, 2H), 1.85-1.89 (m, 2H), 2.64 (t, 2H, J=6.3 Hz), 3.97 (t, 2H, J=6.1 Hz), 5.97 (s, 1H), 6.25 (s, 1H), 6.85 (s, 1H), 6.88 (s, 1H).

Example 10

Preparation of (5R),(6Z)-6-(7-Methyl-6-oxo-5,6,7,8-tetrahydro-imidazo[1,2-a]pyrazin-2-ylmethylene)-7-oxo-4-thia-1-aza-bicyclo[3.2.0]hept-2-ene-2-carboxylic acid sodium salt

Step 1: 5-Methoxy-1-methyl-3,6-dihydro-1H-pyrazin-2-one

The titled compound was prepared in the same way of S. Rajappa and B. G. Advani (*Tetrahedron*. 1973, 29, 1299-1302).

Step 2: 5-Amino-1-methyl-3,6-dihydro-1H-pyrazin-2-one

A mixture of 5-methoxy-1-methyl-3,6-dihydro-1H-pyrazin-2-one (2.3 g) and ammonium chloride (936 mg) in dry ethanol (32 mL) was stirred at room temperature for 1 h and then refluxed for 2 h. The reaction mixture was cooled to room temperature and evaporated under reduced pressure. The residue was triturated with chloroform at room temperature for 30 min. The precipitate was filtered off and dried in vacuo. The 5-amino-1-methyl-3,6-dihydro-1H-pyrazin-2-one hydrochloride was obtained as a pale brown powder (1.7 g, 66%).

A solution of 5-amino-1-methyl-3,6-dihydro-1H-pyrazin-2-one hydrochloride (662 mg) in methanol (10 mL) was added 10% potassium carbonate aqueous solution at 0° F. and then stirred for 40 min at 0□. The mixture was concentrated under reduced pressure. The residue was triturated with chloroform (18 mL) and methanol (2 mL) at room temperature for 30 min. The precipitate was filtered off and dried in vacuo. The compound was obtained as a pale brown powder (515 mg, quantitative).

$^1$H NMR (DMSO-d$^6$) δ 2.88 (s, 3H), 3.94 (s, 2H), 4.42 (s, 2H).

Step 3: 7-Methyl-6-oxo-5,6,7,8-tetrahydro-imidazo[1,2-a]pyrazine-2-carbaldehyde and 7-Methyl-6-oxo-5,6,7,8-tetrahydro-imidazo[1,2-a]pyrazine-3-carbaldehyde The solution of 2-bromo-3-isopropoxy-propenal (1.3 g) in dry acetonitrile (60 mL) was added to the solution of 5-amino-1-methyl-3,6-dihydro-1H-pyrazin-2-one (782 mg) in dry acetonitrile (60 mL) at room temperature. The reaction mixture was stirred at room temperature for 20 h, added triethylamine (0.95 mL) and then refluxed for 2 h. The reaction mixture was cooled to room temperature and then evaporated under reduce pressure. The residue was dissolved in chloroform (10 mL) and washed with 50% $K_2CO_3$ aqueous solution (10 mL). The aqueous layer was extracted with chloroform. The organic layer was dried (MgSO$_4$) and filtered. The filtrate was evaporated under reduce pressure. The residue was applied to silica gel column chromatography and eluted with CHCl$_3$-MeOH (95:5) to obtain the title compound 7-Methyl-6-oxo-5,6,7,8-tetrahydro-imidazo[1,2-a]pyrazine-2-carbaldehyde as a pale yellow solid (541 mg, 49.1%) and its regio isomer 7-Methyl-6-oxo-5,6,7,8-tetrahydro-imidazo[1,2-a]pyrazine-3-carbaldehyde as a pale yellow solid (128 mg, 11.6%).

7-Methyl-6-oxo-5,6,7,8-tetrahydro-imidazo[1,2-a]pyrazine-2-carbaldehyde: $^1$H NMR (CDCl$_3$) δ 3.17 (s, 3H), 4.68 (s, 2H), 4.78 (s, 2H), 7.66 (s, 1H), 9.83 (s, 1H).

7-Methyl-6-oxo-5,6,7,8-tetrahydro-imidazo[1,2-a]pyrazine-3-carbaldehyde: $^1$H NMR (CDCl$_3$) δ 3.16 (s, 3H), 4.70 (s, 2H), 5.03 (s, 2H), 7.82 (s, 1H), 9.73 (s, 1H).

Step 4: (5R,6RS)-6-[Acetoxy-(7-methyl-6-oxo-5,6,7,8-tetrahydro-imidazo[1,2-a]pyrazin-2-yl)-methyl]-6-bromo-7-oxo-4-thia-1-aza-bicyclo[3.2.0]hept-2-ene-2-carboxylic acid 4-nitro-benzyl ester 7-Methyl-6-oxo-5,6,7,8-tetrahydro-imidazo[1,2-a]pyrazine-2-carbaldehyde (319 mg) was added to the dry acetonitrile (32 mL) solution of anhydrous MgBr$_2$ (786 mg) under a nitrogen atmosphere at room temperature. The dry THF solution (32 mL) of (5R,6S)-6-bromo-7-oxo-4-thia-1-aza-bicyclo[3.2.0]hept-2-ene-2-carboxylic acid 4-nitro-benzyl ester (687 mg) was added to the mixture, cooled to −20° C., and triethylamine (0.60 mL) was added in one portion. The reaction vessel was covered with foil to exclude light. The reaction mixture was stirred for 3 h at −20° C. and treated with 4-dimethylaminopyridine (44 mg) and acetic anhydride (0.35 mL) in one portion. The reaction mixture was warmed to 0° C. and stirred for 20 h at 0° C. The mixture was diluted with ethyl acetate and H$_2$O. After separating organic layer, the aqueous layer was extracted with ethyl acetate. The organic layers were combined and washed with 5% citric acid aqueous solution and brine. The organic layer was dried (MgSO$_4$) and filtered. The filtrate was concentrated under reduced pressure. The residue was applied to silica gel column chromatography, then eluted with chloroform. The title compound was obtained as diastereo mixture (yellow amorphous solid; 410 mg, 38%).

$^1$H NMR (6, CDCl$_3$) 2.03 (s, 0.7×3H), 2.09 (s, 0.3×3H), 3.15 (s, 3H), 4.59-4.62 (m, 2H), 4.66 (s, 0.3×2H), 4.67 (s, 0.7×2H), 5.28 (d, 1H, J=13.5 Hz), 5.43 (d, 0.3×1H, J=13.5 Hz), 5.45 (d, 0.7×1H, J=13.5 Hz), 6.07 (s, 0.3×1H), 6.28 (s, 0.7×1H), 6.32 (s, 0.7×1H), 6.83 (s, 0.3×1H), 6.86 (s, 0.3×1H), 7.10 (s, 0.7×1H), 7.44 (s, 0.3×1H), 7.47 (s, 0.7×1H), 7.60 (d, 0.7×2H, J=8.6 Hz), 7.61 (d, 0.3×2H, J=8.6 Hz), 8.24 (d, 2H, J=8.6 Hz),

Step 5: (5R),(6Z)-6-(7-Methyl-6-oxo-5,6,7,8-tetrahydro-imidazo[1,2-a]pyrazin-2-ylmethylene)-7-oxo-4-thia-1-aza-bicyclo[3.2.0]hept-2-ene-2-carboxylic acid sodium salt and (5R),(6E)-6-(7-Methyl-6-oxo-5,6,7,8-tetrahydro-imidazo[1,2-a]pyrazin-2-ylmethylene)-7-oxo-4-thia-1-aza-bicyclo[3.2.0]hept-2-ene-2-carboxylic acid sodium salt (5R,6RS)-6-[Acetoxy-(7-methyl-6-oxo-5,6,7,8-tetrahydro-imidazo[1,2-a]pyrazin-2-yl)-methyl]-6-bromo-7-oxo-4-thia-1-aza-bicyclo[3.2.0]hept-2-ene-2-carboxylic acid 4-nitro-benzyl ester (481 mg) was dissolved in THF (6.7 mL) and acetonitrile (3.1 mL). Freshly activated Zn dust (1.92 g) and 0.5 M phosphate buffer (pH 6.5, 9.9 mL) were added to the mixture. The reaction vessel was covered with foil to exclude light. The reaction mixture was vigorously stirred for 2 h at room temperature. The reaction solution was mixed with ethyl acetate and filtered through a pad of Celite. The pad was washed with water and the aqueous layer was separated. The aqueous layer was cooled to 3° C. and 1 M NaOH was added to adjust pH to 8.0. The mixture was concentrated under high vacuum at 35° C. and lyophilized. The residue was separated by the preparative HPLC (Inertsil ODS-2, GL Science Inc., 10×250 mm, 0.05 mol/L phosphate buffer (pH 7.1): CH$_3$CN=93:7, 4.0 mL/min.). The separated fractions of (5R),(6Z)-6-(7-Methyl-6-oxo-5,6,7,8-tetrahydro-imidazo[1,2-a]pyrazin-2-ylmethylene)-7-oxo-4-thia-1-aza-bicyclo[3.2.0]hept-2-ene-2-carboxylic acid sodium salt and (5R),(6E)-6-(7-Methyl-6-oxo-5,6,7,8-tetrahydro-imidazo[1,2-a]pyrazin-2-ylmethylene)-7-oxo-4-thia-1-aza-bicyclo[3.2.0]hept-2-ene-2-carboxylic acid sodium salt were cooled to 3° C. and 1 M NaOH was added to adjust pH to 8.0 respectively. Each solution was concentrated under high vacuum at 35° C. Each concentrate was applied to Diaion HP-21 (60 mL, Mitsubishi Kasei Co. Ltd.) resin column chromatography. After adsorbing, the column was eluted with water and then with 5% acetonitrile-water. The combined fractions were concentrated under high vacuum at 35° C. and lyophilized to give the title compound (5R),(6Z)-6-(7-Methyl-6-oxo-5,6,7,8-tetrahydro-imidazo[1,2-a]pyrazin-2-ylmethylene)-7-oxo-4-thia-1-aza-bicyclo[3.2.0]hept-2-ene-2-carboxylic acid sodium salt as a yellow amorphous solid (125 mg, 44.4%, Mp 115-117° C. (dec)) and compound (5R),(6E)-6-(7-Methyl-6-oxo-5,6,7,8-tetrahydro-imidazo[1,2-a]pyrazin-2-ylmethylene)-7-oxo-4-thia-1-aza-bicyclo[3.2.0]hept-2-ene-2-carboxylic acid sodium salt as yellow amorphous solid (19 mg, 6.7%) respectively.

Compound (5R),(6Z)-6-(7-Methyl-6-oxo-5,6,7,8-tetrahydro-imidazo[1,2-a]pyrazin-2-ylmethylene)-7-oxo-4-thia-1-aza-bicyclo[3.2.0]hept-2-ene-2-carboxylic acid sodium salt $^1$H NMR (6, D$_2$O) 2.99 (s, 3H), 4.54 (s, 2H), 4.66 (s, 2H), 6.38 (s, 1H), 6.85 (s, 1H), 6.90 (s 1H), 7.30 (s, 1H).

Compound (5R),(6E)-6-(7-Methyl-6-oxo-5,6,7,8-tetrahydro-imidazo[1,2-a]pyrazin-2-ylmethylene)-7-oxo-4-thia-1-aza-bicyclo[3.2.0]hept-2-ene-2-carboxylic acid sodium salt ¹H NMR (6, D₂O) 2.94 (s, 3H), 4.45 (s, 2H), 4.56 (s, 2H), 6.22 (s, 1H), 6.48 (s, 1H), 6.94 (s, 1H), 7.69 (s 1H).

Example 11

Preparation of (5R)(6Z)-6-(6,7-Dihydro-4H-pyrazolo[5,1-c][1,4]thiazin-2-ylmethylene)-7-oxo-4-thia-1-azabicyclo[3.2.0]hept-2-ene-2-carboxylic acid, sodium salt Step 1: (3R)-Thiomorpholine-3-carboxylic acid The titled compound was prepared in the same way of Shiraiwa and co-workers (*Biosci. Biotechnol. Biochem.* 1998, 62, 2382-2387).

Step 2: 3-Oxo-3a,4,6,7-tetrahydro-3H-2-oxa-5-thia-1-aza-7a-azonioindenide

NaNO₂ (3.14 g) was added to the 1 mol/L HCl (33.7 mL) solution of (3R)-thiomorpholine-3-carboxylic acid (4.96 g) under a nitrogen atmosphere at 0° C. and stirred for 0.5 h. The solution was extracted with CHCl₃ (5 times) and the organic layer was washed with brine. The mixture was dried over MgSO₄ and concentrated under reduced pressure to afford crude (3R)-4-nitrosothiomorpholine-3-carboxylic acid as pale yellow crystals.

Trifluoroacetic anhydride (7.07 g) was added to the THF (169 mL) solution of crude (3R)-4-nitrosothiomorpholine-3-carboxylic acid under a nitrogen atmosphere at 0° C. and stirred for 3 h at 0° C. and for 17 h at room temperature. The solution was concentrated under a reduced pressure. The residue was applied to silica gel column chromatography, then the column was eluted with n-hexane-AcOEt (1/1-0/1). The titled compound was obtained as pale brown crystals (3.41 g, 64%).

¹H NMR (CDCl₃) δ 3.15 (t, 2H, J=5.5 Hz), 3.71 (s, 2H), 4.54 (t, 2H, J=5.5 Hz).

Step 3: 6,7-Dihydro-4H-pyrazolo[5,1-c][1,4]thiazine-2-carboxylic acid ethyl ester Ethyl propiolate (2.33 g) was added to the o-xylene (72 mL) solution of 3-oxo-3a,4,6,7-tetrahydro-3H-2-oxa-5-thia-1-aza-7a-azonioindenide (3.41 g) under a nitrogen atmosphere and refluxed for 15 h. The solution was concentrated under a reduced pressure. The residue was applied to silica gel column chromatography, then the column was eluted with n-hexane-AcOEt (2/1-1/1). The titled compound was obtained as yellow oil (3.13 g, 68%), and the other unwanted regio isomer 6,7-dihydro-4H-pyrazolo[5,1-c][1,4]thiazine-3-carboxylic acid ethyl ester was obtained as yellow oil (556 mg, 12%).

¹H NMR (CDCl₃) δ 1.31 (t, 3H, J=7.1 Hz), 3.04 (t, 2H J=5.7 Hz), 3.81 (s, 2H), 4.32 (q, 2H, J=7.1 Hz), 4.40 (t, 2H, J=5.7 Hz), 6.54 (s, 1H).

Step 4: (6,7-Dihydro-4H-pyrazolo[5,1-c][1,4]thiazin-2-yl)methanol

LiBH₄ (cont. 90%) (536 mg) and MeOH (0.9 mL) was added to the THF (59 mL) solution of 6,7-dihydro-4H-pyrazolo[5,1-c][1,4]thiazine-2-carboxylic acid ethyl ester (3.13 g) under a nitrogen atmosphere at room temperature and stirred for 3 h at 40° C. The mixture was quenched with 1 mol/L HCl at pH 1 and stirred for 1 h at room temperature. Solid K₂CO₃ was added to the solution to adjust pH to 8 and the mixture was extracted with AcOEt. The organic layer was dried (K₂CO₃) and filtered. The filtrate was concentrated under reduced pressure to afford titled compound as pale yellow oil (2.51 g, quant.).

¹H NMR (CDCl₃) δ 2.58 (br, 1H), 3.07 (t, 2H, J=5.7 Hz), 3.84 (s, 2H), 4.33 (t, 2H, J=5.7 Hz), 4.63 (d, 2H, J=3.9 Hz), 6.05 (s, 1H).

Step 5: 6,7-Dihydro-4H-pyrazolo[5,1-c][1,4]thiazine-2-carbaldehyde

MnO₂ (activated) (11.46 g) was added to the CHCl₃ (135 mL) solution of (6,7-dihydro-4H-pyrazolo[5,1-c][1,4]thiazin-2-yl)methanol (2.31 g) and refluxed for 1 h under a nitrogen atmosphere. The reaction mixture was filtered through a pad of Celite. The filtrate was concentrated under a reduced pressure. The residue was applied to silica gel column chromatography, then the column was eluted with n-hexane—AcOEt (1/1). The titled compound was obtained as pale yellow crystals (1.78 g, 78%).

¹H NMR (CDCl₃) δ 3.15 (t, 2H, J=5.8 Hz), 3.90 (s, 2H), 4.48 (t, 2H, J=5.8 Hz), 6.58 (s, 1H), 9.92 (s, 1H).

Step 6: (5R)(6Z)-6-(6,7-Dihydro-4H-pyrazolo[5,1-c][1,4]thiazin-2-ylmethylene)-7-oxo-4-thia-1-azabicyclo[3.2.0]hept-2-ene-2-carboxylic acid, sodium salt 6,7-Dihydro-4H-pyrazolo[5,1-c][1,4]thiazine-2-carbaldehyde (841 mg) was added to the dry acetonitrile (39 mL) solution of anhydrous MgBr₂ (1.88 g) under a nitrogen atmosphere at room temperature. The dry THF solution (39 mL) of (5R,6S)-6-bromo-7-oxo-4-thia-1-azabicyclo[3.2.0]hept-2-ene-2-carboxylic acid 4-nitrobenzyl ester (cont. 99.7%) (1.93 g) was added to the mixture, cooled to −20° C., and Et₃N (2.79 mL) was added in one portion. The reaction vessel was covered with foil to exclude light. The reaction mixture was stirred for 3 h at −20° C. and treated with acetic anhydride (0.94 mL) and DMAP (61 mg) in one portion. The reaction mixture was warmed to 0° C. and stirred for 17 h at 0° C. The mixture was diluted with ethyl acetate and washed with 5% citric acid aqueous solution, saturated sodium hydrogen carbonate, water and brine. The organic layer was dried (MgSO₄) and filtered. The filtrate was concentrated under reduced pressure.

The residue was dissolved in THF (83 mL) and acetonitrile (39 mL). Freshly activated Zn dust (7.72 g) was added rapidly with 0.5 M phosphate buffer (pH 6.5, 122 mL). The reaction vessel was covered with foil to exclude light. The reaction mixture was vigorously stirred for 1.5 h at room temperature. The reaction mixture was filtered through a pad of Celite. The filtrate was washed with ethyl acetate and the aqueous layer was separated. The aqueous layer was cooled to 3° C. and 1 M NaOH was added to adjust pH to 8.0. The mixture was concentrated under high vacuum at 35° C. The concentrate was applied to Diaion HP-21 (150 mL, Mitsubishi Kasei Co. Ltd.) resin column chromatography. After adsorbing, the column was eluted with H₂O-MeCN (1/0-85/15). The combined fractions were concentrated under high vacuum at 35° C. and lyophilized to give the title compound as a yellow amorphous solid (371 mg, 22%, pH 8.0).

Mp 190° C. (dec); ¹H NMR (D₂O) δ 3.03 (t, 2H, J=5.7 Hz), 3.75 (s, 2H), 4.22 (t, 2H, J=5.7 Hz), 6.07 (s, 1H), 6.27 (s, 1H), 6.86 (s, 1H), 6.89 (s, 1H).

Example 12

Preparation of (5R)(6Z)-7-Oxo-6-(4H-5-thia-1,6a-diazapentalen-2-ylmethylene)-4-thia-1-azabicyclo[3.2.0]hept-2-ene-2-carboxylic acid, sodium salt

Step 1: 3-Oxo-3a,4-dihydro-3H,6H-2-oxa-5-thia-1-aza-6a-azonio-3a-pentalenide Conc. HCl (15 mL) and $NaNO_2$ (16.6 g) were added to the $H_2O$ (166 mL) solution of L-thioproline (24.3 g) under a nitrogen atmosphere at 0° C. and stirred for 2 h. The solution was extracted with $CH_2Cl_2$, organic layer was dried over $MgSO_4$ and concentrated under reduced pressure to afford the crude N-nitroso derivative as a yellow solid.

Trifluoroacetic anhydride (5.0 mL) was added to the THF (350 mL) solution of crude N-nitrosothioproline under a nitrogen atmosphere at 0° C. and stirred for 5 h at 0° C. The solution was concentrated under reduced pressure. The residue was applied to silica gel column chromatography, then the column was eluted with n-hexane—AcOEt (1:1). The titled compound was obtained as a pale brown solid (4.0 g, 15.1%).

$^1$H NMR ($CDCl_3$): δ4.04 (t, 2H, J=1.7 Hz), 5.40 (t, 2H, J=1.7 Hz).

Step 2: 4H-5-Thia-1,6a-diazapentalen-2-carboxylic acid ethylester

Ethyl propiolate (3.1 mL) was added to the o-xylene (130 mL) solution of 3-oxo-3a,4-dihydro-3H,6H-2-oxa-5-thia-1-aza-6a-azonio-3a-pentalenide (4.0 g) under a nitrogen atmosphere and refluxed for 19 h. The solution was cooled to room temperature and concentrated under reduced pressure. The residue was applied to silica gel column chromatography, then the column was eluted with n-hexane-AcOEt (4:1). The titled compound was obtained as a yellow solid (2.7 g, 49.3%), and 4H-5-thia-1,6a-diazapentalen-3-carboxylic acid ethylester was obtained as pale yellow crystals (1.2 g, 21.7%).

$^1$H NMR ($CDCl_3$) δ1.40 (t, 3H, J=7.1 Hz), 4.11 (d, 2H, J=2.1 Hz), 4.40 (q, 2H, J=7.1 Hz), 5.24 (t, 2H, J=1.6 Hz), 6.61 (s, 1H).

Step 3: (4H-5-Thia-1,6a-diazapentalen-2-yl)methanol $LiBH_4$ (cont. 90%) (459 mg) was added to the ether (126 mL) solution of 4H-5-thia-1,6a-diazapentalen-2-carboxylic acid ethylester (2.5 g) and MeOH (0.77 mL) under a nitrogen atmosphere at room temperature, then refluxed for 1.5 h. The mixture was quenched with 1 mol/L HCl (25 mL) and stirred for 1 h at room temperature. The mixture was neutralized by saturated sodium hydrogen carbonate solution and separated. The aqueous layer was extracted with dichloromethane (10× 25 mL). The organic layer was dried ($MgSO_4$) and filtered. The filtrate was concentrated under reduced pressure. The residue was applied to silica gel column chromatography, then the column was eluted with AcOEt. The titled compound was obtained as a pale yellow solid (1.7 g, 87.9%).

$^1$H NMR ($CDCl_3$) δ 2.95 (t, 1H, J=5.6 Hz), 4.07 (s, 2H), 4.62 (d, 2H, J=5.1 Hz), 5.13 (t, 1H, J=1.6 Hz), 6.04 (s, 1H).

Step 4: 4H-5-Thia-16a-diazapentalen-2-carbaldehyde

The dry dichloromethane (8 mL) solution of dimethylsulfoxide (2.2 mL) was added dropwise to the dry dichloromethane (110 mL) solution of oxalyl chloride (2.0 mL) at −78° C. The reaction mixture was stirred for 15 min at the same temperature. The dry dichloromethane (40 mL) solution of (4H-5-thia-1,6a-diazapentalen-2-yl)methanol, (1.7 g) was added dropwise to the reaction mixture at −78° C., and stirring was continued for an additional 15 min. The reaction mixture was allowed to warm to −45° C. and stirred for 1 h. Triethylamine (11.3 mL) was added dropwise and the reaction mixture was allowed to warm to 0° C. After 20 min, saturated ammonium chloride solution (50 mL) and water (100 mL) were added and separated. The aqueous layer was extracted with AcOEt (3×150 mL). The combined organic layers were washed with water (200 mL) and brine (200 mL), dried ($MgSO_4$) and filtered. The filtrate was concentrated under reduced pressure. The residue was applied to silica gel column chromatography, then the column was eluted with hexane—AcOEt (1:1). The titled compound was obtained as a yellow solid (1.7 g, quant.).

$^1$H NMR ($CDCl_3$) δ 4.13 (s, 2H), 5.26 (d, 2H, J=1.4 Hz), 6.59 (s, 1H), 9.90 (s, 1H).

Step 5; (5R)(6Z)-7-Oxo-6-(4H-5-thia-1,6a-diazapentalen-2-ylmethylene)-4-thia-1-azabicyclo[3.2.0]hept-2-ene-2-carboxylic acid, sodium salt The dry acetonitrile (92 mL) solution of 4H-5-thia-1,6a-diazapentalen-2-carbaldehyde (1.7 g) was added to the dry acetonitrile (92 mL) solution of $MgBr_2$ (5.0 g) under a nitrogen atmosphere at room temperature then the mixture was stirred for 10 min. The dry THF (184 mL) solution of p-nitrobenzyl (5R,6S)-6-bromopenem-3-carboxylate (4.3 g) was added and the mixture was cooled to −20° C. then triethylamine (7.4 mL) was added in one portion. The reaction vessel was covered with foil to exclude light. The reaction mixture was stirred for 3 h at −20° C. and treated with 4-dimethylamino pyridine (138 mg) and acetic anhydride (2.1 mL) in one portion. The reaction mixture was warmed to 0° C. and stirred for 15 h at 0° C. The 1 mol/L Citric acid aqueous solution (1000 mL) was added to the reaction mixture and the aqueous layer was extracted with ethyl acetate (3×400 mL). The combined organic layers were washed with water, saturated sodium hydrogen carbonate and brine, dried ($MgSO_4$) and filtered. The filtrate was concentrated under reduced pressure and crude (5R)-6-[acetoxy-(4H-5-thia-1,6a-diazapentalen-2-yl)methyl]-6-bromo-7-oxo-4-thia-1-azabicyclo[3.2.0]hept-2-ene-2-carboxylic acid p-nitrobenzyl ester was obtained as a brown amorphous solid.

Freshly activated Zn dust (19.3 g) was added rapidly with 0.5 mol/L phosphate buffer (pH 6.5, 100 mL) to the THF (100 mL) solution of crude (5R)-6-[acetoxy-(4H-5-thia-1,6a-diazapentalen-2-yl)methyl]-6-bromo-7-oxo-4-thia-1-azabicyclo[3.2.0]hept-2-ene-2-carboxylic acid p-nitrobenzyl ester. The reaction vessel was covered with foil to exclude light. The reaction mixture was vigorously stirred for 2.5 h at room temperature. The reaction solution was filtered through a pad of Celite and the pad was washed with water (200 mL) and n-butanol (200 mL). The aqueous layer was separated and then the organic layer was extracted with 0.5 mol/L phosphate buffer (pH 6.5, 2×50 mL). The combined aqueous layers were concentrated to 90 g, 1 mol/L NaOH was added to adjust pH to 8.0 and applied to Diaion HP-21 resin (180 mL, Mitsubishi Kasei Co. Ltd.) column chromatography. After adsorbing, the column was eluted with water and then 15% acetonitrile aqueous solution. The combined active fractions were concentrated under high vacuum at 35° C. and lyophilized to give the title compound as a yellow amorphous solid (634 mg, 17.4%, pH 7.25).

Mp 150° C. (dec); $^1$H NMR (D$_2$O) δ4.00 (s, 2H), 5.09 (s, 2H), 6.14 (s, 1H), 6.36 (s, 1H), 6.91 (s, 1H), 6.92 (s, 1H); IR (KBr) 3381, 1752, 1683, 1600, 1558 cm$^{-1}$; λ$^{max}$ (H$_2$O) 292, 196 nm.

Example 13

Preparation of (5R)(6Z)-6-(7H-Imidazo[1,2-c]thiazol-2-ylmethylene)-7-oxo-4-thia-1-azabicyclo[3.2.0] hept-2-ene-2-carboxylic acid, sodium salt Step 1: Thiazolidin-4-one The titled compound was prepared in the same way of Marvin M. and Allen R. Harkness. (*Tetrahedron Letters*. 1994, 35, 6971-6974).

Step 2: Thiazolidine-4-thione

Lawesson's reagents (33.5 g) added to the solution of thiazolidin-4-one (14.2 g) in dry THF (690 mL) and the reaction mixture was refluxed for 2 h. The mixture was cooled to room temperature and evaporated under reduced pressure. The residue was triturated with CHCl$_3$:MeOH=7:3 solution (65 mL) at room temperature for 30 min. The precipitate was filtered off, washed with CHCl$_3$:n-hexane=7:3 solution (15 mL) and dried in vacuo. The thiazolidine-4-thione was obtained as a pale yellow powder (10.7 g, 65%).

$^1$H NMR (CDCl$_3$) δ 4.08 (s, 2H), 4.70 (s, 2H).

Step 3: 4-Methylthio-2,5-dihydro-thiazole

Methyl iodide (28.4 g) was added to the boiling solution of thiazolidine-4-thione (9.5 g) in chloroform (400 mL), and the reaction mixture was refluxed for 1.5 h. To the reaction mixture, an additional methyl iodide (56.8 g) was added in 5 portions at 30-60 min intervals. After refluxing for additional 1 h, the reaction mixture was cooled to room temperature. Then 10% potassium carbonate aqueous solution (200 mL) was added and stirred for 15 min at room temperature. After separating organic layer, the aqueous layer was extracted with CHCl$_3$ (100 mL×3). Organic layers were combined, dried (MgSO$_4$) and filtered. The filtrate was concentrated under reduced pressure and dried in vacuo. After drying, the title compound was obtained as brown oil (11.0 g, quant.).

$^1$H NMR (CDCl$_3$) δ 2.51 (s, 3H), 3.91 (t, 2H, J=3.5 Hz), 5.21 (t, 2H, J=3.5 Hz).

Step 4: Thiazolidin-4-ylideneamine

A mixture of 4-methylthio-2,5-dihydrothiazole (10.7 g) and ammonium chloride (6.4 g) in dry ethanol (400 mL) was refluxed for 27.5 h. The reaction mixture was cooled to room temperature and evaporated under reduced pressure. The residue was dissolved in chloroform (300 mL) and 10% potassium carbonate aqueous solution (200 mL), then stirred for 20 min at room temperature. After separating organic layer, the aqueous layer was extracted with chloroform (100 mL×5). Organic layers were combined, dried (MgSO$_4$) and filtered. The filtrate was concentrated under reduced pressure and dried in vacuo to obtain crude thiazolidin-4-ylideneamine (5.5 g) as a brown solid that included by product, which is an ethoxy derivative and 4-methylthio-2,5-dihydrothiazole, which is the starting material. The ratio of these three compounds was determined to be 61:34:5 respectively by $^1$H-NMR.

$^1$H NMR (CDCl$_3$) δ 3.75 (t, 2H, J=2.8 Hz), 4.97 (t, 2H, J=2.9 Hz).

Step 5: 7H-Imidazo[1,2-c]thiazole-2-carbaldehyde

The solution of 2-bromo-3-isopropoxypropenal (6.9 g) in dry acetonitrile (326 mL) was added to the solution of crude thiazolidin-4-ylideneamine (3.3 g) in dry acetonitrile (326 mL) at room temperature. The reaction mixture was stirred at room temperature for 19.5 h, added triethylamine (4.9 mL) and then refluxed for 2 h. The reaction mixture was cooled to room temperature and then evaporated under reduce pressure. The residue was dissolved in dichloromethane (300 mL) and washed with 50% potassium carbonate aqueous solution (20 g). After filtration and separation, the aqueous layer was extracted with dichloromethane (50 mL×4). The organic layers were combined, dried (MgSO$_4$) and filtered. The filtrate was evaporated under reduced pressure. The residue was applied to silica gel column chromatography and eluted with CHCl$_3$-MeOH (100:3) to obtain crude 7H-Imidazo[1,2-c] thiazole-2-carbaldehyde as a brown solid. The crude product was re-crystallized twice from CHCl$_3$-n-hexane (1$^{st}$: 30:5, 2$^{nd}$: 30:60) at 0° C. to give the required aldehyde as pale brown crystals (Yield: 1.84 g, 15%).

$^1$H NMR (CDCl$_3$) δ 4.09 (t, 2H, J=1.3 Hz), 5.08 (t, 2H, J=1.2 Hz), 7.63 (s, 1H), 9.81 (s, 1H).

Step 6: (5R)(6Z)-6-(7H-Imidazo[1,2-c]thiazol-2-ylmethylene)-7-oxo-4-thia-1-azabicyclo

[3.2.0]hept-2-ene-2-carboxylic acid, sodium salt

7H-Imidazo[1,2-c]thiazole-2-carbaldehyde (841 mg) was added to the dry acetonitrile (116 mL) solution of anhydrous MgBr$_2$ (2.93 g) under a nitrogen atmosphere at room temperature. The dry THF solution (116 mL) of (5R,6S)-6-bromo-7-oxo-4-thia-1-azabicyclo[3.2.0]hept-2-ene-2-carboxylic acid 4-nitrobenzyl ester (cont. 99.7%) (2.51 g) was added to the mixture, cooled to −20° C., and Et$_3$N (2.20 mL) was added in one portion. The reaction vessel was covered with foil to exclude light. The reaction mixture was stirred for 4 h at −20° C. and treated with acetic anhydride (1.26 mL) and DMAP (160 mg) in one portion. The reaction mixture was warmed to 0° C. and stirred for 15 h at 0° C. The mixture was diluted with ethyl acetate and washed with 5% citric acid aqueous solution, saturated sodium hydrogen carbonate, water and brine. The organic layer was dried (MgSO$_4$) and filtered. The filtrate was concentrated under reduced pressure.

The residue was dissolved in THF (53 mL) and acetonitrile (25 mL). Freshly activated Zn dust (15.1 g) and 0.5 M phosphate buffer (pH 6.5, 78 mL) were added to the mixture. The reaction vessel was covered with foil to exclude light. The reaction mixture was vigorously stirred for 1.5 h at room temperature. The reaction mixture was filtered through a pad of Celite. The filtrate was washed with ethyl acetate and the aqueous layer was separated. The aqueous layer was cooled to 3° C. and 1 M NaOH was added to adjust pH to 8.0. The mixture was concentrated under high vacuum at 35° C. The concentrate was applied to Diaion HP-21 (321 mL, Mitsubishi Kasei Co. Ltd.) resin column chromatography. After adsorbing, the column was eluted with H$_2$O-MeCN (1/0-9/1). The combined fractions were concentrated under high vacuum at 35° C. and lyophilized to give the title compound as a yellow amorphous solid (1.1 g, 51%, pH 7.5).

Mp 145° C. (dec); $^1$H NMR (D$_2$O) δ 3.85 (s, 2H), 4.88 (s, 2H), 6.32 (s, 1H), 6.78 (s, 1H), 6.85 (s, 1H), 7.27 (s, 1H).

Example 14

Preparation of (5R,6Z)-7-oxo-6-[(4-oxo-6,7-dihydro-4H-pyrazolo[51-c][1,4]oxazin-2-yl)methylene]-4-thia-1-azabicyclo[3.2.0]hept-2-ene-2-carboxylic Acid.

Step 1: Diethyl 1-(2-{[tert-butyl(dimethyl)silyl]oxy}ethyl)-1H-pyrazole-3,5-dicarboxylate To a solution of diethyl 3,5-pyrazoledicarboxylate (2.17 g, 10 mmol) in acetonitrile (10 ml), under nitrogen, was added potassium carbonate (2.07 g, 15 mmol), and 2-bromoethoxy-t-butyldimethylsilane (2.90 g, 12 mmol). The mixture was stirred at reflux for 18 hr. It was then cooled to room temperature, diluted with ethyl acetate (20 ml), and filtered through Magnesol. The filter pad was eluted with 2×10 ml of ethyl acetate, and the combined filtrate was evaporated. The residue was dissolved in hexanes and passed through a column of silica gel (70 g). After eluting with hexanes (100 ml), the column was eluted with ethyl acetate. The ethyl acetate eluent was evaporated to give 3.71 g of a colorless oil; MS m/e 371 (MH$^+$).

Step 2: 1-(2-{[tert-butyl(dimethyl)silyl]oxy}ethyl)-1H-pyrazole-3,5-dimethanol To a solution of diethyl 1-(2-{[tert-butyl(dimethyl)silyl]oxy}ethyl)-1H-pyrazole-3,5-dicarboxylate (0.74 g, 2 mmol) in methylene chloride (8 ml), under nitrogen, was added 12 ml of a 1.0 M solution of diisobutylaluminum hydride in methylene chloride at 0° C. After stirring at 0° C. for 0.5 hr, the mixture was warmed to room temperature for 0.5 hr. It was then quenched with 15 ml of saturated ammonium chloride solution and extracted with ethyl acetate. The organic extract was washed with brine, dried over anhydrous sodium sulfate, and evaporated to give 0.44 g of a white solid; mp 82-83° C.; MS m/e 287 (MH$^+$).

Step 3: 1-(2-{[tert-butyl(dimethyl)silyl]oxy}ethyl)-1H-pyrazole-3,5-dicarbaldehyde To a stirred solution of 1-(2-{[tert-butyl(dimethyl)silyl]oxy}ethyl)-1H-pyrazole-3,5-dimethanol (1.18 g, 4 mmol) in methylene chloride (20 ml), was added 4-methylmorpholine-N-oxide (2.89 g, 24 mmol) and molecular sieve 4 A (4 g). The reaction mixture was stirred at room temperature for 10 min. and then treated with tetrapropylammonium peruthenate (0.15 g, 0.4 mmol). Stirring was continued for 2 hr. The methylene chloride solution was concentrated and diluted with ether (40 ml). The mixture was filtered through a pad of silica gel (40 g) and the filter pad was eluted with 2×20 ml ether. The combined eluent was washed with 1N HCl and brine, dried over anhydrous sodium sulfate, and evaporated to give 0.79 g of a white solid; mp 63-64° C.; MS m/e 283 (MH$^+$).

Step 4: 4-oxo-6,7-dihydro-4H-pyrazolo[5,1-c][1,4]oxazine-2-carbaldehyde

To a solution of 1-(2-{[tert-butyl(dimethyl)silyl]oxy}ethyl)-1H-pyrazole-3,5-dicarbaldehyde (1.02 g, 6.07 mmol) in THF (30 ml) was added 6.68 ml of a 1.0 M solution of tetrabutylammonium fluoride in THF at 0° C. After stirring for 1 hr, the mixture was treated with 10 ml of saturated ammonium chloride solution and extracted with ethyl acetate. The organic solution was washed with brine, dried over anhydrous sodium sulfate, filtered through Magnesol and evaporated. The crude gum was washed with hexanes, dried in vacuo, and then dissolved in methylene chloride (20 ml). To this solution was added 4-methylmorpholine-N-oxide (2.89 g, 24 mmol) and molecular sieve 4 A (6 g). The mixture was stirred at room temperature for 10 min. and then treated with tetrapropylammonium peruthenate (0.11 g, 0.3 mmol). Stirring was continued for 2 hr. The methylene chloride solution was concentrated and diluted with ethyl acetate (40 ml). The mixture was filtered through a pad of silica gel (40 g) and the filter pad was eluted with 2×20 ml ethyl acetate. The combined eluent was washed with 1N HCl and brine, dried over anhydrous sodium sulfate, and evaporated to give 0.30 g of a white solid; mp 135-136° C.; MS m/e 167 (MH$^+$).

Step 5: 4-nitrobenzyl (5R)-6-[(acetyloxy)(4-oxo-6,7-dihydro-4H-pyrazolo[5,1-c][1,4]oxazin-2-yl)methyl]-6-bromo-7-oxo-4-thia-1-azabicyclo[3.2.0]hept-2-ene-2-carboxylate To a solution of MgBr$_2$ (0.46 g, 2.52 mmol) in acetonitrile (13 ml) under nitrogen was added 4-oxo-6,7-dihydro-4H-pyrazolo[5,1-c][1,4]oxazine-2-carbaldehyde (0.14 g, 0.84 mmol) at room temperature with stirring. A solution of (5R,6S)-6-bromo-7-oxo-4-thia-1-azabicyclo[3.2.0]hept-2-ene-2-carboxylic acid 4-nitrobenzyl ester (0.32 g, 0.84 mmole) in THF (13 ml) was then added, and the mixture was cooled to −20° C. Triethylamine (0.35 ml, 2.52 mmol) was introduced, and the mixture was stirred at −20° C. in the dark for 4 hr. It was then treated with acetic anhydride (0.2 ml, 2.0 mmol), and 4-N,N-dimethylaminopyridine (12 mg, 0.1 mmol), and kept at 0° C. for 18 hr. The mixture was concentrated and the residue was dissolved in ethyl acetate. The ethyl acetate solution was washed with 5% citric acid, saturated sodium bicarbonate solution, and brine, dried over anhydrous sodium sulfate, and evaporated. The crude material was chromatographed with silica gel (EtOAc—CH2Cl2/1:5) to give 0.27 g of an off-white solid; mp 107-110° C.; MS m/e 595 (MH$^+$).

Step 6: (5R,6Z)-7-oxo-6-[(4-oxo-6,7-dihydro-4H-pyrazolo[5,1-c][1,4]oxazin-2-yl)methylene]-4-thia-1-azabicyclo[3.2.0]hept-2-ene-2-carboxylic Acid To a solution of 4-nitrobenzyl (5R)-6-[(acetyloxy)(4-oxo-6,7-dihydro-4H-pyrazolo[5,1-c][1,4]oxazin-2-yl)methyl]-6-bromo-7-oxo-4-thia-1-azabicyclo[3.2.0]hept-2-ene-2-carboxylate (0.22 g, 0.37 mmol) in THF (15 ml), under nitrogen, was added 15 ml of a phosphate buffer solution (0.5M, pH 6.5), and 80 mg of 10% Pd/C. The mixture was hydrogenated at 40-50 psi for 3 hr, and then filtered through Celite. The filter pad was washed with THF, and the filtrate was extracted with ethyl acetate. The organic extract was dried over anhydrous magnesium sulfate and evaporated. The residue was washed with ether to give 0.07 g of a yellow solid; MS m/e 320 (MH$^+$); $^1$H NMR (DMSO-d$_6$) δ 4.55-4.57 (m, 2H), 4.76-4.80 (m, 2H), 6.50 (s, 1H), 6.63 (s, 1H), 7.58 (s, 1H), 7.76 (s, 1H).

Example 15

Preparation of 6-(6,7-Dihydro-4H-thieno[3,2-c]pyran-2-ylmethylene)-7-oxo-4-thia-1-aza-bicyclo[3.2.0]hept-2-ene-2-carboxylic acid

Step 1: Preparation of 6,7-Dihydro-4H-thieno[3,2-c]pyran-2-carbaldehyde

POCl3 (3.83 ml, 50 mmol) was added dropwise to ice cooled DMF (3.85 ml, 50 mmol) within 3 minutes. DCM (20 ml) was added and the bath was removed when the reaction media appeared to be pasty. The reaction was kept at 23° C. for 2 hrs. Then it was cooled to 0° C. again. 4H-pyran-4-one (5 gram, 50 mmol) in 10 ml DCM was then added dropwise within 3 minutes. The reaction was kept at 0° C. for 2 hrs. Pour the mixture onto ice and sodium acetate solution and extract with DCM (2×200). The combined organic layers were dried over magnesium sulfate. Filter off the drying agent and concentrate gave 5.0 gram of product. The compound was dissolved in DCM (200 ml) and was added 6.0 gram of ethyl 2-6,7-Dihydro-4H-thieno[3,2-c]thiopyran-2-carbaldehyde-acetate and 10 ml TEA. The mixture was refluxed for 18 hrs. Then it was washed with water and dried over magnesium sulfate. It was then filtered, concentrated and flash chromatographed with 20 ethyl acetate in hexane. The collected material was dissolved in 100 ml THF and LAH (150 ml, 0.5M in THF) was injected and left at 23° C. for 10 minutes. Then it was refluxed for 18 hrs. Quenched at 23° C. by adding water and eventually 1N HCl to clear up the mixture. Extract with ethyl acetate (2×200 ml) and combined organic layers dried over magnesium sulfate. Filter and concentrate gave 2.3 gram product. The crude material was dissolved in DCM (300 ml) and manganese dioxide (15 gram was added). The reaction was carried on at 23° C. for 0.5 hr. Then 2×15 gram of oxidant was added each half an hour later. The material was then filtered through a pad of celite concentrated. Flash column chromatography gave 1.206 gram (14% yield) oil product.

H-NMR: δ 9.84 (s, 1H), 7.41 (s, 1H), 4.74 (s, 2H), 4.00 (t, 2H, J=5.6 Hz), 2.96 (t, 2H, J=5.6 Hz); MS: 169.1 (M+H)

Step 2: Preparation of 6-(6,7-Dihydro-4H-thieno[3,2-c]pyran-2-ylmethylene)-7-oxo-4-thia-1-aza-bicyclo[3.2.0]hept-2-ene-2-carboxylic acid 6,7-Dihydro-4H-thieno[3,2-c]pyran-2-carbaldehyde (336 mg, 2 mmol) was dissolved in 20 ml acetonitrile and magnesium bromide (516 mg, 2 mmol) was then added under N2 atmosphere. The mixture was stirred at 23° C. for half an hour. 6-Bromo-7-oxo-4-thia-1-aza-bicyclo[3.2.0]hept-2-ene-2-carboxylic acid 4-nitro-benzyl ester (770 mg, 2 mmol) in 20 ml THF was then injected all at once and the mixture was immediately cooled to −20° C./Triethylamine (1 ml) was then injected and the mixture stirred at −20° C. for three hrs. Then acetic anhydride (0.4 ml) was injected and the mixture was stirred at 0° C. for 18 hrs. The reaction media was then diluted with 400 ml ethyl acetate and washed with 100 ml 5% citric acid, 100 ml saturated sodium bicarbonate, and 100 ml brine. The organic layer was then dried over magnesium sulfate, filtered and concentrated. Flash column chromatography using 20% ethyl acetate in hexane gave 491 mg (41%) product. This product was then dissolved in 15 ml THF and 15 ml aqueous phosphate buffer (pH=6.5). The mixture was then subjected to 45 psi hydrogen for one hour with 0.5 gram 10% palladium on carbon. Then it was filtered through a pad of celite and concentrated in vacuo to remove most of the THF. The solution was then cooled to zero degree and basified to pH=8 with 1 N sodium hydroxide. Then it was purified via reverse phase HPLC using 2 liter of water followed by 5% acetonitrile in water. Water was then removed through concentrate in vacuo and 100 mg (38%) of product was collected; MP: >250° C.;

H-NMR: δ 7.36 (s, 1H), 7.15 (s, 1H), 6.55 (s, 1H), 6.44 (s, 1H), 4.61 (s, 2H), 3.88 (m, 2H), 2.86 (m, 2H), 2.27 (m, 2H), 1.43 (t, 3H)

MS: 320.3 (M−H)

Example 16

Preparation of 6-(6,7-Dihydro-4H-thieno[3,2-c]thiopyran-2-ylmethylene)-7-oxo-4-thia-1-aza-bicyclo[3.2.0]hept-2-ene-2-carboxylic acid

Step 1: Preparation of 6,7-Dihydro-4H-thieno[3,2-c]thiopyran-2-carbaldehyde

POCl3 (4.02 ml, 43 mmol) was added dropwise to ice cooled DMF (3.34 ml, 43 mmol) within 3 minutes. DCM (20 ml) was added and the bath was removed when the reaction media appeared to be pasty. The reaction was kept at 23° C. for 2 hrs. Then it was cooled to 0° C. again. Tetrahydro-thiopyran-4-one (5 gram, 43 mmol) in 10 ml DCM was then added dropwise within 3 minutes. The reaction was kept at 0° C. for 2 hrs. Dilute with DCM (250 ml) and then wash with ice cold 200 ml saturated sodium acetate aqueous solution. The organic layer was dried over sodium sulfate. Filter off the drying agent, concentrate and flash column chromatography using 10% ethyl acetate in hexane gave 1.3 gram (8 mmol) of product. The compound was dissolved in DCM (100 ml) and was added 1.2 ml (11 mmol) of ethyl 2-mercapto-acetate and 1 ml TEA. The mixture was refluxed for 18 hrs. Then it was washed with water and dried over magnesium sulfate. Filter, concentrate and flash chromatograph with 20 ethyl acetate in hexane produced 1.1 gram (11% yield) of product H-NMR: δ 6.68 (s, 1H), 4.73 (s, 2H), 3.68 (s, 2H), 3.04 (t, 2H, J=7.6 Hz), 2.91 (t, 2H, J=7.6 Hz).; MS (EI): 185.99 (M+)

The 1.1 gram (4.8 mmol) 6,7-Dihydro-4H-thieno[3,2-c]thiopyran-2-carboxylic acid ethyl ester was dissolved in 100 ml THF and LAH (40 ml, 0.5M in DMG) was injected and the reaction was left at 23° C. for 10 minutes. Then it was refluxed for 18 hrs. Quenched at 23° C. with water (10 ml). The organic layer decanted and the remaining was washed with 20 ml DCM. The combined organic layers dried over sodium sulfate. Filter, concentrate and flash column chromatograph with 10-20% ethyl acetate produced 940 mg crude product. This crude material was dissolved in DCM (40 ml) and manganese dioxide (2 gram was added). The reaction was carried on at 23° C. for half an hour. The material was then filtered through a pad of celite concentrated. Flash column chromatography gave 320 mg (36%) product.

H-NMR: δ 9.82 (s, 1H), 7.46 (s, 1H), 3.56 (s, 2H), 3.15 (t, 2H, J=7.2 Hz), 2.95 (t, 2H, J=7.2 Hz).; MS (EI): 228.02 (M+)

Step 2: Preparation of 6-(6,7-Dihydro-4H-thieno[3,2-c]thiopyran-2-ylmethylene)-7-oxo-4-thia-1-aza-bicyclo[3.2.0]hept-2-ene-2-carboxylic acid 6,7-Dihydro-4H-thieno[3,2-c]thiopyran-2-carbaldehyde (320 mg, 1.72 mmol) was dissolved in 17 ml acetonitrile and magnesium bromide etherate (450 mg, 1.74 mmol) was then added under N2 atmosphere. The mixture was stirred at 23° C. for half an hour. 6-Bromo-7-oxo-4-thia-1-aza-bicyclo[3.2.0]hept-2-ene-2-carboxylic acid 4-nitro-benzyl ester (660 mg, 1.72 mmol) in 17 ml THF was then injected all at once and the mixture was immediately cooled to −20° C./Triethylamine (1 ml) was then injected and the mixture stirred at −20° C. for three hrs. Then acetic anhydride (0.4 ml) was injected and the mixture was stirred at 0° C. for 18 hrs. The reaction media was then diluted with 400 ml ethyl acetate and washed with 100 ml 5% citric acid, 100 ml saturated sodium bicarbonate, and 100 ml brine. The organic layer was then dried over magnesium sulfate, filtered and concentrated. Flash column chromatography using 20% ethyl acetate in hexane gave 461 mg (44%) product. This product was then dissolved in 20 ml THF and 20 ml aqueous phosphate buffer (pH=6.5). The mixture was then subjected to 40 psi hydrogen for one hour and half with 0.5 gram 10% palladium on carbon. Then it was filtered through a pad of celite and concentrated in vacuo to remove most of the THF. The solution was then cooled to zero degree and basified to pH=8 with 1 N sodium hydroxide. Then it was purified via reverse phase HPLC using 2 liter of water followed by 5% acetonitrile in water. Water was then removed through concentrate in vacuo and 21 mg (8.6%) of product was collected.

MP: >250° C.

H-NMR: 7.34 (s, 1H), 7.18 (s, 1H), 6.59 (s, 1H), 6.44 (s, 1H), 3.71 (s, 2H), 2.93 (s, 2H), 2.50 (s, 2H).; MS: 338.0 (M+H)

Example 17

Preparation of 6-(5-Methyl-4,5,6,7-tetrahydro-thieno[3,2-c]pyridin-2-ylmethylene)-7-oxo-4-thia-1-aza-bicyclo[3.2.0]hept-2-ene-2-carboxylic acid Step 1: Preparation of (5-Methyl-4,5,6,7-tetrahydro-thieno[3,2-c]pyridin-2-yl)-methanol 6,7-Dihydro-4H-thieno[3,2-c]pyridine-2,5-dicarboxylic acid diethyl ester (46 gram, 163 mmol) was dissolved in 200 ml THF. The solution was injected LAH (1M, THF) 300 ml at 23° C. Then it was stirred at 23° C. for 18 hrs. The reaction was quenched with 10 ml water and dried directly over sodium sulfate. Filter and concentrate yielded 29.3 gram (160 mmol, 98%) crude product.

H-NMR: 6.55 (s, 1H), 4.70 (s, 2H), 3.41 (s, 2H), 2.86 (t, 2H, J=5.6 Hz), 2.73 (t, 2H, J=5.6 Hz), 2.38 (s, 3H); MS: 184.0 (M+H)

Step 2: Preparation of 5-Methyl-4,5,6,7-tetrahydro-thieno[3,2-c]pyridine-2-carbaldehyde DMSO (1.7 ml, 24 mmol) in 5 ml CH$_2$Cl$_2$ was cooled to −50-60° C. Oxalyl chloride (1 ml, 11 mmol) in 20 ml DCM was then added within 5 minutes at 50° C. The mixture was kept at −50° C. for 5 minutes and then 1.67 gram (9 mmol) of (5-Methyl-4,5,6,7-tetrahydro-thieno[3,2-c]pyridin-2-yl)-methanol in 20 ml DCM was added at 50° C. and the mixture was stirred for another 15 minutes at 50° C. Triethylamine (7 ml) was then added at −50° C. and after 5 minutes the bath was removed and the mixture is naturally warmed up to 23° C. It was washed with 100 ml water and extracted with 100 ml ethyl acetate. The combined organic layers were dried over magnesium sulfate. Filter. Concentrate and flash column chromatograph using 0-15% methanol in ethyl acetate yielded 736 mg (45% yield) product.

H-NMR: 9.81 (s, 1H), 7.42 (s, 1H), 3.56 (s, 2H), 3.00 (t, 2H, J=5.6 Hz), 2.91 (t, 2H, J=5.6 Hz), 2.51 (s, 3H); MS: 182.1 (M+H)

Step 3: Preparation of 6-(5-Methyl-4,5,6,7-tetrahydro-thieno[3,2-c]pyridin-2-ylmethylene)-7-oxo-4-thia-1-aza-bicyclo[3.2.0]hept-2-ene-2-carboxylic acid 2-formyl-6,7-dihydro-4H-thieno[3,2-c]pyridine-5-carboxylic acid ethyl ester (724 mg, 4 mmol) was dissolved in 40 ml acetonitrile and magnesium bromide etherate (1.2 gram, 4.65 mmol) was then added under N2 atmosphere. The mixture was stirred at 23° C. for half an hour. 6-Bromo-7-oxo-4-thia-1-aza-bicyclo[3.2.0]hept-2-ene-2-carboxylic acid 4-nitro-benzyl ester (1.54 gram, 4 mmol) in 40 ml THF was then injected all at once and the mixture was immediately cooled to −20° C. Triethylamine (2 ml) was then injected and the mixture stirred at −20° C. for 3 hrs. Then acetic anhydride (0.66 ml) was injected and the mixture was stirred at 0° C. for 48 hrs. The reaction media was then diluted with 500 ml ethyl acetate and washed with 50 ml 5% citric acid, 50 ml saturated sodium bicarbonate, and 50 ml brine. Another 300 ml ethyl acetate was used to wash each aqueous solution. The combined organic layers were then dried over sodium sulfate. Filter, concentrate, and flash column chromatograph using 20% ethyl acetate in hexane gave 1.56 gram (64% yield) product. This product was then dissolved in 20 ml THF and 20 ml aqueous phosphate buffer (pH=6.5). The mixture was then subjected to 40 psi hydrogen for two hrs with 0.5 gram 10% palladium on carbon. Then it was filtered through a pad of celite and concentrated in vacuo to remove most of the THF. The solution was then cooled to zero degree and basified to pH=8 with 1 N sodium hydroxide. Then it was purified via reverse phase HPLC using 2 liter of water followed by 5% acetonitrile in water. Water was then removed through concentrate in vacuo and 112 mg (13%) of product was collected.

MP: >250° C.

H-NMR: δ 7.48 (s, 1H), 7.37 (s, 1H), 7.21 (s, 1H), 7.10 (s, 1H), 3.41 (s, 2H), 2.88 (s, 2H), 2.68 (s, 2H), 2.37 (s, 3H); MS: 335.0 (M+H)

Example 18

Preparation of 2-(2-Carboxy-7-oxo-4-thia-1-aza-bicyclo[3.2.0]hept-2-en-6-ylidenemethyl)-6,7-dihydro-4H-thieno[3,2-c]pyridine-5-carboxylic acid ethyl ester 2-Formyl-6,7-dihydro-4H-thieno[3,2-c]pyridine-5-carboxylic acid ethyl ester (480 mg, 2 mmol) was dissolved in 20 ml acetonitrile and magnesium bromide etherate (516 mg, 2 mmol) was then added under N2 atmosphere. The mixture was stirred at 23° C. for half an hour. 6-Bromo-7-oxo-4-thia-1-aza-bicyclo[3.2.0]hept-2-ene-2-carboxylic acid 4-nitro-benzyl ester (770 mg, 2 mmol) in 20 ml THF was then injected all at once and the mixture was immediately cooled to −20° C. Triethylamine (1 ml) was then injected and the mixture stirred at −20° C. for 3 hrs. Then acetic anhydride (0.4 ml) was injected and the mixture was stirred at 0° C. for 48 hrs. The reaction media was then diluted with 200 ml ethyl acetate and washed sequentially with 50 ml 5% citric acid, 50 ml saturated sodium bicarbonate, and 50 ml brine. The organic layer was then dried over sodium sulfate. Filter, concentrate, and flash column chromatograph using 20% ethyl acetate in hexane gave 690 mg (50%, yield) product. A fraction of this product (456 mg, 0.69 mmol) was then dissolved in 15 ml THF and 15 ml aqueous phosphate buffer (pH=6.5). The mixture was then subjected to 40 psi hydrogen for two hrs with 0.5 gram 10% palladium on carbon. Then it was filtered through a pad of celite and concentrated in vacuo to remove most of the THF. The solution was then cooled to zero degree and basified to pH=8 with 1 N sodium hydroxide. Then it was purified via reverse phase HPLC using 2 liter of water followed by 5% acetonitrile in water. Water was then removed through concentrate in vacuo and 18 mg (5%) of product was collected.

MP: >250° C.

H-NMR: 7.35 (s, 1H), 7.24 (s, 1H), 6.61 (s, 1H), 6.45 (s, 1H), 4.48 (s, 2H), 4.08 (quartet, 2H, J=7.2 Hz), 3.68 (m, 2H), 2.87 (m, 2H), 1.20 (t, 3H, J=7.2 Hz); MS: 393.0 (M+H)

Example 19

Preparation of 7-Oxo-6-(6,7,8,9-tetrahydro-5H-imidazo[1,2-a]azepin-2-ylmethylene)-4-thia-1-aza-bicyclo[3.2.0]hept-2-ene-2-carboxylic acid Step 1: Preparation of 6,7,8,9-Tetrahydro-5H-imidazo[1,2-a]azepine-2-carbaldehyde Thiocaprolactam (6.45 gram, 50 mmol) was dissolved in 400 ml $CH_2Cl_2$ and methyl iodide (16 ml, 5 eq) was next added. The mixture was stirred under nitrogen for 18 hrs. Then it was treated with 100 ml potassium carbonate (50%, aq.). The organic layer was then dried over magnesium sulfate. After filtration and concentration 7.3 gram of material was obtained. This material was dissolved 300 ml ethanol and 2.83 gram of ammonium chloride was added. The mixture was refluxed for 1 hr. Then the solvent was removed in vacuo. Half of the material was added 200 ml ethanol and then followed by addition of 1.35 gram (25 mmol) sodium methoxide and 4.8 gram (25 mmol) 2-Bromo-3-isopropoxy-propenal and the mixture was stirred at 23° C. for 2 hrs. Then the solvent was removed and 200 ml chloroform was added along with 10 ml triethyl amine. The mixture was refluxed for 2 hrs and then cooled to 23° C. The reaction media was partitioned between 300 ml DCM and 2×150 potassium carbonate (50%). The organic layer was dried over magnesium sulfate. After filtration and concentration 2.1 gram of oil product was obtained.

H-NMR: 9.62 (s, 1H), 7.60 (s, 1H), 6.61 (s, 1H), 6.45 (s, 1H), 4.58 (s, 2H), 2.96 (2m, H), 1.90 (m, 2H), 1.72 (m, 2H); MS: 164.9 (M+H)

Step 2: Preparation of 7-Oxo-6-(6,7,8,9-tetrahydro-5H-imidazo[1,2-a]azepin-2-ylmethylene)-4-thia-1-aza-bicyclo[3.2.0]hept-2-ene-2-carboxylic acid 6,7,8,9-Tetrahydro-5H-imidazo[1,2-a]azepine-2-carbaldehyde (1.312 gram, 8 mmol) was dissolved in 80 ml acetonitrile and magnesium bromide etherate (2.94 gram, 8 mmol) was then added under N2 atmosphere. The mixture was stirred at 23° C. for half an hour. 6-Bromo-7-oxo-4-thia-1-aza-bicyclo[3.2.0]hept-2-ene-2-carboxylic acid 4-nitro-benzyl ester (1.155 gram, 3 mmol) in 60 ml THF was then injected all at once and the mixture was immediately cooled to −20° C. Triethylamine (4 ml) was then injected and the mixture stirred at −20° C. for 4 hrs. Then acetic anhydride (1 ml) was injected and the mixture was stirred at 0° C. for 20 hrs. The reaction media was then diluted with 500 ml ethyl acetate and washed with 100 ml 5% citric acid, 100 ml saturated sodium bicarbonate, and 100 ml brine. The organic layer was then dried over sodium sulfate. Filter, concentrate, and flash column chromatograph using 20% ethyl acetate in hexane gave 800 mg product. This product was then dissolved in 20 ml THF and 20 ml aqueous phosphate buffer (pH=6.5). The mixture was then subjected to 40 psi hydrogen for 1 hr with 0.5 gram 10% palladium on carbon. Then it was filtered through a pad of celite and concentrated in vacuo to remove most of the THF. The solution was then cooled to zero degree and basified to pH=8 with 1 N sodium hydroxide. Then it was purified via reverse phase HPLC using 2 liter of water followed by 5% acetonitrile in water. Water was then removed through concentrate in vacuo and 131 mg (31%) of product was collected.

MP: >250° C.

H-NMR: δ 7.78 (s, 1H), 7.02 (s, 1H), 6.94 (s, 1H), 6.36 (s, 1H), 3.92 (m, 2H), 2.80 (m, 2H), 1.78 (m, 2H), 1.61 (m, 2H), 1.54 (m, 2H); MS: 318.2 (M+H).

Example 20

Preparation of (5R),(6Z)-6-(7-Benzyl-5,6,7,8-tetrahydroimidazo[1,2-a]pyrazin-2-ylmethylene)-7-oxo-4-thia-1-azabicyclo[3.2.0]hept-2-ene-2-carboxylic acid, sodium salt Step 1: 7-Benzyl-5,6,7,8-tetrahydroimidazo[1,2-a]pyrazine-2-carboxylic acid ethyl ester $Et_3N$ (6.27 mL), PhCHO (4.92 mL) were added successively to the EtOH (81 mL) solution of 5,6,7,8-tetrahydroimidazo[1,2-a]pyrazine-2-carboxylic acid ethyl ester, hydrochloride (9.47 g) at room temperature and stirred for 3 h under a nitrogen atmosphere. Then $NaBH_3CN$ (2.97 g) was added to the reaction mixture and stirred for 19 h. The mixture was filtered through a pad of Celite and diluted with $CH_2Cl_2$ and washed with 50% $K_2CO_3$ aq. The organic layer was dried ($K_2CO_3$) and filtered. The filtrate was concentrated under reduced pressure. The residue was applied to silica gel column chromatography, then the column was eluted with $CHCl_3$-acetone (1/0~9/1) and $CHCl_3$-MeOH (19/1~9/1). The titled compound was obtained as pale yellow crystals (4.16 g, 36%).

$^1$H NMR ($CDCl_3$) δ 1.36 (t, 3H, J=7.1 Hz), 2.87 (t, 2H, J=5.2 Hz), 3.71 (s, 2H), 3.75 (s, 2H), 4.01 (m, 2H), 4.34 (q, 2H, J=7.1 Hz), 7.25-7.34 (m, 5H), 7.51 (s, 1H).

Step 2: 7-Benzyl-5,6,7,8-tetrahydroimidazo[1,2-a]pyrazine-2-carbaldehyde 1.01 M solution of DIBAL in toluene (1 mL+0.2 mL+0.3 mL) was added to the dry $CH_2Cl_2$ (5 mL) solution of 7-benzyl-5,6,7,8-tetrahydroimidazo[1,2-a]pyrazine-2-carboxylic acid ethyl ester (283 mg) under a nitrogen atmosphere at −78° C. and stirred for 1.5 h. The mixture was quenched with 1 M HCl (5 mL). The reaction mixture was filtered through a pad of Celite. The filtrate was washed with 50% $K_2CO_3$ aq. and the aqueous layer was extracted with $CH_2Cl_2$. The combined organic layer was dried ($K_2CO_3$) and filtered. The filtrate was concentrated under reduced pressure. The residue was applied to silica gel column chromatography, then the column was eluted with $CHCl_3$-acetone (9/1~4/1) and $CHCl_3$-MeOH (19/1). The titled compound was obtained as colorless crystals (148 mg, 61%).

$^1$H NMR ($CDCl_3$) δ 2.90 (t, 2H, J=5.5 Hz), 3.74 (s, 2H), 3.76 (s, 2H), 4.06 (t, 2H, J=5.5 Hz), 7.28~7.35 (m, 5H), 7.53 (s, 1H), 9.80 (s, 1H).

Step 3: (5R,6RS)-6-[(RS)-Acetoxy(7-benzyl-5,6,7,8-tetrahydroimidazo[1,2-a]pyrazin-2-yl)methyl]-6-bromo-7-oxo-4-thia-1-azabicyclo[3.2.0]hept-2-ene-2-carboxylic acid 4-nitrobenzyl ester (diastereo mixture)

7-Benzyl-5,6,7,8-tetrahydroimidazo[1,2-a]pyrazine-2-carbaldehyde (139 mg) was added to the dry acetonitrile (8.7 mL) solution of anhydrous $MgBr_2$ (325 mg) under a nitrogen atmosphere at room temperature. The dry THF solution (8.7 mL) of (5R,6S)-6-bromo-7-oxo-4-thia-1-azabicyclo[3.2.0]hept-2-ene-2-carboxylic acid 4-nitro-benzyl ester (223 mg) was added to the mixture, cooled to −20° C., and $Et_3N$ (0.24 mL) was added in one portion. The reaction vessel was covered with foil to exclude light. The reaction mixture was stirred for 5 h at −20° C. and treated with acetic anhydride (0.11 mL) and DMAP (7 mg) in one portion. The reaction mixture was warmed to 0° C. and stirred for 15 h at 0° C. The mixture was diluted with ethyl acetate and washed with 5% citric acid aqueous solution, saturated sodium hydrogen carbonate, water and brine. The organic layer was dried ($MgSO_4$) and filtered. The filtrate was concentrated under reduced pressure. The residue was applied to silica gel column chromatography, then the column was eluted with n-hexane—AcOEt (3/1~1/1). The titled compound was obtained as two diastereo mixture (80/20, purple amorphous solid, 233 mg, 61%).

$^1H$ NMR ($CDCl_3$) δ 1.99 (s, 0.8×3H), 2.23 (s, 0.2×3H), 2.83~2.89 (m, 2H), 3.68 (d, 2H, J=4.9 Hz), 3.71 (s, 2H), 3.94~4.13 (m, 2H), 5.27 (d, 1H, J=13.6 Hz), 5.41 (d, 0.2×1H, J=13.6 Hz), 5.45 (d, 0.8×1H, J=13.6 Hz), 6.05 (s, 0.2×1H), 6.28 (s. 0.8×1H), 6.31 (s, 0.8×1H), 6.790 (s, 0.2×1H), 6.793 (s, 0.2×1H), 7.01 (s, 0.8×1H), 7.27~7.36 (m, 5H), 7.42 (s, 0.2×1H), 7.46 (s, 0.8×1H), 7.61 (d, 2H, J=8.6 Hz), 8.22 (d, 2H, J=8.6 Hz).

Step 4: (5R),(6Z)-6-(7-Benzyl-5,6,7,8-tetrahydroimidazo[1,2-a]pyrazin-2-ylmethylene)-7-oxo-4-thia-1-azabicyclo[3.2.0]hept-2-ene-2-carboxylic acid, sodium salt (5R,6RS)-6-[(RS)-Acetoxy(7-benzyl-5,6,7,8-tetrahydroimidazo[1,2-a]pyrazin-2-yl)methyl]-6-bromo-7-oxo-4-thia-1-azabicyclo[3.2.0]hept-2-ene-2-carboxylic acid 4-nitrobenzyl ester (1.27 g) was dissolved in THF (55 mL) and acetonitrile (25 mL). Freshly activated Zn dust (5.08 g) was added rapidly with 0.5 M phosphate buffer (pH 6.5, 80 mL). The reaction vessel was covered with foil to exclude light. The reaction mixture was vigorously stirred for 2 h at room temperature. The reaction mixture was filtered through a pad of Celite. The filtrate was washed with ethyl acetate and the aqueous layer was separated. The aqueous layer was cooled to 3° C. and 1 M NaOH was added to adjust pH to 8.0. The mixture was concentrated under high vacuum at 35° C. The concentrate was applied to Diaion HP-21 (79 mL, Mitsubishi Kasei Co. Ltd.) resin column chromatography. After adsorbing, the column was eluted with $H_2O$-MeCN (1/0~4/1). The combined fractions were concentrated under high vacuum at 35° C. and lyophilized to give the title compound as a yellow amorphous solid (390 mg, 49%, pH 7.7).

Mp 180° C. (dec); $^1H$ NMR ($D_2O$) δ 2.84~2.95 (m, 2H), 3.61 (d, 2H, J=7.2 Hz), 3.67 (s, 2H), 3.96 (t, 2H, J=5.7 Hz), 6.43 (s, 1H), 6.89 (s, 1H), 6.93 (s, 1H), 7.28~7.37 (m, 6H).

Example 21

Preparation of (5R,6Z)-7-oxo-6-{[5-(pyridin-3-ylmethyl)-4,5,6,7-tetrahydrothieno[3,2-c]pyridin-2-yl)]methylene}-7oxo-4-thia-1-azabicyclo[3.2.0]hept-2-ene-2-carboxylic acid

Step 1: 2-Formyl [5-(pyridin-3-ylmethyl)-4,5,6,7-tetrahydrothieno][3,2-c]pyridine To a stirred solution of 2-(formyl)-6,7-dihydrothieno[3,2-c]-5(4H)-pyridine (1.05 g, 5.2 mmol) in DMF (20 ml), 3-picolyl chloride hydrochloride (0.852 g, 5.2 mmol) and N,N-diisopropylethylamine (10 ml, excess) was added at room temperature. The reaction mixture was stirred for 24 hrs and quenched with water. The reaction mixture was extracted with chloroform; washed well with water and dried over anhydrous $MgSO_4$. It was filtered and concentrated. The product was purified by $SiO_2$ column chromatography by eluting it with ethylacetate. Pale yellow semi-solid. Yield: 800 mg, 59%; M+H 259.

Step 2: 4-Nitrobenzy-6-[(acetyloxy)[5(pyridin-3-ylmethyl)-4,5,6,7-tetrahydrothieno[3,2-c]pyridin-2-yl)methyl]-6-bromo-7-oxo-4-thia-1-azabicyclo[3.2.0]hept-2-ene-2-carboxylate 2-Formyl [5-(pyridin-3-ylmethyl)-4,5,6,7-tetrahydrothieno][3,2-c]pyridine (516 mg, 2.0 mmol) and the dry THF solution (20 mL) of (5R,6S)-6-bromo-7-oxo-4-thia-1-aza-bicyclo[3.2.0]hept-2-ene-2-carboxylic acid 4-nitro-benzyl ester (772 mg, 2.0 mmol) were added successively to the dry acetonitrile (15 mL) solution of anhydrous $MgBr_2:O(Et)_2$ (390 mg, 1.5 mmol) under an argon atmosphere at room temperature. After cooling to −20° C., $Et_3N$ (2.0 mL) was added in one portion. The reaction vessel was covered with foil to exclude light. The reaction mixture was stirred for 2 h at −20° C. and treated with acetic anhydride (1.04 mL) in one portion. The reaction mixture was warmed to 0° C. and stirred for 15 h at 0° C. The mixture was diluted with ethyl acetate and washed with 5% citric acid aqueous solution, saturated sodium hydrogen carbonate, and brine. The organic layer was dried ($MgSO_4$) and filtered through a pad of Celite. The pad was washed with ethyl acetate. The filtrate was concentrated under reduced pressure. The residue was applied to silica gel column chromatography, then the column was eluted with ethyl acetate:hexane (1:1). Collected fractions were concentrated under reduced pressure and the mixture of diastereo isomers were taken to next step. Pale yellow amorphous solid; Yield: 700 mg, 51%; M+H 685 and 687.

Step-3: (5R,6Z)-6-{[5-(pyridin-3-ylmethyl)-4,5,6,7-tetrahydrothieno[3,2-c]pyridin-2-yl)]methylene}-7oxo-4-thia-1-azabicyclo[3.2.0]hept-2-ene-2-carboxylic acid 4-Nitrobenzy-6-[(acetyloxy)[5(pyridin-3-ylmethyl)-4,5,6,7-tetrahydrothieno[3,2-c]pyridin-2-yl)methyl]-6-bromo-7-oxo-4-thia-1-azabicyclo[3.2.0]hept-2-ene-2-carboxylate (686 mg, 1.0 mmol) was dissolved in THF (20 mL) and acetonitrile (10 mL). Freshly activated Zn dust (5.2 g) was added rapidly with 0.5 M phosphate buffer (pH 6.5, 28 mL). The reaction vessel was covered with foil to exclude light. The reaction mixture was vigorously stirred for 2 h at room temperature. The reaction mixture was filtered, cooled to 3° C., and 0.1 M NaOH was added to adjust pH to 8.5. The filtrate was washed with ethyl acetate and the aqueous layer was separated. The aqueous layer was concentrated under high vacuum at 35° C. to give yellow precipitate. The product was purified by HP21 resin reverse phase column chromatography. Initially the column was eluted with deionized water (2 lits) and latter with 10% CAN:Water. The fractions containing the product were collected and concentrated at reduced pressure at room temperature. The yellow solid was washed with acetone and filtered. Dried. Yield: 50 mg, 12%; as yellow crystals; mp. 134-136° C.; (M+H) 412.

$^1$H NMR (DMSO-$d_6$) δ d 2.8 (m, 2H), 2.92 (bm, 2H), 3.6 (m, 2H), 3.86 (s, 2H), 6.3 (s, 1H), 6.41 (s, 1H), 7.17 (s, 1H), 7.29 (s, 1H), 7.35 (m, 1H), 7.7 (m, 1H), 8.48 (d, 1H), 8.54 (s, 1H).

Example 22

Preparation of (5R,6Z)-7-oxo-6-{[5-(pyridin-3-ylcarbonyl)-4,5,6,7-tetrahydrothieno[3,2-c]pyridin-2-yl)]methylene}-7oxo-4-thia-1-azabicyclo[3.2.0]hept-2-ene-2-carboxylic acid Step 1: 2-Formyl [5-(pyridin-3-ylcarbonyl)-4,5,6,7-tetrahydrothieno][3,2-c]pyridine To a stirred solution of 2-(formyl)-6,7-dihydrothieno[3,2-c]-5(4H)-pyridine (606 mg, 3.0 mmol) in DMF (20 ml), nicotinoyl chloride hydrochloride (531 mg, 3.0 mmol) and N,N-diisopropylethylamine (10 ml, excess) was added at room temperature. The reaction mixture was stirred for 24 hrs and quenched with water. The reaction mixture was extracted with chloroform; washed well with water and dried over anhydrous MgSO$_4$. It was filtered and concentrated. The product was purified by SiO$_2$ column chromatography by eluting it with ethylacetate. Pale yellow semi-solid. Yield: 600 mg, 73%; M+H 273.

Step 2: 4-Nitrobenzy-6-[(acetyloxy)[5(pyridin-3-ylcarbonyl)-4,5,6,7-tetrahydrothieno[3,2-c]pyridin-2-yl)carbonyl]-6-bromo-7-oxo-4-thia-1-azabicyclo[3.2.0]hept-2-ene-2-carboxylate 2-Formyl [5-(pyridin-3-ylcarbonyl)-4,5,6,7-tetrahydrothieno][3,2-c]pyridine (400 mg, 1.4 mmol) and the dry THF solution (20 mL) of (5R,6S)-6-bromo-7-oxo-4-thia-1-aza-bicyclo[3.2.0]hept-2-ene-2-carboxylic acid 4-nitro-benzyl ester (772 mg, 2.0 mmol) were added successively to the dry acetonitrile (15 mL) solution of anhydrous MgBr$_2$:O(Et)$_2$ (619 mg, 2.4 mmol) under an argon atmosphere at room temperature. After cooling to −20° C., Et$_3$N (2.0 mL) was added in one portion. The reaction vessel was covered with foil to exclude light. The reaction mixture was stirred for 2 h at −20° C. and treated with acetic anhydride (1.04 mL) in one portion. The reaction mixture was warmed to 0° C. and stirred for 15 h at 0° C. The mixture was diluted with ethyl acetate and washed with 5% citric acid aqueous solution, saturated sodium hydrogen carbonate, and brine. The organic layer was dried (MgSO$_4$) and filtered through a pad of Celite. The pad was washed with ethyl acetate. The filtrate was concentrated under reduced pressure. The residue was applied to silica gel column chromatography, then the column was eluted with ethyl acetate:hexane (1:1). Collected fractions were concentrated under reduced pressure and the mixture of diastereo isomers were taken to next step. Pale yellow amorphous solid; Yield: 300 mg, 30%; M.pt. 71° C.; M+H 701.

Step-3: (5R,6Z)-6-{[5-(pyridin-3-ylcarbonyl)-4,5,6,7-tetrahydrothieno[3,2-c]pyridin-2-yl)]methylene}-7oxo-4-thia-1-azabicyclo[3.2.0]hept-2-ene-2-carboxylic acid sodium salt 4-Nitrobenzy-6-[(acetyloxy)[5(pyridin-3-ylcarbonyl)-4,5,6,7-tetrahydrothieno[3,2-c]pyridin-2-yl)methyl]-6-bromo-7-oxo-4-thia-1-azabicyclo[3.2.0]hept-2-ene-2-carboxylate (800 mg, 1.14 mmol) was dissolved in THF (20 mL) and acetonitrile (10 mL). Freshly activated Zn dust (5.2 g) was added rapidly with 0.5 M phosphate buffer (pH 6.5, 28 mL). The reaction vessel was covered with foil to exclude light. The reaction mixture was vigorously stirred for 2 h at room temperature. The reaction mixture was filtered, cooled to 3° C., and 0.1 M NaOH was added to adjust pH to 8.5. The filtrate was washed with ethyl acetate and the aqueous layer was separated. The aqueous layer was concentrated under high vacuum at 35° C. to give yellow precipitate. The product was purified by HP21 resin reverse phase column chromatography. Initially the column was eluted with deionized water (2 lits) and latter with 10% CAN:Water. The fractions containing the product were collected and concentrated at reduced pressure at room temperature. The yellow solid was washed with acetone and filtered. Dried. Yield: 50 mg, 12%; as yellow crystals; mp. 195° C.; (M+H) 426.

Example 23

Preparation of (5R,6Z)-7-oxo-6-{[5-(phenylacetyl)-4,5,6,7-tetrahydrothieno[3,2-c]pyridin-2-yl)]methylene}-7oxo-4-thia-1-azabicyclo[3.2.0]hept-2-ene-2-carboxylic acid Step 1: 2-Formyl [5-(phenylacetyl)-4,5,6,7-tetrahydrothieno][3,2-c]pyridine To a stirred solution of 2-(formyl)-6,7-dihydrothieno[3,2-c]-5(4H)-pyridine (0.41 mg, 2 mmol) in DMF (20 ml), phenyl acetyl chloride (0.35 mg, 2.2 mmol) and N,N-diisopropylethylamine (10 ml, excess) was added at room temperature. The reaction mixture was stirred for 24 hrs and quenched with water. The reaction mixture was extracted with chloroform; washed well with water and dried over anhydrous MgSO$_4$. It was filtered and concentrated. The product was purified by SiO$_2$ column chromatography by eluting it with ethylacetate. White solid. Yield: 510 mg, 89%; M+H 286.

Step 2: 4-Nitrobenzy-6-[(acetyloxy)[5(phenylacetyl)-4,5,6,7-tetrahydrothieno[3,2-c]pyridin-2-yl)methyl]-6-bromo-7-oxo-4-thia-1-azabicyclo[3.2.0]hept-2-ene-2-carboxylate 2-Formyl [5-(phenylacetyl)-4,5,6,7-tetrahydrothieno][3,2-c]pyridine (340 mg, 1.2 mmol) and the dry THF solution (20 mL) of (5R,6S)-6-bromo-7-oxo-4-thia-1-aza-bicyclo[3.2.0]hept-2-ene-2-carboxylic acid 4-nitro-benzyl ester (390 mg, 1.0 mmol) were added successively to the dry acetonitrile (15 mL) solution of anhydrous MgBr$_2$:O(Et)$_2$ (310 mg, 1.2 mmol) under an argon atmosphere at room temperature. After cooling to −20° C., Et$_3$N (2.0 mL) was added in one portion. The reaction vessel was covered with foil to exclude light. The reaction mixture was stirred for 2 h at −20° C. and treated with acetic anhydride (1.04 mL) in one portion. The reaction mixture was warmed to 0° C. and stirred for 15 h at 0° C. The mixture was diluted with ethyl acetate and washed with 5% citric acid aqueous solution, saturated sodium hydrogen carbonate, and brine. The organic layer was dried (MgSO$_4$) and filtered through a pad of Celite. The pad was washed with ethyl acetate. The filtrate was concentrated under reduced pressure. The residue was applied to silica gel column chromatography, then the column was eluted with ethyl acetate:hexane (1:1). Collected fractions were concentrated under reduced pressure and the mixture of diastereo isomers were taken to next step. Pale yellow amorphous solid; Yield: 360 mg, 50%; M+H 713.

Step-3: (5R,6Z)-6-{[5-(phenylacetyl)-4,5,6,7-tetrahydrothieno[3,2-c]pyridin-2-yl)]methylene}-7oxo-4-thia-1-azabicyclo[3.2.0]hept-2-ene-2-carboxylic acid 4-Nitrobenzy-6-[(acetyloxy)[5(phenylacetyl)-4,5,6,7-tetrahydrothieno[3,2-c]pyridin-2-yl)methyl]-6-bromo-7-oxo-4-thia-1-azabicyclo[3.2.0]hept-2-ene-2-carboxylate (300 mg, 0.4 mmol) was dissolved in THF (50 mL) and 0.5 M phosphate buffer (pH 6.5, 28 mL). This was hydrogenated at 40 psi pressure, in the presence of 10% Pd/C (80 mg) for 2 hrs. at the end, reaction mixture was filtered through a pad of celite and concentrated. The separated yellow solid was dissolved in ethyl acetate and washed well with water. The organic layer was dried and concentrated. The separated yellow solid was triturated with diethyl ether and filtered. The yellow solid was washed well with diethyl ether and it was found to be 95% pure compound. Yield: 160 mg, 91%; Yellow solid; mp. 166-169° C.; (M+H) 439.

Example 24

Preparation of (5R),(6Z)-6-(5,5-Dioxo-4,5,6,7-tetrahydro-5λ$^6$-pyrazolo[5,1-c][1,4]thiazin-2-ylmethylene)-7-oxo-4-thia-1-azabicyclo[3.2.0]hept-2-ene-2-carboxylic acid, sodium salt Step 1: 5,5-Dioxo-4,5,6,7-tetrahydro-5λ$^6$-pyrazolo[5,1-c][1,4]thiazine-2-carbaldehyde m-Chloroperbenzoic acid (cont. 69%) (6.36 g) was added to the CH$_2$Cl$_2$ (111 mL) solution of 6,7-dihydro-4H-pyrazolo[5,1-c][1,4]thiazine-2-carbaldehyde (1.86 g) at 0° C. The reaction mixture was stirred for 0.5 h at the same temperature and stirred for 18 h at room temperature. The reaction mixture was concentrated under reduced pressure. The residue was triturated with 10 mL of THF and filtered to obtain crystals. The filtrate was concentrated under reduced pressure. The residue was triturated with 5 mL of THF and filtered to obtain crystals. The combined crystals were dried under reduced pressure to give the titled compound as colorless crystals (1.96 g, 89%).

$^1$H NMR (CDCl$_3$) δ 3.60 (t, 2H, J=6.1 Hz), 4.47 (s, 2H), 4.87 (t, 2H, J=6.1 Hz), 6.71 (s, 1H), 9.94 (s, 1H).

Step 2: (5R,6RS)-6-[(RS)-Acetoxy-(5,5-dioxo-4,5,6,7-tetrahydro-5λ$^6$-pyrazolo[5,1-c][1,4]thiazin-2-yl)-methyl]-6-bromo-7-oxo-4-thia-1-azabicyclo[3.2.0]hept-2-ene-2-carboxylic acid 4-nitrobenzyl ester 5,5-Dioxo-4,5,6,7-tetrahydro-5λ$^6$-pyrazolo[5,1-c][1,4]thiazine-2-carbaldehyde (1.95 g) was added to the dry acetonitrile (112 mL) solution of anhydrous MgBr$_2$ (cont. 98%) (5.48 g) under a nitrogen atmosphere at room temperature. The dry THF solution (112 mL) of (5R,6S)-6-bromo-7-oxo-4-thia-1-azabicyclo[3.2.0]hept-2-ene-2-carboxylic acid 4-nitrobenzyl ester (cont. 96.5%) (3.88 g) was added to the mixture, cooled to –20° C., and Et$_3$N (cont. 99%) (3.79 mL) was added in one portion. The reaction vessel was covered with foil to exclude light. The reaction mixture was stirred for 3 h at –20° C. and treated with acetic anhydride (cont. 97%) (3.79 mL) and DMAP (cont. 99%) (120 mg) in one portion. The reaction mixture was warmed to 0° C. and stirred for 16 h at 0° C. To the reaction mixture was added acetic anhydride (cont. 97%) (0.95 mL) and DMAP (cont. 99%) (120 mg) in one portion. The mixture was diluted with ethyl acetate and washed with 5% citric acid aqueous solution, saturated sodium hydrogen carbonate and brine. The organic layer was dried (MgSO$_4$), followed by concentration under reduced pressure. The residue was purified with a silica-gel column chromatography (CHCl$_3$:acetone=19:1-4:1) to give the titled compound as a pale brown amorphous solid (diastereo-mixture (8:2), 1.35 g, 22%).

$^1$H NMR (CDCl$_3$) δ 2.07 (s, 3H×0.2), 2.25 (s, 3H×0.8), 3.45-3.60 (m, 2H), 4.39 (d, 1H, J=17.0 Hz), 4.44 (d, 1H, J=17.0 Hz), 4.65-4.78 (m, 2H), 5.28 (d, 1H, J=13.5 Hz), 5.43 (d, 1H×0.8, J=13.5 Hz), 5.44 (d, 1H×0.2, J=13.5 Hz), 6.05 (s, 1H×0.8), 6.20 (s, 1H×0.8), 6.22 (s, 1H×0.2H), 6.38 (s, 1H×0.2), 6.39 (s, 1H×0.2), 6.79 (s, 1H×0.8), 7.42 (s, 1H×0.8), 7.44 (s, 1H×0.2), 7.60 (d, 2H, J=8.7 Hz), 8.24 (d, 2H, J=8.7 Hz).

Step 3: (5R),(6Z)-6-(5,5-Dioxo-4,5,6,7-tetrahydro-5λ$^6$-pyrazolo[5,1-c][1,4]thiazin-2-ylmethylene)-7-oxo-4-thia-1-azabicyclo[3.2.0]hept-2-ene-2-carboxylic acid, sodium salt (5R,6RS)-6-[(RS)-Acetoxy-(5,5-dioxo-4,5,6,7-tetrahydro-5□$^6$-pyrazolo[5,1-c][1,4]-thiazin-2-yl)-methyl]-6-bromo-7-oxo-4-thia-1-azabicyclo[3.2.0]hept-2-ene-2-carboxylic acid 4-nitrobenzyl ester (1.33 g) was dissolved in THF (19 mL) and acetonitrile (9 mL). Freshly activated Zn dust (5.32 g) was added rapidly with 0.5 M phosphate buffer (pH 6.5, 27 mL). The reaction vessel was covered with foil to exclude light. The reaction mixture was vigorously stirred for 1.5 h at room temperature. The insoluble material was filtered off and was washed with H$_2$O (27 mL). The filtrate was added H$_2$O (27 mL) and washed with ethyl acetate (27 mL) and the aqueous layer was cooled to 3° C. and 1 M HCl was added to adjust pH to 2.5. The mixture was stirred for 1 d at the same temperature and added H$_2$O (55 mL), then stirred for 4 d at the same temperature. The mixture was stirred for 10 h at room temperature. The resultant mixture was cooled to 3° C. and 1 M NaOH was added to adjust pH to 8. The mixture was concentrated under high vacuum at 35° C. The concentrate was treated to Diaion HP-21 (80 mL, Mitsubishi Kasei Co. Ltd.) resin column chromatography. After adsorbing, the column was eluted with H$_2$O-MeCN (1/0-9/1). The combined fractions were concentrated under high vacuum at 35° C. and lyophilized to give the title compound as a yellow amorphous solid (306 mg, 38%, pH 7.4).

Mp 180° C. (dec); $^1$H NMR (D$_2$O) δ 3.83 (t, 2H, J=6.1 Hz), 4.68 (s, 2H), 4.72 (t, 2H, J=6.1 Hz), 6.37 (s, 1H), 6.40 (s, 1H), 6.95 (s, 1H), 6.98 (s, 1H).

Example 25

Preparation of (5R),(6Z)-7-Oxo-6-(4,5,6,7-tetrahydropyrazolo[1,5-a]pyrazin-2-ylmethylene)-4-thia-1-aza-bicyclo[3.2.0]hept-2-ene-2-carboxylic acid, sodium salt Piperazine-2-carboxylic acid, dihydrochloride The titled compound was prepared in the same way of M. T. Wu and co-workers (*Bioorg. Med. Chem. Lett.* 1993, 3, 2023-2028).

Step 1: piperazine-1,3-dicarboxylic acid 1-(4-nitrobenzyl) ester $CuCO_3.Cu(OH)_2.H_2O$ (15.8 g) was added to the $H_2O$ (275 mL) solution of piperazine-2-carboxylic acid, dihydrochloride (22.3 g), then the mixture was refluxed and stirred for 10 min. The insoluble material was filtered off and was washed with hot $H_2O$ (165 mL). The filtrate was cooled to room temperature, and $NaHCO_3$ (9.2 g) and 1,4-dioxane (220 mL) was added to the dark blue solution. The mixture was cooled to 0° C. and $NaHCO_3$ (18.5 g) and 50% solution of 4-nitrobenzyl chloroformate in 1,4-dioxane (61.7 g) was added to the mixture for 0.5 h. After stirring for additional 1.5 h at 0° C., the precipitate was filtered and washed with cold $H_2O$ (140 mL), EtOH (100 mL), acetone (200 mL) and $Et_2O$ (100 mL), then it was allowed to dry under reduced pressure to obtain the pale blue crystals. The crystals were added to the 1 mol/L HCl (330 mL) solution of EDTA.2Na (20.5 g) for 30 min, and stirred for 2 h at room temperature. The suspension was filtered and the filtered material was diluted with EtOH—$H_2O$ (7:3, 550 mL) and refluxed for 10 min. The reaction mixture was filtered to obtain the colorless crystals. The recrystallization from the filtrate was carried out 3 times to obtain additional crystals. The combined crystals were dried under reduced pressure to obtain the titled compound (26.25 g, 77%) as colorless crystals.

$^1$H NMR ($D_2O$) δ 2.54-2.61 (m, 1H), 2.89 (dt, 2H, J=12.7, 3.4 Hz), 2.97 (br, 1H), 3.13 (br, 1H), 3.62-4.04 (m, 2H), 5.16 (s, 2H), 7.49 (d, 2H, J=8.6 Hz), 8.14 (d, 2H, J=8.6 Hz).

Step 2: 5-(4-Nitrobenzyloxycarbonyl)-3-oxo-3a,4,6,7-tetrahydro-3H-2-oxa-1,5-diaza-7a-azoniainden-3a-ide The $H_2O$ (300 mL) solution of $NaNO_2$ (cont. 98.5%) (6.66 g) was added to the acetic acid (864 mL) solution of piperazine-1,3-dicarboxylic acid 1-(4-nitrobenzyl) ester (26.72 g) under a nitrogen atmosphere at 0° C. for 0.5 h and stirred for 1 h. In addition, the $H_2O$ (132 mL) solution of $NaNO_2$ (cont. 98.5%) (2.41 g) was added to the solution at 0° C. for 0.5 h and stirred for 1 h. The solution was concentrated under reduced pressure and $H_2O$ (500 mL) was added to the residue. The solution was extracted with AcOEt (5 times) and organic layer was washed with brine. The mixture was dried over $MgSO_4$, filtered and concentrated under reduced pressure to afford crude 4-nitrosopiperazine-1,3-dicarboxylic acid 1-(4-nitrobenzyl) ester as pale brown amorphous (27.83 g (gross), 25.77 g (net), 88.2%).

The THF (10 mL) solution of trifluoroacetic anhydride (24.0 g) was added to the THF (371 mL) solution of crude 4-nitrosopiperazine-1,3-dicarboxylic acid 1-(4-nitrobenzyl) ester under a nitrogen atmosphere at 0° C. for 15 min. The solution was stirred for 1.5 h at 0° C. and for 1 h at room temperature. The THF (5 mL) solution of trifluoroacetic anhydride (8.0 g) was added to the solution for 5 min and stirred for 20 h at room temperature. To the solution was added trifluoroacetic anhydride (8.0 g) for 5 min and the solution was stirred for 4 h. The precipitate was filtered and washed with THF and $Et_2O$. The filtrate was concentrated under reduced pressure. The residue was triturated with THF, filtered and washed with $Et_2O$. These materials were combined and dried under reduced pressure to afford the titled compound as colorless crystals (22.3 g, 91%).

$^1$H NMR ($CDCl_3$) δ 4.06 (t, 2H, J=5.4 Hz), 4.37 (t, 2H, J=5.4 Hz), 4.63 (s, 2H), 5.30 (s, 2H), 7.54 (d, 2H, J=8.7 Hz), 8.25 (d, 2H, J=8.7 Hz).

Step 3: 6,7-Dihydro-4H-pyrazolo[1,5-a]pyrazine-2,5-dicarboxylic acid 2-ethyl ester 5-(4-nitrobenzyl) ester Ethyl propiolate (cont. 99%) (8.28 g) was added to the o-xylene (348 mL) solution of 5-(4-nitrobenzyloxycarbonyl)-3-oxo-3a,4,6,7-tetrahydro-3H-2-oxa-1,5-diaza-7a-azoniainden-3a-ide (22.3 g) under a nitrogen atmosphere and refluxed for 16 h. The solution was concentrated under reduced pressure, followed by silica-gel column chromatography 3 times (n-hexane/AcOEt=2/1-1/3). The titled compound was obtained as pale yellow crystals (16.78 g, 64%). Besides, 6,7-dihydro-4H-pyrazolo[1,5-a]pyrazine-3,5-dicarboxylic acid 3-ethyl ester 5-(4-nitrobenzyl) ester was obtained as pale yellow crystals (6.18 g, 24%).

$^1$H NMR ($CDCl_3$) δ 1.39 (t, 3H, J=7.1 Hz), 4.01 (t, 2H, J=5.5 Hz), 4.31 (t, 2H, J=5.5 Hz), 4.40 (q, 2H, J=7.1 Hz), 4.79 (s, 2H), 5.29 (s, 2H), 6.64 (s, 1H), 7.54 (d, 2H, J=8.6 Hz), 8.24 (d, 2H, J=8.6 Hz).

Step 4: 2-Hydroxymethyl-6,7-dihydro-4H-pyrazolo[1,5-a]pyrazine-5-carboxylic acid 4-nitrobenzyl ester $LiBH_4$ (640 mg) and MeOH (1.2 mL) was added to the THF (267 mL) solution of 6,7-dihydro-4H-pyrazolo[1,5-a]pyrazine-2,5-dicarboxylic acid 2-ethyl ester 5-(4-nitrobenzyl) ester (10 g) under a nitrogen atmosphere at room temperature and stirred for 3 h at 40° C. Additional $LiBH_4$ (523 mg) and MeOH (1.0 mL) was added to the solution and stirred for 1 h at 40° C. and 1 h at 50° C. The mixture was acidified with 3 mol/L HCl to pH 2 and stirred for 1 h at room temperature, then solid $K_2CO_3$ was added to the solution to adjust pH to 8. The insoluble material was filtered off and the filtrate was extracted with AcOEt. The organic layer was dried ($K_2CO_3$), and concentrated under reduced pressure. The residue was purified with silica gel column chromatography ($CHCl_3$/MeOH=49/1-19/1) to afford titled compound as pale yellow crystals (8.44 g, 95%).

$^1$H NMR ($CDCl_3$) δ1.69 (br, 1H), 3.98 (t, 2H, J=5.5 Hz), 4.19 (t, 2H, J=5.5 Hz), 4.65 (s, 2H), 4.75 (s, 2H), 5.28 (s, 2H), 6.08 (s, 1H), 7.53 (d, 2H, J=8.7 Hz), 8.24 (d, 2H, J=8.7 Hz).

Step 5: 2-Formyl-6,7-dihydro-4H-pyrazolo[1,5-a]pyrazine-5-carboxylic acid 4-nitrobenzyl ester $MnO_2$ (activated) (84.2 g) was added to the $CHCl_3$-MeOH (95:5, 253 mL) solution of 2-hydroxymethyl-6,7-dihydro-4H-pyrazolo[1,5-a]pyrazine-5-carboxylic acid 4-nitrobenzyl ester (8.42 g), and the mixture was refluxed for 1 h under a nitrogen atmosphere. The reaction mixture was filtered through a pad of Celite. Silica-gel (20 g) was added to the filtrate and the solvent was removed under reduced pressure to give the silica-gel coating with crude reactant. The above silica-gel was adsorbed to silica-gel column chromatography and the column was eluted with CHCl$_3$-MeOH (49/1 to 19/1). The titled compound was obtained as yellow crystals (2.82 g, 34%).

$^1$H NMR (CDCl$_3$) δ 4.05 (t, 2H, J=5.5 Hz), 4.32 (t, 2H, J=5.5 Hz), 4.81 (s, 2H), 5.29 (s, 2H), 6.62 (s, 1H), 7.54 (d, 2H, J=8.7 Hz), 8.24 (d, 2H, J=8.7 Hz), 9.93 (s, 1H).

Step 6; 2-{(RS)-Acetoxy-[(5R,6RS)-6-bromo-2-(4-nitrobenzyloxycarbonyl)-7-oxo-4-thia-1-azabicyclo[3.2.0]hept-2-en-6-yl]-methyl}-6,7-dihydro-4H-pyrazolo[1,5-a]pyrazine-5-carboxylic acid 4-nitrobenzyl ester 2-Formyl-6,7-dihydro-4H-pyrazolo[1,5-a]pyrazine-5-carboxylic acid 4-nitrobenzyl ester (2.71 g) was added to the dry acetonitrile (164 mL) solution of anhydrous MgBr$_2$ (cont. 98%) (6.17 g) under a nitrogen atmosphere at room temperature. The dry THF solution (164 mL) of (5R,6S)-6-bromo-7-oxo-4-thia-1-azabicyclo[3.2.0]hept-2-ene-2-carboxylic acid 4-nitrobenzyl ester (cont. 96.5%) (3.27 g) was added to the mixture, cooled to −20° C., and Et$_3$N (cont. 99%) (9.24 mL) was added in one portion. The reaction vessel was covered with foil to exclude light. The reaction mixture was stirred for 1.5 h at −20° C. and treated with acetic anhydride (cont. 97%) (3.19 mL) and DMAP (cont. 99%) (203 mg) in one portion. The reaction mixture was warmed to 0° C. and stirred for 1 h at 0° C. Acetic anhydride (3.19 mL) was added to the solution and stirred for 15 h at 0° C. The mixture was diluted with ethyl acetate and washed with 5% citric acid aqueous solution, saturated sodium hydrogen carbonate, water and brine. The organic layer was dried (MgSO$_4$), followed by concentration under reduced pressure. The residue was purified with silica-gel column chromatography three times (n-hexane-AcOEt (1/1 to 2/3), CHCl$_3$-acetone (29/1 to 19/1) and CHCl$_3$-acetone (29/1)). The titled compound was obtained as yellow amorphous (diastereo-mixture (64:36), 3.30 g, 53%).

$^1$H NMR (CDCl$_3$) δ 2.06 (s, 3H×0.36), 2.26 (s, 3H×0.64), 3.95-4.04 (m, H), 4.18 (s, 2H), 4.73 (d, 1H, J=18.2 Hz), 4.78 (d, 1H, J=18.2 Hz), 5.28 (d, 1H, J=13.5 Hz), 5.28 (s, 2H), 5.43 (d, 1H×0.64, J=13.5 Hz), 5.44 (d, 1H×0.36), 6.06 (s, 1H×0.64), 6.08 (s, 1H×0.64), 6.24 (s, 1H×0.36), 6.27 (s, 1H×0.36), 6.41 (s, 1H×0.36), 6.79 (s, 1H×0.64), 7.42 (s, 1H×0.64), 7.44 (s, 1H×0.36), 7.53 (d, 2H, J=8.6 Hz), 7.60 (d, 2H, J=8.8 Hz), 8.24 (d, 2H, J=8.8 Hz), 8.24 (d, 2H, J=8.6 Hz).

Step 7: (5R),(6Z)-7-Oxo-6-(4,5,6,7-tetrahydropyrazolo[1,5-a]pyrazin-2-ylmethylene)-4-thia-1-aza-bicyclo[3.2.0]hept-2-ene-2-carboxylic acid, sodium salt To the THF (43 mL) and acetonitrile (20 mL) solution of 2-{(RS)-acetoxy-[(5R,6RS)-6-bromo-2-(4-nitrobenzyloxycarbonyl)-7-oxo-4-thia-1-azabicyclo[3.2.0]hept-2-en-6-yl]-methyl}-6,7-dihydro-4H-pyrazolo[1,5-a]pyrazine-5-carboxylic acid 4-nitrobenzyl ester was added Zn dust (12.36 g) rapidly with 0.5 M phosphate buffer (pH 6.5, 63 mL). The reaction vessel was covered with foil to exclude light. The reaction mixture was vigorously stirred for 1.5 h at room temperature. The insoluble material was filtered off and was washed with H$_2$O (63 mL). The filtrate was washed with ethyl acetate (63 mL) and the aqueous layer was cooled to 3° C. and 1 M HCl was added to adjust pH to 2.5. The mixture was stirred for 4 h at the same temperature and added H$_2$O (63 mL) and 1 M HCl to adjust pH to 2.5, then stirred for 17 h at the same temperature. To the mixture was added 1 M NaOH to adjust pH to 8. The mixture was concentrated under high vacuum at 35° C. The concentrate was treated to Diaion HP-21 (124 mL, Mitsubishi Kasei Co. Ltd.) resin column chromatography. After adsorbing, the column was eluted with H$_2$O-MeCN (1/0-95/5). The combined fractions were concentrated under high vacuum at 35° C. and lyophilized to give the title compound as a yellow amorphous solid (288 mg, 22%, pH 8.8).

Mp 160° C. (dec); $^1$H NMR (D$_2$O) δ 2.94 (t, 2H, J=5.6 Hz), 3.67 (d, 1H, J=17.2 Hz), 3.70 (d, 1H, J=17.2 Hz), 3.82 (t, 2H, J=5.6 Hz), 5.84 (s, 1H), 6.03 (s, 1H), 6.65 (s, 1H), 6.67 (s, 1H).

Example 26

Preparation of (5R)(6Z)-6-(5,5-Dimethyl-4H-1,6a-diazapentalen-2-ylmethylene)-7-oxo-4-thia-1-azabicyclo[3.2.0]hept-2-ene-2-carboxylic acid, sodium salt 5,5-Dimethyl-2-piperidone 5-5-Dimethyl-2-piperadinone was prepared in the method of Nagasawa (J. Med. Chem., 20, 1176 (1977)).

Step 1: 3,3-Dichloro-5,5-dimethyl-2-piperidone

To a cold (0° C.) stirred solution of 5,5-dimethyl-2-piperidone (30.2 g, 0.24 mol) in 475 mL of CHCl$_3$, PCl$_5$ (57.1 g, 0.26 mol) was added at such a rate that the temperature never exceeded 7° C. After the addition was complete, stirring was continued for 10 min. Sulfuryl chloride (96.6 g, 0.72 mol) was slowly added and the mixture was heated under reflux for 1 h. The solution was concentrated under reduced pressure. The residue was cooled in ice and diluted with 250 mL of ice-water. The product was then extracted with CHCl$_3$ (6×250 mL) and the organic layer was dried (MgSO$_4$) and filtered. The filtrate was concentrated under reduced pressure. The residue was applied to silica-gel column chromatography, and then the column was eluted with CHCl$_3$-MeOH (50:1). The titled compound was obtained as a white solid (41.3 g, 88.8%). (J. Med. Chem., 20, 1176 (1977))

$^1$H NMR (CDCl$_3$) δ 1.17 (s, 6H), 2.76 (s, 2H), 3.19 (d, 2H, J=3.0 Hz), 6.82 (brs, 1H).

Step 2: 3-Chloro-5,5-dimethyl-2-piperidone

To 40.8 g (0.21 mol) of 3,3-dichloro-5,5-dimethyl-2-piperidone dissolved in 410 mL of AcOH was added 10% Pd/C (50% wet, 6.2 g) and NaOAc-3H$_2$O (62.4 g, 0.46 mol) and the mixture was hydrogenated at 300 kPa for 20 min. The pressure of hydrogen was adjusted at 300 kPa every 5 min. The catalyst was removed by filtration and the filtrate concentrated under reduced pressure. CHCl$_3$ (400 mL) and water (300 mL) were added to the residue and the aqueous layer was neutralized with 4 mol/L NaOH. The mixture was separated and the aqueous layer was extracted with CHCl$_3$ (5×300 mL) and the organic layer was dried (MgSO$_4$) and filtered. The filtrate was concentrated under reduced pressure. The residue was applied to silica-gel column chromatography, and then the column was eluted with hexane-AcOEt (1:1). The titled compound was obtained as a white solid (20.4 g, 59.9%). (J. Med. Chem., 20, 1176 (1977))

$^1$H NMR (CDCl$_3$) δ 1.10 (s, 3H), 1.12 (s, 3H), 2.02 (dd, 1H, J=10.8, 13.6 Hz), 2.20 (ddd, 1H, J=2.2, 6.7, 13.6 Hz), 2.97 (ddd, 1H, J=2.3, 3.9, 12.1 Hz), 3.22 (d, 1H, J=12.1 Hz), 4.44 (dd, 1H, J=6.8, 10.7 Hz), 6.66 (brs, 1H).

Step 3: 4,4-Dimethylpyrrolidine-2-carboxylic acid

A suspension of 20.4 g (0.13 mol) of 3-chloro-5,5-dimethyl-2-piperidone and 45.2 g (0.14 mol) of Ba(OH)$_3$·8H$_2$O in 252 mL of water was heated in a Parr apparatus at 150° C. for 6 h. Then, 18.6 g (0.14 mol) of ammonium sulphate were added. The precipitate was filtered off, and the solution was concentrated under reduced pressure to dryness. Crude 4,4-dimethylpyrrolidine-2-carboxylic acid was obtained as a white solid (37.5 g). (*J. Med. Chem.*, 20, 1176 (1977), EP 0 447 704 A1, page 17)

$^1$H NMR ($D_2O$) δ 1.10 (s, 3H), 1.11 (s, 3H), 1.88 (dd, 1H, J=7.8, 13.2 Hz), 2.21 (dd, 1H, J=9.2, 13.2 Hz), 3.12 (dd, 2H, J=11.5, 23.5 Hz), 4.22 (dd, 1H, J=8.1, 8.9 Hz).

Step 4: 5,5-Dimethyl-3-oxo-3a,4-dihydro-3H,6H-2-oxa-5-1-aza-6a-azonio-3a-pentalenide To a suspension of 37.5 g of the crude 4,4-dimethylpyrrolidine-2-carboxylic acid in 420 mL of AcOH was added a solution of 13.3 g (0.19 mol) of $NaNO_2$ in 210 mL of water over 15 min at room temperature and stirred for 3 h. The solution was concentrated under reduced pressure. Acetone (250 mL) was added to the residue and the precipitate was filtered off, and the solution was concentrated under reduced pressure to dryness and crude 4,4-dimethyl-1-nitrosopyrrolidine-2-carboxylic acid was obtained as brown oil.

To a solution of crude 4,4-dimethyl-1-nitrosopyrrolidine-2-carboxylic acid in 252 mL of dry THF was added trifluoroacetic anhydride (81.3 g, 0.39 mol) under a nitrogen atmosphere at 0° C. and stirred for 6 h at 0° C. The solution was concentrated under reduced pressure. The residue was applied to silica-gel column chromatography, and then the column was eluted with n-hexane-AcOEt (2:1). The titled compound was obtained as a brown solid (12.0 g, 61.7%).

$^1$H NMR ($CDCl_3$) δ 1.38 (s, 6H), 2.71 (s, 2H), 4.12 (s, 2H).

Step 5: 5,5-Dimethyl-5,6-dihydro-4H-pyrrolo[1,2-b]pyrazole-2-carboxylic acid ethylester A solution of 5,5-dimethyl-3-oxo-3a,4-dihydro-3H,6H-2-oxa-5-1-aza-6a-azonio-3a-pentalenide (10.8 g, 0.07 mol) and ethyl propiolate (10.8 mL, 0.11 mol) in o-xylene (350 mL) was refluxed under a nitrogen atmosphere for 16 h. The solution was cooled to room temperature and concentrated under reduced pressure. The residue was applied to silica gel column chromatography, and then the column was eluted with n-hexane-AcOEt (3:1). The titled compound was obtained as a pale brown solid (4.63 g, 31.7%), and 5,5-dimethyl-5,6-dihydro-4H-pyrrolo[1,2-b]pyrazole-3-carboxylic acid ethylester was obtained as a yellow solid (4.73 g, 32.4%).

5,5-Dimethyl-5,6-dihydro-4H-pyrrolo[1,2-b]pyrazole-2-carboxylic acid ethylester: $^1$H NMR ($CDCl_3$) δ 1.29 (s, 6H), 1.40 (t, 3H, J=7.1 Hz), 2.71 (s, 2H), 3.93 (s, 2H), 4.39 (q, 2H, J=7.1 Hz), 6.54 (s, 1H).

5,5-dimethyl-5,6-dihydro-4H-pyrrolo[1,2-b]pyrazole-3-carboxylic acid ethylester: $^1$H NMR ($CDCl_3$) δ 1.32 (s, 6H), 1.33 (t, 3H, J=7.1 Hz), 2.89 (s, 2H), 3.90 (s, 2H), 4.26 (q, 2H, J=7.1 Hz), 7.90 (s, 1H).

Step 6: 5,5-Dimethyl-5,6-dihydro-4H-pyrrolo[1,2-b]pyrazole-2-carbaldehyde

To 4.63 g (22.2 mmol) of 5,5-dimethyl-5,6-dihydro-4H-pyrrolo[1,2-b]pyrazole-2-carboxylic acid ethylester in 222 mL of dry THF was added $LiAlH_4$ (0.85 g, 22.3 mmol) under a nitrogen atmosphere at 0° C., and then stirred for 1 h. The mixture was quenched with water (5.0 mL) and the precipitate was filtered through a pad of Celite and the pad was washed with water (50 mL) and THF (150 mL). The filtrate was concentrated under reduced pressure, and then water (50 mL) was added. The aqueous layer was extracted with $CHCl_3$ (5×100 mL). The organic layer was dried ($MgSO_4$) and filtered. The filtrate was concentrated under reduced pressure and crude 5,5-Dimethyl-5,6-dihydro-4H-pyrrolo[1,2-b]pyrazole-2-yl)methanol was obtained as a yellow solid (3.19 g).

To 3.19 g of the crude (5,5-dimethyl-5,6-dihydro-4H-pyrrolo[1,2-b]pyrazol-2-yl)methanol in 222 mL of $CHCl_3$ was added activated $MnO_2$ (18.5 g) under a nitrogen atmosphere at room temperature, and then refluxed for 1 h. The mixture was filtered through a pad of Celite and the filtrate was concentrated under reduced pressure. The residue was applied to silica-gel column chromatography, and then the column was eluted with hexane-AcOEt (3:1). The titled compound was obtained as a brown solid (2.48 g, 68.0% from the ester).

$^1$H NMR ($CDCl_3$) δ 1.32 (s, 6H), 2.73 (s, 2H), 3.95 (s, 2H), 6.52 (s, 1H), 9.90 (s, 1H).

Step 7: (5R)(6Z)-6-(5,5-Dimethyl-4H-1,6a-diazapentalen-2-ylmethylene)-7-oxo-4-thia-1-azabicyclo[3.2.0]hept-2-ene-2-carboxylic acid, sodium salt The dry acetonitrile (16 mL) solution of 5,5-dimethyl-5,6-dihydro-4H-pyrrolo[1,2-b]pyrazole-2-carbaldehyde (2.48 g, 15.1 mmol) was added to the dry acetonitrile (90 mL) solution of $MgBr_2$ (3.07 g, 16.4 mmol) under a nitrogen atmosphere at room temperature, and then the mixture was stirred for 15 min. The dry THF (106 mL) solution of p-nitrobenzyl (5R, 6S)-6-bromopenem-3-carboxylate (5.30 g, 13.8 mmol) was added and the mixture was cooled to −20° C., and then triethylamine (4.6 mL, 33.0 mmol) was added in one portion. The reaction vessel was covered with foil to exclude light. The reaction mixture was stirred for 3 h at −20° C. and treated with 4-dimethylamino pyridine (172 mg, 1.4 mmol) and acetic anhydride (2.6 mL, 27.6 mmol) in one portion. The reaction mixture was warmed to 0° C. and stirred for 16 h at 0° C. Ethyl acetate (420 mL) and 1 mol/L citric acid aqueous solution (210 mL) was added to the reaction mixture and separated. The organic layer was washed with saturated sodium hydrogen carbonate and brine, dried ($MgSO_4$) and filtered. The filtrate was concentrated under reduced pressure and crude (5R)-6-[acetoxy-(5,5-dimethyl-4H-1,6a-diazapentalen-2-yl)methyl]-6-bromo-7-oxo-4-thia-1-azabicyclo[3.2.0]hept-2-ene-2-carboxylic acid p-nitrobenzyl ester was obtained as brown amorphous.

Freshly activated Zn dust (32.0 g) was added rapidly with 0.5 mol/L phosphate buffer (pH 6.5, 167 mL) to the THF (114 mL) and acetonitrile (53 mL) solution of crude (5R)-6-[acetoxy-(5,5-dimethyl-4H-1,6a-diazapentalen-2-yl)methyl]-6-bromo-7-oxo-4-thia-1-azabicyclo[3.2.0]hept-2-ene-2-carboxylic acid p-nitrobenzyl ester. The reaction vessel was covered with foil to exclude light. The reaction mixture was vigorously stirred for 1.5 h at room temperature. The reaction solution was cooled at 0° C., and then the pH was adjusted to 8.0. Ethyl acetate (85 mL) was added to the mixture and filtered through a pad of Celite. The pad was washed with water (120 mL). The aqueous layer was separated and then the organic layer was extracted with 0.5 mol/L phosphate buffer (pH 6.5, 2×50 mL). The combined aqueous layers were cooled at 0° C., and then the pH was adjusted to 8.5. The mixture was concentrated to 325 g, and then applied to Diaion HP-21 resin (240 mL, Mitsubishi Kasei Co. Ltd.) column chromatography. After adsorbing, the column was eluted with water (480 mL) and then acetonitrile aqueous solution (10%; 480 mL, 20%; 720 mL). The combined active fractions were concentrated under high vacuum at 35° C. and lyophilized to give the titled compound as a yellow amorphous solid (2.00 g, 42.8%, pH 7.16).

Mp 150° C. (dec); $^1$H NMR (D$_2$O) δ 1.19 (s, 6H), 2.67 (s, 2H), 3.85 (s, 2H), 6.15 (s, 1H), 6.45 (s, 1H), 6.96 (s, 1H), 7.03 (s, 1H); IR (KBr) 3422, 1752, 1683, 1598, 1557 cm$^{-1}$; λ$^{max}$ (H$_2$O) 296, 198 nm.

Example 27

Preparation of (5R),(6Z)-6-(5,6-Dihydro-4H-cyclopenta[b]furan-2-ylmethylene)-7-oxo-4-thia-1-azabicyclo[3.2.0]hept-2-ene-2-carboxylic acid, sodium salt Step 1;
5,6-Dihydro-4H-cyclopenta[b]furan-2-carboxylic acid methyl ester The titled compound was prepared according to the procedure of Tim Johnson and co-workers (Synlett 2001, 5, 646-648).

Step 2:
(5,6-Dihydro-4H-cyclopenta[b]furan-2-yl)methanol 5,6-Dihydro-4H-cyclopenta[b]furan-2-carboxylic acid methyl ester (2.24 g) was added to the THF (59 mL) solution of LiAlH$_4$ (511 mg) under a nitrogen atmosphere at 0° C. and stirred for 1 h at 0° C. The mixture was quenched with 10 mL of water and filtered. The filtrate was concentrated under reduced pressure and the obtained aqueous solution was extracted with CHCl$_3$. The organic layer was washed with brine and dried over MgSO$_4$ and filtered. The filtrate was concentrated to afford titled compound as yellow oil (1.86 g, quant.).

$^1$H NMR (CDCl$_3$) δ 1.66 (t, 1H, J=5.9 Hz), 2.38-2.46 (m, 2H), 2.50-2.55 (m, 2H), 2.65-2.70 (m, 2H), 4.54 (d, 2H, J=5.9 Hz), 6.15 (s, 1H).

Step 3:
5,6-Dihydro-4H-cyclopenta[b]furan-2-carbaldehyde

Activated MnO$_2$ (9.3 g) was added to the CHCl$_3$ (135 mL) solution of (5,6-dihydro-4H-cyclopenta[b]furan-2-yl)methanol (1.86 g) and refluxed for 1 h under a nitrogen atmosphere. The reaction mixture was filtered through a pad of Celite. The filtrate was concentrated under reduced pressure. The residue was applied to silica gel column chromatography, then the column was eluted with n-hexane-AcOEt (9/1-7/1). The titled compound was obtained as yellow crystals (1.51 g, 77%).

$^1$H NMR (CDCl$_3$) δ 2.47-2.57 (m, 2H), 2.63 (t, 2H, J=6.8 Hz), 2.78 (t, 2H, J=7.3 Hz), 7.06 (s, 1H), 9.44 (s, 1H).

Step 4: (5R,6RS)-6-[(RS)-Acetoxy(5,6-dihydro-4H-cyclopenta[b]furan-2-yl)methyl]-6-bromo-7-oxo-4-thia-1-azabicyclo[3.2.0]hept-2-ene-2-carboxylic acid 4-nitrobenzyl ester The acetonitrile solution (50 mL) of 5,6-dihydro-4H-cyclopenta[b]furan-2-carbaldehyde (1.33 g) was added to the dry acetonitrile (101 mL) solution of anhydrous MgBr$_2$ (cont. 98%) (5.52 g) under a nitrogen atmosphere at room temperature. The dry THF solution (151 mL) of (5R,6S)-6-bromo-7-oxo-4-thia-1-azabicyclo[3.2.0]hept-2-ene-2-carboxylic acid 4-nitrobenzyl ester (cont. 96.5%) (3.91 g) was added to the mixture, cooled to −20° C., and Et$_3$N (cont. 99%) (8.28 mL) was added in one portion. The reaction vessel was covered with foil to exclude light. The reaction mixture was stirred for 2 h at −20° C. and treated with acetic anhydride (cont. 97%) (4.13 mL) and DMAP (cont. 99%) (121 mg) in one portion. The reaction mixture was warmed to 0° C. and stirred for 16 h at 0° C. The mixture was diluted with ethyl acetate and washed with 5% aqueous solution of citric acid, saturated sodium hydrogen carbonate and brine. The organic layer was dried (MgSO$_4$) then filtered. The filtrate was concentrated under reduced pressure. The residue was purified with a silica-gel column chromatography (n-hexane:AcOEt=4:1-3:1) to give the titled compound as a brown amorphous solid (3.34 g, 61%).

$^1$H NMR (CDCl$_3$) δ 2.21 (s, 3H), 2.40-2.48 (m, 2H), 2.53 (t, 2H, J=7.0 Hz), 2.69 (t, 2H, J=7.0 Hz), 5.28 (d, 1H, J=13.5 Hz), 5.43 (d, 1H, J=13.5 Hz), 6.00 (s, 1H), 6.37 (s, 1H), 6.71 (s, 1H), 7.41 (s, 1H), 7.60 (d, 2H, J=8.1 Hz), 8.24 (d, 2H, J=8.1 Hz).

Step 5: (5R),(6Z)-6-(5,6-Dihydro-4H-cyclopenta[b]furan-2-ylmethylene)-7-oxo-4-thia-1-azabicyclo[3.2.0]hept-2-ene-2-carboxylic acid, sodium salt (5R,6RS)-6-[(RS)-Acetoxy(5,6-dihydro-4H-cyclopenta[b]furan-2-yl)methyl]-6-bromo-7-oxo-4-thia-1-azabicyclo[3.2.0]hept-2-ene-2-carboxylic acid 4-nitrobenzyl ester (3.28 g) was dissolved in THF (46 mL) and acetonitrile (21 mL). Freshly activated Zn dust (13.12 g) was added rapidly with 0.5 M phosphate buffer (pH 6.5, 67 mL). The reaction vessel was covered with foil to exclude light. The reaction mixture was vigorously stirred for 1.25 h at room temperature. The reaction mixture was filtered through a pad of Celite. The filtrate was washed with ethyl acetate and the aqueous layer was separated. The aqueous layer was cooled to 3° C. and 1 M NaOH was added to adjust pH to 8.0. The mixture was concentrated under high vacuum at 35° C. The concentrate was applied to Diaion HP-21 (181 mL, Mitsubishi Kasei Co. Ltd.) resin column chromatography. After adsorbing, the column was eluted with H$_2$O-MeCN (1/0-85/15). The combined fractions were concentrated under high vacuum at 35° C. and lyophilized to give the titled crude product (288 mg). This was purified by Diaion HP-21 (100 mL, Mitsubishi Kasei Co. Ltd.) resin column chromatography. After adsorbing, the column was eluted with H$_2$O-MeCN (1/0-85/15). The combined fractions were concentrated under high vacuum at 35° C. and lyophilized to give the titled compound as a yellow amorphous solid (185 mg, 10%, pH 7.2).

Mp 170° C. (dec); $^1$H NMR (D$_2$O) δ 2.24-2.30 (m, 2H), 2.37 (t, 2H, J=6.5 Hz), 2.52-2.57 (t, 2H, J=7.1 Hz), 6.32 (s, 1H), 6.55 (s, 1H), 6.73 (s, 1H), 6.86 (s, 1H).

Example 28

Preparation of (5R)(6Z)-6-(4,5-Dihydro-6-thia-1,7a-diazainden-2-ylmethylene)-7-oxo-4-thia-1-azabicyclo[3.2.0]hept-2-ene-2-carboxylic acid, sodium salt Step 1: DL-Tetrahydro-1,3-thiazine-4-carboxylic acid hydrochloride DL-Tetrahydro-1,3-thiazine-4-carboxylic acid hydrochloride was prepared according to the method of Lewis (*J. Med. Chem.*, 21, 1070 (1978)).

Step 2: 4,5-Dihydro-3aH,7H-2-oxa-3-oxo-6-thia-1-aza-7a-azonioinden

To a suspension of DL-tetrahydro-1,3-thiazine-4-carboxylic acid hydrochloride (48.6 g, 0.26 mol) in 666 mL of AcOH was added to the solution of 27.4 g (0.40 mol) of $NaNO_2$ in 333 mL of water over 16 min at room temperature and stirred for 3 h. The solution was concentrated under reduced pressure. Acetone (300 mL) was added to the residue and the precipitate was filtered off. The filtrate was concentrated under reduced pressure to dryness and crude 3-nitroso[1,3]thiazinane-4-carboxylic acid was obtained as brown amorphous solid.

To a solution of crude 3-nitroso[1,3]thiazinane-4-carboxylic acid in 530 mL of dry THF was added trifluoroacetic anhydride (168.4 g, 0.80 mol) over 60 min under a nitrogen atmosphere at 0° C. and stirred for 5 h at 0° C. The solution was concentrated under reduced pressure. The residue was applied to silicagel column chromatography, and then the column was eluted with n-hexane-AcOEt (1:2). The titled compound was obtained as brown powder (28.0 g, 67.0%).

$^1$H NMR ($CDCl_3$) δ 3.00 (t, 2H, J=5.7 Hz), 3.07 (t, 2H, J=5.7 Hz), 5.16 (s, 2H).

Step 3: 4,5-Dihydro-6-thia-1,7a-diazaindene-2-carboxylic acid ethylester

A solution of 4,5-dihydro-3aH,7H-2-oxa-3-oxo-6-thia-1-aza-7a-azonioinden (28.0 g, 0.18 mol) and ethyl propiolate (27.0 mL, 0.27 mol) in o-xylene (590 mL) was refluxed under a nitrogen atmosphere for 16 h. The solution was cooled to room temperature and concentrated under reduced pressure. The residue was applied to silicagel column chromatography, and then the column was eluted with n-hexane-AcOEt (3:1). The titled compound was obtained as pale brown needles (22.1 g, 58.7%), and 4,5-dihydro-6-thia-1,7a-diazaindene-3-carboxylic acid ethylester was obtained as pale brown crystals (12.7 g, 33.9%).

4,5-Dihydro-6-thia-1,7a-diazaindene-2-carboxylic acid ethylester: $^1$H NMR ($CDCl_3$) δ 1.39 (t, 3H, J=7.1 Hz), 2.98 (t, 2H, J=6.1 Hz), 3.21 (t, 2H, J=6.1 Hz), 4.40 (q, 2H, J=7.1 Hz), 5.17 (s, 2H), 6.60 (s, 1H).

4,5-dihydro-6-thia-1,7a-diazaindene-3-carboxylic acid ethylester: $^1$H NMR ($CDCl_3$) δ 1.34 (t, 3H, J=7.1 Hz), 2.99 (t, 2H, J=6.1 Hz), 3.45 (t, 2H, J=6.1 Hz), 4.28 (q, 2H, J=7.1 Hz), 5.11 (s, 2H), 7.85 (s, 1H).

Step 4: 4,5-Dihydro-6-thia-1,7a-diazaindene-2-carbaldehyde

To a 22.1 gram (0.10 mol) of 4,5-dihydro-6-thia-1,7a-diazaindene-2-carboxylic acid ethylester in 520 mL of dry THF was added $LiAlH_4$ (3.95 g, 0.10 mol) under a nitrogen atmosphere at 0° C., and then stirred for 45 min. The mixture was quenched with water (20 mL) and the precipitate was filtered through a pad of Celite and the pad was washed with water (100 mL) and THF (250 mL). The filtrate was concentrated under reduced pressure, and then water (300 mL) was added. The aqueous layer was extracted with $CH_2Cl_2$ (6×500 mL). The organic layer was dried ($MgSO_4$) and filtered. The filtrate was concentrated under reduced pressure and crude was obtained as pale yellow crystals (17.2 g).

To a 17.2 gram of the crude (4,5-dihydro-6-thia-1,7a-diazainden-2-yl)methanol in 520 mL of $CHCl_3$ was added activated $MnO_2$ (88.0 g) under a nitrogen atmosphere at room temperature, and then refluxed for 2 h. The mixture was filtered through a pad of Celite and the filtrate was concentrated under reduced pressure. The residue was applied to silicagel column chromatography, and then the column was eluted with hexane-AcOEt (2:1). The titled compound was obtained as yellow crystals (13.0 g, 74.5%)

$^1$H NMR ($CDCl_3$) δ 3.00 (t, 2H, J=6.0 Hz), 3.23 (t, 2H, J=6.0 Hz), 5.18 (s, 2H), 6.58 (s, 1H), 9.92 (s, 1H).

Step 5: (5R)(6Z)-6-(4,5-Dihydro-6-thia-1,7a-diazainden-2-ylmethylene)-7-oxo-4-thia-1-azabicyclo[3.2.0]hept-2-ene-2-carboxylic acid, sodium salt The dry acetonitrile (11 mL) solution of 4,5-dihydro-6-thia-1,7a-diazaindene-2-carbaldehyde (1.70 g, 10.1 mmol) was added to the dry acetonitrile (60 mL) solution of $MgBr_2$ (2.03 g, 11.0 mmol) under a nitrogen atmosphere at room temperature, and then the mixture was stirred for 10 min. The dry THF (71 mL) solution of p-nitrobenzyl (5R,6S)-6-bromopenem-3-carboxylate (3.55 g, 9.2 mmol) was added and the mixture was cooled to −20° C., and then triethylamine (3.1 mL, 22.2 mmol) was added in one portion. The reaction vessel was covered with foil to exclude light. The reaction mixture was stirred for 3 h at −20° C. and treated with 4-dimethylamino pyridine (0.11 g, 0.9 mmol) and acetic anhydride (1.8 mL, 18.6 mmol) in one portion. The reaction mixture was warmed to 0° C. and stirred for 15 h at 0° C. Ethyl acetate (280 mL) and 1 mol/L citric acid aqueous solution (140 mL) was added to the reaction mixture and separated. The organic layer was washed with saturated sodium hydrogen carbonate and brine, dried ($MgSO_4$) and filtered. The filtrate was concentrated under reduced pressure and crude (5R)-6-[acetoxy-(4,5-dihydro-6-thia-1,7a-diazainden-2-yl)methyl]-6-bromo-7-oxo-4-thia-1-azabicyclo[3.2.0]hept-2-ene-2-carboxylic acid p-nitrobenzyl ester was obtained as brown amorphous solid.

Freshly activated Zn dust (21.4 g) was added rapidly with 0.5 mol/L phosphate buffer (pH 6.5, 112 mL) to the THF (76 mL) and acetonitrile (36 mL) solution of crude (5R)-6-[acetoxy-(4,5-dihydro-6-thia-1,7a-diazainden-2-yl)methyl]-6-bromo-7-oxo-4-thia-1-azabicyclo[3.2.0]hept-2-ene-2-carboxylic acid p-nitrobenzyl ester. The reaction vessel was covered with foil to exclude light. The reaction mixture was vigorously stirred for 1.5 h at room temperature. The reaction solution was cooled at 0° C., and then the pH was adjusted to 8.0. Ethyl acetate (56 mL) was added to the mixture and filtered through a pad of Celite. The pad was washed with water (150 mL). The aqueous layer was separated and then the organic layer was extracted with 0.5 mol/L phosphate buffer (pH 6.5, 2×30 mL). The combined aqueous layers were cooled at 0° C., and then the pH was adjusted to 8.0. The mixture was concentrated to 236 g, and then applied to Diaion HP-21 resin (480 mL, Mitsubishi Kasei Co. Ltd.) column chromatography. After adsorbing, the column was eluted with water (960 mL) and then acetonitrile aqueous solution (5%; 960 mL, 10%; 960 mL, 20%; 960 mL). The combined active fractions were concentrated under high vacuum at 35° C. and lyophilized to give the titled compound as a yellow amorphous solid (1.28 g, 40.5%, pH 7.45).

Mp 200° C. (dec); $^1$H NMR ($D_2O$) δ 2.95 (t, 2H, J=6.1 Hz), 3.12 (t, 2H, J=6.1 Hz), 5.08 (s, 2H), 6.23 (s, 1H), 6.46 (s, 1H), 6.97 (s, 1H), 7.01 (s, 1H); IR (KBr) 3382, 1752, 1684, 1597, 1554 $cm^{-1}$; $\lambda^{max}$ ($H_2O$) 366, 292, 197 nm.

Example 29

Preparation of (5R),(6Z)-6-(6,6-Dimethyl-5,6,7,8-tetrahydroimidazo[1,2-a]pyrizin-2-ylmethylene)-7-oxo-4-thia-1-azabicyclo[3.2.0]hept-2-ene-2-carboxylic acid, sodium salt

Step 1: Preparation of 5,5-Dimethyl-2-piperidone 5-5-Dimethyl-2-piperadinone (1) was prepared in the method of Nagasawa (*J. Med. Chem.*, 23, 1176 (1977)).

Step 2: Preparation of 3,3-Dimethyl-6-methoxy-2,3,4,5-tetrahydropyridine

Trimethyloxonium tetrafluoroborate (97%, 11.9 g, 78 mmol) was added to the dry dichloromethane (156 mL) solution of 5,5-dimethyl-2-piperidone (9.93 g, 78 mmol) at room temperature and stirred for 14 h. The reaction mixture was neutralized with 10% sodium hydrogen carbonate aqueous solution, and the organic layer was separated. The aqueous layer was extracted with ethyl acetate (3×120 mL), then the combined organic layer was washed with 10% sodium hydrogen carbonate aqueous solution and brine. The organic layer was dried ($MgSO_4$) and filtered. The filtrate was concentrated under reduced pressure and the titled compound was obtained as pale yellow oil (9.0 g, 82.0%).

$^1$H NMR ($CDCl_3$) δ 0.92 (s, 6H), 1.49 (t, 2H, J=7.0 Hz), 2.18 (t, 2H, J=7.0 Hz), 3.19 (s, 2H), 3.63 (s, 3H).

Step 3: 5,5-Dimethylpiperidine-2-ylideneamine monohydrochloride

The mixture of 3,3-dimethyl-6-methoxy-2,3,4,5-tetrahydropyridine (9.0 g, 64 mmol) and ammonium chloride (3.4 g, 64 mmol) in dry ethanol (160 mL) was heated to reflux for 2 h. The reaction mixture was then concentrated under reduced pressure and the titled compound was obtained as a white solid (9.9 g, 94.6%).

$^1$H NMR (DMSO-$d^6$) δ 0.95 (s, 6H), 1.52 (t, 2H, J=6.9 Hz), 2.55 (t, 2H, J=6.9 Hz), 2.99 (d, 2H, J=2.1 Hz).

Step 4: 6,6-Dimethyl-5,6,7,8-tetrahydroimidazo[1,2-a]pyridine-2-carbaldehyde & 6,6-Dimethyl-5,6,7,8-tetrahydroimidazo[1,2-a]pyridine-3-carbaldehyde The mixture of 2-bromo-3-hydroxypropenal (10.1 g, 67 mmol), p-toluenesulfonic acid monohydrate (0.13 g, 0.6 mmol) and 2-propanol (12.6 mL, 165 mmol) in cyclohexane (100 mL) was azeotroped until the vapor temperature over 80° C. The reaction mixture was concentrated under reduced pressure. The residue was dissolved in dry EtOH (200 mL). The dry EtOH (350 mL) solution of 5,5-dimethylpiperidine-2-ylideneamine monohydrochloride (9.9 g, 61 mmol) and the dry EtOH (50 mL) solution of NaOMe (28%, 11.7 g, 61 mmol) were added at room temperature. The reaction mixture was stirred at room temperature for 2 h, and then the reaction solution was removed in vacuo. The residue was dissolved in $CHCl_3$ (300 mL) and triethylamine (8.5 mL, 61 mmol) was added, and then the reaction mixture was heated to reflux for 2 h. The reaction mixture was cooled to room temperature, and then the reaction solution was removed in vacuo. The residue was dissolved in $CH_2H_{12}$ (600 mL) and washed with 50% $K_2CO_3$ aqueous solution (2×200 mL). The combined aqueous solution was extracted with $CH_2Cl_2$ (2×200 mL). The combined organic layer was dried ($MgSO_4$) and filtered. The filtrate was concentrated under reduced pressure. The residue was applied to silica gel column chromatography, eluted with $CHCl_3$-methanol (50:1), and the titled compound 6,6-Dimethyl-5,6,7,8-tetrahydroimidazo[1,2-a]pyridine-2-carbaldehyde (brown solid, 4.4 g, 40.7%) and 6,6-Dimethyl-5,6,7,8-tetrahydroimidazo[1,2-a]pyridine-3-carbaldehyde (orange solid, 1.7 g, 15.8%) were obtained.

6,6-Dimethyl-5,6,7,8-tetrahydroimidazo[1,2-a]pyridine-2-carbaldehyde: $^1$H NMR ($CDCl_3$) δ 1.10 (s, 6H), 1.78 (t, 2H, J=6.9 Hz), 2.95 (t, 2H, J=6.9 Hz), 3.71 (s, 2H), 7.46 (s, 1H), 9.83 (s, 1H).

6,6-Dimethyl-5,6,7,8-tetrahydroimidazo[1,2-a]pyridine-3-carbaldehyde: $^1$H NMR ($CDCl_3$) δ 1.09 (s, 6H), 1.74 (t, 2H, J=6.8 Hz), 2.97 (t, 2H, J=6.8 Hz), 4.05 (s, 2H), 7.74 (s, 1H), 9.64 (s, 1H).

Step 5: (5R),(6Z)-6-(6,6-Dimethyl-5,6,7,8-tetrahydroimidazo[1,2-a]pyrizin-2-ylmethylene)-7-oxo-4-thia-1-azabicyclo[3.2.0]hept-2-ene-2-carboxylic acid, sodium salt The dry acetonitrile (28 mL) solution of 6,6-dimethyl-5,6,7,8-tetrahydroimidazo[1,2-a]pyridine-2-carbaldehyde (4.55 g, 26 mmol) was added to the dry acetonitrile (152 mL) solution of $MgBr_2$ (5.22 g, 28 mmol) under a nitrogen atmosphere at room temperature, and then the mixture was stirred for 10 min. The dry THF (180 mL) solution of p-nitrobenzyl (5R,6S)-6-bromopenem-3-carboxylate (8.94 g, 23 mmol) was added and the mixture was cooled to −20° C., and then triethylamine (7.8 mL, 56 mmol) was added in one portion. The reaction vessel was covered with foil to exclude light. The reaction mixture was stirred for 3 h at −20° C. and treated with 4-dimethylamino pyridine (0.29 g, 2.4 mmol) and acetic anhydride (4.4 mL, 47 mmol) in one portion. The reaction mixture was warmed to 0° C. and stirred for 16 h at 0° C. Ethyl acetate (715 mL) was added to the reaction mixture, and then the organic layer was washed with 1 mol/L Citric acid aqueous solution, saturated sodium hydrogen carbonate and brine. The organic layer was dried ($MgSO_4$) and filtered. The filtrate was concentrated under reduced pressure and crude (5R)-6-[acetoxy-(6,6-dimethyl-5,6,7,8-tetrahydroimidazo[1,2-a]pyridin-2-yl)methyl]-6-bromo-7-oxo-4-thia-1-azabicyclo[3.2.0]hept-2-ene-2-carboxylic acid p-nitrobenzyl ester was obtained as brown amorphous solid.

Freshly activated Zn dust (53.6 g) was added rapidly with 0.5 mol/L phosphate buffer (pH 6.5, 282 mL) to the THF (192 mL) and acetonitrile (90 mL) solution of (5R)-6-[acetoxy-(6,6-dimethyl-5,6,7,8-tetrahydroimidazo[1,2-a]pyridin-2-yl)methyl]-6-bromo-7-oxo-4-thia-1-azabicyclo[3.2.0]hept-2-ene-2-carboxylic acid p-nitrobenzyl ester. The reaction vessel was covered with foil to exclude light. The reaction mixture was vigorously stirred for 1.5 h at room temperature. The reaction mixture was cooled at 0° C., and then the pH was adjusted to 7.6. Ethyl acetate (140 mL) was added to the reaction mixture, and then the mixture was filtered through a pad of Celite and the pad was washed with water (200 mL). The aqueous layer was separated and then the organic layer was extracted with 0.5 mol/L phosphate buffer (pH 6.5, 2×50 mL). The pH of the combined aqueous layer was adjusted to 8.1 and the mixture was concentrated to 584 g. 1 mol/L NaOH was added to adjust pH to 8.2 and applied to Diaion HP-21 resin (420 mL, Mitsubishi Kasei Co. Ltd.) column chromatography. After adsorbing, the column was eluted with 2.5% (2 bed volume), 5% (2 bed volume), 10% (1 bed volume) and 20% acetonitrile aqueous solution. The combined active fractions were concentrated under high vacuum at 35° C. and lyophilized to give the crude (5R),(6Z)-6-(6,6-Dimethyl-5,6,7,8-tetrahydroimidazo[1,2-a]pyrizin-2-ylmethylene)-7-oxo- 4-thia-1-azabicyclo[3.2.0]hept-2-ene-2-carboxylic acid, sodium salt as a yellow amorphous solid (1.19 g).

The crude (5R),(6Z)-6-(6,6-Dimethyl-5,6,7,8-tetrahydroimidazo[1,2-a]pyrizin-2-ylmethylene)-7-oxo-4-thia-1-azabicyclo[3.2.0]hept-2-ene-2-carboxylic acid, sodium salt was purified by the preparative HPLC (Mightysil RP-18 GP (5 □m), Kanto Chemical Co. Inc., 35×250 mm, 0.05 mol/L phosphate buffer (pH 7.2): $CH_3CN$=70:30, 20 mL/min.). The purified product was desalted by Diaion HP-21 resin (50 mL) column chromatography and the title compound was obtained 230 mg (2.8%) as a yellow amorphous solid.

Mp 210° C. (dec); $^1$H NMR ($D_2O$) 6; 0.91 (s, 3H), 0.93 (s, 3H), 1.63 (t, 2H, J=6.8 Hz), 2.72 (t, 2H, J=6.8 Hz), 3.60 (s, 2H), 6.44 (s, 1H), 6.90 (s, 1H), 6.91 (s, 1H), 7.19 (s, 1H).

Example 30

Preparation of (5R),(6Z)-6-(5,6-Dihydro-8-H-imidazo[2,1-c][1,4]thiazin-3-ylmethylene)-7-oxo-4-thia-1-azabicyclo[3.2.0]hept-2-ene-2-carboxylic acid The dry acetonitrile (40 mL) solution of 5,6-dihydro-8H-imidazo[2,1-c][1,4]thiazine-3-carbaldehyde (813 mg) was added to the dry acetonitrile (40 mL) solution of $MgBr_2$ (2.2 g) under a nitrogen atmosphere at room temperature then the mixture was stirred for 10 min. The dry THF (80 mL) solution of p-nitrobenzyl (5R,6S)-6-bromopenem-3-carboxylate (2.1 g) was added, the mixture was cooled to −20° C. then triethylamine (1.7 mL) was added in one portion. The reaction vessel was covered with foil to exclude light. The reaction mixture was stirred for 3.5 h at −20° C. and treated with 4,4-dimethylamino pyridine (64 mg) and acetic anhydride (0.9 mL) in one portion. The reaction mixture was warmed to 0° C. and stirred for 14 h at 0° C. 10% Citric acid aqueous solution (500 mL) was added to the reaction mixture and the aqueous layer was extracted with ethyl acetate (3×200 mL). The organic layer was washed with water, saturated sodium hydrogen carbonate and brine, dried ($MgSO_4$) and filtered. The filtrate was concentrated under reduced pressure. The residue was applied to silica gel column chromatography and eluted with $CH_2Cl_2$-acetone (20:1) to obtain crude (5R)-6-[acetoxy-(5,6-dihydro-8H-imidazo[2,1-c][1,4]thiazin-3-yl)methyl]-6-bromo-7-oxo-4-thia-1-azabicyclo[3.2.0]hept-2-ene-2-carboxylic acid p-nitrobenzyl ester as a brown solid.

The solid obtained above chromatography was dissolved in THF (11 mL). Freshly activated Zn dust (1.4 g) was added rapidly with 0.5 mol/L phosphate buffer (pH 6.5, 11 mL). The reaction vessel was covered with foil to exclude light. The reaction mixture was vigorously stirred for 2 h at room temperature. The reaction solution was filtered through a pad of Celite and the pad was washed with water (26 mL) and n-butanol (26 mL). The aqueous layer was separated and then the organic layer was extracted with 0.5 mol/L phosphate buffer (pH 6.5, 2×5 mL). The combined aqueous layer was concentrated to 18 g, 1 mol/L NaOH was added to adjust pH to 7.3 and applied to Diaion HP-21 resin (20 mL, Mitsubishi Kasei Co. Ltd.) column chromatography. After adsorbing, the column was eluted with water and then 5% acetonitrile aqueous solution. The combined active fractions was concentrated under high vacuum at 35° C. and lyophilized to give the title compound as a yellow amorphous solid (81 mg).

Mp 145° C. (dec); $^1$H NMR ($D_2O$) δ 3.05-3.08 (m, 1H), 3.83 (s, 1H), 4.13-4.16 (m, 1H), 6.37 (s, 1H), 6.91 (s, 1H), 7.01 (s, 1H), 7.04 (s, 1H); IR (KBr) 3371, 1770, 1672, 1613 $cm^{-1}$; $\lambda^{max}$ ($H_2O$) 314 nm.

Example 31

Preparation of (5R)(6Z)-7-Oxo-6-(4H-5-thia-1,6a-diazapentalen-2-ylmethylene)-4-thia-1-azabicyclo [3.2.0]hept-2-ene-2-carboxylic acid, sodium salt Step 1: Preparation of 3-Oxo-3a,4-dihydro-3H,6H-2-oxa-5-thia-1-aza-6a-azonio-3a-pentalenide Conc. HCl (15 mL) and $NaNO_2$ (16.6 g) were added to the $H_2O$ (166 mL) solution of L-thioproline (24.3 g) under a nitrogen atmosphere at 0° C. and stirred for 2 h. The solution was extracted with $CH_2Cl_2$, organic layer was dried over $MgSO_4$ and concentrated under reduced pressure to afford the crude N-nitroso compound as a yellow solid.

Trifluoroacetic anhydride (5.0 mL) was added to the THF (350 mL) solution of crude N-nitroso thioproline under a nitrogen atmosphere at 0° C. and stirred for 5 h at 0° C. The solution was concentrated under reduced pressure. The residue was applied to silica gel column chromatography, then the column was eluted with n-hexane—AcOEt (1:1). The titled compound was obtained as a pale brown solid (4.0 g, 15.1%).

$^1$H NMR ($CDCl_3$) δ: 4.04 (t, 2H, J=1.7 Hz), 5.40 (t, 2H, J=1.7 Hz).

Step 2: Preparation of 4H-5-Thia-1,6a-diazapentalen-2-carboxylic acid ethylester Ethyl propiolate (3.1 mL) was added to the oxylene (130 mL) solution of 3-oxo-3a,4-dihydro-3H,6H-2-oxa-5-thia-1-aza-6a-azonio-3a-pentalenide (4.0 g) under a nitrogen atmosphere and refluxed for 19 h. The solution was cooled to room temperature and concentrated under reduced pressure. The residue was applied to silica gel column chromatography, then the column was eluted with n-hexane—AcOEt (4:1). The titled compound was obtained as a yellow solid (2.7 g, 49.3%), and 4H-5-thia-1,6a-diazapentalen-3-carboxylic acid ethylester was obtained as pale yellow crystals (1.2 g, 21.7%).

$^1$H NMR ($CDCl_3$) δ1.40 (t, 3H, J=7.1 Hz), 4.11 (d, 2H, J=2.1 Hz), 4.40 (q, 2H, J=7.1 Hz), 5.24 (t, 2H, J=1.6 Hz), 6.61 (s, 1H).

Step 3: Preparation of (4H-5-Thia-1,6a-diazapentalen-2-yl)methanol $LiBH_4$ (cont. 90%) (459 mg) was added to the ether (126 mL) solution of 4H-5-thia-1,6a-diazapentalen-2-carboxylic acid ethylester (2.5 g) and MeOH (0.77 mL) under a nitrogen atmosphere at room temperature, then refluxed for 1.5 h. The mixture was quenched with 1 mol/L HCl (25 mL) and stirred for 1 h at room temperature. The mixture was neutralized by saturated sodium hydrogen carbonate solution and separated. The aqueous layer was extracted with dichloromethane (10× 25 mL). The organic layer was dried ($MgSO_4$) and filtered. The filtrate was concentrated under reduced pressure. The residue was applied to silica gel column chromatography, then the column was eluted with AcOEt. The titled compound was obtained as a pale yellow solid (1.7 g, 87.9%).

$^1$H NMR ($CDCl_3$): δ 2.95 (t, 1H, J=5.6 Hz), 4.07 (s, 2H), 4.62 (d, 2H, J=5.1 Hz), 5.13 (t, 1H, J=1.6 Hz), 6.04 (s, 1H).

Step 4: Preparation of 4H-5-Thia-1,6a-diazapentalen-2-carbaldehyde

The dry dichloromethane (8 mL) solution of dimethylsulfoxide (2.2 mL) was added dropwise to the dry dichloromethane (110 mL) solution of oxalyl chloride (2.0 mL) at −78° C. The reaction mixture was stirred for 15 min at the same temperature. The dry dichloromethane (40 mL) solution of (4H-5-thia-1,6a-diazapentalen-2-yl)methanol (1.7 g) was added dropwise to the reaction mixture at −78° C., and stirring was continued for an additional 15 min. The reaction mixture was allowed to warm to −45° C. and stirred for 1 h. Triethylamine (11.3 mL) was added dropwise and the reaction mixture was allowed to warm to 0° C. After 20 min, saturated ammonium chloride solution (50 mL) and water (100 mL) were added and separated. The aqueous layer was extracted with AcOEt (3×150 mL). The combined organic layers were washed with water (200 mL) and brine (200 mL), dried ($MgSO_4$) and filtered. The filtrate was concentrated under reduced pressure. The residue was applied to silica gel column chromatography, then the column was eluted with hexane—AcOEt (1:1). The titled compound was obtained as a yellow solid (1.7 g, quant.).

$^1$H NMR ($CDCl_3$) δ4.13 (s, 2H), 5.26 (d, 2H, J=1.4 Hz), 6.59 (s, 1H), 9.90 (s, 1H).

Step 5: Preparation of (5R)(6Z)-7-Oxo-6-(4H-5-thia-1,6a-diazapentalen-2-ylmethylene)-4-thia-1-azabicyclo[3.2.0]hept-2-ene-2-carboxylic acid, sodium salt The dry acetonitrile (92 mL) solution of 4H-5-thia-1,6a-diazapentalen-2-carbaldehyde (1.7 g) was added to the dry acetonitrile (92 mL) solution of $MgBr_2$ (5.0 g) under a nitrogen atmosphere at room temperature then the mixture was stirred for 10 min. The dry THF (184 mL) solution of p-nitrobenzyl (5R,6S)-6-bromopenem-3-carboxylate (4.3 g) was added and the mixture was cooled to −20° C. then triethylamine (7.4 mL) was added in one portion. The reaction vessel was covered with foil to exclude light. The reaction mixture was stirred for 3 h at −20° C. and treated with 4-dimethylamino pyridine (138 mg) and acetic anhydride (2.1 mL) in one portion. The reaction mixture was warmed to 0° C. and stirred for 15 h at 0° C. The 1 mol/L Citric acid aqueous solution (1000 mL) was added to the reaction mixture and the aqueous layer was extracted with ethyl acetate (3×400 mL). The combined organic layers were washed with water, saturated sodium hydrogen carbonate and brine, dried ($MgSO_4$) and filtered. The filtrate was concentrated under reduced pressure and crude (5R)-6-[acetoxy-(4H-5-thia-1,6a-diazapentalen-2-yl)methyl]-6-bromo-7-oxo-4-thia-1-azabicyclo[3.2.0]hept-2-ene-2-carboxylic acid p-nitrobenzyl ester was obtained as a brown amorphous.

Freshly activated Zn dust (19.3 g) was added rapidly with 0.5 mol/L phosphate buffer (pH 6.5, 100 mL) to the THF (100 mL) solution of crude (5R)-6-[acetoxy-(4H-5-thia-1,6a-diazapentalen-2-yl)methyl]-6-bromo-7-oxo-4-thia-1-azabicyclo[3.2.0]hept-2-ene-2-carboxylic acid p-nitrobenzyl ester. The reaction vessel was covered with foil to exclude light. The reaction mixture was vigorously stirred for 2.5 h at room temperature. The reaction solution was filtered through a pad of Celite and the pad was washed with water (200 mL) and n-butanol (200 mL). The aqueous layer was separated and then the organic layer was extracted with 0.5 mol/L phosphate buffer (pH 6.5, 2×50 mL). The combined aqueous layers were concentrated to 90 g, 1 mol/L NaOH was added to adjust pH to 8.0 and applied to Diaion HP-21 resin (180 mL, Mitsubishi Kasei Co. Ltd.) column chromatography. After adsorbing, the column was eluted with water and then 15% acetonitrile aqueous solution. The combined active fractions were concentrated under high vacuum at 35° C. and lyophilized to give the title compound as a yellow amorphous solid (634 mg, 17.4%, pH 7.25).

Mp 150° C. (dec); $^1$H NMR ($D_2O$) δ4.00 (s, 2H), 5.09 (s, 2H), 6.14 (s, 1H), 6.36 (s, 1H), 6.91 (s, 1H), 6.92 (s, 1H); IR (KBr) 3381, 1752, 1683, 1600, 1558 $cm^{-1}$; $\lambda^{max}$ ($H_2O$) 292, 196 nm.

Example 32

Preparation of (5R)(6Z)-6-(2,3-Dihydropyrazolo[5,1-b]thiazol-6-ylmethylene)-7-oxo-4-thia-1-azabicyclo[3.2.0]hept-2-ene-2-carboxylic acid, sodium salt

Step 1: Preparation of 3-Oxo-3a,4-dihydro-3H,6H-2-oxa-4-thia-1-aza-6a-azonio-3a-pentalenide To a suspension of thiazolidine-2-carboxylic acid (39.9 g, 0.30 mol) in 1,000 ml of acetic acid was added a solution of 31.0 g (0.45 mol) of sodium nitrite in 500 ml of water over 13 minutes at room temperature and stirred for 5 hours. The reaction solution was concentrated under reduced pressure. Acetone (500 ml) was added to the residue and the precipitate was filtered through a pad of Celite. The pad was washed with acetone (500 ml). The filtrate was concentrated under reduced pressure to dryness and crude 3-nitrosothiazolidin-2-carboxylic acid was obtained as a yellow solid.

To a solution of crude 3-nitrosothiazolidin-2-carboxylic acid in 600 ml of dry tetrahydrofuran was added trifluoroacetic anhydride (189.6 g, 0.90 mol) over 20 minutes under a nitrogen atmosphere at 0° C. and stirred for 19 hours at 0° C. The solution was concentrated under reduced pressure. The residue was applied to a silica-gel column chromatography, and then the column was eluted with n-hexane-ethyl acetate (1:1). The titled compound was obtained as a pale brown crystal (19.2 g, 44.5%).

$^1$H NMR ($CDCl_3$) δ 3.98 (t, 2H, J=7.7 Hz), 4.65 (t, 2H, J=7.7 Hz).

Step 2: Preparation of 2,3-Dihydropyrazolo[5,1-b]thiazol-6-carboxylic acid ethyl ester and 2,3-dihydropyrazolo[5,1-b]thiazol-7-carboxylic acid ethyl ester Ethyl propiolate (20.3 ml, 0.20 mol) was added to an o-xylene (600 ml) solution of 3-oxo-3a,4-dihydro-3H,6H-2-oxa-4-thia-1-aza-6a-azonio-3a-pentalenide (19.2 g, 0.13 mol) under a nitrogen atmosphere and refluxed for 21 hours. The solution was cooled to room temperature and concentrated under reduced pressure. The residue was applied to a silica gel column chromatography, and then the column was eluted with n-hexane-ethyl acetate (2:21 to 1:1). The mixture of 2,3-Dihydropyrazolo[5,1-b]thiazol-6-carboxylic acid ethyl ester and 2,3-dihydropyrazolo[5,1-b]thiazol-7-carboxylic acid ethyl ester was obtained as a brown oil in the ratio of 1:1.5 respectively. (21.2 g, Yield: 80.0%).

2,3-Dihydropyrazolo[5,1-b]thiazol-6-carboxylic acid ethyl ester; $^1$H NMR ($CDCl_3$) δ1.39 (t, 3H, J=7.1 Hz), 3.82 (t, 2H, J=7.5 Hz), 4.39 (q, 2H, J=7.1 Hz), 4.42 (t, 2H, J=7.5 Hz), 6.52 (s, 1H).

2,3-dihydropyrazolo[5,1-b]thiazol-7-carboxylic acid ethyl ester; $^1$H NMR ($CDCl_3$) δ1.34 (t, 3H, J=7.1 Hz), 3.85 (t, 2H, J=7.8 Hz), 4.28 (q, 2H, J=7.1 Hz), 4.39 (t, 2H, J=7.8 Hz), 7.87 (s, 1H).

Step 3:
2,3-Dihydropyrazolo[5,1-b]thiazol-6-carbaldehyde
and
2,3-dihydro-pyrazolo[5,1-b]thiazol-7-carbaldehyde To the mixture [21.2 g (0.11 mol)] of 2,3-dihydropyrazolo [5,1-b]thiazol-6-carboxylic acid ethyl ester and 2,3-dihydro-pyrazolo[5,1-b]thiazol-7-carboxylic acid ethyl ester in 540 ml of dry tetrahydrofuran was added LiAlH$_4$ (4.05 g, 0.11 mol) under a nitrogen atmosphere at 0° C., and then stirred for 2.5 hours at room temperature. The mixture was quenched with water (15 ml) and the precipitate was filtered through a pad of Celite. The pad was washed with water (100 ml) and tetrahydrofuran (500 ml). The filtrate was concentrated under reduced pressure, and then water (150 ml) was added. The aqueous layer was extracted with dichloromethane (15×250 ml). The combined organic layers were dried (MgSO$_4$) and filtered. The filtrate was concentrated under reduced pressure and a mixture of (2,3-dihydropyrazolo[5,1-b]thiazol-6-yl) methanol and (2,3-dihydropyrazolo[5,1-b]thiazol-7-yl) methanol was obtained as pale brown oil (15.5 g).

To the mixture [15.5 g (0.10 mol)] of (2,3-dihydropyrazolo [5,1-b]thiazol-6-yl)methanol and (2,3-dihydropyrazolo[5,1-b]thiazol-7-yl)methanol in 500 ml of chloroform was added activated MnO$_2$ (77.7 g) under a nitrogen atmosphere at room temperature, and then refluxed for 3 hours. The mixture was filtered through a pad of Celite and the filtrate was concentrated under reduced pressure. The residue was applied to a silica gel column chromatography, and then the column was eluted with hexane-ethyl acetate (2:1 to 1:1). The titled compound 2,3-Dihydropyrazolo[5,1-b]thiazol-6-carbaldehyde was obtained as a yellow crystal (2.50 g, 15.2%) and 2,3-dihydro-pyrazolo[5,1-b]thiazol-7-carbaldehyde was obtained as a pale brown solid (5.57 g, 33.8)

2,3-Dihydropyrazolo[5,1-b]thiazol-6-carbaldehyde; $^1$H NMR (CDCl$_3$) δ 3.86 (t, 2H, J=7.5 Hz), 4.45 (t, 2H, J=7.5 Hz), 6.50 (s, 1H), 9.83 (s, 1H).

2,3-dihydro-pyrazolo[5,1-b]thiazol-7-carbaldehyde_; $^1$H NMR (CDCl$_3$) δ 3.92 (t, 2H, J=7.9 Hz), 4.40 (t, 2H, J=7.9 Hz), 7.91 (s, 1H), 9.76 (s, 1H).

Step 4: Preparation of (5R)(6Z)-6-(2,3-Dihydropyrazolo[5,1-b]thiazol-6-ylmethylene)-7-oxo-4-thia-1-azabicyclo[3.2.0]hept-2-ene-2-carboxylic acid, sodium salt A dry acetonitrile (19 ml) solution of 2,3-dihydropyrazolo [5,1-b]thiazol-6-carbaldehyde (2.50 g, 16.2 mmol) was added to a dry acetonitrile (106 ml) solution of MgBr$_2$ (3.67 g, 19.9 mmol) under a nitrogen atmosphere at room temperature then the mixture was stirred for 10 minutes. A dry tetrahydrofuran (125 ml) solution of p-nitrobenzyl (5R,6S)-6-bromopenem-3-carboxylate (6.23 g, 16.2 mmol) was added and the mixture was cooled to −20° C. then triethylamine (5.4 ml, 38.7 mmol) was added in one portion. The reaction vessel was covered with foil to exclude light. The reaction mixture was stirred for 3 hours at −20° C. and treated with 4-dimethylamino pyridine (198 mg, 1.62 mmol) and acetic anhydride (3.1 ml, 32.9 mmol) in one portion. The reaction mixture was warmed to 0° C. and stirred for 16 hours at 0° C. Ethyl acetate (500 ml) was added to the reaction mixture and then the organic layer was washed with 1 mol/l citric acid aqueous solution, saturated sodium hydrogen carbonate and brine. The organic layer was dried (MgSO$_4$) and filtered. The filtrate was concentrated under reduced pressure and the crude (5R)-6-[acetoxy-(2,3-dihydropyrazolo[5,1-b]thiazol-6-yl)methyl]-6-bromo-7-oxo-4-thia-1-azabicyclo[3.2.0]hept-2-ene-2-carboxylic acid p-nitrobenzyl ester was obtained as a brown amorphous solid.

Freshly activated Zn dust (37.4 g) was added rapidly with 0.5 mol/l phosphate buffer (pH 6.5, 196 ml) to tetrahydrofuran (134 ml) and acetonitrile (62 ml) solution of (5R)-6-[acetoxy-(2,3-dihydropyrazolo[5,1-b]thiazol-6-yl)methyl]-6-bromo-7-oxo-4-thia-1-azabicyclo[3.2.0]hept-2-ene-2-carboxylic acid p-nitrobenzyl ester. The reaction vessel was covered with foil to exclude light. The reaction mixture was vigorously stirred for 1.5 hours at room temperature. The reaction mixture was cooled at 0° C., and then the pH was adjusted to 8.0. Ethyl acetate (100 ml) was added to the reaction mixture. The mixture was filtered through a pad of Celite and the pad was washed with water (300 ml). The aqueous layer was separated and then the organic layer was extracted with 0.5 mol/l phosphate buffer (pH 6.5, 2×50 ml). The pH of the combined aqueous layer was adjusted to 8.0 and the mixture was concentrated to 426 g. The concentrate was adjust pH to 8.0 and applied to Diaion HP-21 resin (540 ml, Mitsubishi Kasei Co. Ltd.) column chromatography. After adsorbing, the column was eluted with water (1 bed volume) and then 5% (2 bed volume), 10% (2 bed volume) and 20% acetonitrile aqueous solution. The combined active fractions were concentrated under high vacuum at 35° C. and lyophilized to give the title compound as a orange amorphous solid (2.09 g, 39.2%, pH 7.10).

Mp 150° C. (dec); $^1$H NMR (D$_2$O) δ 3.75 (t, 2H, J=7.5 Hz), 4.27 (t, 2H, J=7.5 Hz), 6.00 (s, 1H), 6.34 (s, 1H), 6.85 (s, 1H), 6.94 (s, 1H); IR (KBr) 3392, 1755, 1596, 1554 cm$^{-1}$; $\lambda^{max}$ (H$_2$O) 290, 223 nm.

Example 33

Preparation of (5R)(6Z)-6-(2,3-Dihydropyrazolo[5,1-b]oxazol-6-ylmethylene)-7-oxo-4-thia-1-azabicyclo[3.2.0]hept-2-ene-2-carboxylic acid, sodium salt

Step 1: Preparation of ethyl2,3-dihydropyrazolo[5,1-b][1,3]oxazole-6-carboxylate To the stirred suspension of ethyl 5-hydroxy-1H-pyrazole-3-carboxylate (10.34 g, 0.66 mol) and 36.62 g of potassium carbonate in 500 ml of acetonitrile was added 13.68 g of 1,2-dibromoethane, and refluxed for 16 hours. The reaction mixture was allowed to cool to room temperature, then filtered, the solid was washed with acetonitrile. The filtrate was concentrated to an oil. The residue was dissolved in ethyl acetate and extracted with water. The organic phase was dried over MgSO$_4$ and evaporated to dryness. 5.80 g of the desired product was obtained (48%).

Step 2: Preparation of 2,3-dihydropyrazolo[5,1-b][1,3]oxazole-6-methanol

To the stirred solution of ethyl2,3-dihydropyrazolo[5,1-b] [1,3]oxazole-6-carboxylate (5.47 g, 35 mmol) of in 100 ml of THF was added 1.05 g of lithium borohydride and 1.54 g of methanol. The solution was heated at 40 C for 2.5 hour. The reaction was quenched by 1N HCl, and adjusted to pH 1.3 and stirred at room temperature for 1 hour. The reaction mixture was adjusted pH to 8 with k$_2$CO$_3$. The reaction mixture was extracted with ethyl acetate. The organic layer was dried over MgSO$_4$, and concentrated to an oil and column chromatographed to give 2.68 g of the desired product (65%).

Step 3: Preparation of 2,3-dihydropyrazolo[5,1-b][1,3]oxazole-6-carbaldehyde To the stirred solution of 2,3-dihydropyrazolo[5,1-b][1,3]oxazole-6-methanol (2.60 g, 18.5 mmol) in 60 ml of $CH_3Cl$ was added 12.9 g of $MnO_2$. The suspension was refluxed for 1.5 hour under a nitrogen atmosphere. The reaction mixture was filtered through a pad of Celite. The filtrate was concentrated to give yellow oil. The product was purified by chromatography. 2.15 g of the product was obtained (84.3%).

Step 4: 4-Nitrobenzy (5R)-6-[(acetyloxy)(2,3-dihydropyrazolo[5,1-b][1,3]oxazol-6-yl)-)methyl]-6-bromo-7-oxo-4-thia-1-azabicyclo[3.2.0]hept-2-ene-2-carboxylate 2,3-dihydropyrazolo[5,1-b][1,3]oxazole-6-carbaldehyde (607 mg, 4.3 mmol) and the dry THF solution (20 mL) of (5R,6S)-6-bromo-7-oxo-4-thia-1-aza-bicyclo[3.2.0]hept-2-ene-2-carboxylic acid 4-nitro-benzyl ester (1.54 g, 4.6 mmol) were added successively to the dry acetonitrile (15 mL) solution of anhydrous $MgBr_2:O(Et)_2$ (2.21 g, 8.5 mmol) under an argon atmosphere at room temperature. After cooling to −20° C., $Et_3N$ (2.0 mL) was added in one portion. The reaction vessel was covered with foil to exclude light. The reaction mixture was stirred for 2 h at −20° C. and treated with acetic anhydride (1.04 mL) in one portion. The reaction mixture was warmed to 0° C. and stirred for 15 h at 0° C. The mixture was diluted with ethyl acetate and washed with 5% citric acid aqueous solution, saturated sodium hydrogen carbonate, and brine. The organic layer was dried ($MgSO_4$) and filtered through a pad of Celite. The pad was washed with ethyl acetate. The filtrate was concentrated under reduced pressure. The residue was applied to silica gel column chromatography, then the column was eluted with ethyl acetate:hexane (1:1). Collected fractions were concentrated under reduced pressure and the mixture of diastereo isomers were taken to next step. Pale yellow amorphous solid; Yield: 1.9 g, 81%; M+H 566.

H-NMR ($CDCl_3$) 8.24 (2H, d, J=6.6 Hz), 7.60 (2H, d, J=6.6 Hz), 7.44 (1H, s), 6.34 (1H, s), 6.23 (1H, s), 5.56 (1H, s), 5.44 (1H, d, J=10.2 Hz), 5.27 (1H, d J=10.2 Hz), 5.04 (2H, m), 4.30 (2H, m), 2.10 (3H, s).

Anal.Calcd. for $C_{21}H_{17}BrN_4O_8S$: C, 44.61; H, 3.03; N, 9.91.

Found: C, 45.00; H, 3.14; N, 9.53

Step-5: (5R,6Z)-6-(2,3-dihydropyrazolo[5,1-b][1,3]oxazol-6-ylmethylene}-7oxo-4-thia-1-azabicyclo[3.2.0]hept-2-ene-2-carboxylic acid sodium salt 4-Nitrobenzy-6-[(acetyloxy)(2,3-dihydropyrazolo[5,1-b][1,3]oxazol-6-yl)-)methyl]-6-bromo-7-oxo-4-thia-1-azabicyclo[3.2.0]hept-2-ene-2-carboxylate (700 mg, 1.2 mmol) was dissolved in THF (20 mL), acetonitrile (10 mL) and 0.5 M phosphate buffer (pH 6.5, 28 mL) and hydrogenated over 10% Pd/C at 40 psi pressure. After 4 hrs the reaction mixture was filtered, cooled to 3° C., and 0.1 M NaOH was added to adjust pH to 8.5. The filtrate was washed with ethyl acetate and the aqueous layer was separated. The aqueous layer was concentrated under high vacuum at 35° C. to give yellow precipitate. The product was purified by HP21 resin reverse phase column chromatography. Initially the column was eluted with deionized water (2 lits) and latter with 10% acetonitrile:Water. The fractions containing the product were collected and concentrated at reduced pressure at room temperature. The yellow solid was washed with acetone and filtered. Dried. Yield: 276 mg, 73%; as yellow amorphous solid; (M+H+Na) 314.

$^1$H-NMR ($D_2O$); δ 6.97 (1H, s), 6.95 (1H, s), 6.46 (1H, s), 5.56 (1H, s) 5.07 (2H, d, J=6.3 Hz), 4.30 (2H, t, J=6.3 Hz).

Example 34

Preparation of (5R,6Z)-6-[(5-acetyl-4,5,6,7-tetrahydrothieno[3,2-c]pyridin-2-yl)methylene]-oxo-4-thia-1-azabicyclo[3.2.0]hept-2-ene-2-carboxylic acid (E+Z Isomers mixture, Sodium salt)

Step 1: 5-acetyl-4,5,6,7-tetrahydrothieno[3,2-c]pyridine-2-carbaldehyde

To a cold (0° C.) suspension of 1.5 g. (7.4 mmol) of 4,5,6,7-tetrahydrothieno[3,2-c]pyridine-2-carbaldehyde hydrochloride in 50 mL methylene chloride, under $N_2$ atm., dry conditions, was added dropwise under stirring 2.6 mL (2.5 eqs) of triethylamine. RM stirred for 30 min at 0° C. and a solution of 0.7 g. (8.1 mmol, 1.1 eqs) of acetyl chloride in 15 mL methylene chloride was dropwise added, RM allowed to reach RT and stirred for 3 hours. Filtered trough a celite pad, filtrate washed with 3×50 mL water, dried, evaporated, gave 1.1 g. (71.4%) of the title compound, viscous oil, $(M+H)^+$ 210.3.

Step 2: Preparation of 4-nitrobenzyl(5R)-6-[(acetyloxy)(5-acetyl-4,5,6,7-tetrahydrotieno[3,2-c]pyridin-2-yl)methyl]-6-bromo-7-oxo-4-thia-1-azabicyclo[3.2.0]hept-2-ene-2carboxylate 5-acetyl-4,5,6,7-tetrahydrothieno[3,2-c]pyridine-2-carbaldehyde (540 mg, 2.57 mmol) and the dry THF solution (20 mL) of (5R,6S)-6-bromo-7-oxo-4-thia-1-aza-bicyclo[3.2.0]hept-2-ene-2-carboxylic acid 4-nitro-benzyl ester (950 mg, 2.5 mmol) were added successively to the dry acetonitrile (15 mL) solution of anhydrous $MgBr_2:O(Et)_2$ (2.21 g, 8.5 mmol) under an argon atmosphere at room temperature. After cooling to −20° C., $Et_3N$ (2.0 mL) was added in one portion. The reaction vessel was covered with foil to exclude light. The reaction mixture was stirred for 2 h at −20° C. and treated with acetic anhydride (1.04 mL) in one portion. The reaction mixture was warmed to 0° C. and stirred for 15 h at 0° C. The mixture was diluted with ethyl acetate and washed with 5% citric acid aqueous solution, saturated sodium hydrogen carbonate, and brine. The organic layer was dried ($MgSO_4$) and filtered through a pad of Celite. The pad was washed with ethyl acetate. The filtrate was concentrated under reduced pressure. The residue was applied to silica gel column chromatography, then the column was eluted with ethyl acetate:hexane (1:1). Collected fractions were concentrated under reduced pressure and the mixture of diastereo isomers were taken to next step. Pale yellow amorphous solid; Yield: 870 mg, 53%; m.p. 46-48° C.; $(M+H)^+$ 637.6.

1HNMR ($CDCl3$): δ 2.15 (t, 6H); 2.8-3.0 (m, 2H); 3.7-3.9 (m, 2H); 4.58-4.68 (m, 2H); 5.30-5.45 (dd, 2H); 5.85 (d, 1H); 6.71 (s, 1H); 6.95 (s, 1H); 7.35-7.45 (d, 1H); 7.60 (dd, 2H); 8.25 (dd, 2H).

Step 3: (5R,6Z)-6-[(5-acetyl-4,5,6,7-tetrahydrothieno [3,2-c]pyridin-2-yl)methylene]-oxo-4-thia-1-azabicyclo[3.2.0]hept-2-ene-2-carboxylic acid (E+Z Isomers mixture, Sodium salt)

A solution of 0.77 g. (1.21 mmol, 4-nitrobenzyl(5R)-6-[(acetyloxy)(5-acetyl-4,5,6,7-tetrahydrotieno[3,2-c]pyridin-2-yl)methyl]-6-bromo-7-oxo-4-thia-1-azabicyclo[3.2.0.] hept-2-ene-2carboxylate in 40 mL THF and 40 mL phosphate buffer solution (pH=6.36) was hydrogenated at 40 psi for 3 hours in the presence of 0.4 g. Palladium on Carbon 10% catalyst. Reaction mixture was filtrated through celite pad, filtrate adjusted to pH=8.0, concentrated in vacuo, residue purified on a reverse-phase column (amberlite), using 5%. 10% ACN/water mixture as solvent, gave 0.107 g. (23%) of the title compound, reddish crystals, m.p. 362.4° C., (M+H)$^+$ 409.5.

$^1$H NMR: δ 2.08 (s, 3H); 2.80-2.95 (m, 1H); 3.74 (m, 2H); 3.98-4.06 (d, 2H) 6.32-6.42 (s, 1H); 6.50-6.60 (s, 1H); 6.98-7.20 (s, 1H); 7.30-7.40 (s, 1H).

Example 35

Preparation of (5R,6Z)-6-(6,7-dihydro-4H-pyrazolo [5,1-c][1,4]oxazin-2-ylmethylene)-7-oxo-4-thia-1-azabicyclo[3.2.0]hept-2-ene-2-carboxylic acid

Step 1: 4-Nitrosomorpholine-3-carboxylic acid

To a solution of morpholine-3-carboxylic acid (6.96 g, 52 mmol) in water (20 ml), at 0° C. under nitrogen, was added concentrated hydrochloric acid (4 ml), followed by sodium nitrite (5.0 g, 72 mmol) in small portions. The mixture was stirred at 0° C. for 1 hr, and then concentrated under vacuum at 30 to 35° C. The residue was stirred with 200 ml of acetone and filtered. The filtrate was evaporated and the residue treated with 50 ml of THF and concentrated. The process was repeated with 2×50 ml of THF to give 11.87 g of light yellow foam; MS (ESI) m/z 159.2 (M–H).

Step 2: 6,7-Dihydro-4H-[1,2,3]oxadiazolo[4,3-c][1,4]oxazin-8-ium-3-olate

The crude 4-nitrosomorpholine-3-carboxylic acid (11.0 g) from step 1 was dissolved in THF (250 ml) and cooled to 0° C. A solution of trifluoroacetic anhydride (7.4 ml, 52 mmol) in THF (20 ml) was added with stirring over 10 min. The resulting mixture was stirred at 0° C. for 5 hr, and warmed to room temperature for 16 hr. The solvent was evaporated and the residue was diluted with 250 ml of ethyl acetate and stirred with 30 g of anhydrous potassium carbonate. The mixture was filtered through a pad of silica gel and the filtrate evaporated. The residue was washed with a mixture of ethyl acetate-ether to give 3.80 g of a white solid; mp 132-133° C.; MS (ESI) m/z 143.1 (M+H).

Step 3: Ethyl 6,7-dihydro-4H-pyrazolo[5,1-c][1,4] oxazine-2-carboxylate

To a partial solution of 6,7-dihydro-4H-[1,2,3]oxadiazolo [4,3-c][1,4]oxazin-8-ium-3-olate (3.41 g, 24 mmol) in o-xylene (80 ml), was added ethyl propiolate (2.7 ml, 26 mmol). The mixture was stirred at 140° C. for 3 hr. An additional 2.0 ml (19 mmol) of ethyl propiolate was then added and the mixture was stirred at reflux for 18 hr. The final solution was evaporated under vacuum, and the residue was dissolved in a mixture of methylene chloride and hexanes (1:5). The solution was passed through a pad of silica gel and the filter pad was eluted with methylene chloride-hexanes, followed by ethyl acetate. The ethyl acetate eluent was evaporated and the residue washed with hexanes to give 4.10 g of a white solid; mp 63° C.; MS (ESI) m/z 197.1 (M+H).

Step 4: 6,7-Dihydro-4H-pyrazolo[5,1-c][1,4]oxazin-2-ylmethanol

To a solution of ethyl 6,7-dihydro-4H-pyrazolo[5,1-c][1,4]oxazine-2-carboxylate (1.57 g, 8.0 mmol) in methylene chloride (30 ml) was added 24 ml of a 1.0 M solution of diisobutylaluminum hydride in methylene chloride at 0° C., under nitrogen. After stirring for 0.5 hr at 0° C., the mixture was warmed to room temperature for 2 hr. It was then treated with 30 ml of saturated ammonium chloride solution and extracted with ethyl acetate. The organic solution was washed with brine, dried over anhydrous sodium sulfate, filtered and evaporated to give 1.27 g of a colorless oil; MS (ESI) m/z 155.3 (M+H).

Step 5: 6,7-Dihydro-4H-pyrazolo[5,1-c][1,4]oxazine-2-carbaldehyde

To a solution of 6,7-dihydro-4H-pyrazolo[5,1-c][1,4]oxazin-2-ylmethanol (1.08 g, 7.0 mmol) in 1,2-dichloroethane (30 ml) was added 5.4 g of activated manganese dioxide at room temperature with stirring. The mixture was heated to 60° C. for 1 hr and then stirred at room temperature for 16 hr. The final mixture was filtered through a column of silica gel topped with celite. The filter pad was eluted with methylene chloride, followed by ethyl acetate. The ethyl acetate eluent was evaporated and the residue triturated with to give 0.81 g of a white solid; mp 91° C.; MS (ESI) m/z 153.2 (M+H).

Step 6: 4-Nitrobenzyl (5R)-6-[(acetyloxy)(6,7-dihydro-4H-pyrazolo[5,1-c][1,4]oxazin-2-yl)methyl]-6-bromo-7-oxo-4-thia-1-azabicyclo[3.2.0]hept-2-ene-2-carboxylate To a solution of MgBr$_2$ (0.94 g, 5.1 mmol) in acetonitrile (25 ml) under nitrogen was added 6,7-dihydro-4H-pyrazolo [5,1-c][1,4]oxazine-2-carbaldehyde (0.26 g, 1.7 mmol) at room temperature with stirring. A solution of (5R,6S)-6-bromo-7-oxo-4-thia-1-azabicyclo[3.2.0]hept-2-ene-2-carboxylic acid 4-nitrobenzyl ester (0.58 g, 1.5 mmol) in THF (25 ml) was then added, and the mixture was cooled to –20° C. Triethylamine (0.71 ml, 5.1 mmol) was introduced, and the mixture was stirred at –20° C. in the dark for 5 hr. It was then treated with acetic anhydride (0.6 ml, 6.0 mmol), and 4-N,N-dimethylaminopyridine (24 mg, 0.2 mmol), and kept at 0° C. for 18 hr. The mixture was concentrated and the residue was dissolved in ethyl acetate. The ethyl acetate solution was washed with 5% citric acid, saturated sodium bicarbonate solution, and brine, dried over anhydrous sodium sulfate, and evaporated. The crude material was chromatographed with silica gel (EtOAc—CH2Cl2/1:5) to give 0.77 g of a white foam; MS (ESI) m/z 578.9 (M+H).

Step 7: (5R,6Z)-6-(6,7-dihydro-4H-pyrazolo[5,1-c] [1,4]oxazin-2-ylmethylene)-7-oxo-4-thia-1-azabicyclo[3.2.0]hept-2-ene-2-carboxylic acid To a solution of 4-nitrobenzyl (5R)-6-[(acetyloxy)(6,7-dihydro-4H-pyrazolo[5,1-c][1,4]oxazin-2-yl)methyl]-6-bromo-7-oxo-4-thia-1-azabicyclo[3.2.0]hept-2-ene-2-carboxylate (0.35 g, 0.6 mmol) in THF (20 ml), under nitrogen, was added 20 ml of a phosphate buffer solution (0.5M, pH 6.5), and 120 mg of 10% Pd/C. The mixture was hydrogenated at 40-50 psi for 3 hr, and then filtered through Celite. The filter pad was washed with THF, and the filtrate was extracted with ethyl acetate. The organic extract was dried over anhydrous magnesium sulfate and evaporated. The residue was washed with ether to give 0.09 g of a yellow solid; HRMS: calcd for $C_{13}H_{11}N_3O_4S$, 305.0470; found (ESI+), 306.05434; $^1$H NMR (DMSO-$d_6$) δ 4.07-4.09 (t, 2H), 4.13-4.17 (t, 2H), 4.82 (s, 2H), 6.36 (s, 1H), 6.55 (s, 1H), 7.17 (s, 1H), 7.55 (s, 1H), 12.80 (bs, 1H).

Example 36

Preparation of (5R)(6Z)-6-(6, 7-5H-Dihydropyrazolo [5,1-b]oxazin-2-ylmethylene)-7-oxo-4-thia-1-azabicyclo[3.2.0]hept-2-ene-2-carboxylic acid, sodium salt Step 1: Preparation of ethyl 6,7-dihydro-5H-pyrazolo [5,1-b][1,3]oxazine-2-carboxylate To the stirred suspension of ethyl 5-hydroxy-1H-pyrazole-3-carboxylate (10.34 g, 0.66 mol) and 36.62 g of potassium carbonate in 500 ml of acetonitrile was added 14.7 g of 1,3-dibromopropane, and refluxed for 16 hours. The reaction mixture was allowed to cool to room temperature, then filtered, the solid was washed with acetonitrile. The filtrate was concentrated to an oil. The residue was dissolved in ethyl acetate and extracted with water. The organic phase was dried over $MgSO_4$ and evaporated to dryness. 8.80 g of the desired product was obtained (68%), m.p. 44-46° C. (M+H)$^+$ 197.1.

Step 2: Preparation of 2,3-dihydro-5H-pyrazolo[5,1-b][1,3]oxazin-2-yl-methanol

To the stirred solution of 6,7-dihydro-5H-pyrazolo[5,1-b][1,3]oxazine-2-carboxylate: (4.0 g, 20 mmol) of in 100 ml of THF was added 0.71 g of lithium borohydride and 1.03 g of methanol. The solution was heated at 40 C for 2.5 hour. The reaction was quenched by 1N HCl, and adjusted to pH 1.3 and stirred at room temperature for 1 hour. The reaction mixture was adjusted pH to 8 with $k_2CO_3$. The reaction mixture was extracted with ethyl acetate. The organic layer was dried over $MgSO_4$, and concentrated to an oil and column chromatographed to give 2.08 g of the desired product (67%); (M+H) 155.

Step 3: Preparation of 6,7-dihydro-5H-pyrazolo[5,1-b][1,3]oxazine-2-carbaldehyde To the stirred solution of 2,3-dihydro-5H-pyrazolo[5,1-b][1,3]oxazin-2-yl-methanol (2.08 g, 13.5 mmol) in 60 ml of $CH_3Cl$ was added 9.38 g of $MnO_2$. The suspension was refluxed for 2 hour under a nitrogen atmosphere. The reaction mixture was filtered through a pad of Celite. The filtrate was concentrated to give yellow oil. The product was purified by chromatography. 2.15 g of the product was obtained (78%).

Step 4: 4-Nitrobenzy(5R)-6-[(acetyloxy)(6,7-dihydro-5H-pyrazolo[5,1-b][1,3]oxazin-2-yl)methyl]-6-bromo-7-oxo-4-thia-1-azabicyclo[3.2.0]hept-2-ene-2-carboxylate 6,7-dihydro-5H-pyrazolo[5,1-b][1,3]oxazine-2-carbaldehyde (330 mg, 2 mmol) and the dry THF solution (20 mL) of (5R,6S)-6-bromo-7-oxo-4-thia-1-aza-bicyclo[3.2.0]hept-2-ene-2-carboxylic acid 4-nitro-benzyl ester (0.794 g, 2.2 mmol) were added successively to the dry acetonitrile (15 mL) solution of anhydrous $MgBr_2:O(Et)_2$ (1.2 g) under an argon atmosphere at room temperature. After cooling to –20° C., $Et_3N$ (2.0 mL) was added in one portion. The reaction vessel was covered with foil to exclude light. The reaction mixture was stirred for 2 h at –20° C. and treated with acetic anhydride (1.04 mL) in one portion. The reaction mixture was warmed to 0° C. and stirred for 15 h at 0° C. The mixture was diluted with ethyl acetate and washed with 5% citric acid aqueous solution, saturated sodium hydrogen carbonate, and brine. The organic layer was dried ($MgSO_4$) and filtered through a pad of Celite. The pad was washed with ethyl acetate. The filtrate was concentrated under reduced pressure. The residue was applied to silica gel column chromatography, then the column was eluted with ethyl acetate:hexane (1:1). Collected fractions were concentrated under reduced pressure and the mixture of diastereo isomers were taken to next step. Pale yellow amorphous solid; Yield: 0.76 g, 65%; M+H 579.

Step-5: (5R)(6Z)-6-(6, 7-5H-Dihydropyrazolo[5,1-b] oxazin-2-ylmethylene)-7-oxo-4-thia-1-azabicyclo [3.2.0]hept-2-ene-2-carboxylic acid, sodium salt 4-Nitrobenzy(5R)-6-[(acetyloxy)(6,7-dihydro-5H-pyrazolo[5,1-b][1,3]oxazin-2-yl)methyl]-6-bromo-7-oxo-4-thia-1-azabicyclo[3.2.0]hept-2-ene-2-carboxylate (350 mg, 0.6 mmol) was dissolved in THF (20 mL), acetonitrile (10 mL) and 0.5 M phosphate buffer (pH 6.5, 28 mL) and hydrogenated over 10% Pd/C at 40 psi pressure. After 4 hrs the reaction mixture was filtered, cooled to 3° C., and 0.1 M NaOH was added to adjust pH to 8.5. The filtrate was washed with ethyl acetate and the aqueous layer was separated. The aqueous layer was concentrated under high vacuum at 35° C. to give yellow precipitate. The product was purified by HP21 resin reverse phase column chromatography. Initially the column was eluted with deionized water (2 lits) and latter with 10% acetonitrile:Water. The fractions containing the product were collected and concentrated at reduced pressure at room temperature. The yellow solid was washed with acetone and filtered. Dried. Yield: 103 mg, 52%; as yellow amorphous solid; (M+H+Na) 327.

$^1$H-NMR ($D_2O$); δ 6.97 (1H, s), 6.93 (1H, s), 6.47 (1H, s), 5.65 (1H, s) 4.28 (2H, m), 4.10 (2H, m), 2.21 (2H, m).

Example 37

Preparation of (5R),(6Z)-6-[5-(3-carboxypropionyl)-4,5,6,7-tetrahydropyrazolo[1,5-a]pyrazin-2-ylmethylene]-7-oxo-4-thia-1-azabicyclo[3.2.0]hept-2-ene-carboxylic acid, disodium salt The above mentioned compound was prepared by the procedures outlined in all the above examples. Starting from (5R),(6Z)-6-{5-[3-(4-nitrobenzyloxycarbonyl)propionyl]-4, 5,6,7-tetrahydropyrazolo[1,5-a]pyrazin-2-ylmethylene}-7-oxo-4-thia-1-azabicyclo[3.2.0]hept-2-ene-2-carboxylic acid sodium salt (467 mg) and hydrogenating it over Pd/C (10%), 276 mg of (74%) of (5R),(6Z)-6-[5-(3-carboxypropionyl)-4, 5,6,7-tetrahydropyrazolo[1,5-a]pyrazin-2-ylmethylene]-7-oxo-4-thia-1-azabicyclo[3.2.0]hept-2-ene-carboxylic acid, disodium salt was isolated as yellow amorphous solid. Mp. 180° C. (Dec); $^1$H NMR ($D_2O$) □ 2.41 (t, 2H), 2.42 (t, 2H), 2.67 (t, 2H), 2.72 (t, 2H), 3.95-4.09 (m, 2H), 4.18 (t, 2H), 4.28 (t, 2H), 4.75 (s, 2H), 4.87 (s, 2H), 6.33 (s, 1H), 6.34 (s, 1H), 6.53 (s, 1H), 7.00 (s, 1H), 7.09 (s, 1H).

Example 38

Preparation of (5R),(6Z)-6-[5-(2-methoxyacetyl)-4,5,6,7-tetrahydropyrazolo[1,5-a]pyrazin-2-ylmethylene]-7-oxo-4-thia-1-azabicyclo[3.2.0]hept-2-ene-carboxylic acid, sodium salt (5R),(6Z)-7-Oxo-6-(4,5,6,7-tetrahydropyrazolo[1,5-a]pyrazin-2-ylmethylene)-4-thia-1-aza-bicyclo[3.2.0]hept-2-ene-2-carboxylic acid, sodium salt (Example 25)

To the THF (64 mL) and H$_2$O (64 mL) solution of (5R),(6Z)-7-Oxo-6-(4,5,6,7-tetrahydropyrazolo[1,5-a]pyrazin-2-ylmethylene)-4-thia-1-aza-bicyclo[3.2.0]hept-2-ene-2-carboxylic acid, sodium salt (Example 25) (638 mg) was added 0.1 M NaOH aq slowly to adjust pH to 12.5 at 0° C. To the mixture was added methoxyacetyl-chloride (0.28 mL) over 5 min. The mixture was stirred for 0.5 h at 0° C. and methoxyacetylchloride (0.09 mL) was added to the mixture. After stirring the mixture for 0.5 h at the same temperature, 0.1 M NaOH aq was added to adjust pH to 8.05. The mixture was concentrated under high vacuum at 35° C. The concentrate was applied to Diaion HP-21 (78 mL, Mitsubishi Kasei Co. Ltd.) resin column chromatography. After adsorbing, the column was eluted with H$_2$O-MeCN (1:0 to 9:1). The combined fractions were concentrated under high vacuum at 35° C. and lyophilized to give the title compound as a yellow amorphous solid (509 mg, 65%, pH 7.58).

Mp 170° C. (dec); $^1$H NMR (D$_2$O) ☐ 3.28 (s, 3H×½), 3.29 (s, 3H×½), 3.78 (t, 2H×½, J=5.4 Hz), 3.89-3.93 (m, 2H×½), 4.09 (t, 2H×½, J=5.4 Hz), 4.14 (t, 2H×½, J=5.4 Hz), 4.20 (s, 2H×½), 4.25 (s, 2H×½), 4.61 (s, 2H×½), 4.66 (s, 2H×½), 6.19 (s, 1H×½), 6.22 (s, 1H×½), 6.37 (s, 1H×½), 6.372 (s, 1H×½), 6.87 (s, 1H), 6.93 (s, 1H)

Example 39

Preparation of (5R),(6Z)-6-[5-(2-methoxyacetyl)-4,5,6,7-tetrahydropyrazolo[1,5-a]pyrazin-2-ylmethylene]-7-oxo-4-thia-1-azabicyclo[3.2.0]hept-2-ene-carboxylic acid, sodium salt (4,5,6,7-Tetrahydropyrazolo[1,5-a]pyrazin-2-yl)-methanol Methanol (150 ml) was added to the mixture of 2-hydroxymethyl-6,7-dihydro-4H-pyrazolo[1,5-a]pyrazine-5-carboxylic acid 4-nitrobenzyl ester (Example 25) (2.38 g) and 10% Pd—C (50% wet, 1.19 g). The reaction mixture was stirred for 2 hours under a hydrogen atmosphere. The mixture was filtered and concentrated under reduced pressure. The residue was applied to silica-gel column chromatography, then the column was eluted with 50% methanol in chloroform. The titled compound was obtained as a white solid (1.08 g, 98%).

$^1$H NMR (400 MHz, CD$_3$OD) ☐ 3.22-3.25 (m, 2H), 3.99 (s, 2H), 4.03-4.06 (m, 2H), 4.52 (s, 2H), 6.06 (s, 1H).

[5-(4,5-Dihydrothiazol-2-yl)-4,5,6,7-tetrahydropyrazolo[1,5-a]pyrazin-2-yl]-methanol Hydrogen chloride (2 mol/l) solution in diethyl ether (0.7 ml) was added to the methanol (20 ml) solution of (4,5,6,7-tetrahydropyrazolo[1,5-a]pyrazin-2-yl)-methanol (1.08 g) and 2-methylsulfanyl-4,5-dihydrothiazole (1.03 g). The reaction mixture was refluxed for 4 days. The mixture was quenched with small amount of saturated potassium carbonate solution, dried (MgSO$_4$) and filtered. The filtrate was concentrated under reduced pressure. The residue was applied to silica-gel column chromatography, then the column was eluted with 10% methanol in chloroform. The titled compound was obtained as a white solid (1.49 g, 89%).

$^1$H NMR (400 MHz, CDCl$_3$) ☐ 2.04 (brs, 1H), 3.39 (t, 2H, J=7.5 Hz), 3.90 (t, 2H, J=5.3 Hz), 4.06 (t, 2H, J=7.5 Hz), 4.21 (t, 2H, J=5.3 Hz), 4.66 (s, 2H), 4.69 (s, 2H), 6.07 (s, 1H).

(5R),(6Z)-6-[5-(4,5-Dihydrothiazol-2-yl)-4,5,6,7-tetrahydropyrazolo[1,5-a]pyrazin-2-ylmethylene]-7-oxo-4-thia-1-azabicyclo[3.2.0]hept-2-ene-2-carboxylic acid sodium salt The activated manganese (IV) oxide (16.75 g) was added to the mixture of chloroform (180 ml) solution of [5-(4,5-dihydrothiazol-2-yl)-4,5,6,7-tetrahydropyrazolo[1,5-a]pyrazin-2-yl]-methanol (3.35 g) at room temperature. The reaction mixture was refluxed for 1 hour. After refluxing, the mixture was filtered through a pad of Celite and the filtrate was concentrated under reduced pressure. The residue was dried in vacuo and the crude 5-(4,5-dihydrothiazol-2-yl)-4,5,6,7-tetrahydropyrazolo[1,5-a]pyrazine-2-carbaldehyde was obtained as a colorless solid. The crude aldehyde thus obtained (2.56 g) was added to a dry acetonitrile (200 ml) solution of MgBr$_2$ (7.36 g) under a nitrogen atmosphere at room temperature then the mixture was stirred for 10 minutes. A dry THF (200 ml) solution of WLJ 20,014 (4.16 g) was added and the mixture was cooled to −20° C. Then triethylamine (11.3 ml) was added in one portion. The reaction vessel was covered with foil to exclude light. The reaction mixture was stirred for 1.5 hours at −20° C. and treated with 4-dimethylaminopyridine (132 mg) and acetic anhydride (4.2 ml) in one portion. The reaction mixture was warmed to 0° C. and stirred for 20 hours at 0° C. The mixture was diluted with ethyl acetate and washed with 5% citric acid aqueous solution, saturated sodium hydrogen carbonate, and brine. The organic layer was dried (MgSO$_4$) and filtered. The filtrate was concentrated under reduced pressure. The residue was applied to silica gel column chromatography, then eluted with n-hexane-AcOEt (1:2) and chloroform-methanol (9:1). The (5R,6RS)-6-{(RS)-acetoxy-[5-(4,5-dihydrothiazol-2-yl)-4,5,6,7-tetrahydropyrazolo[1,5-a]pyrazin-2-yl]-methyl}-6-bromo-7-oxo-4-thia-1-azabicyclo[3.2.0]hept-2-ene-2-carboxylic acid 4-nitrobenzyl ester was obtained (5.41 g, 75.4%).

The (5R,6RS)-6-{(RS)-acetoxy-[5-(4,5-dihydrothiazol-2-yl)-4,5,6,7-tetrahydropyrazolo[1,5-a]pyrazin-2-yl]-methyl}-6-bromo-7-oxo-4-thia-1-azabicyclo[3.2.0]hept-2-ene-2-carboxylic acid 4-nitrobenzyl ester (5.41 g) was dissolved in THF (76 ml) and acetonitrile (35 ml). Freshly activated Zn dust (21.6 g) and 0.5 mol/l phosphate buffer (pH 6.5, 111 ml) were added to the mixture. The reaction vessel was covered with foil to exclude light. The reaction mixture was vigorously stirred for 2 hours at 30 to 35° C. The reaction mixture was cooled at 0° C., and then the pH was adjusted to 7.6. Ethyl acetate was added to the reaction mixture and filtered through a pad of Celite. The pad was washed with water and the aqueous layer was separated. The aqueous layer was concentrated under high vacuum at 35° C. The concentrate was applied to Diaion HP-21 (170 ml, Mitsubishi Kasei Co. Ltd.) resin column chromatography. After adsorbing, the column was eluted with water and then with 5% to 15% acetonitrile aqueous solution. The combined active fractions was concentrated under high vacuum at 35° C. and lyophilized to give the titled compound as a crude yellow amorphous solid (1.60 g).

The crude compound was purified by preparative HPLC (Mightysil RP-18GP, KANTO CHEMICAL CO., INC., 35×250 mm, 0.05 mol/l phosphate buffer (pH 7.1): acetonitrile=80:20, 25 ml/min) followed by desaltation on Diaion HP-21 resin (150 ml, Mitsubishi Kasei Co. Ltd.) to give the titled compound as a yellow amorphous solid (1.06 g, y. 31.5%, pH 8.33).

Mp 100° C. (dec); $^1$H NMR (D$_2$O) □ 3.18 (t, 2H, J=7.6 Hz), 3.60 (t, 2H, J=5.3 Hz), 3.73 (t, 2H, J=7.6 Hz), 3.94 (t, 2H, J=5.3 Hz), 4.37 (s, 2H), 6.01 (s, 1H), 6.21 (s, 1H), 6.77 (s, 1H), 6.78 (s, 1H); IR (KBr) 3381, 1752, 1606 cm$^{-1}$; max (H$_2$O) 369, 291, 208 nm.

Example 40

Preparation of (5R),(6Z)-6-[5-(2-methoxyacetyl)-4,5,6,7-tetrahydropyrazolo[1,5-a]pyrazin-2-ylmethylene]-7-oxo-4-thia-1-azabicyclo[3.2.0]hept-2-ene-carboxylic acid, sodium salt Preparation of Ethyl 2-[(acetyloxy)((5R)-6-bromo-2-{[(4-nitrobenzyl)oxy]carbonyl}-7-oxo-4-thia-1-azabicyclo[3.2.0]hept-2-en-6-yl)methyl]-4,7-dihydrofuro[2,3-c]pyridine-6(5H)-carboxylate The titled compound was prepared from 0.669 grams of methyl 2-formyl-4,7-dihydrofuro[2,3-c]pyridine-6(5H)-carboxylate and 1.155 grams of 4-nitrobenzyl (5R)-6-bromo-7-oxo-4-thia-1-azabicyclo[3.2.0]hept-2-ene-2-carboxylate yielded 1.65 grams of product (84%), which was used directly for the next step. MS: 652.2 (M+H)

Preparation of (5R,6Z)-6-{[6-(ethoxycarbonyl)-4,5,6,7-tetrahydrofuro[2,3-c]pyridin-2-yl]methylene}-7-oxo-4-thia-1-azabicyclo[3.2.0]hept-2-ene-2-carboxylic acid The title compound was prepared from 1.65 g of ethyl 2-[(acetyloxy)((5R)-6-bromo-2-{[(4-nitrobenzyl)oxy]carbonyl}-7-oxo-4-thia-1-azabicyclo[3.2.0]hept-2-en-6-yl)methyl]-4,7-dihydrofuro[2,3-c]pyridine-6(5H)-carboxylate, yielded 0.386 grams of product (41%). MP: decomposed at 175° C. MS: 375.0 (M−H). H-NMR (D2O): □ 6.91 (s, 1H), 6.84 (s, 1H), 6.62 (s, 1H), 6.39 (s, 1H), 4.41 (b, 2H), 4.04 (q, 2H, J=5 Hz), 3.52 (b, 2H), 2.42 (b, 2H), 1.14 (t, 3H, J=5 Hz),

What is claimed is:

1. A compound of formula I:

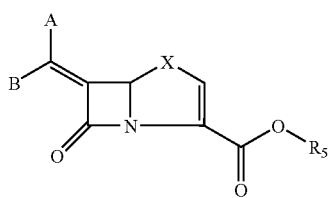

I wherein:
one of A and B is hydrogen and the other is an optionally substituted fused bicyclic heteroaryl group; with the proviso that if the aromatic ring of the bicyclic heteroaryl group is imidazolo, the non-aromatic ring portion may not contain S adjacent to the bridgehead carbon;
X is O;
R$_5$ is H, C1-C6 alkyl, C5-C6 cycloalkyl, or CHR$_3$OCOC1-C6 alkyl; and
R$_3$ is hydrogen, C1-C6 alkyl, C5-C6 cycloalkyl, optionally substituted aryl, or optionally substituted heteroaryl; or a pharmaceutically acceptable salt thereof,
wherein the bicyclic heteroaryl group has the formula 1-A,

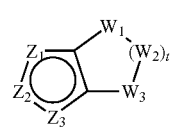

1-A wherein
Z1, Z2 and Z3 are independently CR$_2$, N, O, S or N—R$_1$ except one of Z1-Z3 is carbon and is bonded to the remainder of the molecule;
W$_1$, W$_2$ and W$_3$ are independently CR$_4$R$_4$, S, SO, SO$_2$, O, or N—R$_1$; with the proviso that no S—S or O—O or S—O bond exists in the saturated ring;
t is and integer from 1 to 4;
R$_1$ is H, optionally substituted C1-C6 alkyl, optionally substituted aryl, optionally substituted heteroaryl or mono or bicyclic saturated heterocyclyl, optionally substituted C5-C7 cycloalkyl, optionally substituted C3-C6 alkenyl, optionally substituted C3-C6 alkynyl with the proviso that neither the double bond nor the triple bond should be present at the carbon atom which is directly linked to N; optionally substituted C1-C6 perfluoroalkyl, —S(O)$_p$ optionally substituted alkyl or aryl where p is 0-2, optionally substituted —C(=O)heteroaryl, optionally substituted —C(=O)aryl, optionally substituted —C(=O)C1-C6alkyl, optionally substituted —C(=O)(C5-C6)cycloalkyl, optionally substituted —(C=O) mono or bicyclic saturated heterocyclyl, optionally substituted C1-C6 alkylaryl, optionally substituted C1-C6 alkyl heteroaryl, optionally substituted aryl-C1-C6 alkyl, optionally substituted heteroaryl-C1-C6 alkyl, optionally substituted C1-C6 alkyl mono or bicyclic saturated heterocyclyl, optionally substituted arylalkenyl of 8 to 16 carbon atoms, —CONR$_6$R$_7$, —SO$_2$NR$_6$R$_7$, optionally substituted arylalkyloxyalkyl, optionally substituted -alkyl-O-alkyl-aryl, optionally substituted -alkyl-O-alkyl-heteroaryl, optionally substituted aryloxyalkyl, optionally substituted heteroaryloxyalkyl, optionally substituted aryloxyaryl, optionally substituted aryloxyheteroaryl, optionally substituted C1-C6alkylaryloxyaryl, optionally substituted C1-C6 alkylaryloxyheteroaryl, optionally substituted alkoxycarbonyl, optionally substituted aryloxycarbonyl, or optionally substituted heteroaryloxy carbonyl;
R$_2$ is hydrogen, optionally substituted C1-C6 alkyl, optionally substituted C2-C6 alkenyl, optionally substituted C2-C6 alkynyl, halogen, cyano, NR$_6$R$_7$, optionally substituted C1-C6 alkoxy, hydroxy; optionally substituted aryl, optionally substituted heteroaryl, COOR$_6$, optionally substituted alkyl aryloxy alkylamines, optionally substituted aryloxy, optionally substituted heteroaryloxy, optionally substituted C3-C6 alkenyloxy, optionally substituted C3-C6 alkynyloxy, C1-C6 alkylamino-C1-C6 alkoxy, alkylene dioxy, optionally substituted aryloxy-C1-C6 alkyl amine, C1-C6 perfluoro alkyl, S(O)$_q$-optionally substituted C1-C6 akyl, S(O)$_q$-optionally substituted aryl where q is 0, 1 or 2, CONR$_6$R$_7$, guanidino, optionally substituted C1-C6 alkylaryl, optionally substituted arylalkyl, optionally substituted C1-C6 alkylheteroaryl, optionally substituted heteroaryl-C1-C6 alkyl, optionally substituted C1-C6 alkyl mono or bicyclic saturated heterocyclyl, optionally substituted arylalkenyl of 8 to 16 carbon atoms, $SO_2NR_6R_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, substituted heteroaryloxyaryl, optionally substituted C1-C6alkyl aryloxyaryl, optionally substituted C1-C6 alkylaryloxyheteroaryl, optionally substituted aryloxyalkyl, or optionally substituted heteroaryloxyalkyl;

$R_4$ is H, optionally substituted C1-C6 alkyl, one of $R_4$ is OH, C1-C6 alkoxy, —S—C1-C6 alkyl, $COOR_6$, —$NR_6R_7$, —$CONR_6R_7$; or $R_4R_4$ may together be (=O) or $R_4R_4$ together with the carbon to which they are attached may form a spiro system of five to eight members with or without the presence of heteroatoms selected from N, O, S(=O)n (where n is 0 to 2), and N—$R_1$; and $R_6$ and $R_7$ are independently H, optionally substituted C1-C6 alkyl, optionally substituted aryl, optionally substituted heteroaryl, optionally substituted C1-C6 alkylaryl, optionally substituted arylalkyl, optionally substituted heteroarylalkyl, optionally substituted C1-C6 alkylheteroaryl, or $R_6$ and $R_7$ together with the N to which they are attached, may form a 3-7 membered saturated ring system said ring system in addition to the N to which $R_6$ and $R_7$ are attached optionally having one or two heteroatoms selected from N, O or S.

2. A compound of formula I:

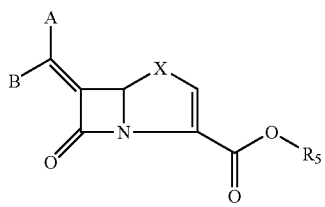

wherein:
one of A and B is hydrogen and the other is an optionally substituted fused bicyclic heteroaryl group; with the proviso that if the aromatic ring of the bicyclic heteroaryl group is imidazolo, the non-aromatic ring portion may not contain S adjacent to the bridgehead carbon;

X is O;

$R_5$ is H, C1-C6 alkyl, C5-6 cycloalkyl, or $CHR_3OCOC1$-C6 alkyl; and $R_3$ is hydrogen, C1-C6 alkyl, C5-C6 cycloalkyl, optionally substituted aryl, or optionally substituted heteroaryl; or a pharmaceutically acceptable salt thereof, wherein the bicyclic heteroaryl group has the formula 1-B,

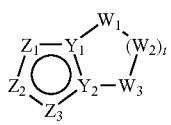

wherein
$Z_1$, $Z_2$ and $Z_3$ are independently $CR_2$, N, O, S or N—$R_1$, except one of $Z_1$, $Z_2$ or $Z_3$ is carbon and is bonded to the remainder of the molecule;

$W_1$, $W_2$ and $W_3$ are each independently $CR_4R_4$, S, SO, $SO_2$, O, or N—$R_1$;

t is and integer from 1 to 4;

$Y_1$ and $Y_2$ are independently N or C, provided at least one of $Y_1$ and $Y_2$ is C;

$R_1$, $R_2$, $R_4$, $R_6$ and $R_7$ are as defined in claim 1.

3. A compound of formula I:

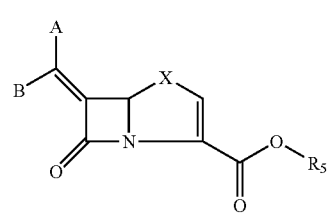

wherein:
one of A and B is hydrogen and the other is an optionally substituted fused bicyclic heteroaryl group;

X is O;

$R_5$ is H, C1-C6 alkyl, C5-C6 cycloalkyl, or $CHR_3OCOC1$-C6alkyl; and $R_3$ is hydrogen, C1-C6 alkyl, C5-C6 cycloalkyl, optionally substituted aryl, or optionally substituted heteroaryl; or a pharmaceutically acceptable salt thereof, wherein the bicyclic heteroaryl group has the formula 1-C,

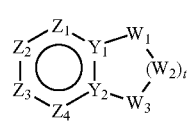

wherein
$Z_1$, $Z_2$, $Z_3$ and $Z_4$ are independently $CR_2$ or N, except one of Z1-Z4 is carbon and is bonded to the remainder of the molecule;

$W_1$, $W_2$ and $W_3$ are each independently $CR_4R_4$, S, SO, $SO_2$, O, or N—$R_1$ with the proviso that no S—S or O—O or S—O bond formation can occur to form the saturated ring system;

$R_1$ is H, optionally substituted C1-C6 alkyl, optionally substituted aryl, optionally substituted heteroaryl or mono or bicyclic saturated heterocyclyl, optionally substituted C5-C7 cycloalkyl, optionally substituted C3-C6 alkenyl, optionally substituted C3-C6 alkynyl with the proviso that neither the double bond nor the triple bond should be present at the carbon atom which is directly linked to N; optionally substituted C1-C6 perfluoroalkyl, —$S(O)_p$ optionally substituted alkyl or aryl where p is 0-2, optionally substituted —C(=O)heteroaryl, optionally substituted —C(=O)aryl, optionally substituted —C(=O)C1-C6alkyl, optionally substituted —C(=O)(C5-C6)cycloalkyl, optionally substituted —C(=O) mono or bicyclic saturated heterocyclyl, optionally substituted C1-C6 alkylaryl, optionally substituted C1-C6 alkyl heteroaryl, optionally substituted aryl-C1-C6 alkyl, optionally substituted heteroaryl-C1-C6 alkyl, optionally substituted C1-C6 alkyl mono or bicyclic saturated heterocyclyl, optionally substituted arylalkenyl of 8 to 16 carbon atoms, —CONR₆R₇, —SO₂NR₆R₇, optionally substituted arylalkyloxyalkyl, optionally substituted -alky-O-alkyl-aryl, optionally substituted -alky-O-alkyl-heteroaryl, optionally substituted aryloxyalkyl, optionally substituted heteroaryloxyalkyl, optionally substituted aryloxyaryl, optionally substituted aryloxyheteroaryl, optionally substituted C1-C6alkylaryloxyaryl, optionally substituted C1-C6 alkylaryloxyheteroaryl, optionally substituted alkoxycarbonyl, optionally substituted aryloxycarbonyl, or optionally substituted heteroaryloxy carbonyl;

$R_2$ is hydrogen, optionally substituted C1-C6 alkyl, optionally substituted C2-C6 alkenyl, optionally substituted C2-C6 alkynyl, halogen, cyano, $NR_6R_7$, optionally substituted C1-C6 alkoxy, hydroxy; optionally substituted aryl, optionally substituted heteroaryl, $COOR_6$, optionally substituted alkyl aryloxy alkylamines, optionally substituted aryloxy, optionally substituted heteroaryloxy, optionally substituted C3-C6 alkenyloxy, optionally substituted C3-C6 alkynyloxy, C1-C6 alkylamino-C1-C6 alkoxy, alkylene dioxy, optionally substituted aryloxy-C1-C6 alkyl amine, C1-C6 perfluoro alkyl, $S(O)_q$-optionally substituted C1-C6 akyl, $S(O)_q$-optionally substituted aryl where q is 0, 1 or 2, $CONR_6R_7$, guanidino, optionally substituted C1-C6 alkylaryl, optionally substituted arylalkyl, optionally substituted C1-C6 alkylheteroaryl, optionally substituted heteroaryl-C1-C6 alkyl, optionally substituted C1-C6 alkyl mono or bicyclic saturated heterocyclyl, optionally substituted arylalkenyl of 8 to 16 carbon atoms, $SO_2NR_6R_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, substituted heteroaryloxyaryl, optionally substituted C1-C6alkyl aryloxyaryl, optionally substituted C1-C6 alkylaryloxyheteroaryl, optionally substituted aryloxyalkyl, optionally substituted heteroaryloxyalkyl;

$R_4$ is H, optionally substituted C1-C6 alkyl, one of $R_4$ is OH, C1-C6 alkoxy, —S—C1-C6 alkyl, $COOR_6$, —$NR_6R_7$, —$CONR_6R_7$; or $R_4R_4$ may together be (=O) or $R_4R_4$ together with the carbon to which they are attached may form a spiro system of five to eight members with or without the presence of heteroatoms selected from N, O, S(=O)n (where n is 0 to 2), and N—$R_1$; and $R_6$ and $R_7$ are independently H, optionally substituted C1-C6 alkyl, optionally substituted aryl, optionally substituted heteroaryl, optionally substituted C1-C6 alkylaryl, optionally substituted arylalkyl, optionally substituted heteroarylalkyl, optionally substituted C1-C6 alkylheteroaryl, or $R_6$ and $R_7$ together with the N to which they are attached, may form a 3-7 membered saturated ring system said ring system in addition to the N to which $R_6$ and $R_7$ are attached optionally having one or two heteroatoms selected from N, O or S;

t is 1-4; and $Y_1$ and $Y_2$ are C.

4. A compound according to claim 1, wherein one of Z2 or Z3 is N, O or S.

5. A compound according to claim 1, wherein at least one of $W_1$, $W_2$ and $W_3$ is $CR_4R_4$.

6. A compound according to claim 5, wherein $W_1$, $W_2$ and $W_3$ are independently $CR_4R_4$.

7. A compound according to claim 1, wherein t is 1,2 or 3.

8. A compound according to claim 2, wherein t is 3.

9. A compound according to claim 2, wherein at least two of $Z_1$, $Z_2$, $Z_3$, $Y_1$ and $Y_2$ are N.

10. A compound according to claim 9, wherein three of $Z_1$, $Z_2$, $Z_3$, $Y_1$ and $Y_2$ are N.

11. A compound according to claim 2, wherein two of $W_1$, $W_2$ and $W_3$ are independently $CR_4R_4$.

12. The compound according to claim 11, wherein $R_4$ is H.

13. The compound according to claim 2, wherein two of $Z_1$, $Z_2$ and $Z_3$ are independently $CR_2$.

14. The compound according to claim 3, wherein three of $Z_1$-$Z_4$ are independently $CR_2$ and the other is C.

15. The compound according to claim 3, wherein at least one of $Z_1$-$Z_4$ is N.

16. The compound according to claim 15, wherein $Z_1$ is N.

17. The compound according to claim 15, wherein two of $Z_1$-$Z_4$ are N.

18. The compound according to claim 15, wherein three of $Z_1$-$Z_4$ are N.

19. A method for the treatment of bacterial infection or disease in a patient in need thereof which comprises providing to said patient an effective amount of a compound of formula I:

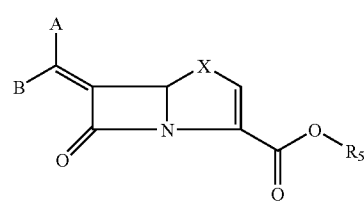

wherein:
one of A and B is hydrogen and the other is an optionally substituted fused bicyclic heteroaryl group; with the proviso that if the aromatic ring of the bicyclic heteroaryl group is imidazolo, the non-aromatic ring portion may not contain S adjacent to the bridgehead carbon;

X is O;

$R_5$ is H, C1-C6 alkyl, C5-C6 cycloalkyl, or $CHR_3OCOC1$-C6 alkyl; and $R_3$ is hydrogen, C1-C6 alkyl, C5-C6 cycloalkyl, optionally substituted aryl, or optionally substituted heteroaryl;

or a pharmaceutically acceptable salt thereof;

wherein the bicyclic heteroaryl group has the formula 1-A,

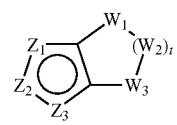

wherein
Z1, Z2 and Z3 are independently $CR_2$, N, O, S or N—$R_1$, except one of Z1-Z3 is carbon and is bonded to the remainder of the molecule;

$W_1$, $W_2$ and $W_3$ are independently $CR_4R_4$, S, SO, $SO_2$, O or N—$R_1$; with the proviso that no S—S or O—O or S—O bond formation can occur to form the saturated ring system;

t is an integer from 1 to 4;

$R_1$ is H, optionally substituted C1-C6 alkyl, optionally substituted aryl, optionally substituted heteroaryl or mono or bicyclic saturated heterocyclyl, optionally substituted C5-C7 cycloalkyl, optionally substituted C3-C6 alkenyl, optionally substituted C3-C6 alkynyl with the proviso that neither the double bond nor the triple bond should be present at the carbon atom which is directly linked to N; optionally substituted C1-C6 perfluoroalkyl, —S(O)$_p$ optionally substituted alkyl or aryl where p is 0-2, optionally substituted —C(=O)heteroaryl, optionally substituted —C(=O)aryl, optionally substituted —C(=O)C1-C6 alkyl, optionally substituted —C(=O)C5-C6cycloalkyl, optionally substituted —C(=O) mono or bicyclic saturated heterocyclyl, optionally substituted C1-C6 alkylaryl, optionally substituted C1-C6 alkyl heteroaryl, optionally substituted arylC1-C6 alkyl, optionally substituted heteroaryl-C1-C6 alkyl, optionally substituted C1-C6 alkyl mono or bicyclic saturated heterocyclyl, optionally substituted arylalkenyl of 8 to 16 carbon atoms, —CONR$_6$R$_7$, —SO$_2$NR$_6$R$_7$, optionally substituted arylalkyloxyalkyl, optionally substituted -alkyl-O-alkyl-aryl, optionally substituted -alkyl-O-alkyl-heteroaryl, optionally substituted aryloxyalkyl, optionally substituted heteroaryloxyalkyl, optionally substituted aryloxyaryl, optionally substituted aryloxyheteroaryl, optionally substituted C1-C6alkylaryloxyaryl, optionally substituted C 1-C6 alkylaryloxyheteroaryl, optionally substituted alkoxycarbonyl, optionally substituted aryloxycarbonyl, or optionally substituted heteroaryloxy carbonyl;

R$_2$ is hydrogen, optionally substituted C1-C6 alkyl, optionally substituted C2-C6 alkenyl, optionally substituted C2-C6 alkynyl, halogen, cyano, NR$_6$R$_7$, optionally substituted C1-C6 alkoxy, hydroxy; optionally substituted aryl, optionally substituted heteroaryl, COOR$_6$, optionally substituted alkyl aryloxy alkylamines, optionally substituted aryloxy, optionally substituted heteroaryloxy, optionally substituted C3-C6 alkenyloxy, optionally substituted C3-C6 alkynyloxy, C1-C6 alkylamino-C1-C6 alkoxy, alkylene dioxy, optionally substituted aryloxy-C1-C6 alkyl amine, C1-C6 perfluoro alkyl, S(O)$_q$-optionally substituted C1-C6 akyl, S(O)$_q$-optionally substituted aryl where q is 0, 1 or 2, CONR$_6$R$_7$, guanidino, optionally substituted C1-C6 alkylaryl, optionally substituted arylalkyl, optionally substituted C1-C6 alkylheteroaryl, optionally substituted heteroarylC1-C6 alkyl, optionally substituted C1-C6 alkyl mono or bicyclic saturated heterocyclyl, optionally substituted arylalkenyl of 8 to 16 carbon atoms, SO$_2$NR$_6$R$_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, substituted heteroaryloxyaryl, optionally substituted C1-C6 alkyl aryloxyaryl, optionally substituted C1-C6 alkylaryloxyheteroaryl, optionally substituted aryloxyalkyl, or optionally substituted heteroaryloxyalkyl;

R$_4$ is H, optionally substituted C1-C6 alkyl, one of R$_4$ is OH, C1-C6 alkoxy, —S—C1-C6 alkyl, COOR$_6$, —NR$_6$R$_7$, —CONR$_6$R$_7$; or R$_4$R$_4$ may together be (=O) or R$_4$R$_4$ together with the carbon to which they are attached may form a spiro system of five to eight members with or without the presence of heteroatoms is selected from N, O, S(=O)n (where n is 0 to 2) and N—R$_1$; and R$_6$ and R$_7$ are independently H, optionally substituted C1-C6 alkyl, optionally substituted aryl, optionally substituted heteroaryl, optionally substituted C1-C6 alkylaryl, optionally substituted arylalkyl, optionally substituted heteroarylalkyl, optionally substituted C1-C6 alkylheteroaryl, or R$_6$ and R$_7$ together with the N to which they are attached, may form a 3-7 membered saturated ring system said ring system in addition to the N to which R$_6$ and R$_7$ are attached optionally having one or two heteroatoms selected from N, O or S.

20. A method for the treatment of bacterial infection or disease in a patient in need thereof which comprises providing to said patient an effective amount of a compound of formula I:

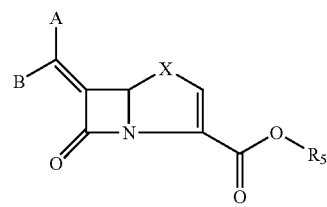

wherein:
one of A and B is hydrogen and the other is an optionally substituted fused bicyclic heteroaryl group; with the proviso that if the aromatic ring of the bicyclic heteroaryl group is imidazolo, the non-aromatic ring portion may not contain S adjacent to the bridgehead carbon;

X is O;

R$_5$ is H, C1-C6 alkyl, C5-C6 cycloalkyl, CHR$_3$OCOC1-C6 alkyl; and

R$_3$ is hydrogen, C1-C6 alkyl, C5-C6 cycloalkyl, optionally substituted aryl, optionally substituted heteroaryl; or a pharmaceutically acceptable salt thereof;

wherein the bicyclic heteroaryl group has the formula 1-B,

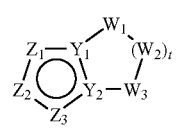

wherein
Z$_1$, Z$_2$ and Z$_3$ are independentl CR$_2$, N, O, S or N—R$_1$, except one of Z$_1$, Z$_2$ or Z$_3$ is carbon and is bonded to the remainder of the molecule;

W$_1$, W$_2$ and W$_3$ are each independently CR$_4$R$_4$, S, SO, SO$_2$, O, or N—R$_1$;

t is and integer from 1 to 4;

Y$_1$ and Y$_2$ are independently N or C, provided at least one of Y$_1$ and Y$_2$ is C;

R$_1$, R$_2$, R$_4$, R$_6$ and R$_7$ are as defined in claim 1.

21. A method for the treatment of bacterial infection or disease in a patient in need thereof which comprises providing to said patient an effective amount of a compound of formula I:

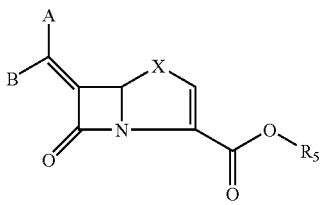

wherein:
one of A and B is hydrogen and the other is an optionally substituted fused bicyclic heteroaryl group;
X is O;
$R_5$ is H, C1-C6 alkyl, C5-C6 cycloalkyl or $CHR_3OCOC1$-C6 alkyl; and
$R_3$ is hydrogen, C1-C6 alkyl, C5-C6 cycloalkyl, optionally substituted aryl or optionally substituted heteroaryl; or a pharmaceutically acceptable salt thereof;
wherein the bicyclic heteroaryl group has the formula 1-C,

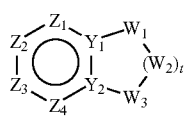

wherein
$Z_1$, $Z_2$, $Z_3$ and $Z_4$ are independently $CR_2$ or N, except one of Z1-Z4 is carbon and is bonded to the remainder of the molecule;
$W_1$, W2 and $W_3$ are each independently $CR_4R_4$, S, SO, $SO_2$, O, or N—$R_1$ with the proviso that no S—S or O—O or S—O bond formation can occur to form the saturated ring system:
t is 1-4;
$Y_1$ and $Y_2$ are C; and
$R_1$ is H, optionally substituted C1-C6 alkyl, optionally substituted aryl, optionally substituted heteroaryl or mono or bicyclic saturated heterocyclyl, optionally substituted C5-C7 cycloalkyl, optionally substituted C3-C6 alkenyl, optionally substituted C3-C6 alkynyl with the proviso that neither the double bond nor the triple bond should be present at the carbon atom which is directly linked to N; optionally substituted C1-C6 perfluoroalkyl, —S(O)$_p$ optionally substituted alkyl or aryl where p is 0-2, optionally substituted —C(=O)heteroaryl, optionally substituted —C(=O)aryl, optionally substituted —C(=O)C1-C6alkyl, optionally substituted —C(=O)(C5-C6)cycloalkyl, optionally substituted —(C=O) mono or bicyclic saturated heterocyclyl, optionally substituted C1-C6 alkylaryl, optionally substituted C1-C6 alkyl heteroaryl, optionally substituted aryl-C1-C6 alkyl, optionally substituted heteroaryl-C1-C6 alkyl, optionally substituted C1-C6 alkyl mono or bicyclic saturated heterocyclyl, optionally substituted arylalkenyl of 8 to 16 carbon atoms, —CONR$_6$,R$_7$, —SO$_2$NR$_6$R$_7$, optionally substituted arylalkyloxyalkyl, optionally substituted -alky-O-alkyl-aryl, optionally substituted -alky-O-alkyl-heteroaryl, optionally substituted aryloxyalkyl, optionally substituted heteroaryloxyalkyl, optionally substituted aryloxyaryl, optionally substituted aryloxyheteroaryl, optionally substituted C1-C6alkylaryloxyaryl, optionally substituted C1-C6 alkylaryloxyheteroaryl, optionally substituted alkoxycarbonyl, optionally substituted aryloxycarbonyl or optionally substituted heteroaryloxy carbonyl;

$R_2$ is hydrogen, optionally substituted C1-C6 alkyl, optionally substituted C2-C6 alkenyl, optionally substituted C2-C6 alkynyl, halogen, cyano, $NR_6R_7$, optionally substituted C1-C6 alkoxy, hydroxy; optionally substituted aryl, optionally substituted heteroaryl, $COOR_6$, optionally substituted aryloxy, optionally, substituted heteroaryloxy, optionally substituted C3-C6 alkenyloxy, optionally substituted C3-C6 alkynyloxy, C1-C6 alkylamino-C1-C6 alkoxy, alkylene dioxy, optionally substituted aryloxy-C1-C6 alkyl amine, C1-C6 perfluoro alkyl, $S(O)_q$-optionally substituted C1-C6 akyl, $S(O)_q$-optionally substituted aryl where q is 0, 1 or 2, $CONR_6R_7$, guanidino, optionally substituted C1-C6 alkylaryl, optionally substituted arylalkyl, optionally substituted C1-C6 alkylheteroaryl, optionally substituted heteroaryl-C1-C6 alkyl, optionally substituted C1-C6 alkyl mono or bicyclic saturated heterocyclyl, optionally substituted arylalkenyl of 8 to 16 carbon atoms, $SO_2NR_6R_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, substituted heteroaryloxyaryl, optionally substituted C1-C6alkyl aryloxyaryl, optionally substituted C1-C6 alkylaryloxyheteroaryl, optionally substituted aryloxyalkyl, or optionally substituted heteroaryloxyalkyl;

$R_4$ is H, optionally substituted C1-C6 alkyl, one of $R_4$ is OH, C1-C6 alkoxy, —S—C1-C6 alkyl, $COOR_6$, —$NR_6R_7$, —$CONR_6R_7$; or $R_4R_4$ may together be (=O) or $R_4R_4$ together with the carbon to which they are attached may form a spiro system of five to eight members with or without the presence of heteroatoms selected from N, O, S(=O)n (where n is 0 to 2), and N—$R_1$; and $R_6$ and $R_7$ are independently H, optionally substituted C1-C6 alkyl, optionally substituted aryl, optionally substituted heteroaryl, optionally substituted C1-C6 alkylaryl, optionally substituted arylalkyl, optionally substituted heteroarylalkyl, optionally substituted C1-C6 alkylheteroaryl, or $R_6$ and $R_7$ together with the N to which they are attached, may form a 3-7 membered saturated ring system said ring system in addition to the N to which $R_6$ and $R_7$ are attached optionally having one or two heteroatoms selected from N, O or S.

22. A method according to any one of claims 19, 20 and 21, wherein the compound is co-administered with a betalactam antibiotic.

23. A method according to claim 22, wherein the ratio of β-lactam antibiotic to the compound is in a range from about 1:1 to 100:1.

24. A method according to claim 22, wherein the ratio of the β-lactam antibiotic to the compound is less than 10:1.

25. A method according to claim 22, wherein the β-lactam antibiotic is selected from a penicillin antibiotic and a cephalosporin antibiotic.

26. A method according to claim 22, wherein the β-lactam antibiotic is selected from piperacillin, amoxycillin, ticarcillin, benzylpenicillins, ampicillin, sulbenicillin, cefatrizine, cephaloridine, cephalothin, cefazolin, cephalexin, cephradine, aztreonam, and latamoxef antibiotic.

27. A method according to claim 22, wherein the betalactam antibiotic is piperacillin or amoxycillin.

28. A method according to claim 22, wherein the betalactam antibiotic is piperacillin and is provided to the patient intravenously.

29. A method according to claim 22, wherein the betalactam antibiotic is amoxycillin and is provided to the patient orally.

30. A pharmaceutical composition comprising: a pharmaceutically acceptable carrier; and an effective amount of a compound of formula I as claimed in any one of claim 1, 2, or 3; or a pharmaceutically acceptable salt of the compound thereof.

31. A composition according to claim 30, further comprising a betalactam antibiotic.

\* \* \* \* \*